US008147822B1

(12) United States Patent
Bell et al.

(10) Patent No.: US 8,147,822 B1
(45) Date of Patent: Apr. 3, 2012

(54) ONCOLYTIC VIRUS

(75) Inventors: John C. Bell, Ontario (CA); Nahum Sonenberg, Quebec (CA); David F. Stojdl, Ontario (CA); Earl G. Brown, Ontario (CA); Harold L. Atkins, Ontario (CA); Ricardo M. Marius, Ontario (CA); Brian D. Lichty, Ontario (CA); Shane B. Knowles, Ontario (CA)

(73) Assignee: Wellstat Biologics Corporation, Gaithersburg, MD (US)

( * ) Notice: Subject to any disclaimer, the term of this patent is extended or adjusted under 35 U.S.C. 154(b) by 1017 days.

(21) Appl. No.: 09/664,444

(22) Filed: Sep. 18, 2000

Related U.S. Application Data

(60) Provisional application No. 60/287,590, filed on Sep. 17, 1999, now abandoned.

(51) Int. Cl.
*A61K 35/76* (2006.01)
(52) U.S. Cl. .................. 424/93.6; 424/204.1; 424/224.1
(58) Field of Classification Search ................. 424/93.1, 424/93.2; 435/235.1, 320.1
See application file for complete search history.

(56) References Cited

U.S. PATENT DOCUMENTS

| 5,124,148 | A | 6/1992 | Csatary et al. |
| 5,215,745 | A | 6/1993 | Csatary et al. |
| 5,273,745 | A | 12/1993 | Schirrmacher |
| 5,585,096 | A | 12/1996 | Martuza et al. |
| 5,602,023 | A | 2/1997 | Csatary |
| 5,677,178 | A | 10/1997 | McCormick |
| 6,033,886 | A | 3/2000 | Conzelmann |
| 6,110,461 | A | 8/2000 | Lee et al. |
| 6,136,307 | A | 10/2000 | Lee et al. |
| 7,192,580 | B2 | 3/2007 | Atkins et al. |
| 2003/0044384 | A1 | 3/2003 | Roberts et al. |
| 2003/0165465 | A1 | 9/2003 | Roberts et al. |
| 2004/0109878 | A1 | 6/2004 | Atkins et al. |
| 2004/0170607 | A1 | 9/2004 | Bell et al. |

FOREIGN PATENT DOCUMENTS

| EP | 0 564 121 A2 | 10/1993 |
| GB | 1069144 | 5/1967 |
| JP | (A) 58-116422 | 7/1993 |
| WO | WO 86/00529 | 1/1986 |
| WO | WO 86/00811 | 2/1986 |
| WO | WO 89/07445 | 8/1989 |
| WO | WO 93/18790 | 9/1993 |
| WO | 94/19022 | 9/1994 |
| WO | WO 94/18992 | 9/1994 |
| WO | WO 94/25627 | 11/1994 |
| WO | WO 95/32706 | 12/1995 |
| WO | WO 96/03997 | 2/1996 |
| WO | 96/26285 | 8/1996 |
| WO | 96/34625 | 11/1996 |
| WO | WO 97/01358 | 1/1997 |
| WO | WO 97/04805 | 2/1997 |
| WO | WO 97/26904 | 7/1997 |
| WO | 99/02657 | 1/1999 |
| WO | WO 99/04026 | 1/1999 |
| WO | WO 99/08692 | 2/1999 |
| WO | 99/18799 | 4/1999 |
| WO | WO 99/29343 | 6/1999 |
| WO | 99/45783 | 9/1999 |
| WO | WO 99/55345 | 11/1999 |
| WO | 99/64068 A1 | 12/1999 |
| WO | WO 00/45853 | 8/2000 |
| WO | 00/54795 | 9/2000 |
| WO | 00/62735 | 10/2000 |

OTHER PUBLICATIONS

Fields Virology $3^{rd}$ Edition. Lippincott, Williams and Wilkins, Philadelphia, PA, 1996, pp. 1140-1141.*
Dermer (Bio/Technology, 1994, vol. 12 p. 320).*
Freshney (Culture of Animal Cells, A Manual of Basic Technique, Alan R. Liss, Inc., 1983, New York, p. 4).*
Jain Scientific American vol. 271 No. 1, pp. 58-65, Jul. 1994.*
Wang et al. (Exp. Opin. Biol. Ther. 2001; 1 (2): 277-290).*
Kelland (Eur. J. Cancer. Apr. 2004; 40 (6): 827-836).*
Voskoglou-Nomikos et al. (Clin. Cancer Res. Sep. 15, 2003; 9: 4227-4239).*
Saijo et al. (Cancer Sci. Oct. 2004; 95 (10): 772-776).*
Schuh (Toxicologic Pathology. 2004; 32 (Suppl. 1): 53-66).*
Bibby (Eur. J. Cancer. Apr. 2004; 40 (6): 852-857).*
Peterson et al. (Eur. J. Cancer. 2004; 40: 837-844).*
Abraham et al, "The Murine PKR Tumor . . . ," Experimental Cell Research, vol. 244, pp. 394-404 (1998), Article No. EX984201.
Abraham, et al, "Characterization of Transgenic Mice with Targeted . . . ," The Journal of Biological Chemistry, vol. 274, No. 9, pp. 5953-5962 (1999).
Beretta et al, "Expression of the protein kinase PKR . . . ," Oncogene, vol. 12, pp. 1593-1596 (1996).
Donze et al, "Abrogation of translation initiation . . . ," Oxford University Press, pp. 3828-3834.
Gale, Jr. et al, "Evidence That Hepatitis C. Virus . . . ," Virology, vol. 230, pp. 217-227 (1997).
Kumar et al, "Double-Stranded RNA-Activated Protein . . . " Molecular and Cellular Biology, pp. 1116-1125 (1999).
Melyille et al, "The molecular chaperone hsp40 . . . ," Proc. Natl. Acad. Sci. USA, vol. 94, pp. 97-102 (1997).
Mundschau et al, "Endogenous inhibitors of hte dsRNA . . . ," Biochimie, vol. 96, pp. 792-800 (1994).
Savinova et al, "Abnormal levels and minimal activity . . . ," The Int'l Journal of Biochemistry & Cell Biology.
Strong et al, "The molecular basis of viral oncolysis . . . ," The EMBO Journal, vol. 71, No. 12, pp. 3351-3362 (1998).
Stojdl et al, "Exploiting tumor-specific defects . . . ," Nature Medicine, vol. 6, No. 7, pp. 821-825 (2000).

(Continued)

*Primary Examiner* — Robert A Zeman
(74) *Attorney, Agent, or Firm* — Douglas A. Golightly

(57) ABSTRACT

The present invention is directed to a method of reducing the viability of a tumor cell involving administering a virus that is not a common human pathogen to the tumor cell. Preferably, the virus exhibits differential susceptibility, in that normal cells are not affected by the virus. This differential susceptibility is more pronounced in the presence of interferon. The tumor cell is characterized by having low levels, or no, PKR activity, or as being PKR−/−, STAT1−/− or both PKR−/− and STAT1−/−. The virus is selected from the group consisting of Rhabdovirus and picornavirus, and preferably is vesicular stomatitis virus (VSV) or a derivative thereof.

41 Claims, 49 Drawing Sheets

OTHER PUBLICATIONS

Figure 1:
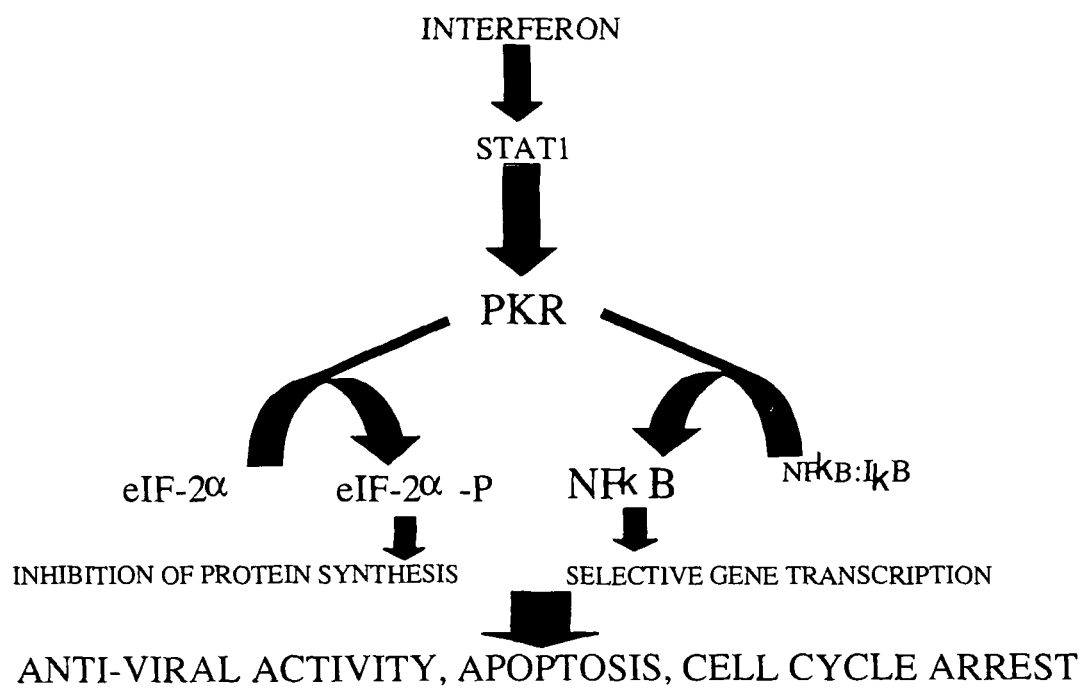

Stojdl et al, "The Murine Double-Stranded RNA-Dependent Protein . . . ," Journal of Virology, vol. 74, No. 20, pp. 9580-9585 (2000).

Lorence, Robert M., et al, Journal of the National Cancer Institute, vol. 86, No. 16, Aug. 17, 1994, pp. 1228-1233, Complete Regression of Human Neuroblastoma Xenografts in Athymic Mice After Local Newcastle Disease Virus Therapy.

Ahlert, T., et al, Cancer Res. 50 (1990), pp. 5962-5968, "Isolation of a Human Melanoma Adapted Newcastle Disease Virus Mutant with Highly Selective Replication Patterns".

Lorence, R.M., et al, *Cancer Research*, 54: 6017-6021, Dec. 1, 1994 "Complete Regression of Human Fibrosarcomaj Xenografts after Local Newcastle Disease Virus Therapy".

Sinkovics et al, "New Developments in the Virus Therapy of Cancer: A Historical Review," Intervirology, vol. 36, pp. 193-214 (1993).

Restifo et al, "A Nonimmunogenic Sarcoma Transduced with the cDNA . . . ," The Journal of Experimental Medicine, vol. 175, pp. 1423-1431 (1992).

Beattie et al, "Host-Range Restriction of Vaccinia Virus . . . ," Virus Genes, vol. 21, No. 1, pp. 89-94 (1996).

Arroyo et al, "Active specific immunotherapy with vaccinia colon . . . ," Cancer Immunol Immunother, vol. 31, pp. 305-311 (1990).

Nickels et al, "Identification of an amino acid change that affects . . . ," Journal of General Virology, vol. 75, pp. 3591-3595 (1995).

Schubert et al, "Primary Structure of the Vesicular . . . ," Journal of Virology, Aug. 1984, pp. 505-514.

Balachandran et al, "Activation of the dsRNA-dependent protein . . . ," The EMBO Journal, vol. 17, No. 23, pp. 6888-6902 (1998).

Durbin et al, "Targeted Disruption of the Mouse *Stat1* Gene Results . . . ," Cell, vol. 84, pp. 443-450 (1996).

Stojdl et al, "Exploiting tumor-specific defects in the interferon pathway . . . ," Nature Medicine, vol. 6, No. 7, pp. 821-825 (2000).

Balachandran et al, "Vesicular Stomatitis Virus . . . ," Life, vol. 50, pp. 135-138 (2000).

Francoeur et al, "The Isolation of Interferon-Inducing Mutants of . . . ," Virology, vol. 160, pp. 236-245 (1987).

Kirn, et al., "Replicating Viruses as Selective Cancer Therapeutics", Molecular Medicine Today, pp. 519-527, Dec. 1996.

Heise, et al., "Onyx-015, an E1B gene-attenuated adenovirus, causes tumor-specific cytolysis and antitumoral efficacy that can be augmented by standard chemotherapeutic agents", Nature Medicine, vol. 3, No. 6, pp. 639-645, Jun. 1997.

Zhang, et al. "Treatment of a human breast cancer xenograft with an adenovirus vector containing an interferon gene results in rapid regression due to viral oncolysis and gene therapy", Proc. Natl. Acad.Sci. USA, vol. 93, pp. 4513-4518, Apr. 1996.

Katze, "Regulation of the interferon-induced PKR: can viruses cope?", Trends in Microbiology, vol. 3, No. 2, pp. 75-78, Feb. 1995.

Maheshwari, et al., "Low Infectivitly of Vesicular Stomatitis Virus (VSV) Particles Released from Interferon-Treated cells is Related to Glycoprotein Deficiency", Biochemical and Biophysical Research Communications, vol. 117, No. 1, pp. 161-168, Nov. 30, 1983.

Chou, et al., "Association of a Mr 90,000 phosphoprotein with protein kinase PKR in cells exhibiting enhancing phosphorylation of translation . . . simplex virus 1", Proc. Natl. Acad. Sci. USA, vol. 92, pp. 10516-10520, Nov. 1995.

Xu, et al., "Primary Leukemia Cells Resistant to x-Interferon in Vitro are Defective in the Activation of the DNA-Bindinf Factor Interferon-Stimulated Gene Factor 3", Blood, vol. 84, No. 6, pp. 1942-1949, Sep. 1994.

Petricoin III, et al., "Human Cancer Cell Lines Express a Negative Transcriptional Regulator of the Interferon Regulatory Factor Family of DNA Binding Proteins", Molecular and Cellular Biology, vol. 14, No. 2, pp. 1477-1486, Feb. 1994.

Symons, et al., "Vaccinia Virus Encodes a Soluble Type I Interferon Receptor of Novel Structure and Board Species Specificity", Cell, vol. 81, pp. 551-560, May 19, 1995.

Linge, et al., "Interferon System Defects in Human Malignant Melanoma", Cancer Research, vol. 55, pp. 4099-4104, Sep. 15, 1995.

Machida, et al. "Effective of Nucleosides on Interferon Production and Development of Antiviral State Induced by Poly I-Poly C", Microbiolo. Immunol., vol. 23 (7), pp. 643-650, 1979.

Tanaka, et al., "Celullar Commitment to Oncogene-Induced Transformation or Apoptosis is Dependent on the Transcription Factor IRF-1", Cell, vol. 77, pp. 829-839, Jun. 17, 1994.

Pennisi, "Will a Twist of Viral Fate Lead to a New Cancer Treatment?", Science, vol. 274, pp. 342-343, Oct. 18,1996.

Bischoff, et al., "An Adenovirus Mutant that Replicates Selectively in p53-Deficient Human Tumor Cells", Science, vol. 274, pp. 373-376, Oct. 18, 1996.

Andreansky, et al., "The application of genetically engineered herpes simplex viruses to the treatment of experimental brain tumors", Proc. Natl. Acad. Sci. USA, vol. 93, pp. 11313-11318, Oct. 1996. Colloquium Paper.

Gastl, et al., "Retroviral Vector-mediated Lymphokine Gene Transfer into Human Renal Cancer Cells", Cancer Research, 52, pp. 6229-6236, Nov. 1992.

Buller, et al., "Cell Proliferative Response to Vaccinia Virus is Mediated by VGF", Virology, vol. 164, pp. 182-192, 1988.

Child, et al., "Insertional Inactivation of the Large Subunit of Ribonucleotide Reductase Encoded by Vaccinia Virus is Associated with Reduced Virulence in Vivo", Virology, vol. 174, pp. 625-629, 1990.

Restifo, et al., "A Nonimmunogenic Sarcoma Transduced with the cDNA for Interferon (Elicits CD8+ T Cells against the Wild-type Tumor . . . Presentation Capability", The Journal of Experimental Medicine, vol. 175, pp. 1423-1431, Jun. 1992.

Buller, et al., "Decreased Virulence of Recombinant Vaccinia Virus Expression Vectors is Associated with a Thymidine Kinase-Negative Phenotype", Nature, vol. 317, pp. 813-815, Oct. 31, 1985.

Haines, et al., "Correlation of the expression of double-stranded RNA-dependent protein kinase (p68) with differentiation in head and neck squamous cell carcinoma", Virchows Archiv B Cell Pathology, vol. 63, pp. 289-295, 1993.

James, et al., "Chromosome 9 Deletion Mapping Reveals Interferon x and Interferon B-1 Gene Deletions in Human Glial Tumors", Cancer Research, vol. 51, pp. 1684-1688, Mar. 15, 1991.

Arroyo, et al., "Active specific immunotherapy with vaccinia colon oncolysate enhances the immunomodulatory and antitumor effects of interleukin-2 and interferon x in a murine hepatic metastasis model", Cancer Immunology Immunotherapy, vol. 31, pp. 305-311, 1990.

Zhang, et al., "High-efficiency gene transfer and high-level expression of wild-type p53 in human lung cancer cells mediated by recombinant adenovirus", Cancer Gene Therapy, vol. 1, No. 1, pp. 5-13, 1994.

Korth, et al., "Cloning, expression, and cellular localization of the oncogenic 58-kDa inhibitor of the RNA-activated human and mouse protein kinase", Gene, vol. 170, pp. 181-188, 1996.

Barber, et al., "The 58-kilodalton inhibitor of the interferon-induced double-straned RNA-activated protein kinases is tetratricopeptide repeat protein with oncogenic properties", Proc. Natl. Acad. Sci. USA, vol. 91, pp. 4278-4282, May 1994.

Matthews, et al., "Adenovirus Virus-Associated RNA and Translation Control", Journal of Virology, vol. 65, No. 11, pp. 5657-5662, Nov. 1991.

Imani, et al., "Inhibitory activity for the interferon-induced protein kinase is associated with the reovirus serotype . . . protein", Proc. Natl. Acad. Sci. USA, vol. 85, pp. 7887-7891, Nov. 1988.

Tanaka, et al., "Immunotherapy of Vaccinia Colon Oncolysate Prepared with Interleukin-2 Gene-Encoded Vaccinia Virus and Interferon-x Increase the Survival of Mice Bearing Syngeneic Colon Adenocarcinoma", Journal of Immunotherapy, vol. 16, No. 4, pp. 283-293, 1994.

Csatary, et al., "Attenuated Veterinary Virus Vaccine for the Treatment of Cancer", Cancer Detection and Prevention, vol. 17, No. 6, pp. 619-627, 1993.

Cassel, et al., "Newcastle Disease Virus as an Antineoplastic Agent", Cancer, vol. 18, No. 7, pp. 863-868, Jul. 1965.

Schirrmacher, et al. "Successful application of non-oncogenic viruses for antimetastatic cancer immunotherapy", Institut for Immunologic and Genetik am Deutschen Krebsforschungszentrum, 6900 Heidelberg, Germany, pp. 19-49, Mar. 13, 1986.

Lorence, et al., "Newcastle Disease Virus as an Antineoplastic Agent: Induction of Tumor Necrosis Factor-x and Augmentation of Its Cytotoxicity", Journal of the National Cancer Institute, vol. 80, No. 16, pp. 1305-1312, Oct. 19, 1988.

Reichard, et al., "Newcastle Disease Virus Selectively Kills Human Tumor Cells", Journal of Surgical Research, vol. 52, pp. 448-453, 1992.

Eaton, et al., "Contribution of Antiviral Immunity to Oncolysis by Newcastle Disease Virus in a Murine Lymphoma", Journal of the National Cancer Institute, vol. 39, No. 6, Dec. 1967.

Beverley, et al., "Immune Responses in Mice to Tumor Challenge After Immunization with Newcastle Disease Virus-Infected or X-Irradiated Tumor Cells or Cell Fractions", Int. Journal of Cancer, vol. 11, pp. 212-223, 1973.

Shoham, et al., "Augmentation of Tumor Cell Immunogenicity by Viruses—An Approach to Specific Immunotherapy of Cancer", Nat. Immun. Cell Growth Regul., vol. 9, pp. 165-172, 1990.

Bart, et al., "Role of Interferon in the Anti-Melanoma Effects of Poly(I).Poly(C) and Newcastle Disease Virus", Nature New Biology, vol. 245, No, 147, pp. 229-230, Oct. 24, 1973.

Sinkovics, et al., "New Developments in the Virus Therapy of Cancer: A Historical Review", Intervirology, vol. 36, pp. 193-214, 1993.

Murray, et al., "Viral Oncolysate in the Management of Malignant Melanoma", Cancer, vol. 40, No. 2, pp. 680-686, Aug. 1977.

Cassel, "A Phase II Study on the Postsurgical Management of Stage Malignant Melanoma with a Newcastle Disease Virus Oncolysate", Cancer, vol. 52, pp. 856-860, Sep. 1, 1983.

Cassel, "A Ten-Year Follow-Up on Stage II Malignant Melanoma Patients Treated Postsurgically with Newcastle Disease Virus Oncolysate", Med. Oncol. & Tumor Pharmacother., vol. 9, No. 4, pp. 169-171, 1992.

Bohle, et al. "Postoperative Active Specific Immunization in Colorectal Cancer Patients with Virus-Modified Autologous Tumor-Cell Vaccine", Cancer, vol. 66, No. 7, pp. 1517-1523, Oct. 1, 1990.

Eaton, et al., "Autoimmunity Induced by Injection of Virus-Modified Cell Membrane Antigens in Syngeneic Mice", Infection and Immunity, vol. 15, No. 1, pp. 322-328, Jan. 1977.

Wheelock, et al, "Observation on the Repeated Administration of Viruses to a Patient with Acute Leukemia", The New England Journal of Medicine, vol. 271, No. 13, pp. 645-651, Sep. 24, 1964.

Csatary, "Viruses in the Treatment of Cancer", The Lancet, p. 825, Oct. 9, 1971.

Kenney, et al., "Viruses as Oncolytic Agents: A New Age for "Therapeutic" Viruses?", JNCL Editorial Issue 16, pp. 1-3, Jun. 20, 1997.

Rodriguez, et al., "Prostate Attenuated Replication Competent Adenovirus (ARCA) CN706: A Selective Cytotoxic for Prostate-specific Antigen-postive Prostate Cancer Cells", Cancer Research, vol. 57, pp. 2559-2563, Jul. 1997.

Martuza, "Novel Treatment Approach for Malignant Brain Tumors Developed at Gerogetown", Georgetown University Medical Center, pp. 1-8, Oct. 1995.

Mineta, et al., "Attenuated multi-mutated herpes simplex virus-1 for the treatment of malignant gliomas", Nature Medicine, vol. 1, No. 9, pp. 938-943, Sep. 1995.

Zhenxiang, et al., "Studies on Viral Immunotherapy of Ascitic Tumors in Mice. I. Results of Treatment on Viruses of Ehrlich and S180 Ascitic Tumor Cells" ACTA Academiae Medicine Sinicae, vol. 6, No. 3, Jun. 1984.

Ganly, et al., "Phase I trial of intratumoral injection with an E1B-attenuated adenovirus, ONYX-015, in patients with recurrent p53(-) head and neck cancer", Proceedings of ASCO, vol. 16, p. 433a, 1997. Abstract 1362.

Kirn, et al., "ONYX-015, A selectively replicating adenovirus, has antitumoral activity following IV administration alone and in combination with cheomtherapy", Proceedings of ASCO, vol. 16, p. 433a, 1997. Abstract 1564.

Izbicka, et al., "'Effects of ONYX adenovirus preparations on human tumor colony forming units", Proceedings of ASCO, vol. 16, p. 433a, 1997. Abstract 1554.

Kirn, et al., "ONYX-015 selectively replicates in and lyses cells lacking functional p53", Proceedings for the American Association for Cancer Research, vol. 37, p. 352, Mar. 1996. Abstract 2400.

Field, et al., "The pathogenicity of thymidine kinase-deficient mutants of herpes simplex virus in mice", J. Hyg., Camb., vol. 81, pp. 267-277, 1978.

Spriggs, et al., "Attenuated reovirus type 3 strains generated by selection of haemagglutinin antigenic variants", Nature, vol. 297, pp. 68-70, May 6, 1982.

Goldstein, et al., "Factor(s) Presented in Herpes Simplex Virus Type 1-Infected Cells Can Compensate for the Loss of the Large Subunit of the Viral Ribonucleotide Reductase: Characterization of an ICP6 Deletion Mutant", Virology, vol. 166, pp. 41-51, 1988.

Perkus, et al., "Deletion of 55 Open Reading Frames from the Termini of Vaccinia Virus", Virology, vol. 180, pp. 406-410, 1991.

Meignier, et al., "In Vivo Behavior of Genetically Engineered Herpes Simplex Viruses R7017 and R7020. II. Studies in Immunocompetent and Immunosuppressed Owl Monkeys (*Aotus trivirgatus*)", The Journal of Infectious Disease, vol. 162, pp. 313-312, 1990.

Hughes, et al., "Vaccinia Virus Encodes an Active Thymidylate Kinase that Complements a cdc8 Mutant of *Saccharomyces cerevisiae*", Journal of Biological Chemistry, vol. 266, No. 30, pp. 20103-20109, Oct. 25, 1991.

Kerr, et al. "Vaccina DNA ligase complements *Saccharomyces cerevisiae* cdc9, localizes in cytoplasmic factories and affects virulence and virus sensitivity to DNA damaging agents", The EMBO Journal, vol. 10, No. 13, pp. 4343-4350, 1991.

Clark, et al. "Protective Effect of WC3 Vaccine Against Rotavirus Diarrhea in Infants During a Predominantly Serotype1 Rotavirus Season", Journal of Infectious Diseases, vol. 158, No. 3, pp. 570-587, Sep. 1988.

Takafuji, et al., "Simultaneous Administration of Live, Enteric-Coated Adenovirus Types 4, 7, and 21 Vaccines: Safety and Immunogenicity", Journal of Infectious Diseases, vol. 140, No. 1, pp. 48-53, Jul. 1979.

Taylor, et al., "Virus-Induced Regression of Tumor Growth", Journal of the National Cancer Institute, vol. 44, pp. 515-519, Mar. 1970.

Beattie, et al., "Host-Range Restriction of Vaccinia Virus E3L-Specific Deletion Mutants", Virus Genes, vol. 12, No. 1, pp. 89-94, 1966.

Howard, et al., "Retrovirus-Meidated Gene Transfer of the Human . . . Gene: A Therapy for Cancer", Annals New York Academy of Sciences, Duke University Medical Center, pp. 167-187.

Suskind, et al., US Dept. of Health, Education & Welfare, N.I.H., National Institute of Allergy and Infectious Disease, and N.C.I, Bethesda, MD., Viral Agents Oncolytic for Human Tumors in Heterologous Host: Oncolytic Effect of Coxsackie B. Viruses, pp. 309-318, Oct. 29, 1956.

Bluming, et al., "Regression of Burkitt's Lymphoma . . . Association with Measles Infection" The Lancet, pp. 105-106, Jul. 10, 1971.

Pasquinucci, et al., "Possible Effect of Measles on Leukemia", The Lancet, p. 136, Jan. 16, 1971.

Gross, "Measles and Leukaemia", The Lancet, pp. 397-398, Feb. 20, 1971.

Shingu, "Therapeutic effects of *Bovine enterovirus* infection on rabbits with experimentally induced adult T cell leukaemia", Journal of General Virology, vol. 72, pp. 2031-2034, 1991.

Faaberg, et al., "Strain Variation and Nuclear Association of Newcastle Disease Virus Matrix Protein", Journal of Virology, vol. 62, No. 2, pp. 586-593, Feb. 1988.

Holzaepfel, et al., "The Use of APC3 Virus as a Cancericidal Agent", Cancer, vol. 10, pp. 577-580, May-Jun. 1957.

Smith, et al., "Studies on the Use of Viruses in the Treatment of Carcinoma of the Cervix", Cancer, vol. 9, pp. 1211-1218, Nov.-Dec. 1956.

Rukavishnikova, et al. "Some Immunological Mechanisms of the Influenza Virus Antitumour Effect", Acta Virol., vol. 20, pp. 387-394, 1976.

Verma, et al., "Gene therapy-promises, problem and prospects", Nature, vol. 389, pp. 239-242, Sep. 18, 1997.

Asada, "Treatment of Human Cancer with Mumps Virus", Cancer, vol. 34, pp. 1907-1928, Dec. 1974.

Sreevalsan, "Chapter 14 Biologic Therapy with Interferon-x and B: Preclinical Studies", Biologic Therapy of Cancer: Principles and Practice, pp. 347-364.

Stoner, et al., "Effect of Neuraminidase Pretreatment on the Susceptibility of Normal and Transformed Mammalian Cells to *Bovine enterovirus* 261", Nautre, vol. 245, pp. 319-320, Oct. 12, 1973.

Joklik, "Interferons", Chapter 16, Second Edition, pp. 382-410, 1990.

Schnell, et al., "Construction of a Novel Virus that Targets HIV-1 Infected Cells and Controls HIV-1 Infection", Cell, vol. 90, pp. 849-857, Sep. 5, 1997.

Kirchner, et al., "Adjuvant treatment of locally advanced renal cancer with autologous virus-modified tumor vaccines", World J. Urol., vol. 13, pp. 171-173, 1995.

Murphy, et al., "Virus Taxonomy", Virology, Second Edition, Chapter 2, pp. 9-35, 1990.

Csatary, "Viruses in the Treatment of Cancer", The Lancet, p. 825, Oct. 9, 1971.

Hashiro, et al., "The Preferential Cytotoxicity of Reovirus for Certain Transformed Cell Lines", Archives of Virology, vol. 54, pp. 307-315, 1977.

Zhang, Attenuated newcastle disease virus for induction of interferons to combat neoplasm or viral disease, Database Caplus, on STN Colombus (OH): Chemical Abstract Serice, DN 116: 104333, CN 1054192A, Abstract, Apr. 9, 1991.

Gresser, et al., "Exogenous Interferon and Inducers of Interferon in the Treatment of Balb/c Mice inoculated with RC19 Tumor Cells", Nature, vol. 223, pp. 844-845, Aug. 1969.

Csatary, et al., "Virus Vaccines for the Treatment of Cancer", Orvosi Hetilap, vol. 131, pp. 2585-2588, 1990.

Eck, et al., "Gene-Based Therapy", Goodman & Gilman's The Pharmacological Basis of Therapeutics, Ninth Edition, Chapter 5, 1996.

Weber, et al., "Mechanisms of Tumor Metastasis to Bone", Critical Reviews in Eukaryotic Gene Expression, 2000, vol. 10, No. 3-4, pp. 281-302.

Rummel, et al., "Future Paradigm of Autologous Bone Marrow Transplantation: Tumor Purging and Ex Vivo Production of Normal Stem and Progenitor Cells", Journal of Hematotherapy,1994, vol. 3, pp. 213-218.

Pending claims from U.S. Appl. No. 11/671,498.

Barber, VSV-tumor selective replication and protein translation, Oncogene (2005) 24, 7710-7719.

Ce'Saire et al., Oncolytic activity of vesicular stomatitis virus in primary adult T-cell leukemia, Oncogene (2006) 25, 349-358.

Garber, China Approves World's First Oncolytic Virus Therapy for Cancer Treatment, Journal of the National Cancer Institute, vol. 98, No. 5:298-300 (2006).

Lichty, Vesicular Stomatitis Virus: A Potential Therapeutic Virus for the Treatment of Hematologic Malignancy, Human Gene Therapy 15:821-831 (2004).

Nemunaitis, Phase II Trial of Intratumoral Administration of ONYX-015, a Replication-Selective Adenovirus, in Patients With Refractory Head and Neck Cancer, Journal of Clinical Oncology, vol. 19, No. 2 (Jan. 2001): pp. 289-298.

Obuchi, Development of Recombinant Vesicular Stomatitis Viruses That Exploit Defects in Host Defense to Augmen Specific Oncolytic Activity, Journal of Virology, (2003), p. 8843-8856.

Pecora, Phase I Trial of Intravenous Administration of PV701, an Oncolytic Virus, in Patients With Advanced Solid Cancers, Journal of Clinical Oncology, vol. 20, No. 9 (2002): pp. 2251-2266.

Porosnicu, The Oncolytic Effect of Recombinant Vesicular Stomatitis Virus is Enhanced by Expression of the Fusion Cytosine Deaminase/Uracil Phosphoribosyltransferase Suicide Gene, Cancer Research, 63, 8366-8376, (2003).

Stojdl, VSV strains with defects in their ability to shutdown innate immunity are potent systemic anti-cancer agents, Cancer Research 4:263-275 (2003).

Fenglan et al., "Studies on Combined Treatment of Cyclophosphamide and Virus in Mice Transplanted with S180 Ascitic Tumor Cells", Acta Academiae Medicinae Sinicae, vol. 7, No. 5, 1985, pp. 376-379.

Reichard et al., "Newcastle Disease Virus Selectively Kills Human Tumor Cells", The Association for Academic Surgery, Twenty-Fifth Annual Meeting, Colorado Springs, Colorado, Nov. 20-23, 1991, p. 152.

Kubo, 1976, Unverified English translation of Japanese Patent Application Publication No. JP S51-73117.

Office Action dated Sep. 18, 2007 for U.S. Appl. No. 11/685,483.

Office Action dated Dec. 6, 2006 for U.S. Appl. No. 10/743,649.

Ahmed, et al., "Ability of the Matrix Protein of Vesicular Stomatitis Virus to Suppress Beta Interferon Gene Expression is Genetically Correlated with the Inhibition of Host RNA and Protein Synthesis", Journal of Virology, vol. 77, No. 8, 2003, 4646-4657.

Coukos, et al., "Use of Carrier Cells to Deliver a Replication-Selective Herpes Simplex Virus-1 Mutant for the Intraperitoneal Therapy of Epithelial Ovarian Cancer", Clinical Cancer Research, vol. 5, Jun. 1999, pp. 1523-1537.

Desforges, et al. "Different Host-Cell Shutoff Strategies Related to the Matrix Protein lead to Persistence of Vesicular Stomatitis Virus Mutants on Fibroblast Cells", Virus Res., 76(1), Jul. 2001, pp. 87-102. (Abstract).

Ferran, et al., "The Vesicular Stomatitis Virus Matrix Protein Inhibits Transcription from the Human Beta Interferon Promoter", Journal of Virology, vol. 71, No. 1, 1997, pp. 371-377.

Marcus, et al., "Interferon Induction by Viruses. III. Vesicular Stomatitis Virus: Interferon-Inducing Particle Activity Requires Partial Transcription of Gene N", J. Gen. Virol., 47(1), 1980, pp. 89-96. (Abstract).

Pasternak, et al., "Stress-Induced Increase of Hexose Transport as a Novel Index of Cytopathic Effects in Virus-Infected Cells: Role of the L Protein in the Action of Vesicular Stomatitis Virus", Virology, 166(2), 1988, pp. 379-386. (Abstract).

Stanners, et al., "Analysis of VSV Mutant with Attenuated Cytopathogenicity: Mutation in Viral Function, P, for Inhibition of Protein Synthesis", Cell, 11(2), 1977, pp. 273-281. (Abstract).

Winship, et al., "Distinctive Characteristics of Crude Interferon from Virus-Infected Guinea-Pig Embryo Fibroblasts", Journal of General Virology, vol. 65, 1984, pp. 843-847. (Abstract).

Current Office Action (Mar. 27, 2008) and Pending claims (filed Jan. 7, 2008) for U.S. Appl. No. 10/743,649.

Pending claims (filed Jan. 17, 2008) for U.S. Appl. No. 11/685,483.

"Notice to Authors" Virology (Aug. 1987) 159:2.

"Notice to Authors" Virology (Sep. 1987) 160:1.

"Notice to Authors" Virology (Sep. 1988) 166:1.

"Notice to Authors" Virology (Oct. 1988) 166:2.

"Instructions to authors" The Journal of General Virology (1980) 47(1):i-ii.

"Instructions to authors" The Journal of General Virology (1984) 65(1):i-ii.

"Instructions to authors" Journal of Virology (Jan 1997):i-xi.

"Information for Contributors (1977)" Cell (Jan. 1977).

Hudson et al. "Cloning and Expression of a Viral Phosphoprotein: Structure Suggests Vesicular Stomatitis Virus NS May Function by Mimicking an RNA Template" J. Gen. Virol. (1986) 67:1571-9.

Francoeur et al. "The Isolation of Interferon-Inducing Mutants of Vesicular Stomatitis Virus with Altered Viral P Function for the Inhibition of Total Protein Synthesis" Virology (1987) 160(1):236-245.

Kalvakolanu, et al., "Differentiation-dependent activation of interferon-stimulated gene factors and transcription factor NF-kB in mouse embryonal carinoma cells", Proc. Natl. Acad. Sci. USA, vol. 90, pp. 3167-3171, Apr. 1993.

Foy, et al., "In Vivo CD40-gp39 Interactoiuns are Essential for Thymus-Dependent Humoral Immunity, II. Prologed Suppression of the Humoral Immune Response by an Antibody to the Ligand for CD40,gp39", J. Exp. Med., vol. 178, pp. 1567-1575, Nov. 1993.

Blaese,et al., "In situ Delivery of Suicide Genes for Cancer Treatment", European Journal of Cancer, vol. 30A., No. 8, pp. 1190-1193, 1994.

Zhang, et al., "Gene Therapy with an adeno-associated virus carrying an Interferon gene results in tumor growth suppression and regression", Cancer Gene Therapy, vol. 3, No. 1, pp. 31-38, 1996.

Peplinski, et al., "Prevention of Murine Breast Cancer by Vaccination with Tumor Cells Modified by Cytokine-Producing Recombinant Vaccinia Viruses", Annals of Surgical Oncology, vol. 3, No. 1, pp. 15-23.

Cotran, et al., "Kinetics of Tumor Cell Growth", Robbins Pathologic Basis of Disease, 4th Edition, p. 251.

Schloer, et al., "Relationship of Plaque Size and Virulence for Chickens for 14 Representative Newcastle Disease Virus Strains", Journal of Virology, vol. 2, No. 1, pp. 40-47, Jan. 1968.

Tait, et al., "A Phase I Trial of Retroviral BRCA1sv Gene Therapy in Ovarian Cancer", Clinical Cancer Research, vol. 3, pp. 1959-1968, Nov. 1997.

Martuza, et al., "Experimental Therapy of Human Glioma by Means of a Genetically Engineered Virus Mutant", Science, vol. 252, pp. 854-855, May 10, 1991.
Hanson, et al., "Identification of Vaccine Strains of Newcastle Disease Virus", Science, vol. 122, pp. 156-157, Jul. 22, 1955.
Chambers, et al., "Comparison of genetically engineered herpes simplex viruses for the treatment of brain tumors in a scid mouse model of human malignant glioma", Pro. Natl. Acad. Sci. USA, vol. 92, pp. 1411-1415, Feb. 1995.

* cited by examiner

VSV INFECTION OF KB CELLS

VSV moi 1 PFU/18HRS

MOCK INFECTED

FIGURE 3C

FIGURE 10B

```
                  1                                                          60
GenBank N nucl.   ATGTCTGTTACAGTCAAGAGAATCATTGACAACACAGTCATAGTTCCAAAACTTCCTGCA
     HR N nucl.   ATGTCTGTTACAGTCAAGAGAATCATTGCCAACACAGTCATAGTTCCAAAACTTCCTGCA
     M2 N nucl.   ATGTCTGTTACAGTCAAGAGAATCATTGACAACACAGTCATAGTTCCAAAACTTCCTGCA
     M3 N nucl.   ATGTCTGTTACAGTCAAGAGAATCATTGACAACACAGTCATAGTTCCAAAACTTCCTGCA
     M4 N nucl.   ............................................................

61                                                        120
GenBank N nucl.   AATGAGGATCCAGTGGAATACCCGGCAGATTACTTCAGAAAATCAAAGGAGATTCCTCTT
     HR N nucl.   AATGAGGATCCAGTGGAATACCCGGCAGATTACTTCAGAAAATCAAAGGAGATTCCTCTT
     M2 N nucl.   AATGAGGATCCAGTGGAATACCCGGCAGATTACTTCAGAAAATCAAAGGAGATTCCTCTT
     M3 N nucl.   AATGAGGATCCAGTGGAATACCCGGCAGATTACTTCAGAAAATCAAAGGAGATTCCTCTT
     M4 N nucl.   ............................................................

121                                                       180
GenBank N nucl.   TACATCAATACTACAAAAAGTTTGTCAGATCTAAGAGGATATGTCTACCAAGGCCTCAAA
     HR N nucl.   TACATCAATACTACAAAAAGTTTGTCAGATCTAAGAGGATATGTCTACCAAGGCCTCAAA
     M2 N nucl.   TACATCAATACTACAAAAAGTTTGTCAGATCTAAGAGGATATGTCTACCAAGGCCTCAAA
     M3 N nucl.   TACATCAATACTACAAAAAGTTTGTCAGATCTAAGAGGATATGTCTACCAAGGCCTCAAA
     M4 N nucl.   ............................................................

181                                                       240
GenBank N nucl.   TCCGGAAATGTATCAATCATACATGTCAACAGCTACTTGTATGGAGCATTAAAGGACATC
     HR N nucl.   TCCGGAAATGTATCAATCATACATGTCAACAGCTACTTGTATGGAGCATTGAAGGACATC
     M2 N nucl.   TCCGGAAATGTATCAATCATACATGTCAACAGCTACTTGTATGGAGCATTGAAGGACATC
     M3 N nucl.   TCCGGAAATGTATCAATCATACATGTCAACAGCTACTTGTATGGAGCATTGAAGGACATC
     M4 N nucl.   ............TCAATCATACATGTCAACAGCTACTTGTATGGAGCATTGAAGGACATC 241                                                       300
GenBank N nucl.   CGGGGTAAGTTGGATAAAGATTGGTCAAGTTTCGGAATAAACATCGGGAAAGCAGGGGAT
     HR N nucl.   CGGGGTAAGTTGGATAAAGATTGGTCAAGTTTCGGAATAAACATCGGGAAGGCAGGGGAT
     M2 N nucl.   CGGGGTAAGTTGGATAAAGATTGGTCAAGTTTCGGAATAAACATCGGGAAGGCAGGGGAT
     M3 N nucl.   CGGGGTAAGTTGGATAAAGATTGGTCAAGTTTCGGAATAAACATCGGGAAGGCAGGGGAT
     M4 N nucl.   CGGGGTAAGTTGGATAAAGATTGGTCAAGTTTCGGAATAAACATCGGGAAGGCAGGGGAT 301                                                       360
GenBank N nucl.   ACAATCGGAATATTTGACCTTGTATCCTTGAAAGCCCTGGACGGCGTACTTCCAGATGGA
     HR N nucl.   ACAATCGGAATATTTGACCTTGTATCCTTGAAAGCCCTGGACGGTGTACTTCCAGATGGA
     M2 N nucl.   ACAATCGGAATATTTGACCTTGTATCCTTGAAAGCCCTGGACGGTGTACTTCCAGATGGA
     M3 N nucl.   ACAATCGGAATATTTGACCTTGTATCCTTGAAAGCCCTGGACGGTGTACTTCCAGATGGA
     M4 N nucl.   ACAATCGGAATATTTGACCTTGTATCCTTGAAAGCCCTGGACGGTGTACTTCCAGATGGA 361                                                       420
GenBank N nucl.   GTATCGGATGCTTCCAGAACCAGCGCAGATGACAAATGGTTGCCTTTGTATCTACTTGGC
     HR N nucl.   GTATCGGATGCTTCCAGAACCAGCGCAGATGACAAATGGTTGCCTTTGTATCTACTTGGC
     M2 N nucl.   GTATCGGATGCTTCCAGAACCAGCGCAGATGACAAATGGTTGCCTTTGTATCTACTTGGC
     M3 N nucl.   GTATCGGATGCTTCCAGAACCAGCGCAGATGACAAATGGTTGCCTTTGTATCTACTTGGC
     M4 N nucl.   GTATCGGATGCTTCCAGAACCAGCGCAGATGACAAATGGTTGCCTTTGTATCTACTTGGC 421                                                       480
GenBank N nucl.   TTATACAGAGTGGGCAGAACACAAATGCCTGAATACAGAAAAAAGCTCATGGATGGGCTG
     HR N nucl.   TTATACAGAGTGGGCAGAACACAAATGCCTGAATACAGAAAAAGGCTCATGGATGGGCTG
     M2 N nucl.   TTATACAGAGTGGGCAGAACACAAATGCCTGAATACAGAAAAAGGCTCATGGATGGGCTG
     M3 N nucl.   TTATACAGAGTGGGCAGAACACAAATGCCTGAATACAGAAAAAGGCTCATGGATGGGCTG
     M4 N nucl.   TTATACAGAGTGGGCAGAACACAAATGCCTGAATACAGAAAAAGGCTCATGGATGGGCTG
```

FIGURE 14-1

```
                481                                                         540
GenBank N nucl. ACAAATCAATGCAAAATGATCAATGAACAGTTTGAACCTCTTGTGCCAGAAGGTCGTGAC
     HR N nucl. ACAAATCAATGCAAAATGATCAATGAACAGTTTGAACCTCTTGTGCCAGAAGGTCGTGAC
     M2 N nucl. ACAAATCAATGCAAAATGATCAATGAACAGTTTGAACCTCTTGTGCCAGAAGGTCGTGAC
     M3 N nucl. ACAAATCAATGCAAAATGATCAATGAACAGTTTGAACCTCTTGTGCCAGAAGGTCGTGAC
     M4 N nucl. ACAAATCAATGCAAAATGATCAATGAACAGTTTGAACCTCTTGTGCCAGAAGGTCGTGAC 541                                                         600
GenBank N nucl. ATTTTTGATGTGTGGGGAAATGACAGTAATTACACAAAAATTGTCGCTGCAGTGGACATG
     HR N nucl. ATTTTTGATGTGTGGGGAAATGACAGTAATTACACAAAAATTGTCGCTGCAGTGGACATG
     M2 N nucl. ATTTTTGATGTGTGGGGAAATGACAGTAATTACACAAAAATTGTCGCTGCAGTGGACATG
     M3 N nucl. ATTTTTGATGTGTGGGGAAATGACAGTAATTACACAAAAATTGTCGCTGCAGTGGACATG
     M4 N nucl. ATTTTTGATGTGTGGGGAAATGACAGTAATTACACAAAAATTGTCGCTGCAGTGGACATG 601                                                         660
GenBank N nucl. TTCTTCCACATGTTCAAAAAACATGAATGTGCCTCGTTCAGATACGGAACTATTGTTTCC
     HR N nucl. TTCTTCCACATGTTCAAAAAACATGAATGTGCCTCGTTCAGATACGGAACTATTGTTTCC
     M2 N nucl. TTCTTCCACATGTTCAAAAAACATGAATGTGCCTCGTTCAGATACGGAACTATTGTTTCC
     M3 N nucl. TTCTTCCACATGTTCAAAAAACATGAATGTGCCTCGTTCAGATACGGAACTATTGTTTCC
     M4 N nucl. TTCTTCCACATGTTCAAAAAACATGAATGTGCCTCGTTCAGATACGGAACTATTGTTTCC 661                                                         720
GenBank N nucl. AGATTCAAAGATTGTGCTGCATTGGCAACATTTGGACACCTCTGCAAAATAACCGGAATG
     HR N nucl. AGATTCAAAGATTGTGCTGCATTGGCAACATTTGGACACCTCTGCAAAATAACCGGAATG
     M2 N nucl. AGATTCAAAGATTGTGCTGCATTGGCAACATTTGGACACCTCTGCAAAATAACCGGAATG
     M3 N nucl. AGATTCAAAGATTGTGCTGCATTGGCAACATTTGGACACCTCTGCAAAATAACCGGAATG
     M4 N nucl. AGATTCAAAGATTGTGCTGCATTGGCAACATTTGGACACCTCTGCAAAATAACCGGAATG 721                                                         780
GenBank N nucl. TCTACAGAAGATGTAACGACCTGGATCTTGAACCGAGAAGTTGCAGATGAAATGGTCCAA
     HR N nucl. TCTACAGAAGATGTAACGACCTGGATCTTGAACCGAGAAGTTGCAGATGAGATGGTCCAA
     M2 N nucl. TCTACAGAAGATGTAACGACCTGGATCTTGAACCGAGAAGTTGCAGATGAGATGGTCCAA
     M3 N nucl. TCTACAGAAGATGTAACGACCTGGATCTTGAACCGAGAAGTTGCAGATGAGATGGTCCAA
     M4 N nucl. TCTACAGAAGATGTAACGACCTGGATCTTGAACCGAGAAGTTGCAGATGAGATGGTCCAA 781                                                         840
GenBank N nucl. ATGATGCTTCCAGGCCAAGAAATTGACAAGGCCGATTCATACATGCCTTATTTGATCGAC
     HR N nucl. ATGATGCTTCCAGGCCAAGAAATTGACAAGGCCGATTCATACATGCCTTATTTGATCGAC
     M2 N nucl. ATGATGCTTCCAGGCCAAGAAATTGACAAGGCCGATTCATACATGCCTTATTTGATCGAC
     M3 N nucl. ATGATGCTTCCAGGCCAAGAAATTGACAAGGCCGATTCATACATGCCTTATTTGATCGAC
     M4 N nucl. ATGATGCTTCCAGGCCAAGAAATTGACAAGGCCGATTCATACATGCCTTATTTGATCGAC 841                                                         900
GenBank N nucl. TTTGGATTGTCTTCTAAGTCTCCATATTCTTCCGTCAAAAACCCTGCCTTCCACTTCTGG
     HR N nucl. TTTGGATTGTCTTCTAAGTCTCCATATTCTTCCGTCAAAAACCCTGCCTTCCACTTCTGG
     M2 N nucl. TTTGGATTGTCTTCTAAGTCTCCATATTCTTCCGTCAAAAACCCTGCCTTCCACTTCTGG
     M3 N nucl. TTTGGATTGTCTTCTAAGTCTCCATATTCTTCCGTCAAAAACCCTGCCTTCCACTTCTGG
     M4 N nucl. TTTGGATTGTCTTCTAAGTCTCCATATTCTTCCGTCAAAAACCCTGCCTTCCACTTCTGG
```

FIGURE 14-2

```
                901                                                          960
GenBank N nucl. GGGCAATTGACAGCTCTTCTGCTCAGATCCACCAGAGCAAGGAATGCCCGACAGCCTGAT
     HR N nucl. GGGCAATTGACAGCTCTTCTGCTCAGATCCACCAGAGCAAGGAATGCCCGACAGCCTGAT
     M2 N nucl. GGGCAATTGACAGCTCTTCTGCTCAGATCTACCAGAGCAAGGAATGCCCGACAGCCTGAT
     M3 N nucl. GGGCAATTGACAGCTCTTCTGCTCAGATCCACCAGAGCAAGGAATGCCCGACAGCCTGAT
     M4 N nucl. GGGCAATTGAC.................................................T 961                                                         1020
GenBank N nucl. GACATTGAGTATACATCTCTTACTACAGCAGGTTTGTTGTACGCTTATGCAGTAGGATCC
     HR N nucl. GACATTGAGTATACATCTCTTACTACAGCAGGTTTGTTGTACGCTTATGCAGTAGGATCC
     M2 N nucl. GACATTGAGTATACATCTCTTACTACAGCAGGTTTGTTGTACGCTTATGCAGTAGGATCC
     M3 N nucl. GACATTGAGTATACATCTCTTACTACAGCAGGTTTGTTGTACGCTTATGCAGTAGGATCC
     M4 N nucl. GACATTGAGTATACATCTCNTACTACAGCAGGTTTGTTGTACGCTTATGCAGTAGGATCC 1021                                                        1080
GenBank N nucl. TCTGCCGACTTGGCACAACAGTTTTGTGTTGGAGATAACAAATACACTCCAGATGATAGT
     HR N nucl. TCTGCTGACTTGGCACAACAGTTTTGTGTTGGAGATAGCAAATACACTCCAGATGATAGT
     M2 N nucl. TCTGCTGACTTGGCACAACAGTTTTGTGTTGGAGATAGCAAATACACTCCAGATGATAGT
     M3 N nucl. TCTGCTGACTTGGCACAACAGTTTTGTGTTGGAGATAGCAAATACACTCCAGATGATAGT
     M4 N nucl. TCTGCTGACTTGGCACANCAGTTTTGTGTTGGAGATAGCAAATACACTCCAGATGATAGT 1081                                                        1140
GenBank N nucl. ACCGGAGGATTGACGACTAATGCACCGCCACAAGGCAGAGATGTGGTCGAATGGCTCGGA
     HR N nucl. ACCGGAGGATTGACGACTAATGCACCGCCACAAGGCAGAGATGTGGTCGAATGGCTCGGA
     M2 N nucl. ACCGGAGGATTGACGACTAATGCACCGCCACAAGGCAGAGATGTGGTCGAATGGCTCGGA
     M3 N nucl. ACCGGAGGATTGACGACTAATGCACCGCCACAAGGCAGAGATGTGGTCGAATGGCTCGGA
     M4 N nucl. ACCGGAGGATTGACGACTAATGCACCGCCACAAGGCAGAGATGTGGTCGAATGGCTCGGA 1141                                                        1200
GenBank N nucl. TGGTTTGAAGATCAAAACAGAAAACCGACTCCTGATATGATGCAGTATGCGAAAAGAGCA
     HR N nucl. TGGTTTGAAGATCAAAACAGAAAACCGACTCCTGATATGATGCAGTATGCGAAACGAGCA
     M2 N nucl. TGGTTTGAAGATCAAAACAGAAAACCGACTCCTGATATGATGCAGTATGCGAAACGAGCA
     M3 N nucl. TGGTTTGAAGATCAAAACAGAAAACCGACTCCTGATATGATGCAGTATGCGAAACGAGCA
     M4 N nucl. TGGTTTGAAGATCAAAACAGAAAACCGACTCCTGATATGATGCAGTATGCGAAACGAGCA 1201                                                        1260
GenBank N nucl. GTCATGTCACTGCAAGGCCTAAGAGAGAAGACAATTGGCAAGTATGCTAAGTCAGAATTT
     HR N nucl. GTCATGTCACTGCAAGGCCTAAGAGAGAAGACAATTGGCAAGTATGCTAAGTCAGAATTT
     M2 N nucl. GTCATGTCACTGCAAGGCCTAAGAGAGAAGACAATTGGCAAGTATGCTAAGTCAGAATTT
     M3 N nucl. GTCATGTCACTGCAAGGCCTAAGAGAGAAGACAATTGGCAAGTATGCTAAGTCAGAATTT
     M4 N nucl. GTCATGTCACTGCAAGGCCTAAGAGAGAAGACAATTGGCAAGTATGCTAAGTCAGAATTT 1261    1269
GenBank N nucl. GACAAATGA
     HR N nucl. GACAAATGA
     M2 N nucl. GACAAATGA
     M3 N nucl. GACAAATGA
     M4 N nucl. GACAAATGA
```

FIGURE 14-3

```
                   1                                                          60
GenBank N a.a.     MSVTVKRIIDNTVIVPKLPANEDPVEYPADYFRKSKEIPLYINTTKSLSDLRGYVYQGLK
     HR N a.a.    MSVTVKRIIANTVIVPKLPANEDPVEYPADYFRKSKEIPLYINTTKSLSDLRGYVYQGLK
     M3 N a.a.    MSVTVKRIIDNTVIVPKLPANEDPVEYPADYFRKSKEIPLYINTTKSLSDLRGYVYQGLK
     M4 N a.a.    ............................................................

61                                                        120
GenBank N a.a.    SGNVSIIHVNSYLYGALKDIRGKLDKDWSSFGINIGKAGDTIGIFDLVSLKALDGVLPDG
     HR N a.a.    SGNVSIIHVNSYLYGALKDIRGKLDKDWSSFGINIGKAGDTIGIFDLVSLKALDGVLPDG
     M3 N a.a.    SGNVSIIHVNSYLYGALKDIRGKLDKDWSSFGINIGKAGDTIGIFDLVSLKALDGVLPDG
     M4 N a.a.    ....SIIHVNSYLYGALKDIRGKLDKDWSSFGINIGKAGDTIGIFDLVSLKALDGVLPDG 121                                                       180
GenBank N a.a.    VSDASRTSADDKWLPLYLLGLYRVGRTQMPEYRKKLMDGLTNQCKMINEQFEPLVPEGRD
     HR N a.a.    VSDASRTSADDKWLPLYLLGLYRVGRTQMPEYRKRLMDGLTNQCKMINEQFEPLVPEGRD
     M3 N a.a.    VSDASRTSADDKWLPLYLLGLYRVGRTQMPEYRKRLMDGLTNQCKMINEQFEPLVPEGRD
     M4 N a.a.    VSDASRTSADDKWLPLYLLGLYRVGRTQMPEYRKRLMDGLTNQCKMINEQFEPLVPEGRD 181                                                       240
GenBank N a.a.    IFDVWGNDSNYTKIVAAVDMFFHMFKKHECASFRYGTIVSRFKDCAALATFGHLCKITGM
     HR N a.a.    IFDVWGNDSNYTKIVAAVDMFFHMFKKHECASFRYGTIVSRFKDCAALATFGHLCKITGM
     M3 N a.a.    IFDVWGNDSNYTKIVAAVDMFFHMFKKHECASFRYGTIVSRFKDCAALATFGHLCKITGM
     M4 N a.a.    IFDVWGNDSNYTKIVAAVDMFFHMFKKHECASFRYGTIVSRFKDCAALATFGHLCKITGM 241                                                       300
GenBank N a.a.    STEDVTTWILNREVADEMVQMMLPGQEIDKADSYMPYLIDFGLSSKSPYSSVKNPAFHFW
     HR N a.a.    STEDVTTWILNREVADEMVQMMLPGQEIDKADSYMPYLIDFGLSSKSPYSSVKNPAFHFW
     M3 N a.a.    STEDVTTWILNREVADEMVQMMLPGQEIDKADSYMPYLIDFGLSSKSPYSSVKNPAFHFW
     M4 N a.a.    STEDVTTWILNREVADEMVQMMLPGQEIDKADSYMPYLIDFGLSSKSPYSSVKNPAFHFW 301                                                       360
GenBank N a.a.    GQLTALLLRSTRARNARQPDDIEYTSLTTAGLLYAYAVGSSADLAQQFCVGDNKYTPDDS
     HR N a.a.    GQLTALLLRSTRARNARQPDDIEYTSLTTAGLLYAYAVGSSADLAQQFCVGDSKYTPDDS
     M3 N a.a.    GQLTALLLRSTRARNARQPDDIEYTSLTTAGLLYAYAVGSSADLAQQFCVGDSKYTPDDS
     M4 N a.a.    GQLT...............DIEYTSXTTAGLLYAYAVGSSADLAXQFCVGDSKYTPDDS 361                                                       420
GenBank N a.a.    TGGLTTNAPPQGRDVVEWLGWFEDQNRKPTPDMMQYAKRAVMSLQGLREKTIGKYAKSEF
     HR N a.a.    TGGLTTNAPPQGRDVVEWLGWFEDQNRKPTPDMMQYAKRAVMSLQGLREKTIGKYAKSEF
     M3 N a.a.    TGGLTTNAPPQGRDVVEWLGWFEDQNRKPTPDMMQYAKRAVMSLQGLREKTIGKYAKSEF
     M4 N a.a.    TGGLTTNAPPQGRDVVEWLGWFEDQNRKPTPDMMQYAKRAVMSLQGLREKTIGKYAKSEF 421  423
GenBank N a.a.    DK.
     HR N a.a.    DK.
     M3 N a.a.    DK.
     M4 N a.a.    DK.
```

FIGURE 15

```
                    1                                                          60
GenBank P nucl.    ATGGATAATCTCACAAAAGTTCGTGAGTATCTCAAGTCCTATTCTCGTCTGGATCAGGCG
     HR P nucl.    ATGGATAATCTCACAAAAGTTCGTGAGTATCTCAAGTCCTATTCTCGTCTAGATCAGGCG
     M2 P nucl.    ATGGATAATCTCACAAAAGTTCGTGAGTATCTCAAGTCCTATTCTCGTCTAGATCAGGCG
     M3 P nucl.    ATGGATAATCTCACAAAAGTTCGTGAGTATCTCAAGTCCTATTCTCGTCTAGATCAGGCG
     M4 P nucl.    ATGGATAATCTCACAAAAGTTCGTGAGTATCTCAAGTCCTATTCTCGTCTAGATCAGGCG 61                                                         120
GenBank P nucl.    GTAGGAGAGATAGATGAGATCGAAGCACAACGAGCTGAAAAGTCCAATTATGAGTTGTTC
     HR P nucl.    GTAGGAGAGATAGATGAGATCGAAGCACAACGAGCTGAAAAGTCCAATTATGAGTTGTTC
     M2 P nucl.    GTAGGAGAGATAGATGAGATCGAAGCACAACGAGCTGAAAAGTCCAATTATGAGTTGTTC
     M3 P nucl.    GTAGGAGAGATAGATGAGATCGAAGCACAACGAGCTGAAAAGTCCAATTATGAGTTGTTC
     M4 P nucl.    GTAGGAGAGATAGATGAGATCGAAGCACAACGAGCTGAAAAGTCCAATTATGAGTTGTTC 121                                                        180
GenBank P nucl.    CAAGAGGATGGAGTGGAAGAGCATACTAAGCCCTCTTATTTTCAGGCAGCAGATGATTCT
     HR P nucl.    CAAGAGGACGGAGTGGAAGAGCATACTAGGCCCTCTTATTTTCAGGCAGCAGATGATTCT
     M2 P nucl.    CAAGAGGACGGAGTGGAAGAGCATACTAGGCCCTCTTATTTTCAGGCAGCAGATGATTCT
     M3 P nucl.    CAAGAGGACGGAGTGGAAGAGCATACTAGGCCCTCTTATTTTCAGGCAGCAGATGATTCT
     M4 P nucl.    CAAGAGGACGGAGTGGAAGAGCATACTAGGCCCTCTTATTTTCAGGCAGCAGATGATTCT 181                                                        240
GenBank P nucl.    GACACAGAATCTGAACCAGAAATTGAAGACAATCAAGGTTTGTATGCACAGGATCCAGAA
     HR P nucl.    GACACAGAATCTGAACCAGAAATTGAAGACAATCAAGGCTTGTATGTACCAGATCCGGAA
     M2 P nucl.    GACACAGAATCTGAACCAGAAATTGAAGACAATCAAGGCTTGTATGTACCAGATCCGGAA
     M3 P nucl.    GACACAGAATCTGAACCAGAAATTGAAGACAATCAAGGCTTGTATGTACCAGATCCGGAA
     M4 P nucl.    GACACAGAATCTGAACCAGAAATTGAAGACAATCAAGGCTTGTATGTACCAGATCCGGAA 241                                                        300
GenBank P nucl.    GCTGAGCAAGTTGAAGGCTTTATACAGGGGCCTTTAGATGACTATGCAGATGAGGAAGTG
     HR P nucl.    GCTGAGCAAGTTGAAGGCTTTATACAGGGGCCTTTAGATGACTATGCGGATGAGGACGTG
     M2 P nucl.    GCTGAGCAAGTTGAAGGCTTTATACAGGGGCCTTTAGATGACTATGCGGATGAGGACGTG
     M3 P nucl.    GCTGAGCAAGTTGAAGGCTTTATACAGGGGCCTTTAGATGACTATGCGGATGAGGACGTG
     M4 P nucl.    GCTGAGCAAGTTGAAGGCTTTATACAGGGGCCTTTAGATGACTATGCGGATGAGGACGTG 301                                                        360
GenBank P nucl.    GATGTTGTATTTACTTCGGACTGGAAACCACCTGAGCTTGAATCTGACGAGCATGGAAAG
     HR P nucl.    GATGTTGTATTCACTTCGGACTGGAAACAGCCTGAGCTTGAATCCGACGAGCATGGAAAG
     M2 P nucl.    GATGTTGTATTCACTTCGGACTGGAAACAGCCTGAGCTTGAATCCGACGAGCATGGAAAG
     M3 P nucl.    GATGTTGTATTCACTTCGGACTGGAAACAGCCTGAGCTTGAATCCGACGAGCATGGAAAG
     M4 P nucl.    GATGTTGTATTCACTTCGGACTGGAAACAGCCTGAGCTTGAATCCGACGAGCATGGAAAG 361                                                        420
GenBank P nucl.    ACCTTACGGTTGACATCGCCAGAGGGTTTAAGTGGAGAGCAGAAATCCCAGTGGCTTTCG
     HR P nucl.    ACCTTACGGTTGACATTGCCAGAGGGTTTAAGTGGAGAGCAGAAATCCCAGTGGCTTTTG
     M2 P nucl.    ACCTTACGGTTGACATTGCCAGAGGGTTTAAGTGGAGAGCAGAAATCCCAGTGGCTTTTG
     M3 P nucl.    ACCTTACGGTTGACATTGCCAGAGGGTTTAAGTGGAGAGCAGAAATCCCAGTGGCTTTTG
     M4 P nucl.    ACCTTACGGTTGACATTGCCAGAGGGTTTAAGTGGAGAGCAGAAATCCCAGTGGCTTTTG
```

FIGURE 16-1

```
              421                                                           480
GenBank P nucl. ACGATTAAAGCAGTCGTGCAAAGTGCCAAATACTGGAATCTGGCAGAGTGCACATTTGAA
     HR P nucl. ACGATTAAAGCAGTCGTTCAAAGTGCCAAACACTGGAATCTGGCAGAGTGCACATTTGAA
     M2 P nucl. ACGATTAAAGCAGTCGTTCAAAGTGCCAAACACTGGAATCTGGCAGAGTGCACATTTGAA
     M3 P nucl. ACGATTAAAGCAGTCGTTCAAAGTGCCAAACACTGGAATCTGGCAGAGTGCACATTTGAA
     M4 P nucl. ACGATTAAAGCAGTCGTTCAAAGTGCCAAACACTGGAATCTGGCAGAGTGCACATTTGAA 481                                                           540
GenBank P nucl. GCATCGGGAGAAGGGGTCATTATGAAGGAGCGCCAGATAACTCCGGATGTATATAAGGTC
     HR P nucl. GCATCGGGAGAAGGGGTCATCATAAAAAAGCGCCAGATAACTCCGGATGTATATAAGGTC
     M2 P nucl. GCATCGGGAGAAGGGGTCATCATAAAAAAGCGCCAGATAACTCCGGATGTATATAAGGTC
     M3 P nucl. GCATCGGGAGAAGGGGTCATCATAAAAAAGCGCCAGATAACTCCGGATGTATATAAGGTC
     M4 P nucl. GCATCGGGAGAAGGGGTCATCATAAAAAAGCGCCAGATAACTCCGGATGTATATAAGGTC 541                                                           600
GenBank P nucl. ACTCCAGTGATGAACACACATCCGTCCCAATCAGAAGCAGTATCAGATGTTTGGTCTCTC
     HR P nucl. ACTCCAGTGATGAACACACATCCGTCCCAATCAGAAGCCGTATCAGATGTTTGGTCTCTC
     M2 P nucl. ACTCCAGTGATGAACACACATCCGTCCCAA..............................
     M3 P nucl. ACTCCAGTGATGAACACACATCCGTCCCAATCGGAAGCCGTATCAGATGTTTGGTCTCTC
     M4 P nucl. ACTCCAGTGATGAACACACATCCGTCCCAATCAGAAGCCGTATCAGATGTTTGGTCTCTC 601                                                           660
GenBank P nucl. TCAAAGACATCCATGACTTTCCAACCCAAGAAAGCAAGTCTTCAGCCTCTCACCATATCC
     HR P nucl. TCAAAGACATCCATGACTTTCCAACCCAAGAAAGCAAGTCTTCAGCCTCTCACCATATCC
     M2 P nucl. ............................................................
     M3 P nucl. TCAAAGACATCCATGACTTTCCAACCCAAGAAAGCAAGTCTTCAGCCTCTCACCATATCC
     M4 P nucl. TCAAAGACATCCATGACTTTCCAACCCAAGAAAGCAAGTCTTCAGCCTCTCACCATATCC 661                                                           720
GenBank P nucl. TTGGATGAATTGTTCTCATCTAGAGGAGAGTTCATCTCTGTCGGAGGTGACGGACGAATG
     HR P nucl. TTGGATGAATTGTTCTCATCTAGAGGAGAATTCATCTCTGTCGGAGGTAACGGACGAATG
     M2 P nucl. ............................................................
     M3 P nucl. TTGGATGAATTGTTCTCATCTAGAGGAGAATTCATCTCTGTCGGAGGTAACGGACGAATG
     M4 P nucl. TTGGATGAATTGTTCTCATCTAGAGGAGAATTCATCTCTGTCGGAGGTAACGGACGAATG 721                                                           780
GenBank P nucl. TCTCATAAAGAGGCCATCCTGCTCGGCCTGAGATACAAAAAGTTGTACAATCAGGCGAGA
     HR P nucl. TCTCATAAAGAGGCCATCCTGCTCGGTCTGAGGTACAAAAAGTTGTACAATCAGGCGAGA
     M2 P nucl. ............................................................
     M3 P nucl. TCTCATAAAGAGGCCATCCTGCTCGGTCTGAGGTACAAAAAGTTGTACAATCAGGCGAGA
     M4 P nucl. TCTCATAAAGAGGCCATCCTGCTCGGTCTGAGGTACAAAAAGTTGTACAATCAGGCGAGA 781         798
GenBank P nucl. GTCAAATATTCTCTGTAG
     HR P nucl. GTCAAATATTCTCTGTAG
     M2 P nucl. ..................
     M3 P nucl. GTCAAATATTCTCTGTAG
     M4 P nucl. GTCAAATATTCTCTGTAG
```

FIGURE 16-2

```
                    1                                                          60
GenBank P a.a.      MDNLTKVREYLKSYSRLDQAVGEIDEIEAQRAEKSNYELFQEDGVEEHT KPSYFQAADDS
     HR P a.a.      MDNLTKVREYLKSYSRLDQAVGEIDEIEAQRAEKSNYELFQEDGVEEHTRPSYFQAADDS
     M2 P a.a.      MDNLTKVREYLKSYSRLDQAVGEIDEIEAQRAEKSNYELFQEDGVEEHTRPSYFQAADDS
     M3 P a.a.      MDNLTKVREYLKSYSRLDQAVGEIDEIEAQRAEKSNYELFQEDGVEEHTRPSYFQAADDS
     M4 P a.a.      MDNLTKVREYLKSYSRLDQAVGEIDEIEAQRAEKSNYELFQEDGVEEHTRPSYFQAADDS 61                                                         120
GenBank P a.a.      DTESEPEIEDNQGLY ACDPEAEQVEGFIQGPLDDYADE EVDVVFTSDWK PPELESDEHGK
     HR P a.a.      DTESEPEIEDNQGLYVPDPEAEQVEGFIQGPLDDYADEDVDVVFTSDWKQPELESDEHGK
     M2 P a.a.      DTESEPEIEDNQGLYVPDPEAEQVEGFIQGPLDDYADEDVDVVFTSDWKQPELESDEHGK
     M3 P a.a.      DTESEPEIEDNQGLYVPDPEAEQVEGFIQGPLDDYADEDVDVVFTSDWKQPELESDEHGK
     M4 P a.a.      DTESEPEIEDNQGLYVPDPEAEQVEGFIQGPLDDYADEDVDVVFTSDWKQPELESDEHGK 121                                                        180
GenBank P a.a.      TLRLT SPEGLSGEQKSQWL STIKAVVQSAK YWNLAECTFEASGEGVI MKERQITPDVYKV
     HR P a.a.      TLRLTLPEGLSGEQKSQWLLTIKAVVQSAKHWNLAECTFEASGEGVIIKKRQITPDVYKV
     M2 P a.a.      TLRLTLPEGLSGEQKSQWLLTIKAVVQSAKHWNLAECTFEASGEGVIIKKRQITPDVYKV
     M3 P a.a.      TLRLTLPEGLSGEQKSQWLLTIKAVVQSAKHWNLAECTFEASGEGVIIKKRQITPDVYKV
     M4 P a.a.      TLRLTLPEGLSGEQKSQWLLTIKAVVQSAKHWNLAECTFEASGEGVIIKKRQITPDVYKV 181                                                        240
GenBank P a.a.      TPVMNTHPSQSEAVSDVWSLSKTSMTFQPKKASLQPLTISLDELFSSRGEFISVGG DGRM
     HR P a.a.      TPVMNTHPSQSEAVSDVWSLSKTSMTFQPKKASLQPLTISLDELFSSRGEFISVGGNGRM
     M2 P a.a.      TPVMNTHPSQ..................................................
     M3 P a.a.      TPVMNTHPSQSEAVSDVWSLSKTSMTFQPKKASLQPLTISLDELFSSRGEFISVGGNGRM
     M4 P a.a.      TPVMNTHPSQSEAVSDVWSLSKTSMTFQPKKASLQPLTISLDELFSSRGEFISVGGNGRM 241              266
GenBank P a.a.      SHKEAILLGLRYKKLYNQARVKYSL
     HR P a.a.      SHKEAILLGLRYKKLYNQARVKYSL
     M2 P a.a.      .........................
     M3 P a.a.      SHKEAILLGLRYKKLYNQARVKYSL
     M4 P a.a.      SHKEAILLGLRYKKLYNQARVKYSL
```

FIGURE 17

```
                    1                                                          60
GenBank M nucl.     ATGAGTTCCTTAAAGAAGATTCTCGGTCTGAAGGGGAAAGGTAAGAAATCTAAGAAATTA
     HR M nucl.     ATGAGTTCCTTAAAGAAGATTCTCGGTCTGAAGGGGAAAGGTAAGAAATCTAAGAAATTA
     M3 M nucl.     ATGAGTTCCTTAAAGAAGATTCTCGGTCTGAAGGGGAAAGGTAAGAAATCTAAGAAATTA
     M4 M nucl.     ATGAGTTCCTTAAAGAAGATTCTCGGTCTGAAGGGGAAAGGTAAGAAATCTAAGAAATTA 61                                                         120
GenBank M nucl.     GGGATCGCACCACCCCCTTATGAAGAGGACACTAGCATGGAGTATGCTCCGAGCGCTCCA
     HR M nucl.     GGGATCGCACCACCCCCTTATGAAGAGGACACTAACATGGAGTATGCTCCGAGCGCTCCA
     M3 M nucl.     GGGATCGCACCACCCCCTTATGAAGAGGACACTAACATGGAGTATGCTCCGAGCGCTCCA
     M4 M nucl.     GGGATCGCACCACCCCCTTATGAAGAGGACACTAACATGGAGTATGCTCCGAGCGCTCCA 121                                                        180
GenBank M nucl.     ATTGACAAATCCTATTTTGGAGTTGACGAGATGGACACCTATGATCCGAATCAATTAAGA
     HR M nucl.     ATTGACAAATCCTATTTTGGAGTTGACGAGATGGACACTCATGATCCGCATCAATTAAGA
     M3 M nucl.     ATTGACAAATCCTATTTTGGAGTTGACGAGGGGACACTCATGATCCGCATCAATTAAGA
     M4 M nucl.     ATTGACAAATCCTATTTTGGAGTTGACGAGATGGACACTCATGATCCGCATCAATTAAGA 181                                                        240
GenBank M nucl.     TATGAGAAATTCTTCTTTACAGTGAAAATGACGGTTAGATCTAATCGTCCGTTCAGAACA
     HR M nucl.     TATGAGAAATTCTTCTTTACAGTGAAAATGACGGTTAGATCTAATCGTCCGTTCAGAACA
     M3 M nucl.     TATGAGAAATTCTTCTTTACAGTGAAAATGACGGTTAGATCTAATCGTCCGTTCAGAACA
     M4 M nucl.     TATGAGAAATTCTTCTTTACAGTGAAAATGACGGTTAGATCTAATCGTCCGTTCAGAACA 241                                                        300
GenBank M nucl.     TACTCAGATGTGGCAGCCGCTGTATCCCATTGGGATCACATGTACATCGGAATGGCAGGG
     HR M nucl.     TACTCAGATGTGGCAGCCGCTGTATCCCATTGGGATCACATGTACATCGGAATGGCAGGG
     M3 M nucl.     TACTCAGATGTGGCAGCCGCTGTATCCCATTGGGATCACATGTACATCGGAATGGCAGGG
     M4 M nucl.     TACTCAGATGTGGCAGCCGCTGTATCCCATTGGGATCACATGTACATCGGAATGGCAGGG 301                                                        360
GenBank M nucl.     AAACGTCCCTTCTACAAAATCTTGGCTTTTTTGGGTTCTTCTAATCTAAAGGCCACTCCA
     HR M nucl.     AAACGTCCCTTCTACAAGATCTTGGCTTTTTTGGGTTCTTCTAATCTAAAGGCCACTCCA
     M3 M nucl.     AAACGTCCCTTCTACAAGATCTTGGCTTTTTTGGGTTCTTCTAATCTAAAGGCCACTCCA
     M4 M nucl.     AAACGTCCCTTCTACAAGATCTTGGCTTTTTTGGGTTCTTCTAATCTAAAGGCCACTCCA 361                                                        420
GenBank M nucl.     GCGGTATTGGCAGATCAAGGTCAACCAGAGTATCACACTCACTGCGAAGGCAGGGCTTAT
     HR M nucl.     GCGGTATTGGCAGATCAAGGTCAACCAGAGTATCACGCTCACTGTGAAGGCAGGGCTTAT
     M3 M nucl.     GCGGTATTGGCAGATCAAGGTCAACCAGAGTATCACGCTCACTGTGAAGGCAGGGCTTAT
     M4 M nucl.     GCGGTATTGGCAGATCAAGGTCAACCAGAGTATCACGCTCACTGTGAAGGCAGGGCTTAT 421                                                        480
GenBank M nucl.     TTGCCACATAGGATGGGGAAGACCCCTCCCATGCTCAATGTACCAGAGCACTTCAGAAGA
     HR M nucl.     TTGCCACACAGAATGGGGAAGACCCCTCCCATGCTCAATGTACCAGAGCACTTCAGAAGA
     M3 M nucl.     TTGCCACACAGAATGGGGAAGACCCCTCCCATGCTCAATGTACCAGAGCACTTCAGAAGA
     M4 M nucl.     TTGCCACACAGAATGGGGAAGACCCCTCCCATGCTCAATGTACCAGAGCACTTCAGAAGA 481                                                        540
GenBank M nucl.     CCATTCAATATAGGTCTTTACAAGGGAACGATTGAGCTCACAATGACCATCTACGATGAT
     HR M nucl.     CCATTCAATATAGGTCTTTACAAGGGAACGGTTGAGCTCACAATGACCATCTACGATGAT
     M3 M nucl.     CCATTCAATATAGGTCTTTACAAGGGAACGGTTGAGCTCACAATGACCATCTACGATGAT
     M4 M nucl.     CCATTCAATATAGGTCTTTACAAGGGAACGGTTGAGCTCACAATGACCATCTACGATGAT
```

FIGURE 18-1

```
                541                                                          600
GenBank M nucl. GAGTCACTGGAAGCAGCTCCTATGATCTGGGATCATTTCAATTCTTCCAAATTTTCTGAT
     HR M nucl. GAGTCACTGGAAGCAGCTCCTATGATCTGGGATCATTTCAATTCTTCCAAATTTTCTGAT
     M3 M nucl. GAGTCACTGGAAGCAGCTCCTATGATCTGGGATCATTTCAATTCTTCCAAATTTTCTGAT
     M4 M nucl. GAGTCACTGGAAGCAGCTCCTATGATCTGGGATCATTTCAATTCTTCCAAATTTTCTGAT 601                                                          660
GenBank M nucl. TTCAGAGAGAAGGCCTTAATGTTTGGCCTGATTGTCGAGAAAAAGGCATCTGGAGCGTGG
     HR M nucl. TTCAGAGAGAAGGCCTTAATGTTTGGCCTGATTGTCGAGAAAAAGGCATCTGGAGCTTGG
     M3 M nucl. TTCAGAGAGAAGGCCTTAATGTTTGGCCTGATTGTCGAGAAAAAGGCATCTGGAGCTTGG
     M4 M nucl. TTCAGAGAGAAGGCCTTAATGTTTGGCCTGATTGTCGAGAAAAAGGCATCTGGAGCTTGG 661                           690
GenBank M nucl. GTCCTGGATTCTATCAGCCACTTCAAATGA
     HR M nucl. GTCCTGGATTCTGTCAGCCACTTCAAATGA
     M3 M nucl. GTCCTGGATTCTGTCAGCCACTTCAAATGA
     M4 M nucl. GTCCTGGATTCTGTCAGCCACTTCAAATGA
```

FIGURE 18-2

```
                   1                                                          60
GenBank M a.a.    MSSLKKILGLKGKGKKSKKLGIAPPPYEEDTSMEYAPSAPIDKSYFGVDEMDTYDPNQLR
     HR M a.a.    MSSLKKILGLKGKGKKSKKLGIAPPPYEEDTNMEYAPSAPIDKSYFGVDEMDTHDPHQLR
     M4 M a.a.    MSSLKKILGLKGKGKKSKKLGIAPPPYEEDTNMEYAPSAPIDKSYFGVDEMDTHDPHQLR
     M3 M a.a.    MSSLKKILGLKGKGKKSKKLGIAPPPYEEDTNMEYAPSAPIDKSYFGVDERDTHDPHQLR 61                                                        120
GenBank M a.a.    YEKFFFTVKMTVRSNRPFRTYSDVAAAVSHWDHMYIGMAGKRPFYKILAFLGSSNLKATP
     HR M a.a.    YEKFFFTVKMTVRSNRPFRTYSDVAAAVSHWDHMYIGMAGKRPFYKILAFLGSSNLKATP
     M4 M a.a.    YEKFFFTVKMTVRSNRPFRTYSDVAAAVSHWDHMYIGMAGKRPFYKILAFLGSSNLKATP
     M3 M a.a.    YEKFFFTVKMTVRSNRPFRTYSDVAAAVSHWDHMYIGMAGKRPFYKILAFLGSSNLKATP 121                                                       180
GenBank M a.a.    AVLADQGQPEYHTHCEGRAYLPHRMGKTPPMLNVPEHFRRPFNIGLYKGTTELTMTIYDD
     HR M a.a.    AVLADQGQPEYHAHCEGRAYLPHRMGKTPPMLNVPEHFRRPFNIGLYKGTVELTMTIYDD
     M4 M a.a.    AVLADQGQPEYHAHCEGRAYLPHRMGKTPPMLNVPEHFRRPFNIGLYKGTVELTMTIYDD
     M3 M a.a.    AVLADQGQPEYHAHCEGRAYLPHRMGKTPPMLNVPEHFRRPFNIGLYKGTVELTMTIYDD 181                                    230
GenBank M a.a.    ESLEAAPMIWDHFNSSKFSDFREKALMFGLIVEKKASGAWVLDSISHFK.
     HR M a.a.    ESLEAAPMIWDHFNSSKFSDFREKALMFGLIVEKKASGAWVLDSVSHFK.
     M4 M a.a.    ESLEAAPMIWDHFNSSKFSDFREKALMFGLIVEKKASGAWVLDSVSHFK.
     M3 M a.a.    ESLEAAPMIWDHFNSSKFSDFREKALMFGLIVEKKASGAWVLDSVSHFK.
```

FIGURE 19

```
               1                                                          60
GenBank G nucl. ATGAAGTGCCTTTTGTACTTAGCCTTTTTATTCATTGGGGTGAATTGCAAGTTCACCATA
     HR G nucl. ATGAAGTGCCTTTTGKACTTAGCTTTTTATTCATCGGGGTGAATTGCAAGTTCACCATA
     M2 G nucl. ............................................................
     M3 G nucl. ATGAAGTGCCTTTTGTACTTAGCTTTTTATTCATCGGGGTGAATTGCAAGTTCACCATA
     M4 G nucl. ATGAAGTGCCTTTTGTACTTAGCTTTTTATTCATCGGGGTGAATTGCAAGTTCACCATA 61                                                         120
GenBank G nucl. GTTTTTCCACACAACCAAAAAGGAAACTGGAAAAATGTTCCTTCTAATTACCATTATTGC
     HR G nucl. GTTTTTCCATACAACCAAAAAGGAAACTGGAAAAATGTTCCTTCCAATTACCATTATTGC
     M2 G nucl. ............................................................
     M3 G nucl. GTTTTTCCATACAACCCAAAAGGAAACTGGAAAAATGTTCCTTCCAATTACCATTATTGC
     M4 G nucl. GTTTTTCCATACAACCAAAAAGGAAACTGGAAAAATGTTCCTTCCAATTACCATTATTGC 121                                                        180
GenBank G nucl. CCGTCAAGCTCAGATTTAAATTGGCATAATGACTTAATAGGCACAGCCATACAAGTCAAA
     HR G nucl. CCGTCAAGCTCAGATTTAAATTGNCATAATGACTTAATAGGCACAGCCTTACAAGTCAAA
     M2 G nucl. ............................................................
     M3 G nucl. CCGTCAAGCTCAGATTTAAATTGGCATAATGACTTAATAGGCACAGCCTTACAAGTCAAA
     M4 G nucl. CCGTCAAGCTCAGATTTAAATTGGCATAATGACTTAATAGGCACAGCCTTACAGGTCAAA 181                                                        240
GenBank G nucl. ATGCCCAAGAGTCACAAGGCTATTCAAGCAGACGGTTGGATGTGTCATGCTTCCAAATGG
     HR G nucl. ATGCCCAAGAGTCACAAGGCTATTCAAGCAGACGGTTGGATGTGTCATGCTTCCAAATGG
     M2 G nucl. ............................................................
     M3 G nucl. ATGCCCAAGAGTCACAAGGCTATTCAAGCAGACGGTTGGATGTGTCATGCTTCCAAATGG
     M4 G nucl. ATGCCCAAGAGTCACAAGGCTATTCAAGCAGACGGTTGGATGTGTCATGCTTCCAAATGG 241                                                        300
GenBank G nucl. GTCACTACTTGTGATTTCCGCTGGTATGGACCGAAGTATATAACACAGTCCATCCGATCC
     HR G nucl. GTCACTACTTGTGATTTCCGCTGGTACGGACCGAAGTATATAACACATTCCATCCGATCC
     M2 G nucl. ............................................................
     M3 G nucl. GTCACTACTTGTGATTTCCGCTGGTACGGACCGAAGTATATAACACATTCCATCCGATCC
     M4 G nucl. GTCACTACTTGTGATTTCCGCTGGTACGGACCGAAGTATATAACACATTCCATCCGATCC 301                                                        360
GenBank G nucl. TTCACTCCATCTGTAGAACAATGCAAGGAAAGCATTGAACAAACGAAACAAGGAACTTGG
     HR G nucl. TTCACTCCATCTGTAGAACAATGCAAGGAAAGCATTGAACAAACGAAACAAGGAACTTGG
     M2 G nucl. ............................................................
     M3 G nucl. TTCACTCCATCTGTAGAACAATGCAAGGAAAGCATTGAACAAACGAAACAAGGAACTTGG
     M4 G nucl. TTCACTCCATCTGTAGAACAATGCAAGGAAAGCATTGAACAAACGAAACAAGGAACTTGG 361                                                        420
GenBank G nucl. CTGAATCCAGGCTTCCCTCCTCAAAGTTGTGGATATGCAACTGTGACGGATGCCGAAGCA
     HR G nucl. CTGAATCCAGGCTTCCCTCCTCAAAGTTGTGGATATGCAACTGTGACGGATGCTGAAGCA
     M2 G nucl. ............................................................
     M3 G nucl. CTGAATCCAGGCTTCCCTCCTCAAAGTTGTGGATATGCAACTGTGACGGATGCTGAAGCA
     M4 G nucl. CTGAATCCAGGCTTCCCTCCTCAAAGTTGTGGATATGCAACTGTGACGGATGCTGAAGCA 421                                                        480
GenBank G nucl. GTGATTGTCCAGGTGACTCCTCACCATGTGCTGGTTGATGAATACACAGGAGAATGGGTT
     HR G nucl. GCGATTGTCCAGGTGACTCCTCACCATGTGCTTGTTGATGAATACACAGGAGAATGGGTT
     M2 G nucl. ............................................................
     M3 G nucl. GCGATTGTCCAGGTGACTCCTCACCATGTGCTTGTTGATGAATACACAGGAGAATGGGTT
     M4 G nucl. GCGATTGTCCAGGTGACTCCTCACCATGTGCTTGTTGATGAATACACAGGAGAATGGGTT
```

FIGURE 20-1

```
               481                                                          540
GenBank G nucl. GATTCACAGTTCATCAACGGAAAATGCAGCAATTACATATGCCCCACTGTCCATAACTCT
     HR G nucl. GATTCACAGTTCATCAACGGAAAATGCAGCAATGACATATGCCCCACTGTCCATAACTCC
     M2 G nucl. ............................................................
     M3 G nucl. GATTCACAGTTCATCAACGGAAAATGCAGCAATGACATATGCCCCACTGTCCATAACTCC
     M4 G nucl. GATTCACAGTTCATCAACGGAAAATGCAGCAATGACATATGCCCCACTGTCCATAACTCC 541                                                          600
GenBank G nucl. ACAACCTGGCATTCTGACTATAAGGTCAAAGGGCTATGTGATTCTAACCTCATTTCCATG
     HR G nucl. ACAACCTGGCATTCCGACTATAAGGTCAAAGGGCTATGTGATTCTAACCTCATTTCCATG
     M2 G nucl. ............................................................
     M3 G nucl. ACAACCTGGCATTCCGACTATAAGGTCAAAGGGCTATGTGATTCTAACCTCATTTCCATG
     M4 G nucl. ACAACCTGGCATTCCGACTATAAGGTCAAAGGGCTATGTGATTCTAACCTCATTTCCATG 601                                                          660
GenBank G nucl. GACATCACCTTCTTCTCAGAGGACGGAGAGCTATCATCCCTGGGAAAGGAGGGCACAGGG
     HR G nucl. GACATCACCTTCTTCTCAGAGGACGGAGAGCTATCATCCCTAGGAAAGGAGGGCACAGGG
     M2 G nucl. ............................................................
     M3 G nucl. GACATCACCTTCTTCTCAGAGGACGGAGAGCTATCATCCCTAGGAAAGGAGGGCACAGGG
     M4 G nucl. GACATCACCTTCTTCTCAGAGGACGGAGAGCTATCATCCCTAGGAAAGGAGGGCACAGGG 661                                                          720
GenBank G nucl. TTCAGAAGTAACTACTTTGCTTATGAAACTGGAGCCAAGGCCTGCAAAATGCAATACTGC
     HR G nucl. TTCAGAAGTAACTACTTTGCTTATGAAACTGGAGACAAGGCCTGCAAAATGCAGTACTGC
     M2 G nucl. ............................................................
     M3 G nucl. TTCAGAAGTAACTACTTTGCTTATGAAACTGGAGACAAGGCCTGCAAAATGCAGTACTGC
     M4 G nucl. TTCAGAAGTAACTACTTTGCTTATGAAACTGGAGACAAGGCCTGCAAAATGCAGTACTGC 721                                                          780
GenBank G nucl. AAGCATTGGGGAGTCAGACTCCCATCAGGTGTCTGGTTCGAGATGGCTGATAAGGATCTC
     HR G nucl. AAGCGTTGGGGAGTCAGACTCCCATCAGGTGTCTGGTTCGAGATGGCTGATAAGGATCTC
     M2 G nucl. ............................................................
     M3 G nucl. AAGCATTGGGGAGTCAGACTCCCATCAGGTGTCTGGTTCGAGATGGCTGATAAGGATCTC
     M4 G nucl. AAGCGTTGGGGAGTCAGACTCCCATCAGGTGTCTGGTTCGGATGGCTGATAAGGATCTC 781                                                          840
GenBank G nucl. TTTGCTGCAGCCAGATTCCCTGAATGCCCAGAAGGGTCAAGTATCTCTGCTCCATCTCAG
     HR G nucl. TTTGCTGCAGCCAGATTCCCTGAATGCCCAGAAGGGTCAAGTATCTCTGCTCCATCTCAG
     M2 G nucl. ....................................................CCATCTCAG
     M3 G nucl. TTTGCTGCAGCCAGATTCCCTGAATGCCCAGAAGGGTCAAGTATCTCTGCTCCATCTCAG
     M4 G nucl. TTTGCTGCAGCCAGATTCCCTGAATGCCCAGAAGGGTCAAGTATCTCTGCTCCATCTCAG 841                                                          900
GenBank G nucl. ACCTCAGTGGATGTAAGTCTAATTCAGGACGTTGAGAGGATCTTGGATTATTCCCTCTGC
     HR G nucl. ACCTCAGTGGATGTAAGTCTCATTCAGGACGTTGAGAGGATCTTG...............
     M2 G nucl. ACCTCAGTGGATGTAAGTCTCATTCAGGACGTTGAGAGGATCTTGGATTATTCCCTCTGC
     M3 G nucl. ACCTCAGTGGATGTAAGTCTCATTCAGGACGTTGAGAGGATCTTGGATTATTCCCTCTGC
     M4 G nucl. ACCTCAGTGGATGTAAGTCTCATTCAGGACGTTGAGAGGATCT.................
```

FIGURE 20-2

```
             901                                                        960
GenBank G nucl.  CAAGAAACCTGGAGCAAAATCAGAGCGGGTCTTCCAATCTCTCCAGTGGATCTCAGCTAT
     HR G nucl.  ............................................................
     M2 G nucl.  CAAGAAACCTGGAGCAAAATCAGAGCGGGTCTTCCCATCTCTCCAGTGGATCTCAGCTAT
     M3 G nucl.  CAAGAAACCTGGAGCAAAATCAGAGCGGGTCTTCCCATCTCTCCAGTGGATCTCAGCTAT
     M4 G nucl.  ............................................................

961                                                       1020
GenBank G nucl.  CTTGCTCCTAAAAACCCAGGAACCGGTCCTGCTTTCACCATAATCAATGGTACCCTAAAA
     HR G nucl.  ............................................................
     M2 G nucl.  CTTGCTCCTAAAAACCCAGGAACCGGTCCTGTCTTTACCATAATCAATGGTACCCTAAAA
     M3 G nucl.  CTTGCTCCTAAAAACCCAGGAACCGGTCCTGCTTTCACCATAATCAATGGTACCCTAAAA
     M4 G nucl.  ............................................................

1021                                                       1080
GenBank G nucl.  TACTTTGAGACCAGATACATCAGAGTCGATATTGCTGCTCCAATCCTCTCAAGAATGGTC
     HR G nucl.  ............................................................
     M2 G nucl.  TACTTTGAGACCAGATACATCAGAGTCGATATTGCTGCTCCAATCCTCTCAAGAATGGTC
     M3 G nucl.  TACTTTGAGACCAGATACATCAGAGTCGATATTGCTGCTCCAATCCTCTCAAGAATGGTC
     M4 G nucl.  TACTTTGAGACCAGATACATCAGAGTCGATATTGCTGCTCCAATCCTCTCAAGAATGGTC 1081                                                       1140
GenBank G nucl.  GGAATGATCAGTGGAACTACCACAGAAAGGGAACTGTGGGATGACTGGGCACCATATGAA
     HR G nucl.  ............................................................
     M2 G nucl.  GGAATGATCAGTGGAACTACCACAGAAAGGGAACTGTGGGATGACTGGGCTCCATATGAA
     M3 G nucl.  GGAATGATCAGTGGAACTACCACAGAAAGGGAACTGTGGGATGACTGGGCTCCATATGAA
     M4 G nucl.  GGAATGATCAGTGGAACTACCACAGAAAGGGAACTGTGGGATGACTGGGCTCCATATGAA 1141                                                       1200
GenBank G nucl.  GACGTGGAAATTGGACCCAATGGAGTTCTGAGGACCAGTTCAGGATATAAGTTTCCTTTA
     HR G nucl.  ............................................................
     M2 G nucl.  GACGTGGAAATTGGACCCAATGGAGTTCTGAGGACCAGTTCAGGATATAAGTTTCCTTTA
     M3 G nucl.  GACGTGGAAATTGGACCCAATGGAGTTCTGAGGACCAGTTCAGGATATAAGTTTCCTTTA
     M4 G nucl.  GACGTGGAAATTGGACCCAATGGAGTTCTGAGGACCAGTTCAGGATATAAGTTTCCTTTA 1201                                                       1260
GenBank G nucl.  TACATGATTGGACATGGTATGTTGGACTCCGATCTTCATCTTAGCTCAAAGGCTCAGGTG
     HR G nucl.  ............................................................
     M2 G nucl.  TATATGATTGGACATGGTATGTTGGACTCCGATCTTCATCTTAGCTCAAAGGCTCAGGTG
     M3 G nucl.  TATATGATTGGACATGGTATGTTGGACTCCGATCTTCATCTTAGCTCAAAGGCTCAGGTG
     M4 G nucl.  TATATGATTGGACATGGTATGTTGGACTCCGATCTTCATCTTAGCTCAAAGGCTCAGGTG 1261                                                       1320
GenBank G nucl.  TTCGAACATCCTCACATTCAAGACGCTGCTTCGCAACTTCCTGATGATGAGAGTTTATTT
     HR G nucl.  ............................................................
     M2 G nucl.  TTTGAACATCCTCACATTCAAGACGCTGCTTCGCAGCTTCCTGATGATGAGACTTTATTT
     M3 G nucl.  TTTGAACATCCTCACATTCAAGACGCTGHTGCGCAGCTTCCTGATGATGAGACTTTATTT
     M4 G nucl.  TTTGAACATCCTCACATTCAAGACGCTGCTTCGCAGCTTCCTGATGATGAGACTTTATTT
```

FIGURE 20-3

```
                    1321                                                        1380
GenBank G nucl.     TTTGGTGATACTGGGCTATCCAAAAATCCAATCGAGCTTGTAGAAGGTTGGTTCAGTAGT
    HR  G nucl.     ............................................................
    M2  G nucl.     TTTGGTGATACTGGGCTATCCAAAAATCCAATCGAGTTTGTAGAAGGTTGGTTCAGTAGT
    M3  G nucl.     TTTGGTGATACTGGGCTATCCAAAAATCCAATCGAGTTTGTAGAAGGTTGGTTCAGTAGT
    M4  G nucl.     TTTGGTGATACTGGGCTATCCAAAAATCCAATCGAGTTTGTAGAAGGTTGGTTCAGTAGT 1381                                                        1440
GenBank G nucl.     TGGAAAAGCTCTATTGCCTCTTTTTTCTTTATCATAGGGTTAATCATTGGACTATTCTTG
    HR  G nucl.     ............................................................
    M2  G nucl.     TGGAAGAGCTCTATTGCCTCTTTTTTCTTTATCATAGGGTTAATCATTGGACTATTCTTG
    M3  G nucl.     TGGAAGAGCTCTATTGCCTCTTTTTTCTTTATCATAGGGTTAATCATTGGACTATTCTTG
    M4  G nucl.     TGGAAGAGCTCTATTGCCTCTTTTTTCTTTATCATAGGGTTAATCATTGGACTATTCTTG 1441                                                        1500
GenBank G nucl.     GTTCTCCGAGTTGGTATCCATCTTTGCATTAAATTAAAGCACACCAAGAAAAGACAGATT
    HR  G nucl.     ............................................................
    M2  G nucl.     GTTCTCCGAGTTGGTATTTATCTTTGCATTAAATTAAAGCACACCAAGAAAAGACAGATT
    M3  G nucl.     GTTCTCCGAGTTGGTATTTATCTTTGCATTAAATTAAAGCACACCAAGAAAAGACAGATT
    M4  G nucl.     GTTCTCCGAGTTGGTATTTATCTTTGCATTAAATTAAAGCACACCAAGAAAAGACAGATT 1501                                    1536
GenBank G nucl.     TATACAGACATAGAGATGAACCGACTTGCAAAGTAA
    HR  G nucl.     ....................................
    M2  G nucl.     TATACAGACATAGAGATGAACCGACTTGGGAAGTAA
    M3  G nucl.     TATACAGACATAGAGATGAACCGACTTGGGAAGTAA
    M4  G nucl.     TATACAGACATAGAGATGAACCGACTTGGGAAGTAA
```

FIGURE 20-4

|  |  | 1 | 60 |
| --- | --- | --- | --- |

```
GenBank G a.a.  MKCLLYLAFLFIGVNCKFTIVFPHNQKGNWKNVPSNYHYCPSSSDLNWHNDLIGTATQVK
     HR G a.a.  MKCLLXLAFLFIGVNCKFTIVFPYNQKGNWKNVPSNYHYCPSSSDLNXHNDLIGTALQVK
     M2 G a.a.  ............................................................
     M3 G a.a.  MKCLLYLAFLFIGVNCKFTIVFPYNRKGNWKNVPSNYHYCPSSSDLNWHNDLIGTALQVK
     M4 G a.a.  MKCLLYLAFLFIGVNCKFTIVFPYNQKGNWKNVPSNYHYCPSSSDLNWHNDLIGTALQVK 61                                                         120
GenBank G a.a.  MPKSHKAIQADGWMCHASKWVTTCDFRWYGPKYITQSIRSFTPSVEQCKESIEQTKQGTW
     HR G a.a.  MPKSHKAIQADGWMCHASKWVTTCDFRWYGPKYITHSIRSFTPSVEQCKESIEQTKQGTW
     M2 G a.a.  ............................................................
     M3 G a.a.  MPKSHKAIQADGWMCHASKWVTTCDFRWYGPKYITHSIRSFTPSVEQCKESIEQTKQGTW
     M4 G a.a.  MPKSHKAIQADGWMCHASKWVTTCDFRWYGPKYITHSIRSFTPSVEQCKESIEQTKQGTW 121                                                        180
GenBank G a.a.  LNPGFPPQSCGYATVTDAEAVIVQVTPHHVLVDEYTGEWVDSQFINGKCSNVICPTVHNS
     HR G a.a.  LNPGFPPQSCGYATVTDAEAAIVQVTPHHVLVDEYTGEWVDSQFINGKCSNDICPTVHNS
     M2 G a.a.  ............................................................
     M3 G a.a.  LNPGFPPQSCGYATVTDAEAAIVQVTPHHVLVDEYTGEWVDSQFINGKCSNDICPTVHNS
     M4 G a.a.  LNPGFPPQSCGYATVTDAEAAIVQVTPHHVLVDEYTGEWVDSQFINGKCSNDICPTVHNS 181                                                        240
GenBank G a.a.  TTWHSDYKVKGLCDSNLISMDITFFSEDGELSSLGKEGTGFRSNYFAYETGGKACKMQYC
     HR G a.a.  TTWHSDYKVKGLCDSNLISMDITFFSEDGELSSLGKEGTGFRSNYFAYETGDKACKMQYC
     M2 G a.a.  ............................................................
     M3 G a.a.  TTWHSDYKVKGLCDSNLISMDITFFSEDGELSSLGKEGTGFRSNYFAYETGDKACKMQYC
     M4 G a.a.  TTWHSDYKVKGLCDSNLISMDITFFSEDGELSSLGKEGTGFRSNYFAYETGDKACKMQYC 241                                                        300
GenBank G a.a.  KHWGVRLPSGVWFEMADKDLFAAARFPECPEGSSISAPSQTSVDVSLIQDVERILDYSLC
     HR G a.a.  KRWGVRLPSGVWFEMADKDLFAAARFPECPEGSSISAPSQTSVDVSLIQDVERIL.....
     M2 G a.a.  ...........................PSQTSVDVSLIQDVERILDYSLC
     M3 G a.a.  KHWGVRLPSGVWFEMADKDLFAAARFPECPEGSSISAPSQTSVDVSLIQDVERILDYSLC
     M4 G a.a.  KRWGVRLPSGVWFGMADKDLFAAARFPECPEGSSISAPSQTSVDVSLIQDVERI......

301                                                        360
GenBank G a.a.  QETWSKIRAGLPISPVDLSYLAPKNPGTGPAFTIINGTLKYFETRYIRVDIAAPILSRMV
     HR G a.a.  ............................................................
     M2 G a.a.  QETWSKIRAGLPISPVDLSYLAPKNPGTGPVFTIINGTLKYFETRYIRVDIAAPILSRMV
     M3 G a.a.  QETWSKIRAGLPISPVDLSYLAPKNPGTGPAFTIINGTLKYFETRYIRVDIAAPILSRMV
     M4 G a.a.  ..............................................YFETRYIRVDIAAPILSRMV 361                                                        420
GenBank G a.a.  GMISGTTTERELWDDWAPYEDVEIGPNGVLRTSSGYKFPLYMIGHGMLDSDLHLSSKAQV
     HR G a.a.  ............................................................
     M2 G a.a.  GMISGTTTERELWDDWAPYEDVEIGPNGVLRTSSGYKFPLYMIGHGMLDSDLHLSSKAQV
     M3 G a.a.  GMISGTTTERELWDDWAPYEDVEIGPNGVLRTSSGYKFPLYMIGHGMLDSDLHLSSKAQV
     M4 G a.a.  GMISGTTTERELWDDWAPYEDVEIGPNGVLRTSSGYKFPLYMIGHGMLDSDLHLSSKAQV
```

FIGURE 21-1

```
                 421                                                        480
GenBank G a.a.   FEHPHIQDAASQLPDDESLFFGDTGLSKNPIELVEGWFSSWKSSIASFFFIIGLIIGLFL
     HR G a.a.   ............................................................
     M2 G a.a.   FEHPHIQDAASQLPDDETLFFGDTGLSKNPIEFVEGWFSSWKSSIASFFFIIGLIIGLFL
     M3 G a.a.   FEHPHIQDAXAQLPDDETLFFGDTGLSKNPIEFVEGWFSSWKSSIASFFFIIGLIIGLFL
     M4 G a.a.   FEHPHIQDAASQLPDDETLFFGDTGLSKNPIEFVEGWFSSWKSSIASFFFIIGLIIGLFL 481                              512
GenBank G a.a.   VLRVGIHLCIKLKHTKKRQIYTDIEMNRLGK
     HR G a.a.   ...............................
     M2 G a.a.   VLRVGIYLCIKLKHTKKRQIYTDIEMNRLGK
     M3 G a.a.   VLRVGIYLCIKLKHTKKRQIYTDIEMNRLGK
     M4 G a.a.   VLRVGIYLCIKLKHTKKRQIYTDIEMNRLGK
```

FIGURE 21-2

```
              1                                                            60
GenBank L nucl.  ATGGAAGTCCACGATTTTGAGACCGACGAGTTCAATGATTTCAATGAAGATGACTATGCC
HR L nucl.       ............................................................
M2 L nucl.       ATGGAAGTCCACGATTTTGAGACCGACGAGTTCAATGATTTCAATGAAGATGACTATGCC
M4 L nucl.       ATGGAAGTCCACGATTTTGAGACCGACGAGTTCAATGATTTCAATGAAGATGACTATGCC 61                                                           120
GenBank L nucl.  ACAAGAGAATTCCTGAATCCCGATGAGCGCATGACGTACTTGAATCATGCTGATTACAAT
HR L nucl.       ............................................................
M2 L nucl.       ACAAGAGAATTCCTGAATCCCGATGAGCGCATGACGTACTTGAATCATGCTGATTACAAT
M4 L nucl.       ACAAGAGAATTCCTGAATCCCGATGAGCGCATGACGTACTTGAATCATGCTGATTACAAT 121                                                          180
GenBank L nucl.  TTGAATTCTCCTCTAATTAGTGATGATATTGACAATTTGATCAGGAAATTCAATTCTCTT
HR L nucl.       ............................................................
M2 L nucl.       TTGAATTCTCCTCTAATTAGTGATGATATTGACAATTTGATCAGGAAATTCAATTCTCTT
M4 L nucl.       TTGAATTCTCCTCTAATTAGTGATGATATTGACAATTTGATCAGGAAATTCAATTCTCTT 181                                                          240
GenBank L nucl.  CCGATTCCCTCGATGTGGGATAGTAAGAACTGGGATGGAGTTCTTGAGATGTTAACATCA
HR L nucl.       ............................................................
M2 L nucl.       CCGATTCCCTCGATGTGGGATAGTAAGAACTGGGATGGAGTTCTTGAGATGTTAACATCA
M4 L nucl.       CCGATTCCCTCGATGTGGGATAGTAAGAACTGGGATGGAGTTCTTGAGATGTTAACATCA 241                                                          300
GenBank L nucl.  TGTCAAGCCAATCCCATCTCAACATCTCAGATGCATAAATGGATGGGAAGTTGGTTAATG
HR L nucl.       ............................................................
M2 L nucl.       TGTCAAGCCAATCCCATCTCAACATCTCAGATGCATAAATGGATGGGAAGTTGGTTAATG
M4 L nucl.       TGTCAAGCCAATCCCATCTCAACATCTCAGATGCATAAATGGATGGGAAGTTGGTTAATG 301                                                          360
GenBank L nucl.  TCTGATAATCATGATGCCAGTCAAGGGTATAGTTTTTTACATGAAGTGGACAAAGAGGCA
HR L nucl.       ............................................................
M2 L nucl.       TCTGATAATCATGATGCCAGTCAAGGGTATAGTTTTTTACATGAAGTG............
M4 L nucl.       TCTGATAATCATGATGCCAGTCAAGGGTATAGTTTTTTACATGAAGTGGACAAAGAGGCA 361                                                          420
GenBank L nucl.  GAAATAACATTTGACGTGGTGGAGACCTTCATCCGCGGCTGGGGCAACAAACCAATTGAA
HR L nucl.       ............................................................
M2 L nucl.       ............................................................
M4 L nucl.       GAAATAACATTTGACGTGGTGGAGACCTTCATCCGCGGCTGGGGCAACAAACCAATTGAA 421                                                          480
GenBank L nucl.  TACATCAAAAAGGAAAGATGGACTGACTCATTCAAAATTCTCGCTTATTTGTGTCAAAAG
HR L nucl.       ............................................................
M2 L nucl.       ............................................................
M4 L nucl.       TACATCAAAAAGGAAAGATGGACTGACTCATTCAAAATTCTCGCTTATTTGTGTCAAAAG 481                                                          540
GenBank L nucl.  TTTTTGGACTTACACAAGTTGACATTAATCTTAAATGCTGTCTCTGAGGTGGAATTGCTC
HR L nucl.       ............................................................
M2 L nucl.       ............................................................
M4 L nucl.       TTTTTGGACTTACACAAGTTGACATTAATCTTAAATGCTGTCTCTGAGGTGGAATTGCTC
```

FIGURE 22-1

```
                    541                                                         600
GenBank L nucl.     AACTTGGCGAGGACTTTCAAAGGCAAAGTCAGAAGAAGTTCTCATGGAACGAACATATGC
HR L nucl.          ............................................................
M2 L nucl.          ............................................................
M4 L nucl.          AACTTGGCGAGGACTTTCAAAGGCAAAGTCAGAAGAAGTTCTCATGGAACGAACATATGC 601                                                         660
GenBank L nucl.     AGGATTAGGGTTCCCAGCTTGGGTCCTACTTTTATTTCAGAAGGATGGGCTTACTTCAAG
HR L nucl.          ............................................................
M2 L nucl.          ............................................................
M4 L nucl.          AGGCTTAGGGTTCCCAGCTTGGGTCCTACTTTTATTTCAGAAGGATGGGCTTACTTCAAG 661                                                         720
GenBank L nucl.     AAACTTGATATTCTAATGGACCGAAACTTTCTGTTAATGGTCAAAGATGTGATTATAGGG
HR L nucl.          ............................................................
M2 L nucl.          ............................................................
M4 L nucl.          AAACTTGATATTCTAATGGACCGAAACTTTCTGTTAATGGTCAAAGATGTGATTATAGGG 721                                                         780
GenBank L nucl.     AGGATGCAAACGGTGCTATCCATGGTATGTAGAATAGACAACCTGTTCTCAGAGCAAGAC
HR L nucl.          ............................................................
M2 L nucl.          ............................................................
M4 L nucl.          AGGATGCAAACGGTGCTATCCATGGTATGTAGAATAGACAACCTGTTCTCAGAGCAAGAC 781                                                         840
GenBank L nucl.     ATCTTCTCCCTTCTAAATATCTACAGAATTGGAGATAAAATTGTGGAGAGGCAGGGAAAT
HR L nucl.          ............................................................
M2 L nucl.          ............................................................
M4 L nucl.          ATCTTCTCCCTTCTAAATATCTACAGAATTGGAGATAAAATTGTGGAGAGGCAGGGAAAT 841                                                         900
GenBank L nucl.     TTTTCTTATGACTTGATTAAAATGGTGGAACCGATATGCAACTTGAAGCTGATGAAATTA
HR L nucl.          ............................................................
M2 L nucl.          ............................................................
M4 L nucl.          TTTTCTTATGACTTGATTAAAATGGTGGAACCGATATGCAACTTGAGGCTGATGAAATTA 901                                                         960
GenBank L nucl.     GCAAGAGAATCAAGGCCTTTAGTCCCACAATTCCCTCATTTTGAAAATCATATCAAGACT
HR L nucl.          ............................................................
M2 L nucl.          ............................................................
M4 L nucl.          GCAAGAGAATCAAGGCCTTTAGTCCCACAATTCCCTCATTTTGAAAATCATATCAAGACT 961                                                         1020
GenBank L nucl.     TCTGTTGATGAAGGGGCAAAAATTGACCGAGGTATAAGATTCCTCCATGATCAGATAATG
HR L nucl.          ............................................................
M2 L nucl.          ............................................................
M4 L nucl.          TCTGTTGATGAAGGGGCAAAAATTGACCGAGGTATAAGATTCCTCCATGATCAGATAATG
```

FIGURE 22-2

```
                1021                                                       1080
GenBank L nucl. AGTGTGAAAACAGTGGATCTCACACTGGTGATTTATGGATCGTTCAGACATTGGGGTCAT
HR L nucl.      ........................................CATTGGGGTCAT
M2 L nucl.      ............................................................
M4 L nucl.      AGTGTGAAAACAGTGGATCTCACACTGGTGATTTATGGATCGTTCAGACATTGGGGTCAT 1081                                                       1140
GenBank L nucl. CCTTTTATAGATTATTACACTGGACTAGAAAAATTACATTCCCAAGTAACCATGAAGAAA
HR L nucl.      CCTTTTATAGATTATTACGCTGGWCTAGAAAAATTACATTCCCAAGTWACCATKAAGAAA
M2 L nucl.      ............................................................
M4 L nucl.      CCTTTTATAGATTATTACGCTGGACTAGAAAAATTACATTCCCAAGTAACCATGAAGAAA 1141                                                       1200
GenBank L nucl. GATATTGATGTGTCATATGCAAAAGCACTTGCAAGTGATTTAGCTCGGATTGTTCTATTT
HR L nucl.      GATATTGATGTGTCATATGCRAAAGCACTTGCAAGTGATTTAGCTCGGATTGTTCTATTT
M2 L nucl.      ............................................................
M4 L nucl.      GATATTGATGTGTCATATGCAAAAGCACTTGCAAGTGATTTAGCTCGGATTGTTCTATTT 1201                                                       1260
GenBank L nucl. CAACAGTTCAATGATCATAAAAAGTGGTTCGTGAATGGAGACTTGCTCCCTCATGATCAT
HR L nucl.      CAACAGTTCAATGATCATAMAAAGTGGTTCGTGAATGGAGACTTGCTCCCTCATGATCAT
M2 L nucl.      ............................................................
M4 L nucl.      CAACAGTTCAATGATCATAAAAAGTGGTTCGTGAATGGAGACTTGCTCCCTCATGATCAT 1261                                                       1320
GenBank L nucl. CCCTTTAAAAGTCATGTTAAAGAAAATACATGGCCCACAGCTGCTCAAGTTCAAGATTTT
HR L nucl.      CCCTTTAAAAGTCATGTTAAAGAAAATACATGGCCCACAGCTGCTCAAGTTCAAGATTTT
M2 L nucl.      ............................................................
M4 L nucl.      CCCTTTAAAAGTCATGTTAAAGAAAATACATGGCCCACAGCTGCTCAAGTTCAAGATTTT 1321                                                       1380
GenBank L nucl. GGAGATAAATGGCATGAACTTCCGCTGATTAAATGTTTTGAAATACCCGACTTACTAGAC
HR L nucl.      GGAGATAAATGGCATGAACTTCCGCTGATTAAATGTTTTGAAATACCCGACTTACTAGAC
M2 L nucl.      ............................................................
M4 L nucl.      GGAGATAAATGGCATGAACTTCCGCTGATTAAATGTTTTGAAATACCCGACTTACTAGAC 1381                                                       1440
GenBank L nucl. CCATCGATAATATACTCTGACAAAAGTCATTCAATGAATAGGTCAGAGGTGTTGAAACAT
HR L nucl.      CCATCGATAATATACTCTGACAAAAGTCATTCAATGAATAGGTCAGAGGTGTTGAAACAT
M2 L nucl.      ............................................................
M4 L nucl.      CCATCGATAATATACTCTGACAAAAGTCATTCAATGAATAGGTCAGAGGTGTTGAAACAT 1441                                                       1500
GenBank L nucl. GTCCGAATGAATCCGAACACTCCTATCCCTAGTAAAAAGGTGTTGCAGACTATGTTGGAC
HR L nucl.      GTCCGAATGAATCCGAACACTCCTATCCCTAGTAAAAAGGTGTTGCAGACTATGTTGGAC
M2 L nucl.      ............................................................
M4 L nucl.      GTCCGAATGAATCCGAACACTCCTATCCCTAGTAAAAAGGTGTTGCAGACTATGTTGGAC
```

FIGURE 22-3

```
                          1501                                                        1560
GenBank L nucl.   ACAAAGGCTACCAATTGGAAAGAATTTCTTAAAGAGATTGATGAGAAGGGCTTAGATGAT
HR L nucl.        ACAAAGGCTACCAATTGGAAAGAATTTCTTAAAGAGATTGATGAGAAGGGCTTAGATGAT
M2 L nucl.        ............................................................
M4 L nucl.        ACAAAGGCTACCAATTGGAAAGAATTTCTTAAAGAGATTGATGAGAAGGGCTTAGATGAT 1561                                                        1620
GenBank L nucl.   GATGATCTAATTATTGGTCTTAAAGGAAAGGAGAGGGAACTGAAGTTGGCAGGTAGATTT
HR L nucl.        GATGATCTAATTATTGGTCTTAAAGGAAAGGAGAGGGAACTGAAGTTGGCAGGTAGATTT
M2 L nucl.        ............................................................
M4 L nucl.        GATGATCTAATTATTGGTCTTAAAGGAAAGGAGAGGGAACTGAAGTTGGCAGGTAGATTT 1621                                                        1680
GenBank L nucl.   TTCTCCCTAATGTCTTGGAAATTGCGAGAATACTTTGTAATTACCGAATATTTGATAAAG
HR L nucl.        TTCTCCCTAATGTCTTGGAAATTGCGAGAATACTTTGTAATTACCGAATATTTGATAAAG
M2 L nucl.        ............................................................
M4 L nucl.        TTCTCCCTAATGTCTTGGAAATTGCGAGAATACTTTGTAATTACCGAATATTTGATAAAG 1681                                                        1740
GenBank L nucl.   ACTCATTTCGTCCCTATGTTTAAAGGCCTGACAATGGCGGACGATCTAACTGCAGTCATT
HR L nucl.        ACTCATTTCGTCCCTATGTTTAAAGGCCTGACAATGGCGGACGATCTAACTGCAGTCATT
M2 L nucl.        ............................................................
M4 L nucl.        ACTCATTTCGTCCCTATGTTTAAAGGCCTGACAATGGCGGACGATCTAACTGCAGTCATT 1741                                                        1800
GenBank L nucl.   AAAAAGATGTTAGATTCCTCATCCGGCCAAGGATTGAAGTCATATGAGGCAATTTGCATA
HR L nucl.        AAAAAGATGTTAGATTCCTCATCCGGCCAAGGATTGAAGTCATATGAGGCAATTTGCATA
M2 L nucl.        ............................................................
M4 L nucl.        AAAAAGATGTTAGATTCCTCATCCGGCCAAGGATTGAAGTCATATGAGGCAATTTGCATA 1801                                                        1860
GenBank L nucl.   GCCAATCACATTGATTACGAAAAATGGAATAACCACCAAAGGAAGTTATCAAACGGCCCA
HR L nucl.        GCCAATCACATTGATTACGAAAAATGGAATAACCACCAAAGGAAGTTATCAAACGGCCCA
M2 L nucl.        ............................................................
M4 L nucl.        GCCAATCACATTGATTACGAAAAATGGAATAACCACCAAAGGAAGTTATCAAACGGCCCA 1861                                                        1920
GenBank L nucl.   GTGTTCCGAGTTATGGGCCAGTTCTTAGGTTATCCATCCTTAATCGAGAGAACTCATGAA
HR L nucl.        GTGTTCCGAGTTATGGGCCAGTTCTTAGGTTATCCATCCTTAATCGAGAGAACTCATGAA
M2 L nucl.        ............................................................
M4 L nucl.        GTGTTCCGAGTTATGGGCCAGTTCTTAGGTTATCCATCCTTAATCGAGAGAACTCATGAA 1921                                                        1980
GenBank L nucl.   TTTTTTGAGAAAAGTCTTATATACTACAATGGAAGACCAGACTTGATGCGTGTTCACAAC
HR L nucl.        TTTTTTGAGAAAAGTCTTATATACTACAATGGAAGACCAGACTTGATGCGTGTTCACAAC
M2 L nucl.        ............................................................
M4 L nucl.        TTTTTTGAGAAAAGTCTTATATACTACAATGGAAGACCAGACTTGATGCGTGTTCACAAC 1981                                                        2040
GenBank L nucl.   AACACACTGATCAATTCAACCTCCCAACGAGTTTGTTGGCAAGGACAAGAGGGTGGACTG
HR L nucl.        AACACACTGATCAATTCAACCTCCCAACGAGTTTGTTGGCAAGGACAAGAGGGTGGACTG
M2 L nucl.        ............................................................
M4 L nucl.        AACACACTGATCAATTCAACCTCCCAACGAGTTTGTTGGCAAGGACAAGAGGGTGGACTG
```

FIGURE 22-4

```
                    2041                                                    2100
GenBank L nucl.     GAAGGTCTACGGCAAAAAGGATGGACTATCCTCAATCTACTGGTTATTCAAAGAGAGGCT
HR L nucl.          GAAGGTCTACGGCAAAAAGGATGGAGTATCCTCAATCTACTGGTTATTCAAAGAGAGGCT
M2 L nucl.          ............................................................
M4 L nucl.          GAAGGTCTACGGCAAAAAGGATGGAGTATCCTCAATCTACTGGTTATTCAAAGAGAGGCT 2101                                                    2160
GenBank L nucl.     AAAATCAGAAACACTGCTGTCAAAGTCTTGGCACAAGGTGATAATCAAGTTATTTGCACA
HR L nucl.          AAAATCAGAAACACTGCTGTCAAAGTCTTGGCACAAGGTGATAATCAAGTTATTTGCACA
M2 L nucl.          ............................................................
M4 L nucl.          AAAATCAGAAACACTGCTGTCAAAGTCTTGGCACAAGGTGATAATCAAGTTATTTGCACA 2161                                                    2220
GenBank L nucl.     CAGTATAAAACGAAGAAATCGAGAAACGTTGTAGAATTACAGGGTGCTCTCAATCAAATG
HR L nucl.          CAGTATAAAACGAAGAAATCGAGAAACGTTGTAGAATTACAGGGTGCTCTCAATCAAATG
M2 L nucl.          ............................................................
M4 L nucl.          CAGTATAAAACGAAGAAATCGAGAAACGTTGTAGAATTACAGGGTGCTCTCAATCAAATG 2221                                                    2280
GenBank L nucl.     GTTTCTAATAATGAGAAAATTATGACTGCAATCAAAATAGGGACAGGGAAGTTAGGACTT
HR L nucl.          GTTTCTAATAATGAGAAAATTATGACTGCAATCAAAATAGGGACAGGGAAGTTAGGACTT
M2 L nucl.          ............................................................
M4 L nucl.          GTTTCTAATAATGAGAAAATTATGACTGCAATCAAAATAGGGACAGGGAAGTTAGGACTT 2281                                                    2340
GenBank L nucl.     TTGATAAATGACGATGAGACTATGCAATCTGCAGATTACTTGAATTATGGAAAAATACCG
HR L nucl.          TTGATAAATGACGATGAGACTATGCAATCTGCAGATTACTTGAATTATGGAAAAATACCG
M2 L nucl.          ............................................................
M4 L nucl.          TTGATAAATGACGATGAGACTATGCAATCTGCAGATTACTTGAATTATGGAAAAATACCA 2341                                                    2400
GenBank L nucl.     ATTTTCCGTGGAGTGATTAGAGGGTTAGAGACCAAGAGATGGTCACGAGTGACTTGTGTC
HR L nucl.          ATTTTCCGTGGAGTGATTAGAGGGTTAGAGACCAAGAGATGGTCACGAGTGACTTGTGTC
M2 L nucl.          ............................................................
M4 L nucl.          ATTTTCCGTGGAGTGATTAGAGGGTTAGAGACCAAGAGATGGTCACGAGTGACTTGTGTC 2401                                                    2460
GenBank L nucl.     ACCAATGACCAAATACCCACTTGTGCTAATATAATGAGCTCAGTTTCCACAAATGCTCTC
HR L nucl.          ACCAATGACCAAATACCCACTTGTGCTAATATAATGAGCTCAGTTTCCACAAATGCTCTC
M2 L nucl.          ............................................................
M4 L nucl.          ACCAATGACCAAATACCCACTTGTGCTAATATAATGAGCTCAGTTTCCACAAATGCTCTC 2461                                                    2520
GenBank L nucl.     ACCGTAGCTCATTTTGCTGAGAACCCAATCAATGCCATGATACAGTACAATTATTTTGGG
HR L nucl.          ACCGTAGCTCATTTTGCTGAGAACCCAATCAATGCCATGATACAGTACAATTATTTTGGG
M2 L nucl.          ............................................................
M4 L nucl.          ACCGTAGCTCATTTTGCTGAGAACCCAATCAATGCCATGATACAGTACAATTATTTTGGG 2521                                                    2580
GenBank L nucl.     ACATTTGCTAGACTCTTGTTGATGATGCATGATCCTGCTCTTCGTCAATCATTGTATGAA
HR L nucl.          ACATTTGCTAGACTCTTGTTGATGATGCATGATCCTGCTCTTCGTCAATCATTGTATGAA
M2 L nucl.          ............................................................
M4 L nucl.          ACATTTGCTAGACTCTTGTTGATGATGCATGATCCTGCTCTTCGTCAATCATTGTATGAA
```

FIGURE 22-5

```
                       2581                                                   2640
GenBank L nucl.        GTTCAAGATAAGATACCGGGCTTGCACAGTTCTACTTTCAAATACGCCATGTTGTATTTG
HR L nucl.             GTTCAAGATAAGATACCGGGCTTGCACAGTTCTACTTTCAAATACGCCATGTTGTATTTG
M2 L nucl.             ............................................................
M4 L nucl.             GTTCAAGATAAGATACCGGGCTTGCACAGTTCTACTTTCAAATACGCCATGTTGTATTTG 2641                                                   2700
GenBank L nucl.        GACCCTTCCATTGGAGGAGTGTCGGGCATGTCTTTGTCCAGGTTTTTGATTAGAGCCTTC
HR L nucl.             GACCCTTCCATTGGAGGAGTGTCGGGCATGTCTTTGTCCAGGTTTTTGATTAGAGCCTTC
M2 L nucl.             ............................................................
M4 L nucl.             GACCCTTCCATTGGAGGAGTGTCGGGCATGTCTTTGTCCAGGTTTTTGATTAGAGCCTTC 2701                                                   2760
GenBank L nucl.        CCAGATCCCGTAACAGAAAGTCTCTCATTCTGGAGATTCATCCATGTACATGCTCGAAGT
HR L nucl.             CCAGATCCCGTAACAGAAAGTCTCTCATTCTGGAGATTCATCCATGTACATGCTCGAAGT
M2 L nucl.             ............................................................
M4 L nucl.             CCAGATCCCGTAACAGAAAGTCTCTCATTCTGGAGATTCATCCATGTACATGCTCGAAGT 2761                                                   2820
GenBank L nucl.        GAGCATCTGAAGGAGATGAGTGCAGTATTTGGAAACCCCGAGATAGCCAAGTTTCGAATA
HR L nucl.             GAGCATCTGAAGGAGATGAGTGCAGTATTTGGAAACCCCGAGATAGCCAAGTTTCGAATA
M2 L nucl.             ............................................................
M4 L nucl.             GAGCATCTGAAGGAGATGAGTGCAGTATTTGGAAACCCCGAGATAGCCAAGTTTCGAATA 2821                                                   2880
GenBank L nucl.        ACTCACATAGACAAGCTAGTAGAAGATCCAACCTCTCTGAACATCGCTATGGGAATGAGT
HR L nucl.             ACTCACATAGACAAGCTAGTAGAAGATCCAACCTCTCTGAACATCGCTATGGGAATGAGT
M2 L nucl.             ............................................................
M4 L nucl.             ACTCACATAGACAAGCTAGTAGAAGATCCAACCTCTCTGAACATCGCTATGGGAATGAGT 2881                                                   2940
GenBank L nucl.        CCAGCGAACTTGTTAAAGACTGAGGTTAAAAAATGCTTAATCGAATCAAGACAAACCATC
HR L nucl.             CCAGCGAACTTGTTAAAGACTGAGGTTAAAAAATGCTTAATCGAATCAAGACAAACCATC
M2 L nucl.             ............................................................
M4 L nucl.             CCAGCGAACTTGTTAAAGACTGAGGTTAAAAAATGCTTAATCGAATCAAGACAAACCATC 2941                                                   3000
GenBank L nucl.        AGGAACCAGGTGATTAAGGATGCAACCATATATTTGTATCATGAAGAGGATCGGCTCAGA
HR L nucl.             AGGAACCAGGTGATTAAGGATGCAACCATATATTTGTATCATGAAGAGGATCGGCTCAGA
M2 L nucl.             ............................................................
M4 L nucl.             AGGAACCAGGTGATTAAGGATGCAACCATATATTTGTATCATGAAGAGGATCGGCTCAGA 3001                                                   3060
GenBank L nucl.        AGTTTCTTATGGTCAATAAATCCTCTGTTCCCTAGATTTTTAAGTGAATTCAAATCAGGC
HR L nucl.             AGTTTCTTATGGTCAATAAATCCTCTGTTCCCTAGATTTTTAAGTGAATTCAAATCAGGC
M2 L nucl.             ............................................................
M4 L nucl.             AGTTTCTTATGGTCAATAAATCCTCTGTTCCCTAGATTTTTAAGTGAATTCAAATCAGGC 3061                                                   3120
GenBank L nucl.        ACTTTTTTGGGAGTCGCAGACGGGCTCATCAGTCTATTTCAAAATTCTCGTACTATTCGG
HR L nucl.             ACTTTTTTGGGAGTCGCAGACGGGCTCATCAGTCTATTTCAAAATTCTCGTACTATTCGG
M2 L nucl.             ............................................................
M4 L nucl.             ACTTTTTTGGGAGTCGCAGACGGGCTCATCAGTCTATTTCAAAATTCTCGTACTATTCGG
```

FIGURE 22-6

```
                 3121                                                        3180
GenBank L nucl.  AACTCCTTTAAGAAAAAGTATCATAGGGAATTGGATGATTTGATTGTGAGGAGTGAGGTA
HR L nucl.       AACTCCTTTAAGAAAAAGTATCATAGGGAATTGGATGATTTGATTGTGAGGAGTGAGGTA
M2 L nucl.       ............................................................
M4 L nucl.       AACTCCTTTAAGAAAAAGTATCATAGGGAATTGGATGATTTGATTGTGAGGAGTGAGGTA 3181                                                        3240
GenBank L nucl.  TCCTCTTTGACACATTTAGGGAAACTTCATTTGAGAAGGGGATCATGTAAAATGTGGACA
HR L nucl.       TCCTCTTTGACACATTTAGGGAAACTTCATTTGAGAAGGGGATCATGTAAAATGTGGACA
M2 L nucl.       ............................................................
M4 L nucl.       TCCTCTTTGACACATTTAGGGAAACTTCATTTGAGAAGGGGATCATGTAAAATGTGGACA 3241                                                        3300
GenBank L nucl.  TGTTCAGCTACTCATGCTGACACATTAAGATACAAATCCTGGGGCCGTACAGTTATTGGG
HR L nucl.       TGTTCAGCTACTCATGCTGACACATTAAGATACAAATCCTGGGGCCGTACAGTTATTGGG
M2 L nucl.       ............................................................
M4 L nucl.       TGTTCAGCTACTCATGCTGACACATTAAGATACAAATCCTGGGGCCGTACAGTTATTGGG 3301                                                        3360
GenBank L nucl.  ACAACTGTACCCCATCCATTAGAAATGTTGGGTCCACAACATCGAAAAGAGACTCCTTGT
HR L nucl.       ACAACTGTACCCCATCCATTAGAAATGTTGGGTCCACAACATCGAAAAGAGACTCCTTGT
M2 L nucl.       ............................................................
M4 L nucl.       ACAACTGTACCCCATCCATTAGAAATGTTGGGTCCACAACATCGAAAAGAGACTCCTTGT 3361                                                        3420
GenBank L nucl.  GCACCATGTAACACATCAGGGTTCAATTATGTTTCTGTGCATTGTCCAGACGGGATCCAT
HR L nucl.       GCACCATGTAACACATCAGGGTTCAATTATGTTTCTGTGCATTGTCCAGACGGGATCCAT
M2 L nucl.       ............................................................
M4 L nucl.       GCACCATGTAACACATCAGGGTTCAATTATGTTTCTGTGCATTGTCCAGACGGGATCCAT 3421                                                        3480
GenBank L nucl.  GACGTCTTTAGTTCACGGGGACCATTGCCTGCTTATCTAGGGTCTAAAACATCTGAATCT
HR L nucl.       GACGTCTTTAGTTCACGGGGACCATTGCCTGCTTATCTAGGGTCTAAAACATCTGAATCT
M2 L nucl.       ............................................................
M4 L nucl.       GACGTCTTTAGTTCACGGGGACCATTGCCTGCTTATCTAGGGTCTAAAACATCTGAATCT 3481                                                        3540
GenBank L nucl.  ACATCTATTTTGCAGCCTTGGGAAAGGGAAAGCAAAGTCCCACTGATTAAAAGAGCTACA
HR L nucl.       ACATCTATTTTGCAGCCTTGGGAAAGGGAAAGCAAAGTCCCACTGATTAAAAGAGCTACA
M2 L nucl.       ............................................................
M4 L nucl.       ACATCTATTTTGCAGCCTTGGGAAAGGGAAAGCAAAGTCCCACTGATTAAAAGAGCTACA 3541                                                        3600
GenBank L nucl.  CGTCTTAGAGATGCTATCTCTTGGTTTGTTGAACCCGACTCTAAACTAGCAATGACTATA
HR L nucl.       CGTCTTAGAGATGCTATCTCTTGGTTTGTTGAACCCGACTCTAAACTAGCAATGACTATA
M2 L nucl.       ............................................................
M4 L nucl.       CGTCTTAGAGATGCTATCTCTTGGTTTGTTGAACCCGACTCTAAACTAGCAATGACTATA 3601                                                        3660
GenBank L nucl.  CTTTCTAACATCCACTCTTTAACAGGCGAAGAATGGACCAAAAGGCAGCATGGGTTCAAA
HR L nucl.       CTTTCTAACATCCACTCTTTAACAGGCGAAGAATGGACCAAAAGGCAGCATGGGTTCAAA
M2 L nucl.       ............................................................
M4 L nucl.       CTTTCTAACATCCACTCTTTAACAGGCGAAGAATGGACCAAAAGGCAGCATGGGTTCAAA
```

FIGURE 22-7

```
                    3661                                                        3720
GenBank L nucl.     AGAACAGGGTCTGCCCTTCATAGGTTTTCGACATCTCGGATGAGCCATGGTGGGTTCGCA
HR L nucl.          AGAACAGGGTCTGCCCTTCATAGGTTTTCGACATCTCGGATGAGCCATGGTGGGTTCGCA
M2 L nucl.          ............................................................
M4 L nucl.          AGAACAGGGTCTGCCCTTCATAGGTTTTCGACATCTCGGATGAGCCATGGTGGGTTCGCA 3721                                                        3780
GenBank L nucl.     TCTCAGAGCACTGCAGCATTGACCAGGTTGATGGCAACTACAGACACCATGAGGGATCTG
HR L nucl.          TCTCAGAGCACTGCAGCATTGACCAGGTTGATGGCAACTACAGACACCATGAGGGATCTG
M2 L nucl.          ............................................................
M4 L nucl.          TCTCAGAGCACTGCAGCATTGACCAGGTTGATGGCAACTACAGACACCATGAGGGATCTG 3781                                                        3840
GenBank L nucl.     GGAGATCAGAATTTCGACTTTTTATTCCAAGCAACGTTGCTCTATGCTCAAATTACCACC
HR L nucl.          GGAGATCAGAATTTCGACTTTTTATTCCAGGCAACGTTGCTCTATGCTCAGATTACCACC
M2 L nucl.          ............................................................
M4 L nucl.          GGAGATCAGAATTTCGACTTTTTATTCCANGCAACGTTGCTCTATGCTCANATTACCACC 3841                                                        3900
GenBank L nucl.     ACTGTTGCAAGAGACGGATGGATCACCAGTTGTACAGATCATTATCATATTGCCTGTAAG
HR L nucl.          ACTGTTGCAAGAGACGGATGGATCACCAGTTGTACAGATCATTATCATATTGCCTGTAAG
M2 L nucl.          ............................................................
M4 L nucl.          ACTGTTGCAAGAGACGGATGGATCACCAGTTGTACAGATCATTATCATATTGCCTGTAAG 3901                                                        3960
GenBank L nucl.     TCCTGTTTGAGACCCATAGAAGAGATCACCCTGGACTCAAGTATGGACTACACGCCCCCA
HR L nucl.          TCCTGTTTGAGACCCATAGAAGAGATCACCCTGGACTCAAGTATGGACTACACGCCCCCA
M2 L nucl.          ............................................................
M4 L nucl.          TCCTGTTTGAGACCCATAGAAGAGATCACCCTGGACTCAAGTATGGACTACACGCCCCCA 3961                                                        4020
GenBank L nucl.     GATGTATCCCATGTGCTGAAGACATGGAGGAATGGGGAAGGTTCGTGGGGACAAGAGATA
HR L nucl.          GATGTATCCCATGTGCTGAAGACATGGAGGAATGGGGAAGGTTCGTGGGGACAAGAGATA
M2 L nucl.          ............................................................
M4 L nucl.          GATGTATCCCATGTGCTGAAGACATGGAGGAATGGGGAAGGTTCGTGGGGACAAGAGATA 4021                                                        4080
GenBank L nucl.     AAACAGATCTATCCTTTAGAAGGGAATTGGAAGAATTTAGCACCTGCTGAGCAATCCTAT
HR L nucl.          AAACAGATCTATCCTTTAGAAGGGAATTGGAAGAATTTAGCACCTGCTGAGCAATCCTAT
M2 L nucl.          ............................................................
M4 L nucl.          AAACAGATCTATCCTTTAGAAGGGAATTGGAAGAATTTAGCACCTGCTGAGCAATCCTAT 4081                                                        4140
GenBank L nucl.     CAAGTCGGCAGATGTATAGGTTTTCTATATGGAGACTTGGCGTATAGAAAATCTACTCAT
HR L nucl.          CAAGTCGGCAGATGTATAGGTTTTCTATATGGAGACTTGGCGTATAGAAAATCTACTCAT
M2 L nucl.          ............................................................
M4 L nucl.          CAAGTCGGCAGATGTATAGGTTTTCTATATGGAGACTTGGCGTATAGAAAATCTACTCAT 4141                                                        4200
GenBank L nucl.     GCCGAGGACAGTTCTCTATTTCCTCTATCTATACAAGGTCGTATTAGAGGTCGAGGTTTC
HR L nucl.          GCCGAGGACAGTTCTCTATTTCCTCTATCTATACAAGGTCGTATTAGAGGTCGAGGTTTC
M2 L nucl.          ............................................................
M4 L nucl.          GCCGAGGACAGTTCTCTATTTCCTCTATCTATACAAGGTCGTATTAGAGGTCGAGGTTTC
```

FIGURE 22-8

```
                      4201                                                    4260
GenBank L nucl.       TTAAAAGGGTTGCTAGACGGATTAATGAGAGCAAGTTGCTGCCAAGTAATACACCGGAGA
HR L nucl.            TTAAAAGGGTTGCTAGACGGATTAATGAGAGCAAGTTGCTGCCAAGTAATACACCGGAGA
M2 L nucl.            ............................................................
M4 L nucl.            TTAAAAGGGTTGCTAGACGGATTAATGAGAGCAAGTTGCTGCCAAGTAATACACCGGAGA 4261                                                    4320
GenBank L nucl.       AGTCTGGCTCATTTGAAGAGGCCGGCCAACGCAGTGTACGGAGGTTTGATTTACTTGATT
HR L nucl.            AGTCTGGCTCATTTGAAGAGGCCGGCCAACGCAGTGTACGGAGGTTTGATTTACTTGATT
M2 L nucl.            ............................................................
M4 L nucl.            AGTCTGGCTCATTTGAAGAGGCCGGCCAACGCAGTGTACGGAGGTTTGATTTACTTGATT 4321                                                    4380
GenBank L nucl.       GATAAATTGAGTGTATCACCTCCATTCCTTTCTCTTACTAGATCAGGACCTATTAGAGAC
HR L nucl.            GATAAATTGAGTGTATCACCTCCATTCCTTTCTCTTACTAGATCAGGACCTATTAGAGAC
M2 L nucl.            ............................................................
M4 L nucl.            GATAAATTGAGTGTATCACCTCCATTCCTTTCTCTTACTAGATCAGGACCTATTAGAGAC 4381                                                    4440
GenBank L nucl.       GAATTAGAAACGATTCCCCACAAGATCCCAACCTCCTATCCGACAAGCAACCGTGATATG
HR L nucl.            GAATTAGAAACGATTCCCCACAAGATCCCAACCTCCTATCCGACAAGCAACCGTGATATG
M2 L nucl.            ............................................................
M4 L nucl.            GAATTAGAAACGATTCCCCACAAGATCCCAACCTCCTATCCGACAAGCAACCGTGATATG 4441                                                    4500
GenBank L nucl.       GGGGTGATTGTCAGAAATTACTTCAAATACCAATGCCGTCTAATTGAAAAGGGAAAATAC
HR L nucl.            GGGGTGATTGTCAGAAATTACTTCAAATACCAATGCCGTCTAATTGAAAAGGGAAAATAC
M2 L nucl.            ............................................................
M4 L nucl.            GGGGTGATTGTCAGAAATTACTTCAAATACCAATGCCGTCTAATTGAAAAGGGAAAATAC 4501                                                    4560
GenBank L nucl.       AGATCACATTATTCACAATTATGGTTATTCTCAGATGTCTTATCCATAGACTTCATTGGA
HR L nucl.            AGATCACATTATTCACAATTATGGTTATTCTCAGATGTCTTATCCATAGACTTCATTGGA
M2 L nucl.            ............................................................
M4 L nucl.            AGATCACATTATTCACAATTATGGTTATTCTCAGATGTCTTATCCATAGACTTCATTGGA 4561                                                    4620
GenBank L nucl.       CCATTCTCTATTTCCACCACCCTCTTGCAAATCCTATACAAGCCATTTTTATCTGGGAAA
HR L nucl.            CCATTCTCTATTTCCACCACCCTCTTGCAAATCCTATACAAGCCATTTTTATCTGGGAAA
M2 L nucl.            ............................................................
M4 L nucl.            CCATTCTCTATTTCCACCACCCTCTTGCAAATCCTATACAAGCCATTTTTATCTGGGAAA 4621                                                    4680
GenBank L nucl.       GATAAGAATGAGTTGAGAGAGCTGGCAAATCTTTCTTCATTGCTAAGATCAGGAGAGGGG
HR L nucl.            GATAAGAATGAGTTGAGAGAGCTGGCAAATCTTTCTTCATTGCTAAGATCAGGAGAGGGG
M2 L nucl.            ............................................................
M4 L nucl.            GATAAGAATGAGTTGAGAGAGCTGGCAAATCTTTCTTCATTGCTAAGATCAGGAGAGGGG 4681                                                    4740
GenBank L nucl.       TGGGAAGACATACATGTGAAATTCTTCACCAAGGACATATTATTGTGTCCAGAGGAAATC
HR L nucl.            TGGGAAGACATACATGTGAAATTCTTCACCAAGGACATATTATTGTGTCCAGAGGAAATC
M2 L nucl.            ............................................................
M4 L nucl.            TGGGAAGACATACATGTGAAATTCTTCACCAAGGACATATTATTGTGTCCAGAGGAAATC
```

FIGURE 22-9

```
                    4741                                                        4800
GenBank L nucl.     AGACATGCTTGCAAGTTCGGGATTGCTAAGGATAATAATAAAGACATGAGCTATCCCCCT
HR L nucl.          AGACATGCTTGCAAGTTCGGGATTGCTAAGGATAATAATAAAGACATGAGCTATCCCCCT
M2 L nucl.          ............................................................
M4 L nucl.          AGACATGCTTGCAAGTTCGGGATTGCTAAGGATAATAATAAAGACATGAGCTATCCCCCT 4801                                                        4860
GenBank L nucl.     TGGGGAAGGGAATCCAGAGGGACAATTACAACAATCCCTGTTTATTATACGACCACCCCT
HR L nucl.          TGGGGAAGGGAATCCAGAGGGACAATTACAACAATCCCTGTTTATTATACGACCACCCCT
M2 L nucl.          ............................................................
M4 L nucl.          TGGGGAAGGGAATCCAGAGGGACAATTACAACAATCCCTGTTTATTATACGACCACCCCT 4861                                                        4920
GenBank L nucl.     TACCCAAAGATGCTAGAGATGCCTCCAAGAATCCAAAATCCCCTGCTGTCCGGAATCAGG
HR L nucl.          TACCCAAAGATGCTAGAGATGCCTCCAAGAATCCAAAATCCCCTGCTGTCCGGAATCAGG
M2 L nucl.          ............................................................
M4 L nucl.          TACCCAAAGATGCTAGAGATGCCTCCAAGAATCCAAAATCCCCTGCTGTCCGGAATCAGG 4921                                                        4980
GenBank L nucl.     TTGGGCCAATTACCAACTGGCGCTCATTATAAAATTCGGAGTATATTACATGGAATGGGA
HR L nucl.          TTGGGCCAGTTACCAACTGGCGCTCATTATAAAATTCGGAGTATATTACATGGAATGGGA
M2 L nucl.          ............................................................
M4 L nucl.          TTGGGCCAGTTACCAACTGGCGCTCATTATAAAATTCGGAGTATATTACATGGAATGGGA 4981                                                        5040
GenBank L nucl.     ATCCATTACAGGGACTTCTTGAGTTGTGGAGACGGCTCCGGAGGGATGACTGCTGCATTA
HR L nucl.          ATCCATTACAGGGACTTCTTGAGTTGTGGAGACGGCTCCGGAGGGATGACTGCTGCATTA
M2 L nucl.          ............................................................
M4 L nucl.          ATCCATTACAGGGACTTCTTGAGTTGTGGAGACGGCTCCGGAGGGATGACTGCTGCATTA 5041                                                        5100
GenBank L nucl.     CTACGAGAAAATGTGCATAGCAGAGGAATATTCAATAGTCTGTTAGAATTATCAGGGTCA
HR L nucl.          CTACGAGAAAATGTGCATAGCAGAGGAATATTCAATAGTCTGTTAGAATTATCAGGGTCA
M2 L nucl.          ............................................................
M4 L nucl.          CTACGAGAAAATGTGCATAGCAGAGGAATATTCAATAGTCTGTTAGAATTATCAGGGTCA 5101                                                        5160
GenBank L nucl.     GTCATGCGAGGCGCCTCTCCTGAGCCCCCCAGTGCCCTAGAAACTTTAGGAGGAGATAAA
HR L nucl.          GTCATGCGAGGCGCCTCTCCTGAGCCCCCCAGTGCCCTAGAAACTTTAGGAGGAGATAAA
M2 L nucl.          ............................................................
M4 L nucl.          GTCATGCGAGGCGCCTCTCCTGAGCCCCCCAGTGCCCTAGAAACTTTAGGAGGAGATAAA 5161                                                        5220
GenBank L nucl.     TCGAGATGTGTAAATGGTGAAACATGTTGGGAATATCCATCTGACTTATGTGACCCAAGG
HR L nucl.          TCGAGATGTGTAAATGGTGAAACATGTTGGGAATATCCATCTGACTTATGTGACCCAAGG
M2 L nucl.          ............................................................
M4 L nucl.          TCGAGATGTGTAAATGGTGAAACATGTTGGGAATATCCATCTGACTTATGTGACCCAAGG 5221                                                        5280
GenBank L nucl.     ACTTGGGACTATTTCCTCCGACTCAAAGCAGGCTTGGGGCTTCAAATTGATTTAATTGTA
HR L nucl.          ACTTGGGACTATTTCCTCCGACTCAAAGCAGGCTTGGGGCTTCAAATTGATTTAATTGTA
M2 L nucl.          ............................................................
M4 L nucl.          ACTTGGGACTATTTCCTCCGACTCAAAGCAGGCTTGGGGCTTCAAATTGATTTAATTGTA
```

FIGURE 22-10

```
                    5281                                                        5340
GenBank L nucl.     ATGGATATGGAAGTTCGGGATTCTTCTACTAGCCTGAAAATTGAGACGAATGTTAGAAAT
HR L nucl.          ATGGATATGGAAGTTCGGGATTCTTCTACTAGCCTGAAAATTGAGACGAATGTTAGAAAT
M2 L nucl.          ............................................................
M4 L nucl.          ATGGATATGGAAGTTCGGGATTCTTCTACTAGCCTGAAAATTGAGACGAATGTTAGAAAT 5341                                                        5400
GenBank L nucl.     TATGTGCACCGGATTTTGGATGAGCAAGGAGTTTTAATCTACAAGACTTATGGAACATAT
HR L nucl.          TATGTGCACCGGATTTTGGATGAGCAAGGAGTTTTAATCTACAAGACTTATGGAACATAT
M2 L nucl.          ............................................................
M4 L nucl.          TATGTGCACCGGATTTTGGATGAGCAAGGAGTTTTAATCTACAAGACTTATGGAACATAT 5401                                                        5460
GenBank L nucl.     ATTTGTGAGAGCGAAAAGAATGCAGTAACAATCCTTGGTCCCATGTTCAAGACGGTCGAC
HR L nucl.          ATTTGTGAGAGCGAAAAGAATGCAGTAACAATCCTTGGTCCCATGTTCAAGACGGTCGAC
M2 L nucl.          ............................................................
M4 L nucl.          ATTTGTGAGAGCGAAAAGAATGCAGTAACAATCCTTGGTCCCATGTTCAAGACGGTCGAC 5461                                                        5520
GenBank L nucl.     TTAGTTCAAACAGAATTTAGTAGTTCTCAAACGTCTGAAGTATATATGGTATGTAAAGGT
HR L nucl.          TTAGTTCAAACAGAATTTAGTAGTTCTCAAACGTCTGAAGTATATATGGTATGTAAAGGT
M2 L nucl.          ............................................................
M4 L nucl.          TTAGTTCAAACAGAATTTAGTAGTTCTCAAACGTCTGAAGTATATATGGTATGTAAAGGT 5521                                                        5580
GenBank L nucl.     TTGAAGAAATTAATCGATGAACCCAATCCCGATTGGTCTTCCATCAATGAATCCTGGAAA
HR L nucl.          TTGAAGAAATTAATCGATGAACCCAATCCCGATTGGTCTTCCATCAATGAATCCTGGAAA
M2 L nucl.          ............................................................
M4 L nucl.          TTGAAGAAATTAATCGATGAACCCAATCCCGATTGGTCTTCCATCAATGAATCCTGGAAA 5581                                                        5640
GenBank L nucl.     AACCTGTACGCATTCCAGTCATCAGAACAGGAATTTGCCAGAGCAAAGAAGGTTAGTACA
HR L nucl.          AACCTGTACGCATTCCAGTCATCAGAACAGGAATTTGCCAGAGCAAAGAAGGTTAGTACA
M2 L nucl.          ............................................................
M4 L nucl.          AACCTGTACGCATTCCAGTCATCAGAACAGGAATTTGCCAGAGCAAAGAAGGTTAGTACA 5641                                                        5700
GenBank L nucl.     TACTTTACCTTGACAGGTATTCCCTCCCAATTCATTCCTGATCCTTTTGTAAACATTGAG
HR L nucl.          TACTTTACCTTGACAGGTATTCCCTCCCAATTCATTCCTGATCCTTTTGTGAACATTGAG
M2 L nucl.          ............................................................
M4 L nucl.          TACTTTACCTTGACAGGTATTCCCTCCCAATTCATTCCTGATCCTTTTGTGAACATTGAG 5701                                                        5760
GenBank L nucl.     ACTATGCTACAAATATTCGGAGTACCCACGGGTGTGTCTCATGCGGCTGCCTTAAAATCA
HR L nucl.          ACTATGCTACAAATATTCGGAGTACCCACGGGTGTGTCTCATGCGGCTGCCTTAAAATCA
M2 L nucl.          ............................................................
M4 L nucl.          ACTATGCTACAAATATTCGGAGTACCCACGGGTGTGTCTCATGCGGCTGCCTTAAAATCA 5761                                                        5820
GenBank L nucl.     TCTGATAGACCTGCAGATTTATTGACCATTAGCCTTTTTTATATGGCGATTATATCGTAT
HR L nucl.          TCTGATAGACCTGCAGATTTATTGACCATTAGCCTTTTTTATATGGCGATTATATCGTAT
M2 L nucl.          ............................................................
M4 L nucl.          TCTGATAGACCTGCAGATTTATTGACCATTAGCCTTTTTTATATGGCGATTATATCGTAT
```

FIGURE 22-11

```
                     5821                                                        5880
GenBank L nucl.      TATAACATCAATCATATCAGAGTAGGACCGATACCTCCGAACCCCCCATCAGATGGAATT
HR L nucl.           TATAACATCAATCATATCAGAGTAGGACCGATACCTCCGAACCCCCCATCAGATGGAATT
M2 L nucl.           ............................................................
M4 L nucl.           TATAACATCAATCATATCAGAGTAGGACCGATACCTCCGAACCCCCCATCAGATGGAATT 5881                                                        5940
GenBank L nucl.      GCACAAAATGTGGGGATCGCTATAACTGGTATAAGCTTTTGGCTGAGTTTGATGGAGAAA
HR L nucl.           GCACAAAATGTGGGGATCGCTATAACTGGTATAAGCTTTTGGCTGAGTTTGATGGAGAAA
M2 L nucl.           ............................................................
M4 L nucl.           GCACAAAATGTGGGGATCGCTATAACTGGTATAAGCTTTTGGCTGAGTTTGATGGAGAAA 5941                                                        6000
GenBank L nucl.      GACATTCCACTATATCAACAGTGTTTAGCAGTTATCCAGCAATCATTCCCGATTAGGTGG
HR L nucl.           GACATTCCACTATATCAACAGTGTTTAGCAGTTATCCAGCAATCATTCCCGATTAGGTGG
M2 L nucl.           ............................................................
M4 L nucl.           GACATTCCACTATATCAACAGTGTTTAGCAGTTATCCAGCAATCATTCCCGATTAGGTGG 6001                                                        6060
GenBank L nucl.      GAGGCTGTTTCAGTAAAAGGAGGATACAAGCAGAAGTGGAGTACTAGAGGTGATGGGCTC
HR L nucl.           GAGGCTGTTTCAGTAAAAGGAGGATACAAGCAGAAGTGGAGTACTAGAGGTGATGGGCTC
M2 L nucl.           ............................................................
M4 L nucl.           GAGGCTGTTTCAGTAAAAGGAGGATACAAGCAGAAGTGGAGTACTAGAGGTGATGGGCTC 6061                                                        6120
GenBank L nucl.      CCAAAAGATACCCGAACTTCAGACTCCTTGGCCCCAATCGGGAACTGGATCAGATCTCTG
HR L nucl.           CCAAAAGATACCCGAATTTCAGACTCCTTGGCCCCAATCGGGAACTGGATCAGATCTCTG
M2 L nucl.           ............................................................
M4 L nucl.           CCAAAAGATACCCGAATTTCAGACTCCTTGGCCCCAATCGGGAACTGGATCAGATCTCTG 6121                                                        6180
GenBank L nucl.      GAATTGGTCCGAAACCAAGTTCGTCTAAATCCATTCAATGAGATCTTGTTCAATCAGCTA
HR L nucl.           GAATTGGTCCGAAACCAAGTTCGTCTAAATCCATTCAATGAGATCTTGTTCAATCAGCTA
M2 L nucl.           ............................................................
M4 L nucl.           GAATTGGTCCGAAACCAAGTTCGTCTAAATCCATTCAATGAGATCTTGTTCAATCAGCTA 6181                                                        6240
GenBank L nucl.      TGTCGTACAGTGGATAATCATTTGAAATGGTCAAATTTGCGAACAAACACAGGAATGATT
HR L nucl.           TGTCGTACAGTGGATAATCATTTGAAATGGTCAAATTTGCGAAAAAACACAGGAATGATT
M2 L nucl.           ............................................................
M4 L nucl.           TGTCGTACAGTGGATAATCATTTGAAATGGTCAAATTTGCGAAAAAACACAGGAATGATT 6241                                                        6300
GenBank L nucl.      GAATGGATCAATAGACGAATTTCAAAAGAAGACCGGTCTATACTGATGTTGAAGAGTGAC
HR L nucl.           GAATGGATCAATAGACGAATTTCAAAAGAAGACCGGTCTATACTGATGTTGAAGAGTGAC
M2 L nucl.           ............................................................
M4 L nucl.           GAATGGATCAATAGACGAATTTCAAAAGAAGACCGGTCTATACTGATGTTGAAGAGTGAC
```

FIGURE 22-12

```
                   6301                                                  6360
GenBank L nucl.    CTACACGAGGAAAACTCTTGGAGAGATTAA..............................
HR L nucl.         CTACATGAGGAAAACTCTTGGAGAGATTAAAAAATCATGAGGAGACTCCAAACTTTAAGT
M2 L nucl.         ............................................................
M4 L nucl.         CTACATGAGGAAAACTCTTGGAGAGATTAA..............................

6361                          6395
GenBank L nucl.    ...................................
HR L nucl.         ATGAAAAAAACTTTGATCCTTAAGACCCTCTTGTG
M2 L nucl.         ...................................
M4 L nucl.         ...................................
```

FIGURE 22-13

```
                    1                                                           60
GenBank L  a.a.    MEVHDFETDEFNDFNEDDYATREFLNPDERMTYLNHADYNLNSPLISDDIDNLIRKFNSL
HR L a.a.          ............................................................
M4 L a.a.          MEVHDFETDEFNDFNEDDYATREFLNPDERMTYLNHADYNLNSPLISDDIDNLIRKFNSL 61                                                          120
GenBank L  a.a.    PIPSMWDSKNWDGVLEMLTSCQANPISTSQMHKWMGSWLMSDNHDASQGYSFLHEVDKEA
HR L a.a.          ............................................................
M4 L a.a.          PIPSMWDSKNWDGVLEMLTSCQANPISTSQMHKWMGSWLMSDNHDASQGYSFLHEVDKEA 121                                                         180
GenBank L  a.a.    EITFDVVETFIRGWGNKPIEYIKKERWTDSFKILAYLCQKFLDLHKLTLILNAVSEVELL
HR L a.a.          ............................................................
M4 L a.a.          EITFDVVETFIRGWGNKPIEYIKKERWTDSFKILAYLCQKFLDLHKLTLILNAVSEVELL 181                                                         240
GenBank L  a.a.    NLARTFKGKVRRSSHGTNICRIRVPSLGPTFISEGWAYFKKLDILMDRNFLLMVKDVIIG
HR L a.a.          ............................................................
M4 L a.a.          NLARTFKGKVRRSSHGTNICRIRVPSLGPTFISEGWAYFKKLDILMDRNFLLMVKDVIIG 241                                                         300
GenBank L  a.a.    RMQTVLSMVCRIDNLFSEQDIFSLLNIYRIGDKIVERQGNFSYDLIKMVEPICNLKLMKL
HR L a.a.          ............................................................
M4 L a.a.          RMQTVLSMVCRIDNLFSEQDIFSLLNIYRIGDKIVERQGNFSYDLIKMVEPICNLRLMKL 301                                                         360
GenBank L  a.a.    ARESRPLVPQFPHFENHIKTSVDEGAKIDRGIRFLHDQIMSVKTVDLTLVIYGSFRHWGH
HR L a.a.          ........................................................HWGH
M4 L a.a.          ARESRPLVPQFPHFENHIKTSVDEGAKIDRGIRFLHDQIMSVKTVDLTLVIYGSFRHWGH 361                                                         420
GenBank L  a.a.    PFIDYYTGLEKLHSQVTMKKDIDVSYAKALASDLARIVLFQQFNDHKKWFVNGDLLPHDH
HR L a.a.          PFIDYYAGLEKLHSQVTXKKDIDVSYAKALASDLARIVLFQQFNDHXKWFVNGDLLPHDH
M4_L.pro           PFIDYYAGLEKLHSQVTMKKDIDVSYAKALASDLARIVLFQQFNDHKKWFVNGDLLPHDH 421                                                         480
GenBank L  a.a.    PFKSHVKENTWPTAAQVQDFGDKWHELPLIKCFEIPDLLDPSIIYSDKSHSMNRSEVLKH
HR L a.a.          PFKSHVKENTWPTAAQVQDFGDKWHELPLIKCFEIPDLLDPSIIYSDKSHSMNRSEVLKH
M4 L a.a.          PFKSHVKENTWPTAAQVQDFGDKWHELPLIKCFEIPDLLDPSIIYSDKSHSMNRSEVLKH 481                                                         540
GenBank L  a.a.    VRMNPNTPIPSKKVLQTMLDTKATNWKEFLKEIDEKGLDDDDLIIGLKGKERELKLAGRF
HR L a.a.          VRMNPNTPIPSKKVLQTMLDTKATNWKEFLKEIDEKGLDDDDLIIGLKGKERELKLAGRF
M4 L a.a.          VRMNPNTPIPSKKVLQTMLDTKATNWKEFLKEIDEKGLDDDDLIIGLKGKERELKLAGRF 541                                                         600
GenBank L  a.a.    FSLMSWKLREYFVITEYLIKTHFVPMFKGLTMADDLTAVIKKMLDSSSGQGLKSYEAICI
HR L a.a.          FSLMSWKLREYFVITEYLIKTHFVPMFKGLTMADDLTAVIKKMLDSSSGQGLKSYEAICI
M4 L a.a.          FSLMSWKLREYFVITEYLIKTHFVPMFKGLTMADDLTAVIKKMLDSSSGQGLKSYEAICI
```

FIGURE 23-1

```
              601                                                         660
GenBank L a.a. ANHIDYEKWNNHQRKLSNGPVFRVMGQFLGYPSLIERTHEFFEKSLIYYNGRPDLMRVHN
HR L a.a.      ANHIDYEKWNNHQRKLSNGPVFRVMGQFLGYPSLIERTHEFFEKSLIYYNGRPDLMRVHN
M4 L a.a.      ANHIDYEKWNNHQRKLSNGPVFRVMGQFLGYPSLIERTHEFFEKSLIYYNGRPDLMRVHN 661                                                         720
GenBank L a.a. NTLINSTSQRVCWQGQEGGLEGLRQKGWTILNLLVIQREAKIRNTAVKVLAQGDNQVICT
HR L a.a.      NTLINSTSQRVCWQGQEGGLEGLRQKGWSILNLLVIQREAKIRNTAVKVLAQGDNQVICT
M4 L a.a.      NTLINSTSQRVCWQGQEGGLEGLRQKGWSILNLLVIQREAKIRNTAVKVLAQGDNQVICT 721                                                         780
GenBank L a.a. QYKTKKSRNVVELQGALNQMVSNNEKIMTAIKIGTGKLGLLINDDETMQSADYLNYGKIP
HR L a.a.      QYKTKKSRNVVELQGALNQMVSNNEKIMTAIKIGTGKLGLLINDDETMQSADYLNYGKIP
M4 L a.a.      QYKTKKSRNVVELQGALNQMVSNNEKIMTAIKIGTGKLGLLINDDETMQSADYLNYGKIP 781                                                         840
GenBank L a.a. IFRGVIRGLETKRWSRVTCVTNDQIPTCANIMSSVSTNALTVAHFAENPINAMIQYNYFG
HR L a.a.      IFRGVIRGLETKRWSRVTCVTNDQIPTCANIMSSVSTNALTVAHFAENPINAMIQYNYFG
M4 L a.a.      IFRGVIRGLETKRWSRVTCVTNDQIPTCANIMSSVSTNALTVAHFAENPINAMIQYNYFG 841                                                         900
GenBank L a.a. TFARLLLMMHDPALRQSLYEVQDKIPGLHSSTFKYAMLYLDPSIGGVSGMSLSRFLIRAF
HR L a.a.      TFARLLLMMHDPALRQSLYEVQDKIPGLHSSTFKYAMLYLDPSIGGVSGMSLSRFLIRAF
M4 L a.a.      TFARLLLMMHDPALRQSLYEVQDKIPGLHSSTFKYAMLYLDPSIGGVSGMSLSRFLIRAF 901                                                         960
GenBank L a.a. PDPVTESLSFWRFIHVHARSEHLKEMSAVFGNPEIAKFRITHIDKLVEDPTSLNIAMGMS
HR L a.a.      PDPVTESLSFWRFIHVHARSEHLKEMSAVFGNPEIAKFRITHIDKLVEDPTSLNIAMGMS
M4 L a.a.      PDPVTESLSFWRFIHVHARSEHLKEMSAVFGNPEIAKFRITHIDKLVEDPTSLNIAMGMS 961                                                        1020
GenBank L a.a. PANLLKTEVKKCLIESRQTIRNQVIKDATIYLYHEEDRLRSFLWSINPLFPRFLSEFKSG
HR L a.a.      PANLLKTEVKKCLIESRQTIRNQVIKDATIYLYHEEDRLRSFLWSINPLFPRFLSEFKSG
M4 L a.a.      PANLLKTEVKKCLIESRQTIRNQVIKDATIYLYHEEDRLRSFLWSINPLFPRFLSEFKSG 1021                                                       1080
GenBank L a.a. TFLGVADGLISLFQNSRTIRNSFKKKYHRELDDLIVRSEVSSLTHLGKLHLRRGSCKMWT
HR L a.a.      TFLGVADGLISLFQNSRTIRNSFKKKYHRELDDLIVRSEVSSLTHLGKLHLRRGSCKMWT
M4 L a.a.      TFLGVADGLISLFQNSRTIRNSFKKKYHRELDDLIVRSEVSSLTHLGKLHLRRGSCKMWT 1081                                                       1140
GenBank L a.a. CSATHADTLRYKSWGRTVIGTTVPHPLEMLGPQHRKETPCAPCNTSGFNYVSVHCPDGIH
HR L a.a.      CSATHADTLRYKSWGRTVIGTTVPHPLEMLGPQHRKETPCAPCNTSGFNYVSVHCPDGIH
M4 L a.a.      CSATHADTLRYKSWGRTVIGTTVPHPLEMLGPQHRKETPCAPCNTSGFNYVSVHCPDGIH 1141                                                       1200
GenBank L a.a. DVFSSRGPLPAYLGSKTSESTSILQPWERESKVPLIKRATRLRDAISWFVEPDSKLAMTI
HR L a.a.      DVFSSRGPLPAYLGSKTSESTSILQPWERESKVPLIKRATRLRDAISWFVEPDSKLAMTI
M4 L a.a.      DVFSSRGPLPAYLGSKTSESTSILQPWERESKVPLIKRATRLRDAISWFVEPDSKLAMTI
```

FIGURE 23-2

|  | 1201 | 1260 |
|---|---|---|
| GenBank L a.a. | LSNIHSLTGEEWTKRQHGFKRTGSALHRFSTSRMSHGGFASQSTAALTRLMATTDTMRDL | |
| HR L a.a. | LSNIHSLTGEEWTKRQHGFKRTGSALHRFSTSRMSHGGFASQSTAALTRLMATTDTMRDL | |
| M4 L a.a. | LSNIHSLTGEEWTKRQHGFKRTGSALHRFSTSRMSHGGFASQSTAALTRLMATTDTMRDL | |

|  | 1261 | 1320 |
|---|---|---|
| GenBank L a.a. | GDQNFDFLFQATLLYAQITTTVARDGWITSCTDHYHIACKSCLRPIEEITLDSSMDYTPP | |
| HR L a.a. | GDQNFDFLFQATLLYAQITTTVARDGWITSCTDHYHIACKSCLRPIEEITLDSSMDYTPP | |
| M4 L a.a. | GDQNFDFLF[X]ATLLYA[X]ITTTVARDGWITSCTDHYHIACKSCLRPIEEITLDSSMDYTPP | |

|  | 1321 | 1380 |
|---|---|---|
| GenBank L a.a. | DVSHVLKTWRNGEGSWGQEIKQIYPLEGNWKNLAPAEQSYQVGRCIGFLYGDLAYRKSTH | |
| HR L a.a. | DVSHVLKTWRNGEGSWGQEIKQIYPLEGNWKNLAPAEQSYQVGRCIGFLYGDLAYRKSTH | |
| M4 L a.a. | DVSHVLKTWRNGEGSWGQEIKQIYPLEGNWKNLAPAEQSYQVGRCIGFLYGDLAYRKSTH | |

|  | 1381 | 1440 |
|---|---|---|
| GenBank L a.a. | AEDSSLFPLSIQGRIRGRGFLKGLLDGLMRASCCQVIHRRSLAHLKRPANAVYGGLIYLI | |
| HR L a.a. | AEDSSLFPLSIQGRIRGRGFLKGLLDGLMRASCCQVIHRRSLAHLKRPANAVYGGLIYLI | |
| M4 L a.a. | AEDSSLFPLSIQGRIRGRGFLKGLLDGLMRASCCQVIHRRSLAHLKRPANAVYGGLIYLI | |

|  | 1441 | 1500 |
|---|---|---|
| GenBank L a.a. | DKLSVSPPFLSLTRSGPIRDELETIPHKIPTSYPTSNRDMGVIVRNYFKYQCRLIEKGKY | |
| HR L a.a. | DKLSVSPPFLSLTRSGPIRDELETIPHKIPTSYPTSNRDMGVIVRNYFKYQCRLIEKGKY | |
| M4 L a.a. | DKLSVSPPFLSLTRSGPIRDELETIPHKIPTSYPTSNRDMGVIVRNYFKYQCRLIEKGKY | |

|  | 1501 | 1560 |
|---|---|---|
| GenBank L a.a. | RSHYSQLWLFSDVLSIDFIGPFSISTTLLQILYKPFLSGKDKNELRELANLSSLLRSGEG | |
| HR L a.a. | RSHYSQLWLFSDVLSIDFIGPFSISTTLLQILYKPFLSGKDKNELRELANLSSLLRSGEG | |
| M4 L a.a. | RSHYSQLWLFSDVLSIDFIGPFSISTTLLQILYKPFLSGKDKNELRELANLSSLLRSGEG | |

|  | 1561 | 1620 |
|---|---|---|
| GenBank L a.a. | WEDIHVKFFTKDILLCPEEIRHACKFGIAKDNNKDMSYPPWGRESRGTITTIPVYYTTTP | |
| HR L a.a. | WEDIHVKFFTKDILLCPEEIRHACKFGIAKDNNKDMSYPPWGRESRGTITTIPVYYTTTP | |
| M4 L a.a. | WEDIHVKFFTKDILLCPEEIRHACKFGIAKDNNKDMSYPPWGRESRGTITTIPVYYTTTP | |

|  | 1621 | 1680 |
|---|---|---|
| GenBank L a.a. | YPKMLEMPPRIQNPLLSGIRLGQLPTGAHYKIRSILHGMGIHYRDFLSCGDGSGGMTAAL | |
| HR L a.a. | YPKMLEMPPRIQNPLLSGIRLGQLPTGAHYKIRSILHGMGIHYRDFLSCGDGSGGMTAAL | |
| M4 L a.a. | YPKMLEMPPRIQNPLLSGIRLGQLPTGAHYKIRSILHGMGIHYRDFLSCGDGSGGMTAAL | |

|  | 1681 | 1740 |
|---|---|---|
| GenBank L a.a. | LRENVHSRGIFNSLLELSGSVMRGASPEPPSALETLGGDKSRCVNGETCWEYPSDLCDPR | |
| HR L a.a. | LRENVHSRGIFNSLLELSGSVMRGASPEPPSALETLGGDKSRCVNGETCWEYPSDLCDPR | |
| M4 L a.a. | LRENVHSRGIFNSLLELSGSVMRGASPEPPSALETLGGDKSRCVNGETCWEYPSDLCDPR | |

|  | 1741 | 1800 |
|---|---|---|
| GenBank L a.a. | TWDYFLRLKAGLGLQIDLIVMDMEVRDSSTSLKIETNVRNYVHRILDEQGVLIYKTYGTY | |
| HR L a.a. | TWDYFLRLKAGLGLQIDLIVMDMEVRDSSTSLKIETNVRNYVHRILDEQGVLIYKTYGTY | |
| M4 L a.a. | TWDYFLRLKAGLGLQIDLIVMDMEVRDSSTSLKIETNVRNYVHRILDEQGVLIYKTYGTY | |

|  | 1801 | 1860 |
|---|---|---|
| GenBank L a.a. | ICESEKNAVTILGPMFKTVDLVQTEFSSSQTSEVYMVCKGLKKLIDEPNPDWSSINESWK | |
| HR L a.a. | ICESEKNAVTILGPMFKTVDLVQTEFSSSQTSEVYMVCKGLKKLIDEPNPDWSSINESWK | |
| M4 L a.a. | ICESEKNAVTILGPMFKTVDLVQTEFSSSQTSEVYMVCKGLKKLIDEPNPDWSSINESWK | |

FIGURE 23-3

```
            1861                                                        1920
GenBank L a.a.  NLYAFQSSEQEFARAKKVSTYFTLTGIPSQFIPDPFVNIETMLQIFGVPTGVSHAAALKS
HR L a.a.       NLYAFQSSEQEFARAKKVSTYFTLTGIPSQFIPDPFVNIETMLQIFGVPTGVSHAAALKS
M4 L a.a.       NLYAFQSSEQEFARAKKVSTYFTLTGIPSQFIPDPFVNIETMLQIFGVPTGVSHAAALKS 1921                                                        1980
GenBank L a.a.  SDRPADLLTISLFYMAIISYYNINHIRVGPIPPNPPSDGIAQNVGIAITGISFWLSLMEK
HR L a.a.       SDRPADLLTISLFYMAIISYYNINHIRVGPIPPNPPSDGIAQNVGIAITGISFWLSLMEK
M4 L a.a.       SDRPADLLTISLFYMAIISYYNINHIRVGPIPPNPPSDGIAQNVGIAITGISFWLSLMEK 1981                                                        2040
GenBank L a.a.  DIPLYQQCLAVIQQSFPIRWEAVSVKGGYKQKWSTRGDGLPKDTRTSDSLAPIGNWIRSL
HR L a.a.       DIPLYQQCLAVIQQSFPIRWEAVSVKGGYKQKWSTRGDGLPKDTRISDSLAPIGNWIRSL
M4 L a.a.       DIPLYQQCLAVIQQSFPIRWEAVSVKGGYKQKWSTRGDGLPKDTRISDSLAPIGNWIRSL 2041                                                        2100
GenBank L a.a.  ELVRNQVRLNPFNEILFNQLCRTVDNHLKWSNLRRNTGMIEWINRRISKEDRSILMLKSD
HR L a.a.       ELVRNQVRLNPFNEILFNQLCRTVDNHLKWSNLRKNTGMIEWINRRISKEDRSILMLKSD
M4 L a.a.       ELVRNQVRLNPFNEILFNQLCRTVDNHLKWSNLRKNTGMIEWINRRISKEDRSILMLKSD 2101    2110
GenBank L a.a.  LHEENSWRD
HR L a.a.       LHEENSWRD
M4 L a.a.       LHEENSWRD
```

FIGURE 23-4

SEQUENCE LISTING

```
<160> NUMBER OF SEQ ID NOS: 52

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Thr Thr His Arg His His Thr Ser Asn Cys
  1               5                  10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Leu Asn Ala His Arg Thr Thr His His His Cys
  1               5                  10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys His Gly Leu His Ser Asn Met Arg His Cys
  1               5                  10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys His His His His Arg Leu Asn Cys
  1               5
```

```
<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys His Ser His His His Arg Gly Cys
  1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Trp Asp His His Asn His His Cys
  1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Asp Asn Asn His His His His Cys
  1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys His His His Arg Ile Ser Ser His Cys
  1               5                  10

<210> SEQ ID NO 9
<211> LENGTH: 1269
<212> TYPE: DNA
<213> ORGANISM: Vesicular stomatitis virus

<400> SEQUENCE: 9
atgtctgtta cagtcaagag aatcattgac aacacagtca tagttccaaa acttcctgca      60
aatgaggatc cagtggaata cccggcagat tacttcagaa aatcaaagga gattcctctt     120
tacatcaata ctacaaaaag tttgtcagat ctaagaggat atgtctacca aggcctcaaa     180
tccggaaatg tatcaatcat acatgtcaac agctacttgt atggagcatt aaaggacatc     240
cggggtaagt tggataaaga ttggtcaagt tcggaataa acatcgggaa agcaggggat     300
acaatcggaa tatttgacct tgtatccttg aaagccctgg acggcgtact ccagatgga     360 gtatcggatg cttccagaac cagcgcagat gacaaatggt tgccttttgta tctacttggc     420 ttatacagag tgggcagaac acaaatgcct gaatacagaa aaaagctcat ggatgggctg     480
acaaatcaat gcaaaatgat caatgaacag tttgaacctc ttgtgccaga aggtcgtgac     540
```

```
atttttgatg tgtggggaaa tgacagtaat tacacaaaaa ttgtcgctgc agtggacatg      600
ttcttccaca tgttcaaaaa acatgaatgt gcctcgttca gatacggaac tattgtttcc      660
agattcaaag attgtgctgc attggcaaca tttggacacc tctgcaaaat aaccggaatg      720
tctacagaag atgtaacgac ctggatcttg aaccgagaag ttgcagatga atggtccaa       780
atgatgcttc caggccaaga aattgacaag gccgattcat acatgcctta tttgatcgac      840
tttggattgt cttctaagtc tccatattct tccgtcaaaa accctgcctt ccacttctgg      900
gggcaattga cagctcttct gctcagatcc accagagcaa ggaatgcccg acagcctgat      960
gacattgagt atacatctct tactacagca ggtttgttgt acgcttatgc agtaggatcc     1020
tctgccgact tggcacaaca gttttgtgtt ggagataaca aatacactcc agatgatagt     1080
accggaggat tgacgactaa tgcaccgcca caaggcagag atgtggtcga atggctcgga     1140
tggtttgaag atcaaaacag aaaaccgact cctgatatga tgcagtatgc gaaaagagca     1200
gtcatgtcac tgcaaggcct aagagagaag acaattggca agtatgctaa gtcagaattt     1260
gacaaatga                                                             1269

<210> SEQ ID NO 10
<211> LENGTH: 1269
<212> TYPE: DNA
<213> ORGANISM: Vesicular stomatitis virus

<400> SEQUENCE: 10
atgtctgtta cagtcaagag aatcattgcc aacacagtca tagttccaaa acttcctgca       60
aatgaggatc cagtggaata cccggcagat tacttcagaa aatcaaagga gattcctctt      120
tacatcaata ctacaaaaag tttgtcagat ctaagaggat atgtctacca aggcctcaaa      180
tccggaaatg tatcaatcat acatgtcaac agctacttgt atggagcatt gaaggacatc      240
cggggtaagt tggataaaga ttggtcaagt ttccggaataa acatcgggaa ggcaggggat      300
acaatcggaa tatttgacct tgtatccttg aaagccctgg acggtgtact tccagatgga      360
gtatcggatg cttccagaac cagcgcagat gacaaatggt tgcctttgta tctacttggc      420
ttatacagag tgggcagaac acaaatgcct gaatacagaa aaaggctcat ggatgggctg      480
acaaatcaat gcaaaatgat caatgaacag tttgaacctc ttgtgccaga aggtcgtgac      540
atttttgatg tgtggggaaa tgacagtaat tacacaaaaa ttgtcgctgc agtggacatg      600
ttcttccaca tgttcaaaaa acatgaatgt gcctcgttca gatacggaac tattgtttcc      660
agattcaaag attgtgctgc attggcaaca tttggacacc tctgcaaaat aaccggaatg      720
tctacagaag atgtaacgac ctggatcttg aaccgagaag ttgcagatga atggtccaa       780
atgatgcttc caggccaaga aattgacaag gccgattcat acatgcctta tttgatcgac      840
tttggattgt cttctaagtc tccatattct tccgtcaaaa accctgcctt ccacttctgg      900
gggcaattga cagctcttct gctcagatcc accagagcaa ggaatgcccg acagcctgat      960
gacattgagt atacatctct tactacagca ggtttgttgt acgcttatgc agtaggatcc     1020
tctgctgact tggcacaaca gttttgtgtt ggagatagca aatacactcc agatgatagt     1080
accggaggat tgacgactaa tgcaccgcca caaggcagag atgtggtcga atggctcgga     1140
tggtttgaag atcaaaacag aaaaccgact cctgatatga tgcagtatgc gaaacgagca     1200
gtcatgtcac tgcaaggcct aagagagaag acaattggca agtatgctaa gtcagaattt     1260
gacaaatga                                                             1269
```

```
<210> SEQ ID NO 11
<211> LENGTH: 1269
<212> TYPE: DNA
<213> ORGANISM: Vesicular stomatitis virus

<400> SEQUENCE: 11
atgtctgtta cagtcaagag aatcattgac aacacagtca tagttccaaa acttcctgca      60
aatgaggatc cagtggaata cccggcagat tacttcagaa aatcaaagga gattcctctt     120
tacatcaata ctacaaaaag tttgtcagat ctaagaggat atgtctacca aggcctcaaa     180
tccggaaatg tatcaatcat acatgtcaac agctacttgt atggagcatt gaaggacatc     240
cggggtaagt tggataaaga ttggtcaagt tcggaataa acatcgggaa ggcaggggat      300
acaatcggaa tatttgacct tgtatccttg aaagccctgg acggtgtact tccagatgga     360
gtatcggatg cttccagaac cagcgcagat gacaaatggt tgcctttgta tctacttggc     420
ttatacagag tgggcagaac acaaatgcct gaatacagaa aaaggctcat ggatgggctg     480
acaaatcaat gcaaaatgat caatgaacag tttgaacctc ttgtgccaga aggtcgtgac     540
atttttgatg tgtggggaaa tgacagtaat tacacaaaaa ttgtcgctgc agtggacatg     600
ttcttccaca tgttcaaaaa acatgaatgt gcctcgttca gatacggaac tattgtttcc     660
agattcaaag attgtgctgc attggcaaca tttggacacc tctgcaaaat aaccggaatg     720
tctacagaag atgtaacgac ctggatcttg aaccgagaag ttgcagatga gatggtccaa     780
atgatgcttc aggccaaga aattgacaag gccgattcat acatgccta tttgatcgac        840 tttggattgt cttctaagtc tccatattct tccgtcaaaa accctgcctt ccacttctgg     900
gggcaattga cagctcttct gctcagatct accagagcaa ggaatgcccg acagcctgat     960
gacattgagt atacatctct tactacagca ggtttgttgt acgcttatgc agtaggatcc    1020
tctgctgact tggcacaaca gttttgtgtt ggagatagca aatacactcc agatgatagt    1080
accggaggat tgacgactaa tgcaccgcca caaggcagag atgtggtcga atggctcgga    1140
tggtttgaag atcaaaacag aaaaccgact cctgatatga tgcagtatgc gaaacgagca    1200
gtcatgtcac tgcaaggcct aagagagaag acaattggca gtatgctaa gtcagaattt     1260 gacaaatga                                                             1269

<210> SEQ ID NO 12
<211> LENGTH: 1269
<212> TYPE: DNA
<213> ORGANISM: Vesicular stomatitis virus

<400> SEQUENCE: 12
atgtctgtta cagtcaagag aatcattgac aacacagtca tagttccaaa acttcctgca      60
aatgaggatc cagtggaata cccggcagat tacttcagaa aatcaaagga gattcctctt     120
tacatcaata ctacaaaaag tttgtcagat ctaagaggat atgtctacca aggcctcaaa     180
tccggaaatg tatcaatcat acatgtcaac agctacttgt atggagcatt gaaggacatc     240
cggggtaagt tggataaaga ttggtcaagt tcggaataa acatcgggaa ggcaggggat      300
acaatcggaa tatttgacct tgtatccttg aaagccctgg acggtgtact tccagatgga     360
gtatcggatg cttccagaac cagcgcagat gacaaatggt tgcctttgta tctacttggc     420
ttatacagag tgggcagaac acaaatgcct gaatacagaa aaaggctcat ggatgggctg     480
acaaatcaat gcaaaatgat caatgaacag tttgaacctc ttgtgccaga aggtcgtgac     540
atttttgatg tgtggggaaa tgacagtaat tacacaaaaa ttgtcgctgc agtggacatg     600
ttcttccaca tgttcaaaaa acatgaatgt gcctcgttca gatacggaac tattgtttcc     660
```

```
agattcaaag attgtgctgc attggcaaca tttggacacc tctgcaaaat aaccggaatg    720
tctacagaag atgtaacgac ctggatcttg aaccgagaag ttgcagatga gatggtccaa    780
atgatgcttc caggccaaga aattgacaag gccgattcat acatgcctta tttgatcgac    840
tttggattgt cttctaagtc tccatattct tccgtcaaaa accctgcctt ccacttctgg    900
gggcaattga cagctcttct gctcagatcc accagagcaa ggaatgcccg acagcctgat    960
gacattgagt atacatctct tactacagca ggtttgttgt acgcttatgc agtaggatcc   1020
tctgctgact tggcacaaca gttttgtgtt ggagatagca aatacactcc agatgatagt   1080
accggaggat tgacgactaa tgcaccgcca caaggcagag atgtggtcga atggctcgga   1140
tggtttgaag atcaaaacag aaaaccgact cctgatatga tgcagtatgc gaaacgagca   1200
gtcatgtcac tgcaaggcct aagagagaag acaattggca agtatgctaa gtcagaattt   1260
gacaaatga                                                           1269

<210> SEQ ID NO 13
<211> LENGTH: 1029
<212> TYPE: DNA
<213> ORGANISM: Vesicular stomatitis virus
<220> FEATURE:
<221> NAME/KEY: modified_base
<222> LOCATION: (1)..(1029)
<223> OTHER INFORMATION: "n" represents a, t, c, g, other or unknown

<400> SEQUENCE: 13
tcaatcatac atgtcaacag ctacttgtat ggagcattga aggacatccg gggtaagttg     60
gataaagatt ggtcaagttt cggaataaac atcgggaagg caggggatac aatcggaata    120
tttgaccttg tatccttgaa agccctggac ggtgtacttc cagatggagt atcggatgct    180
tccagaacca gcgcagatga caaatggttg cctttgtatc tacttggctt atacagagtg    240
ggcagaacac aaatgcctga atacagaaaa aggctcatgg atgggctgac aaatcaatgc    300
aaaatgatca atgaacagtt tgaacctctt gtgccagaag gtcgtgacat ttttgatgtg    360
tggggaaatg acagtaatta cacaaaaatt gtcgctgcag tggacatgtt cttccacatg    420
ttcaaaaaac atgaatgtgc ctcgttcaga tacggaacta ttgttttccag attcaaagat    480 tgtgctgcat tggcaacatt tggacaccctc tgcaaaataa ccggaatgtc tacagaagat    540
gtaacgacct ggatcttgaa ccgagaagtt gcagatgaga tggtccaaat gatgcttcca    600
ggccaagaaa ttgacaaggc cgattcatac atgccttatt tgatcgactt tggattgtct    660
tctaagtctc catattcttc cgtcaaaaac cctgccttcc acttctgggg gcaattgact    720
gacattgagt atacatctcn tactacagca ggtttgttgt acgcttatgc agtaggatcc    780
tctgctgact tggcacanca gttttgtgtt ggagatagca aatacactcc agatgatagt    840
accggaggat tgacgactaa tgcaccgcca caaggcagag atgtggtcga atggctcgga    900
tggtttgaag atcaaaacag aaaaccgact cctgatatga tgcagtatgc gaaacgagca    960
gtcatgtcac tgcaaggcct aagagagaag acaattggca agtatgctaa gtcagaattt   1020
gacaaatga                                                           1029

<210> SEQ ID NO 14
<211> LENGTH: 422
<212> TYPE: PRT
<213> ORGANISM: Vesicular stomatitis virus

<400> SEQUENCE: 14

Met Ser Val Thr Val Lys Arg Ile Ile Asp Asn Thr Val Ile Val Pro
```

-continued

```
  1               5                  10                 15
Lys Leu Pro Ala Asn Glu Asp Pro Val Glu Tyr Pro Ala Asp Tyr Phe
             20                  25                 30

Arg Lys Ser Lys Glu Ile Pro Leu Tyr Ile Asn Thr Thr Lys Ser Leu
             35                  40                 45

Ser Asp Leu Arg Gly Tyr Val Tyr Gln Gly Leu Lys Ser Gly Asn Val
             50                  55                 60

Ser Ile Ile His Val Asn Ser Tyr Leu Tyr Gly Ala Leu Lys Asp Ile
 65                  70                 75                 80

Arg Gly Lys Leu Asp Lys Asp Trp Ser Ser Phe Gly Ile Asn Ile Gly
             85                  90                 95

Lys Ala Gly Asp Thr Ile Gly Ile Phe Asp Leu Val Ser Leu Lys Ala
             100                 105                110

Leu Asp Gly Val Leu Pro Asp Gly Val Ser Asp Ala Ser Arg Thr Ser
             115                 120                125

Ala Asp Asp Lys Trp Leu Pro Leu Tyr Leu Leu Gly Leu Tyr Arg Val
             130                 135                140

Gly Arg Thr Gln Met Pro Glu Tyr Arg Lys Lys Leu Met Asp Gly Leu
145                 150                 155                160

Thr Asn Gln Cys Lys Met Ile Asn Glu Gln Phe Glu Pro Leu Val Pro
             165                 170                175

Glu Gly Arg Asp Ile Phe Asp Val Trp Gly Asn Asp Ser Asn Tyr Thr
             180                 185                190

Lys Ile Val Ala Ala Val Asp Met Phe Phe His Met Phe Lys Lys His
             195                 200                205

Glu Cys Ala Ser Phe Arg Tyr Gly Thr Ile Val Ser Arg Phe Lys Asp
             210                 215                220

Cys Ala Ala Leu Ala Thr Phe Gly His Leu Cys Lys Ile Thr Gly Met
225                 230                 235                240

Ser Thr Glu Asp Val Thr Thr Trp Ile Leu Asn Arg Glu Val Ala Asp
             245                 250                255

Glu Met Val Gln Met Met Leu Pro Gly Gln Glu Ile Asp Lys Ala Asp
             260                 265                270

Ser Tyr Met Pro Tyr Leu Ile Asp Phe Gly Leu Ser Ser Lys Ser Pro
             275                 280                285

Tyr Ser Ser Val Lys Asn Pro Ala Phe His Phe Trp Gly Gln Leu Thr
             290                 295                300

Ala Leu Leu Leu Arg Ser Thr Arg Ala Arg Asn Ala Arg Gln Pro Asp
305                 310                 315                320

Asp Ile Glu Tyr Thr Ser Leu Thr Thr Ala Gly Leu Leu Tyr Ala Tyr
             325                 330                335

Ala Val Gly Ser Ser Ala Asp Leu Ala Gln Gln Phe Cys Val Gly Asp
             340                 345                350

Asn Lys Tyr Thr Pro Asp Asp Ser Thr Gly Gly Leu Thr Thr Asn Ala
             355                 360                365

Pro Pro Gln Gly Arg Asp Val Val Glu Trp Leu Gly Trp Phe Glu Asp
             370                 375                380

Gln Asn Arg Lys Pro Thr Pro Asp Met Met Gln Tyr Ala Lys Arg Ala
385                 390                 395                400

Val Met Ser Leu Gln Gly Leu Arg Glu Lys Thr Ile Gly Lys Tyr Ala
             405                 410                415

Lys Ser Glu Phe Asp Lys
             420
```

-continued

<210> SEQ ID NO 15
<211> LENGTH: 422
<212> TYPE: PRT
<213> ORGANISM: Vesicular stomatitis virus

<400> SEQUENCE: 15

Met Ser Val Thr Val Lys Arg Ile Ile Ala Asn Thr Val Ile Val Pro
1               5                   10                  15

Lys Leu Pro Ala Asn Glu Asp Pro Val Glu Tyr Pro Ala Asp Tyr Phe
            20                  25                  30

Arg Lys Ser Lys Glu Ile Pro Leu Tyr Ile Asn Thr Thr Lys Ser Leu
        35                  40                  45

Ser Asp Leu Arg Gly Tyr Val Tyr Gln Gly Leu Lys Ser Gly Asn Val
    50                  55                  60

Ser Ile Ile His Val Asn Ser Tyr Leu Tyr Gly Ala Leu Lys Asp Ile
65                  70                  75                  80

Arg Gly Lys Leu Asp Lys Asp Trp Ser Ser Phe Gly Ile Asn Ile Gly
                85                  90                  95

Lys Ala Gly Asp Thr Ile Gly Ile Phe Asp Leu Val Ser Leu Lys Ala
            100                 105                 110

Leu Asp Gly Val Leu Pro Asp Gly Val Ser Asp Ala Ser Arg Thr Ser
        115                 120                 125

Ala Asp Asp Lys Trp Leu Pro Leu Tyr Leu Leu Gly Leu Tyr Arg Val
    130                 135                 140

Gly Arg Thr Gln Met Pro Glu Tyr Arg Lys Arg Leu Met Asp Gly Leu
145                 150                 155                 160

Thr Asn Gln Cys Lys Met Ile Asn Glu Gln Phe Glu Pro Leu Val Pro
                165                 170                 175

Glu Gly Arg Asp Ile Phe Asp Val Trp Gly Asn Asp Ser Asn Tyr Thr
            180                 185                 190

Lys Ile Val Ala Ala Val Asp Met Phe Phe His Met Phe Lys Lys His
        195                 200                 205

Glu Cys Ala Ser Phe Arg Tyr Gly Thr Ile Val Ser Arg Phe Lys Asp
    210                 215                 220

Cys Ala Ala Leu Ala Thr Phe Gly His Leu Cys Lys Ile Thr Gly Met
225                 230                 235                 240

Ser Thr Glu Asp Val Thr Thr Trp Ile Leu Asn Arg Glu Val Ala Asp
                245                 250                 255

Glu Met Val Gln Met Met Leu Pro Gly Gln Glu Ile Asp Lys Ala Asp
            260                 265                 270

Ser Tyr Met Pro Tyr Leu Ile Asp Phe Gly Leu Ser Ser Lys Ser Pro
        275                 280                 285

Tyr Ser Ser Val Lys Asn Pro Ala Phe His Phe Trp Gly Gln Leu Thr
    290                 295                 300

Ala Leu Leu Leu Arg Ser Thr Arg Ala Arg Asn Ala Arg Gln Pro Asp
305                 310                 315                 320

Asp Ile Glu Tyr Thr Ser Leu Thr Thr Ala Gly Leu Leu Tyr Ala Tyr
                325                 330                 335

Ala Val Gly Ser Ser Ala Asp Leu Ala Gln Gln Phe Cys Val Gly Asp
            340                 345                 350

Ser Lys Tyr Thr Pro Asp Asp Ser Thr Gly Gly Leu Thr Thr Asn Ala
        355                 360                 365

Pro Pro Gln Gly Arg Asp Val Val Glu Trp Leu Gly Trp Phe Glu Asp
    370                 375                 380

-continued

Gln Asn Arg Lys Pro Thr Pro Asp Met Met Gln Tyr Ala Lys Arg Ala
385                 390                 395                 400

Val Met Ser Leu Gln Gly Leu Arg Glu Lys Thr Ile Gly Lys Tyr Ala
            405                 410                 415

Lys Ser Glu Phe Asp Lys
            420

<210> SEQ ID NO 16
<211> LENGTH: 422
<212> TYPE: PRT
<213> ORGANISM: Vesicular stomatitis virus

<400> SEQUENCE: 16

Met Ser Val Thr Val Lys Arg Ile Ile Asp Asn Thr Val Ile Val Pro
1               5                   10                  15

Lys Leu Pro Ala Asn Glu Asp Pro Val Glu Tyr Pro Ala Asp Tyr Phe
            20                  25                  30

Arg Lys Ser Lys Glu Ile Pro Leu Tyr Ile Asn Thr Thr Lys Ser Leu
        35                  40                  45

Ser Asp Leu Arg Gly Tyr Val Tyr Gln Gly Leu Lys Ser Gly Asn Val
    50                  55                  60

Ser Ile Ile His Val Asn Ser Tyr Leu Tyr Gly Ala Leu Lys Asp Ile
65                  70                  75                  80

Arg Gly Lys Leu Asp Lys Asp Trp Ser Ser Phe Gly Ile Asn Ile Gly
                85                  90                  95

Lys Ala Gly Asp Thr Ile Gly Ile Phe Asp Leu Val Ser Leu Lys Ala
            100                 105                 110

Leu Asp Gly Val Leu Pro Asp Gly Val Ser Asp Ala Ser Arg Thr Ser
        115                 120                 125

Ala Asp Asp Lys Trp Leu Pro Leu Tyr Leu Leu Gly Leu Tyr Arg Val
    130                 135                 140

Gly Arg Thr Gln Met Pro Glu Tyr Arg Lys Arg Leu Met Asp Gly Leu
145                 150                 155                 160

Thr Asn Gln Cys Lys Met Ile Asn Glu Gln Phe Glu Pro Leu Val Pro
                165                 170                 175

Glu Gly Arg Asp Ile Phe Asp Val Trp Gly Asn Asp Ser Asn Tyr Thr
            180                 185                 190

Lys Ile Val Ala Ala Val Asp Met Phe Phe His Met Phe Lys Lys His
        195                 200                 205

Glu Cys Ala Ser Phe Arg Tyr Gly Thr Ile Val Ser Arg Phe Lys Asp
    210                 215                 220

Cys Ala Ala Leu Ala Thr Phe Gly His Leu Cys Lys Ile Thr Gly Met
225                 230                 235                 240

Ser Thr Glu Asp Val Thr Thr Trp Ile Leu Asn Arg Glu Val Ala Asp
                245                 250                 255

Glu Met Val Gln Met Met Leu Pro Gly Gln Glu Ile Asp Lys Ala Asp
            260                 265                 270

Ser Tyr Met Pro Tyr Leu Ile Asp Phe Gly Leu Ser Ser Lys Ser Pro
        275                 280                 285

Tyr Ser Ser Val Lys Asn Pro Ala Phe His Phe Trp Gly Gln Leu Thr
    290                 295                 300

Ala Leu Leu Leu Arg Ser Thr Arg Ala Arg Asn Ala Arg Gln Pro Asp
305                 310                 315                 320

Asp Ile Glu Tyr Thr Ser Leu Thr Thr Ala Gly Leu Leu Tyr Ala Tyr
                325                 330                 335

```
Ala Val Gly Ser Ser Ala Asp Leu Ala Gln Gln Phe Cys Val Gly Asp
            340                 345                 350

Ser Lys Tyr Thr Pro Asp Ser Thr Gly Gly Leu Thr Thr Asn Ala
            355                 360                 365

Pro Pro Gln Gly Arg Asp Val Val Glu Trp Leu Gly Trp Phe Glu Asp
            370                 375                 380

Gln Asn Arg Lys Pro Thr Pro Asp Met Met Gln Tyr Ala Lys Arg Ala
385                 390                 395                 400

Val Met Ser Leu Gln Gly Leu Arg Glu Lys Thr Ile Gly Lys Tyr Ala
                405                 410                 415

Lys Ser Glu Phe Asp Lys
            420

<210> SEQ ID NO 17
<211> LENGTH: 342
<212> TYPE: PRT
<213> ORGANISM: Vesicular stomatitis virus
<220> FEATURE:
<221> NAME/KEY: MOD_RES
<222> LOCATION: (1)..(342)
<223> OTHER INFORMATION: "Xaa" represents any, other or unknown amino
      acid

<400> SEQUENCE: 17

Ser Ile Ile His Val Asn Ser Tyr Leu Tyr Gly Ala Leu Lys Asp Ile
1               5                   10                  15

Arg Gly Lys Leu Asp Lys Asp Trp Ser Ser Phe Gly Ile Asn Ile Gly
            20                  25                  30

Lys Ala Gly Asp Thr Ile Gly Ile Phe Asp Leu Val Ser Leu Lys Ala
        35                  40                  45

Leu Asp Gly Val Leu Pro Asp Gly Val Ser Asp Ala Ser Arg Thr Ser
    50                  55                  60

Ala Asp Asp Lys Trp Leu Pro Leu Tyr Leu Leu Gly Leu Tyr Arg Val
65                  70                  75                  80

Gly Arg Thr Gln Met Pro Glu Tyr Arg Lys Arg Leu Met Asp Gly Leu
                85                  90                  95

Thr Asn Gln Cys Lys Met Ile Asn Glu Gln Phe Glu Pro Leu Val Pro
            100                 105                 110

Glu Gly Arg Asp Ile Phe Asp Val Trp Gly Asn Asp Ser Asn Tyr Thr
        115                 120                 125

Lys Ile Val Ala Ala Val Asp Met Phe Phe His Met Phe Lys Lys His
    130                 135                 140

Glu Cys Ala Ser Phe Arg Tyr Gly Thr Ile Val Ser Arg Phe Lys Asp
145                 150                 155                 160

Cys Ala Ala Leu Ala Thr Phe Gly His Leu Cys Lys Ile Thr Gly Met
                165                 170                 175

Ser Thr Glu Asp Val Thr Thr Trp Ile Leu Asn Arg Glu Val Ala Asp
            180                 185                 190

Glu Met Val Gln Met Met Leu Pro Gly Gln Glu Ile Asp Lys Ala Asp
        195                 200                 205

Ser Tyr Met Pro Tyr Leu Ile Asp Phe Gly Leu Ser Ser Lys Ser Pro
    210                 215                 220

Tyr Ser Ser Val Lys Asn Pro Ala Phe His Phe Trp Gly Gln Leu Thr
225                 230                 235                 240

Asp Ile Glu Tyr Thr Ser Xaa Thr Thr Ala Gly Leu Leu Tyr Ala Tyr
                245                 250                 255

Ala Val Gly Ser Ser Ala Asp Leu Ala Xaa Gln Phe Cys Val Gly Asp
```

```
                    260                 265                 270
Ser Lys Tyr Thr Pro Asp Asp Ser Thr Gly Gly Leu Thr Thr Asn Ala
            275                 280                 285

Pro Pro Gln Gly Arg Asp Val Val Glu Trp Leu Gly Trp Phe Glu Asp
            290                 295                 300

Gln Asn Arg Lys Pro Thr Pro Asp Met Met Gln Tyr Ala Lys Arg Ala
305                 310                 315                 320

Val Met Ser Leu Gln Gly Leu Arg Glu Lys Thr Ile Gly Lys Tyr Ala
            325                 330                 335

Lys Ser Glu Phe Asp Lys
            340
```

<210> SEQ ID NO 18
<211> LENGTH: 798
<212> TYPE: DNA
<213> ORGANISM: Vesicular stomatitis virus

<400> SEQUENCE: 18

| | | | | | |
|---|---|---|---|---|---|
| atggataatc | tcacaaaagt | tcgtgagtat | ctcaagtcct | attctcgtct | ggatcaggcg | 60 |
| gtaggagaga | tagatgagat | cgaagcacaa | cgagctgaaa | agtccaatta | tgagttgttc | 120 |
| caagaggatg | gagtggaaga | gcatactaag | ccctcttatt | ttcaggcagc | agatgattct | 180 |
| gacacagaat | ctgaaccaga | aattgaagac | aatcaaggtt | tgtatgcaca | ggatccagaa | 240 |
| gctgagcaag | ttgaaggctt | tatacagggg | cctttagatg | actatgcaga | tgaggaagtg | 300 |
| gatgttgtat | ttacttcgga | ctggaaacca | cctgagcttg | aatctgacga | gcatggaaag | 360 |
| accttacggt | tgacatcgcc | agagggttta | agtggagagc | agaaatccca | gtggcttttcg | 420 |
| acgattaaag | cagtcgtgca | aagtgccaaa | tactggaatc | tggcagagtg | cacatttgaa | 480 |
| gcatcgggag | aaggggtcat | tatgaaggag | cgccagataa | ctccggatgt | atataaggtc | 540 |
| actccagtga | tgaacacaca | tccgtcccaa | tcagaagcag | tatcagatgt | ttggtctctc | 600 |
| tcaaagacat | ccatgacttt | ccaacccaag | aaagcaagtc | ttcagcctct | caccatatcc | 660 |
| ttggatgaat | tgttctcatc | tagaggagag | ttcatctctg | tcggaggtga | cggacgaatg | 720 |
| tctcataaag | aggccatcct | gctcggcctg | agatacaaaa | agttgtacaa | tcaggcgaga | 780 |
| gtcaaatatt | ctctgtag | | | | | 798 |

<210> SEQ ID NO 19
<211> LENGTH: 798
<212> TYPE: DNA
<213> ORGANISM: Vesicular stomatitis virus

<400> SEQUENCE: 19

| | | | | | |
|---|---|---|---|---|---|
| atggataatc | tcacaaaagt | tcgtgagtat | ctcaagtcct | attctcgtct | agatcaggcg | 60 |
| gtaggagaga | tagatgagat | cgaagcacaa | cgagctgaaa | agtccaatta | tgagttgttc | 120 |
| caagaggacg | gagtggaaga | gcatactagg | ccctcttatt | ttcaggcagc | agatgattct | 180 |
| gacacagaat | ctgaaccaga | aattgaagac | aatcaaggct | tgtatgtacc | agatccggaa | 240 |
| gctgagcaag | ttgaaggctt | tatacagggg | cctttagatg | actatgcgga | tgaggacgtg | 300 |
| gatgttgtat | tcacttcgga | ctggaaacag | cctgagcttg | aatccgacga | gcatggaaag | 360 |
| accttacggt | tgacattgcc | agagggttta | agtggagagc | agaaatccca | gtggctttg | 420 |
| acgattaaag | cagtcgttca | aagtgccaaa | cactggaatc | tggcagagtg | cacatttgaa | 480 |
| gcatcgggag | aaggggtcat | cataaaaaag | cgccagataa | ctccggatgt | atataaggtc | 540 |
| actccagtga | tgaacacaca | tccgtcccaa | tcagaagccg | tatcagatgt | ttggtctctc | 600 |

```
tcaaagacat ccatgacttt ccaacccaag aaagcaagtc ttcagcctct caccatatcc    660
ttggatgaat tgttctcatc tagaggagaa ttcatctctg tcggaggtaa cggacgaatg    720
tctcataaag aggccatcct gctcggtctg aggtacaaaa agttgtacaa tcaggcgaga    780
gtcaaatatt ctctgtag                                                  798
```

<210> SEQ ID NO 20
<211> LENGTH: 570
<212> TYPE: DNA
<213> ORGANISM: Vesicular stomatitis virus

<400> SEQUENCE: 20

```
atggataatc tcacaaaagt tcgtgagtat ctcaagtcct attctcgtct agatcaggcg     60
gtaggagaga tagatgagat cgaagcacaa cgagctgaaa agtccaatta tgagttgttc    120
caagaggacg gagtggaaga gcatactagg ccctcttatt ttcaggcagc agatgattct    180
gacacagaat ctgaaccaga aattgaagac aatcaaggct gtatgtacc agatccggaa     240 gctgagcaag ttgaaggctt tatacagggg cctttagatg actatgcgga tgaggacgtg    300
gatgttgtat tcacttcgga ctggaaacag cctgagcttg aatccgacga gcatggaaag    360
accttacggt tgacattgcc agagggttta agtggagagc agaaatccca gtggcttttg    420
acgattaaag cagtcgttca aagtgccaaa cactggaatc tggcagagtg cacatttgaa    480
gcatcgggag aaggggtcat cataaaaaag cgccagataa ctccggatgt atataaggtc    540
actccagtga tgaacacaca tccgtcccaa                                     570
```

<210> SEQ ID NO 21
<211> LENGTH: 798
<212> TYPE: DNA
<213> ORGANISM: Vesicular stomatitis virus

<400> SEQUENCE: 21

```
atggataatc tcacaaaagt tcgtgagtat ctcaagtcct attctcgtct agatcaggcg     60
gtaggagaga tagatgagat cgaagcacaa cgagctgaaa agtccaatta tgagttgttc    120
caagaggacg gagtggaaga gcatactagg ccctcttatt ttcaggcagc agatgattct    180
gacacagaat ctgaaccaga aattgaagac aatcaaggct gtatgtacc agatccggaa     240 gctgagcaag ttgaaggctt tatacagggg cctttagatg actatgcgga tgaggacgtg    300
gatgttgtat tcacttcgga ctggaaacag cctgagcttg aatccgacga gcatggaaag    360
accttacggt tgacattgcc agagggttta agtggagagc agaaatccca gtggcttttg    420
acgattaaag cagtcgttca aagtgccaaa cactggaatc tggcagagtg cacatttgaa    480
gcatcgggag aaggggtcat cataaaaaag cgccagataa ctccggatgt atataaggtc    540
actccagtga tgaacacaca tccgtcccaa tcggaagccg tatcagatgt ttggtctctc    600
tcaaagacat ccatgacttt ccaacccaag aaagcaagtc ttcagcctct caccatatcc    660
ttggatgaat tgttctcatc tagaggagaa ttcatctctg tcggaggtaa cggacgaatg    720
tctcataaag aggccatcct gctcggtctg aggtacaaaa agttgtacaa tcaggcgaga    780
gtcaaatatt ctctgtag                                                  798
```

<210> SEQ ID NO 22
<211> LENGTH: 798
<212> TYPE: DNA
<213> ORGANISM: Vesicular stomatitis virus

<400> SEQUENCE: 22

-continued

```
atggataatc tcacaaaagt tcgtgagtat ctcaagtcct attctcgtct agatcaggcg     60
gtaggagaga tagatgagat cgaagcacaa cgagctgaaa agtccaatta tgagttgttc    120
caagaggacg gagtggaaga gcatactagg ccctcttatt ttcaggcagc agatgattct    180
gacacagaat ctgaaccaga aattgaagac aatcaaggct tgtatgtacc agatccggaa    240
gctgagcaag ttgaaggctt tatacagggg cctttagatg actatgcgga tgaggacgtg    300
gatgttgtat tcacttcgga ctggaaacag cctgagcttg aatccgacga gcatggaaag    360
accttacggt tgacattgcc agagggttta gtggagagc agaaatccca gtggcttttg     420
acgattaaag cagtcgttca aagtgccaaa cactggaatc tggcagagtg cacatttgaa    480
gcatcgggag aagggtcat cataaaaaag cgccagataa ctccggatgt atataaggtc     540
actccagtga tgaacacaca tccgtcccaa tcagaagccg tatcagatgt ttggtctctc    600
tcaaagacat ccatgacttt ccaacccaag aaagcaagtc ttcagcctct caccatatcc    660
ttggatgaat tgttctcatc tagaggagaa ttcatctctg tcggaggtaa cggacgaatg    720
tctcataaag aggccatcct gctcggtctg aggtacaaaa agttgtacaa tcaggcgaga    780
gtcaaatatt ctctgtag                                                  798
```

<210> SEQ ID NO 23
<211> LENGTH: 265
<212> TYPE: PRT
<213> ORGANISM: Vesicular stomatitis virus

<400> SEQUENCE: 23

```
Met Asp Asn Leu Thr Lys Val Arg Glu Tyr Leu Lys Ser Tyr Ser Arg
 1               5                  10                  15

Leu Asp Gln Ala Val Gly Glu Ile Asp Glu Ile Glu Ala Gln Arg Ala
            20                  25                  30

Glu Lys Ser Asn Tyr Glu Leu Phe Gln Glu Asp Gly Val Glu Glu His
        35                  40                  45

Thr Lys Pro Ser Tyr Phe Gln Ala Ala Asp Asp Ser Asp Thr Glu Ser
    50                  55                  60

Glu Pro Glu Ile Glu Asp Asn Gln Gly Leu Tyr Ala Gln Asp Pro Glu
65                  70                  75                  80

Ala Glu Gln Val Glu Gly Phe Ile Gln Gly Pro Leu Asp Asp Tyr Ala
                85                  90                  95

Asp Glu Glu Val Asp Val Val Phe Thr Ser Asp Trp Lys Pro Pro Glu
            100                 105                 110

Leu Glu Ser Asp Glu His Gly Lys Thr Leu Arg Leu Thr Ser Pro Glu
        115                 120                 125

Gly Leu Ser Gly Glu Gln Lys Ser Gln Trp Leu Ser Thr Ile Lys Ala
    130                 135                 140

Val Val Gln Ser Ala Lys Tyr Trp Asn Leu Ala Glu Cys Thr Phe Glu
145                 150                 155                 160

Ala Ser Gly Glu Gly Val Ile Met Lys Glu Arg Gln Ile Thr Pro Asp
                165                 170                 175

Val Tyr Lys Val Thr Pro Val Met Asn Thr His Pro Ser Gln Ser Glu
            180                 185                 190

Ala Val Ser Asp Val Trp Ser Leu Ser Lys Thr Ser Met Thr Phe Gln
        195                 200                 205

Pro Lys Lys Ala Ser Leu Gln Pro Leu Thr Ile Ser Leu Asp Glu Leu
    210                 215                 220

Phe Ser Ser Arg Gly Glu Phe Ile Ser Val Gly Gly Asp Gly Arg Met
```

```
                225                 230                 235                 240
Ser His Lys Glu Ala Ile Leu Leu Gly Leu Arg Tyr Lys Lys Leu Tyr
                245                 250                 255

Asn Gln Ala Arg Val Lys Tyr Ser Leu
            260                 265

<210> SEQ ID NO 24
<211> LENGTH: 265
<212> TYPE: PRT
<213> ORGANISM: Vesicular stomatitis virus

<400> SEQUENCE: 24

Met Asp Asn Leu Thr Lys Val Arg Glu Tyr Leu Lys Ser Tyr Ser Arg
  1               5                  10                  15

Leu Asp Gln Ala Val Gly Glu Ile Asp Glu Ile Glu Ala Gln Arg Ala
             20                  25                  30

Glu Lys Ser Asn Tyr Glu Leu Phe Gln Glu Asp Gly Val Glu Glu His
         35                  40                  45

Thr Arg Pro Ser Tyr Phe Gln Ala Ala Asp Asp Ser Asp Thr Glu Ser
     50                  55                  60

Glu Pro Glu Ile Glu Asp Asn Gln Gly Leu Tyr Val Pro Asp Pro Glu
 65                  70                  75                  80

Ala Glu Gln Val Glu Gly Phe Ile Gln Gly Pro Leu Asp Asp Tyr Ala
                 85                  90                  95

Asp Glu Asp Val Asp Val Val Phe Thr Ser Asp Trp Lys Gln Pro Glu
            100                 105                 110

Leu Glu Ser Asp Glu His Gly Lys Thr Leu Arg Leu Thr Leu Pro Glu
        115                 120                 125

Gly Leu Ser Gly Glu Gln Lys Ser Gln Trp Leu Leu Thr Ile Lys Ala
    130                 135                 140

Val Val Gln Ser Ala Lys His Trp Asn Leu Ala Glu Cys Thr Phe Glu
145                 150                 155                 160

Ala Ser Gly Glu Gly Val Ile Ile Lys Lys Arg Gln Ile Thr Pro Asp
                165                 170                 175

Val Tyr Lys Val Thr Pro Val Met Asn Thr His Pro Ser Gln Ser Glu
            180                 185                 190

Ala Val Ser Asp Val Trp Ser Leu Ser Lys Thr Ser Met Thr Phe Gln
        195                 200                 205

Pro Lys Lys Ala Ser Leu Gln Pro Leu Thr Ile Ser Leu Asp Glu Leu
    210                 215                 220

Phe Ser Ser Arg Gly Glu Phe Ile Ser Val Gly Gly Asn Gly Arg Met
225                 230                 235                 240

Ser His Lys Glu Ala Ile Leu Leu Gly Leu Arg Tyr Lys Lys Leu Tyr
                245                 250                 255

Asn Gln Ala Arg Val Lys Tyr Ser Leu
            260                 265

<210> SEQ ID NO 25
<211> LENGTH: 190
<212> TYPE: PRT
<213> ORGANISM: Vesicular stomatitis virus

<400> SEQUENCE: 25

Met Asp Asn Leu Thr Lys Val Arg Glu Tyr Leu Lys Ser Tyr Ser Arg
  1               5                  10                  15

Leu Asp Gln Ala Val Gly Glu Ile Asp Glu Ile Glu Ala Gln Arg Ala
             20                  25                  30
```

```
Glu Lys Ser Asn Tyr Glu Leu Phe Gln Glu Asp Gly Val Glu Glu His
             35                  40                  45

Thr Arg Pro Ser Tyr Phe Gln Ala Ala Asp Asp Ser Asp Thr Glu Ser
 50                      55                  60

Glu Pro Glu Ile Glu Asp Asn Gln Gly Leu Tyr Val Pro Asp Pro Glu
 65                      70                  75                  80

Ala Glu Gln Val Glu Gly Phe Ile Gln Gly Pro Leu Asp Asp Tyr Ala
                     85                  90                  95

Asp Glu Asp Val Asp Val Val Phe Thr Ser Asp Trp Lys Gln Pro Glu
                100                 105                 110

Leu Glu Ser Asp Glu His Gly Lys Thr Leu Arg Leu Thr Leu Pro Glu
            115                 120                 125

Gly Leu Ser Gly Glu Gln Lys Ser Gln Trp Leu Leu Thr Ile Lys Ala
            130                 135                 140

Val Val Gln Ser Ala Lys His Trp Asn Leu Ala Glu Cys Thr Phe Glu
145                 150                 155                 160

Ala Ser Gly Glu Gly Val Ile Ile Lys Lys Arg Gln Ile Thr Pro Asp
                165                 170                 175

Val Tyr Lys Val Thr Pro Val Met Asn Thr His Pro Ser Gln
            180                 185                 190
```

<210> SEQ ID NO 26
<211> LENGTH: 265
<212> TYPE: PRT
<213> ORGANISM: Vesicular stomatitis virus

<400> SEQUENCE: 26

```
Met Asp Asn Leu Thr Lys Val Arg Glu Tyr Leu Lys Ser Tyr Ser Arg
  1               5                  10                  15

Leu Asp Gln Ala Val Gly Glu Ile Asp Glu Ile Glu Ala Gln Arg Ala
                 20                  25                  30

Glu Lys Ser Asn Tyr Glu Leu Phe Gln Glu Asp Gly Val Glu Glu His
             35                  40                  45

Thr Arg Pro Ser Tyr Phe Gln Ala Ala Asp Asp Ser Asp Thr Glu Ser
 50                      55                  60

Glu Pro Glu Ile Glu Asp Asn Gln Gly Leu Tyr Val Pro Asp Pro Glu
 65                      70                  75                  80

Ala Glu Gln Val Glu Gly Phe Ile Gln Gly Pro Leu Asp Asp Tyr Ala
                     85                  90                  95

Asp Glu Asp Val Asp Val Val Phe Thr Ser Asp Trp Lys Gln Pro Glu
                100                 105                 110

Leu Glu Ser Asp Glu His Gly Lys Thr Leu Arg Leu Thr Leu Pro Glu
            115                 120                 125

Gly Leu Ser Gly Glu Gln Lys Ser Gln Trp Leu Leu Thr Ile Lys Ala
            130                 135                 140

Val Val Gln Ser Ala Lys His Trp Asn Leu Ala Glu Cys Thr Phe Glu
145                 150                 155                 160

Ala Ser Gly Glu Gly Val Ile Ile Lys Lys Arg Gln Ile Thr Pro Asp
                165                 170                 175

Val Tyr Lys Val Thr Pro Val Met Asn Thr His Pro Ser Gln Ser Glu
            180                 185                 190

Ala Val Ser Asp Val Trp Ser Leu Ser Lys Thr Ser Met Thr Phe Gln
            195                 200                 205

Pro Lys Lys Ala Ser Leu Gln Pro Leu Thr Ile Ser Leu Asp Glu Leu
210                 215                 220
```

```
Phe Ser Ser Arg Gly Glu Phe Ile Ser Val Gly Gly Asn Gly Arg Met
225                 230                 235                 240

Ser His Lys Glu Ala Ile Leu Leu Gly Leu Arg Tyr Lys Lys Leu Tyr
            245                 250                 255

Asn Gln Ala Arg Val Lys Tyr Ser Leu
        260                 265

<210> SEQ ID NO 27
<211> LENGTH: 265
<212> TYPE: PRT
<213> ORGANISM: Vesicular stomatitis virus

<400> SEQUENCE: 27

Met Asp Asn Leu Thr Lys Val Arg Glu Tyr Leu Lys Ser Tyr Ser Arg
1               5                   10                  15

Leu Asp Gln Ala Val Gly Glu Ile Asp Glu Ile Glu Ala Gln Arg Ala
            20                  25                  30

Glu Lys Ser Asn Tyr Glu Leu Phe Gln Glu Asp Gly Val Glu Glu His
        35                  40                  45

Thr Arg Pro Ser Tyr Phe Gln Ala Ala Asp Asp Ser Asp Thr Glu Ser
    50                  55                  60

Glu Pro Glu Ile Glu Asp Asn Gln Gly Leu Tyr Val Pro Asp Pro Glu
65                  70                  75                  80

Ala Glu Gln Val Glu Gly Phe Ile Gln Gly Pro Leu Asp Asp Tyr Ala
                85                  90                  95

Asp Glu Asp Val Asp Val Val Phe Thr Ser Asp Trp Lys Gln Pro Glu
            100                 105                 110

Leu Glu Ser Asp Glu His Gly Lys Thr Leu Arg Leu Thr Leu Pro Glu
        115                 120                 125

Gly Leu Ser Gly Glu Gln Lys Ser Gln Trp Leu Leu Thr Ile Lys Ala
    130                 135                 140

Val Val Gln Ser Ala Lys His Trp Asn Leu Ala Glu Cys Thr Phe Glu
145                 150                 155                 160

Ala Ser Gly Glu Gly Val Ile Ile Lys Lys Arg Gln Ile Thr Pro Asp
                165                 170                 175

Val Tyr Lys Val Thr Pro Val Met Asn Thr His Pro Ser Gln Ser Glu
            180                 185                 190

Ala Val Ser Asp Val Trp Ser Leu Ser Lys Thr Ser Met Thr Phe Gln
        195                 200                 205

Pro Lys Lys Ala Ser Leu Gln Pro Leu Thr Ile Ser Leu Asp Glu Leu
    210                 215                 220

Phe Ser Ser Arg Gly Glu Phe Ile Ser Val Gly Gly Asn Gly Arg Met
225                 230                 235                 240

Ser His Lys Glu Ala Ile Leu Leu Gly Leu Arg Tyr Lys Lys Leu Tyr
            245                 250                 255

Asn Gln Ala Arg Val Lys Tyr Ser Leu
        260                 265

<210> SEQ ID NO 28
<211> LENGTH: 690
<212> TYPE: DNA
<213> ORGANISM: Vesicular stomatitis virus

<400> SEQUENCE: 28
atgagttcct taaagaagat tctcggtctg aagggaaag gtaagaaatc taagaaatta      60
gggatcgcac caccccctta tgaagaggac actagcatgg agtatgctcc gagcgctcca     120
```

| attgacaaat cctatttgg agttgacgag atggacacct atgatccgaa tcaattaaga | 180 |
| tatgagaaat tcttctttac agtgaaaatg acggttagat ctaatcgtcc gttcagaaca | 240 |
| tactcagatg tggcagccgc tgtatcccat tgggatcaca tgtacatcgg aatggcaggg | 300 |
| aaacgtccct tctacaaaat cttggctttt ttgggttctt ctaatctaaa ggccactcca | 360 |
| gcggtattgg cagatcaagg tcaaccagag tatcacactc actgcgaagg cagggcttat | 420 |
| ttgccacata ggatggggaa gaccctccc atgctcaatg taccagagca cttcagaaga | 480 |
| ccattcaata taggtcttta caagggaacg attgagctca caatgaccat ctacgatgat | 540 |
| gagtcactgg aagcagctcc tatgatctgg gatcatttca attcttccaa attttctgat | 600 |
| ttcagagaga aggccttaat gtttggcctg attgtcgaga aaaaggcatc tggagcgtgg | 660 |
| gtcctggatt ctatcagcca cttcaaatga | 690 |

<210> SEQ ID NO 29
<211> LENGTH: 690
<212> TYPE: DNA
<213> ORGANISM: Vesicular stomatitis virus

<400> SEQUENCE: 29

| atgagttcct taagaagat tctcggtctg aaggggaaag gtaagaaatc taagaaatta | 60 |
| gggatcgcac caccccctta tgaagaggac actaacatgg agtatgctcc gagcgctcca | 120 |
| attgacaaat cctattttgg agttgacgag atggacactc atgatccgca tcaattaaga | 180 |
| tatgagaaat tcttctttac agtgaaaatg acggttagat ctaatcgtcc gttcagaaca | 240 |
| tactcagatg tggcagccgc tgtatcccat tgggatcaca tgtacatcgg aatggcaggg | 300 |
| aaacgtccct tctacaagat cttggctttt ttgggttctt ctaatctaaa ggccactcca | 360 |
| gcggtattgg cagatcaagg tcaaccagag tatcacgctc actgtgaagg cagggcttat | 420 |
| ttgccacaca gaatggggaa gaccctccc atgctcaatg taccagagca cttcagaaga | 480 |
| ccattcaata taggtcttta caagggaacg gttgagctca caatgaccat ctacgatgat | 540 |
| gagtcactgg aagcagctcc tatgatctgg gatcatttca attcttccaa attttctgat | 600 |
| ttcagagaga aggccttaat gtttggcctg attgtcgaga aaaaggcatc tggagcttgg | 660 |
| gtcctggatt ctgtcagcca cttcaaatga | 690 |

<210> SEQ ID NO 30
<211> LENGTH: 690
<212> TYPE: DNA
<213> ORGANISM: Vesicular stomatitis virus

<400> SEQUENCE: 30

| atgagttcct taagaagat tctcggtctg aaggggaaag gtaagaaatc taagaaatta | 60 |
| gggatcgcac caccccctta tgaagaggac actaacatgg agtatgctcc gagcgctcca | 120 |
| attgacaaat cctattttgg agttgacgag agggacactc atgatccgca tcaattaaga | 180 |
| tatgagaaat tcttctttac agtgaaaatg acggttagat ctaatcgtcc gttcagaaca | 240 |
| tactcagatg tggcagccgc tgtatcccat tgggatcaca tgtacatcgg aatggcaggg | 300 |
| aaacgtccct tctacaagat cttggctttt ttgggwtctt ctaatctaaa ggccactcca | 360 |
| gcggtattgg cagatcaagg tcaaccagag tatcacgctc actgtgaagg cagggcttat | 420 |
| ttgccacaca gaatggggaa gaccctccc atgctcaatg taccagagca cttcagaaga | 480 |
| ccattcaata taggtcttta caagggaacg gttgagctca caatgaccat ctacgatgat | 540 |
| gagtcactgg aagcagctcc tatgatctgg gatcatttca attcttccaa attttctgat | 600 |

```
ttcagagaga aggccttaat gtttggcctg attgtcgaga aaaaggcatc tggagcttgg      660
gtcctggatt ctgtcagcca cttcaaatga                                      690

<210> SEQ ID NO 31
<211> LENGTH: 690
<212> TYPE: DNA
<213> ORGANISM: Vesicular stomatitis virus

<400> SEQUENCE: 31
atgagttcct taaagaagat tctcggtctg aaggggaaag gtaagaaatc taagaaatta       60
gggatcgcac cacccccctta tgaagaggac actaacatgg agtatgctcc gagcgctcca     120
attgacaaat cctattttgg agttgacgag atggacactc atgatccgca tcaattaaga     180
tatgagaaat tcttctttac agtgaaaatg acgttagat ctaatcgtcc gttcagaaca      240
tactcagatg tggcagccgc tgtatcccat tgggatcaca tgtacatcgg aatggcaggg     300
aaacgtccct tctacaagat cttggctttt ttgggttctt ctaatctaaa ggccactcca     360
gcggtattgg cagatcaagg tcaaccagag tatcacgctc actgtgaagg cagggcttat     420
ttgccacaca gaatggggaa gacccctccc atgctcaatg taccagagca cttcagaaga     480
ccattcaata taggtcttta caagggaacg gttgagctca caatgaccat ctacgatgat     540
gagtcactgg aagcagctcc tatgatctgg gatcatttca attcttccaa attttctgat     600
ttcagagaga aggccttaat gtttggcctg attgtcgaga aaaaggcatc tggagcttgg     660
gtcctggatt ctgtcagcca cttcaaatga                                      690

<210> SEQ ID NO 32
<211> LENGTH: 229
<212> TYPE: PRT
<213> ORGANISM: Vesicular stomatitis virus

<400> SEQUENCE: 32

Met Ser Ser Leu Lys Lys Ile Leu Gly Leu Lys Gly Lys Gly Lys Lys
1               5                  10                   15

Ser Lys Lys Leu Gly Ile Ala Pro Pro Tyr Glu Glu Asp Thr Ser
            20                  25                  30

Met Glu Tyr Ala Pro Ser Ala Pro Ile Asp Lys Ser Tyr Phe Gly Val
        35                  40                  45

Asp Glu Met Asp Thr Tyr Asp Pro Asn Gln Leu Arg Tyr Glu Lys Phe
    50                  55                  60

Phe Phe Thr Val Lys Met Thr Val Arg Ser Asn Arg Pro Phe Arg Thr
65                  70                  75                  80

Tyr Ser Asp Val Ala Ala Ala Val Ser His Trp Asp His Met Tyr Ile
                85                  90                  95

Gly Met Ala Gly Lys Arg Pro Phe Tyr Lys Ile Leu Ala Phe Leu Gly
            100                 105                 110

Ser Ser Asn Leu Lys Ala Thr Pro Ala Val Leu Ala Asp Gln Gly Gln
        115                 120                 125

Pro Glu Tyr His Thr His Cys Glu Gly Arg Ala Tyr Leu Pro His Arg
    130                 135                 140

Met Gly Lys Thr Pro Pro Met Leu Asn Val Pro Glu His Phe Arg Arg
145                 150                 155                 160

Pro Phe Asn Ile Gly Leu Tyr Lys Gly Thr Ile Glu Leu Thr Met Thr
                165                 170                 175

Ile Tyr Asp Asp Glu Ser Leu Glu Ala Ala Pro Met Ile Trp Asp His
            180                 185                 190
```

```
Phe Asn Ser Ser Lys Phe Ser Asp Phe Arg Glu Lys Ala Leu Met Phe
            195                 200                 205

Gly Leu Ile Val Glu Lys Lys Ala Ser Gly Ala Trp Val Leu Asp Ser
            210                 215                 220

Ile Ser His Phe Lys
225

<210> SEQ ID NO 33
<211> LENGTH: 229
<212> TYPE: PRT
<213> ORGANISM: Vesicular stomatitis virus

<400> SEQUENCE: 33

Met Ser Ser Leu Lys Lys Ile Leu Gly Leu Lys Gly Lys Gly Lys Lys
  1               5                  10                  15

Ser Lys Lys Leu Gly Ile Ala Pro Pro Tyr Glu Glu Asp Thr Asn
             20                  25                  30

Met Glu Tyr Ala Pro Ser Ala Pro Ile Asp Lys Ser Tyr Phe Gly Val
            35                  40                  45

Asp Glu Met Asp Thr His Asp Pro His Gln Leu Arg Tyr Glu Lys Phe
        50                  55                  60

Phe Phe Thr Val Lys Met Thr Val Arg Ser Asn Arg Pro Phe Arg Thr
 65                  70                  75                  80

Tyr Ser Asp Val Ala Ala Val Ser His Trp Asp His Met Tyr Ile
                85                  90                  95

Gly Met Ala Gly Lys Arg Pro Phe Tyr Lys Ile Leu Ala Phe Leu Gly
            100                 105                 110

Ser Ser Asn Leu Lys Ala Thr Pro Ala Val Leu Ala Asp Gln Gly Gln
            115                 120                 125

Pro Glu Tyr His Ala His Cys Glu Gly Arg Ala Tyr Leu Pro His Arg
            130                 135                 140

Met Gly Lys Thr Pro Pro Met Leu Asn Val Pro Glu His Phe Arg Arg
145                 150                 155                 160

Pro Phe Asn Ile Gly Leu Tyr Lys Gly Thr Val Glu Leu Thr Met Thr
                165                 170                 175

Ile Tyr Asp Asp Glu Ser Leu Glu Ala Ala Pro Met Ile Trp Asp His
            180                 185                 190

Phe Asn Ser Ser Lys Phe Ser Asp Phe Arg Glu Lys Ala Leu Met Phe
            195                 200                 205

Gly Leu Ile Val Glu Lys Lys Ala Ser Gly Ala Trp Val Leu Asp Ser
            210                 215                 220

Val Ser His Phe Lys
225

<210> SEQ ID NO 34
<211> LENGTH: 229
<212> TYPE: PRT
<213> ORGANISM: Vesicular stomatitis virus

<400> SEQUENCE: 34

Met Ser Ser Leu Lys Lys Ile Leu Gly Leu Lys Gly Lys Gly Lys Lys
  1               5                  10                  15

Ser Lys Lys Leu Gly Ile Ala Pro Pro Tyr Glu Glu Asp Thr Asn
             20                  25                  30

Met Glu Tyr Ala Pro Ser Ala Pro Ile Asp Lys Ser Tyr Phe Gly Val
            35                  40                  45
```

```
Asp Glu Met Asp Thr His Asp Pro His Gln Leu Arg Tyr Glu Lys Phe
 50                  55                  60
Phe Phe Thr Val Lys Met Thr Val Arg Ser Asn Arg Pro Phe Arg Thr
 65                  70                  75                  80
Tyr Ser Asp Val Ala Ala Ala Val Ser His Trp Asp His Met Tyr Ile
                 85                  90                  95
Gly Met Ala Gly Lys Arg Pro Phe Tyr Lys Ile Leu Ala Phe Leu Gly
                100                 105                 110
Ser Ser Asn Leu Lys Ala Thr Pro Ala Val Leu Ala Asp Gln Gly Gln
             115                 120                 125
Pro Glu Tyr His Ala His Cys Glu Gly Arg Ala Tyr Leu Pro His Arg
         130                 135                 140
Met Gly Lys Thr Pro Pro Met Leu Asn Val Pro Glu His Phe Arg Arg
145                 150                 155                 160
Pro Phe Asn Ile Gly Leu Tyr Lys Gly Thr Val Glu Leu Thr Met Thr
                165                 170                 175
Ile Tyr Asp Asp Glu Ser Leu Glu Ala Ala Pro Met Ile Trp Asp His
             180                 185                 190
Phe Asn Ser Ser Lys Phe Ser Asp Phe Arg Glu Lys Ala Leu Met Phe
         195                 200                 205
Gly Leu Ile Val Glu Lys Lys Ala Ser Gly Ala Trp Val Leu Asp Ser
     210                 215                 220
Val Ser His Phe Lys
225

<210> SEQ ID NO 35
<211> LENGTH: 229
<212> TYPE: PRT
<213> ORGANISM: Vesicular stomatitis virus

<400> SEQUENCE: 35

Met Ser Ser Leu Lys Lys Ile Leu Gly Leu Lys Gly Lys Gly Lys Lys
  1               5                  10                  15
Ser Lys Lys Leu Gly Ile Ala Pro Pro Pro Tyr Glu Glu Asp Thr Asn
                 20                  25                  30
Met Glu Tyr Ala Pro Ser Ala Pro Ile Asp Lys Ser Tyr Phe Gly Val
             35                  40                  45
Asp Glu Arg Asp Thr His Asp Pro His Gln Leu Arg Tyr Glu Lys Phe
 50                  55                  60
Phe Phe Thr Val Lys Met Thr Val Arg Ser Asn Arg Pro Phe Arg Thr
 65                  70                  75                  80
Tyr Ser Asp Val Ala Ala Ala Val Ser His Trp Asp His Met Tyr Ile
                 85                  90                  95
Gly Met Ala Gly Lys Arg Pro Phe Tyr Lys Ile Leu Ala Phe Leu Gly
                100                 105                 110
Ser Ser Asn Leu Lys Ala Thr Pro Ala Val Leu Ala Asp Gln Gly Gln
             115                 120                 125
Pro Glu Tyr His Ala His Cys Glu Gly Arg Ala Tyr Leu Pro His Arg
         130                 135                 140
Met Gly Lys Thr Pro Pro Met Leu Asn Val Pro Glu His Phe Arg Arg
145                 150                 155                 160
Pro Phe Asn Ile Gly Leu Tyr Lys Gly Thr Val Glu Leu Thr Met Thr
                165                 170                 175
Ile Tyr Asp Asp Glu Ser Leu Glu Ala Ala Pro Met Ile Trp Asp His
             180                 185                 190
```

```
Phe Asn Ser Ser Lys Phe Ser Asp Phe Arg Glu Lys Ala Leu Met Phe
    195                 200                 205
Gly Leu Ile Val Glu Lys Lys Ala Ser Gly Ala Trp Val Leu Asp Ser
    210                 215                 220
Val Ser His Phe Lys
225
```

<210> SEQ ID NO 36
<211> LENGTH: 1536
<212> TYPE: DNA
<213> ORGANISM: Vesicular stomatitis virus

<400> SEQUENCE: 36

```
atgaagtgcc ttttgtactt agccttttta ttcattgggg tgaattgcaa gttcaccata    60
gttttttccac acaaccaaaa aggaaactgg aaaaatgttc cttctaatta ccattattgc   120
ccgtcaagct cagatttaaa ttggcataat gacttaatag gcacagccat acaagtcaaa   180
atgcccaaga gtcacaaggc tattcaagca gacggttgga tgtgtcatgc ttccaaatgg   240
gtcactactt gtgatttccg ctggtatgga ccgaagtata acacagtc catccgatcc    300
ttcactccat ctgtagaaca atgcaaggaa agcattgaac aaacgaaaca aggaacttgg   360
ctgaatccag gcttccctcc tcaaagttgt ggatatgcaa ctgtgacgga tgccgaagca   420
gtgattgtcc aggtgactcc tcaccatgtg ctggttgatg aatacacagg agaatgggtt   480
gattcacagt tcatcaacgg aaaatgcagc aattacatat gccccactgt ccataactct   540
acaacctggc attctgacta taaggtcaaa gggctatgtg attctaacct catttccatg   600
gacatcacct tcttctcaga ggacggagag ctatcatccc tgggaaagga gggcacaggg   660
ttcagaagta actactttgc ttatgaaact ggaggcaagg cctgcaaaat gcaatactgc   720
aagcattggg gagtcagact cccatcaggt gtctggttcg agatggctga taaggatctc   780
tttgctgcag ccagattccc tgaatgccca gaagggtcaa gtatctctgc tccatctcag   840
acctcagtgg atgtaagtct aattcaggac gttgagagga tcttggatta ttccctctgc   900
caagaaacct ggagcaaaat cagagcgggt cttccaatct ctccagtgga tctcagctat   960
cttgctccta aaaacccagg aaccggtcct gcttcacca taatcaatgg taccctaaaa  1020
tactttgaga ccagatacat cagagtcgat attgctgctc caatcctctc aagaatggtc  1080
ggaatgatca gtggaactac cacagaaagg gaactgtggg atgactgggc accatatgaa  1140
gacgtggaaa ttgacccaa tggagttctg aggaccagtt caggatataa gtttcctta   1200
tacatgattg gacatggtat gttggactcc gatcttcatc ttagctcaaa ggctcaggtg  1260
ttcgaacatc ctcacattca agacgctgct tcgcaacttc ctgatgatga gagtttattt  1320
tttggtgata ctgggctatc caaaaatcca atcgagcttg tagaaggttg gttcagtagt  1380
tggaaaagct ctattgcctc ttttttcttt atcatagggt taatcattgg actattcttg  1440
gttctccgag ttggtatcca tctttgcatt aaattaaagc acaccaagaa agacagatt   1500
tatacagaca tagagatgaa ccgacttgga aagtaa                             1536
```

<210> SEQ ID NO 37
<211> LENGTH: 885
<212> TYPE: DNA
<213> ORGANISM: Vesicular stomatitis virus
<220> FEATURE:
<221> NAME/KEY: modified_base
<222> LOCATION: (1)..(885)
<223> OTHER INFORMATION: "n" represents a, t, c, g, other or unknown

<400> SEQUENCE: 37

```
atgaagtgcc ttttgkactt agctttttta ttcatcgggg tgaattgcaa gttcaccata      60
gttttttccat acaaccaaaa aggaaactgg aaaaatgttc cttccaatta ccattattgc    120
ccgtcaagct cagatttaaa ttgncataat gacttaatag gcacagcctt acaagtcaaa    180
atgcccaaga gtcacaaggc tattcaagca gacggttgga tgtgtcatgc ttccaaatgg    240
gtcactactt gtgatttccg ctggtacgga ccgaagtata acacattc catccgatcc      300
ttcactccat ctgtagaaca atgcaaggaa agcattgaac aaacgaaaca aggaacttgg    360
ctgaatccag gcttccctcc tcaaagttgt ggatatgcaa ctgtgacgga tgctgaagca    420
gcgattgtcc aggtgactcc tcaccatgtg cttgttgatg aatacacagg agaatgggtt    480
gattcacagt tcatcaacgg aaaatgcagc aatgacatat gccccactgt ccataactcc    540
acaacctggc attccgacta aaggtcaaa gggctatgtg attctaacct catttccatg     600
gacatcacct tcttctcaga ggacggagag ctatcatccc taggaaagga gggcacaggg    660
ttcagaagta actactttgc ttatgaaact ggagacaagg cctgcaaaat gcagtactgc    720
aagcgttggg gagtcagact cccatcaggt gtctggttcg agatggctga taaggatctc    780
tttgctgcag ccagattccc tgaatgccca gaagggtcaa gtatctctgc tccatctcag    840
acctcagtgg atgtaagtct cattcaggac gttgagagga tcttg                    885

<210> SEQ ID NO 38
<211> LENGTH: 705
<212> TYPE: DNA
<213> ORGANISM: Vesicular stomatitis virus

<400> SEQUENCE: 38
ccatctcaga cctcagtgga tgtaagtctc attcaggacg ttgagaggat cttggattat     60
tccctctgcc aagaaacctg gagcaaaatc agagcgggtc ttcccatctc tccagtggat    120
ctcagctatc ttgctcctaa aaacccagga accggtcctg tctttaccat aatcaatggt    180
accctaaaat actttgagac cagatacatc agagtcgata ttgctgctcc aatcctctca    240
agaatggtcg gaatgatcag tggaactacc acagaaaggg aactgtggga tgactgggct    300
ccatatgaag acgtggaaat tggacccaat ggagttctga ggaccagttc aggatataag    360
tttccttta atatgattgg acatggtatg ttggactccg atcttcatct tagctcaaag    420
gctcaggtgt ttgaacatcc tcacattcaa gacgctgctt cgcagcttcc tgatgatgag    480
actttatttt tggtgatac tgggctatcc aaaaatccaa tcgagtttgt agaaggttgg    540
ttcagtagtt ggaagagctc tattgcctct ttttctttta tcatagggtt aatcattgga    600
ctattcttgg ttctccgagt tggtatttat cttttgcatta aattaaagca caccaagaaa    660
agacagattt atacagacat agagatgaac cgacttggga agtaa                   705

<210> SEQ ID NO 39
<211> LENGTH: 1536
<212> TYPE: DNA
<213> ORGANISM: Vesicular stomatitis virus

<400> SEQUENCE: 39
atgaagtgcc ttttgtactt agctttttta ttcatcgggg tgaattgcaa gttcaccata      60
gttttttccat acaaccgaaa aggaaactgg aaaaatgttc cttccaatta ccattattgc    120
ccgtcaagct cagatttaaa ttggcataat gacttaatag gcacagcctt acaagtcaaa    180
atgcccaaga gtcacaaggc tattcaagca gacggttgga tgtgtcatgc ttccaaatgg    240
gtcactactt gtgatttccg ctggtacgga ccgaagtata acacattc catccgatcc      300
```

```
ttcactccat ctgtagaaca atgcaaggaa agcattgaac aaacgaaaca aggaacttgg      360
ctgaatccag gcttccctcc tcaaagttgt ggatatgcaa ctgtgacgga tgctgaagca      420
gcgattgtcc aggtgactcc tcaccatgtg cttgttgatg aatacacagg agaatgggtt      480
gattcacagt tcatcaacgg aaaatgcagc aatgacatat gccccactgt ccataactcc      540
acaacctggc attccgacta taaggtcaaa gggctatgtg attctaacct catttccatg      600
gacatcacct tcttctcaga ggacggagag ctatcatccc taggaaagga gggcacaggg      660
ttcagaagta actactttgc ttatgaaact ggagacaagg cctgcaaaat gcagtactgc      720
aagcattggg gagtcagact cccatcaggt gtctggttcg agatggctga taaggatctc      780
tttgctgcag ccagattccc tgaatgccca gaagggtcaa gtatctctgc tccatctcag      840
acctcagtgg atgtaagtct cattcaggac gttgagagga tcttggatta ttccctctgc      900
caagaaacct ggagcaaaat cagagcgggt cttcccatct ctccagtgga tctcagctat      960
cttgctccta aaaacccagg aaccggtcct gctttcacca taatcaatgg taccctaaaa     1020
tactttgaga ccagatacat cagagtcgat attgctgctc caatcctctc aagaatggtc     1080
ggaatgatca gtggaactac cacagaaagg gaactgtggg atgactgggc tccatatgaa     1140
gacgtggaaa ttggacccaa tggagttctg aggaccagtt caggatataa gtttcctttta     1200
tatatgattg acatggtat gttggactcc gatcttcatc ttagctcaaa ggctcaggtg     1260
tttgaacatc ctcacattca agacgctght gcgcagcttc ctgatgatga actttatttt     1320
tttggtgata ctgggctatc caaaaatcca atcgagtttg tagaaggttg gttcagtagt     1380
tggaagagct ctattgcctc tttttttcttt atcatagggt taatcattgg actattcttg     1440
gttctccgag ttggtattta tctttgcatt aaattaaagc acaccaagaa aagacagatt     1500
tatacagaca tagagatgaa ccgacttggg aagtaa                                1536

<210> SEQ ID NO 40
<211> LENGTH: 1399
<212> TYPE: DNA
<213> ORGANISM: Vesicular stomatitis virus

<400> SEQUENCE: 40
atgaagtgcc ttttgtactt agcttttttta ttcatcgggg tgaattgcaa gttcaccata       60
gttttttccat acaaccaaaa aggaaactgg aaaaatgttc cttccaatta ccattattgc      120
ccgtcaagct cagatttaaa ttggcataat gacttaatag gcacagcctt acaggtcaaa      180
atgcccaaga gtcacaaggc tattcaagca gacggttgga tgtgtcatgc ttccaaatgg      240
gtcactactt tgtgatttcg ctggtacgga ccgaagtata taacacattc catccgatcc      300
ttcactccat ctgtagaaca atgcaaggaa agcattgaac aaacgaaaca aggaacttgg      360
ctgaatccag gcttccctcc tcaaagttgt ggatatgcaa ctgtgacgga tgctgaagca      420
gcgattgtcc aggtgactcc tcaccatgtg cttgttgatg aatacacagg agaatgggtt      480
gattcacagt tcatcaacgg aaaatgcagc aatgacatat gccccactgt ccataactcc      540
acaacctggc attccgacta taaggtcaaa gggctatgtg attctaacct catttccatg      600
gacatcacct tcttctcaga ggacggagag ctatcatccc taggaaagga gggcacaggg      660
ttcagaagta actactttgc ttatgaaact ggagacaagg cctgcaaaat gcagtactgc      720
aagcgttggg gagtcagact cccatcaggt gtctggttcg ggatggctga taaggatctc      780
tttgctgcag ccagattccc tgaatgccca gaagggtcaa gtatctctgc tccatctcag      840
acctcagtgg atgtaagtct cattcaggac gttgagagga tcttactttg agaccagata      900
```

-continued

```
catcagagtc gatattgctg ctccaatcct ctcaagaatg gtcggaatga tcagtggaac    960
taccacagaa agggaactgt gggatgactg ggctccatat gaagacgtgg aaattggacc   1020
caatggagtt ctgaggacca gttcaggata taagtttcct ttatatatga ttggacatgg   1080
tatgttggac tccgatcttc atcttagctc aaaggctcag gtgtttgaac atcctcacat   1140
tcaagacgct gcttcgcagc ttcctgatga tgagacttta ttttttggtg atactgggct   1200
atccaaaaat ccaatcgagt ttgtagaagg ttggttcagt agttggaaga gctctattgc   1260 ctctttttc tttatcatag ggttaatcat tggactattc ttggttctcc gagttggtat   1320
ttatctttgc attaaattaa agcacaccaa gaaaagacag atttatacag acatagagat   1380
gaaccgactt gggaagtaa                                                1399
```

<210> SEQ ID NO 41
<211> LENGTH: 511
<212> TYPE: PRT
<213> ORGANISM: Vesicular stomatitis virus

<400> SEQUENCE: 41

```
Met Lys Cys Leu Leu Tyr Leu Ala Phe Leu Phe Ile Gly Val Asn Cys
  1               5                  10                  15

Lys Phe Thr Ile Val Phe Pro His Asn Gln Lys Gly Asn Trp Lys Asn
             20                  25                  30

Val Pro Ser Asn Tyr His Tyr Cys Pro Ser Ser Ser Asp Leu Asn Trp
         35                  40                  45

His Asn Asp Leu Ile Gly Thr Ala Ile Gln Val Lys Met Pro Lys Ser
     50                  55                  60

His Lys Ala Ile Gln Ala Asp Gly Trp Met Cys His Ala Ser Lys Trp
 65                  70                  75                  80

Val Thr Thr Cys Asp Phe Arg Trp Tyr Gly Pro Lys Tyr Ile Thr Gln
                 85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Val Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
        195                 200                 205

Gly Glu Leu Ser Ser Leu Gly Lys Glu Gly Thr Gly Phe Arg Ser Asn
    210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285
```

```
Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
                340                 345                 350

Ala Pro Ile Leu Ser Arg Met Val Gly Met Ile Ser Gly Thr Thr Thr
                355                 360                 365

Glu Arg Glu Leu Trp Asp Asp Trp Ala Pro Tyr Glu Asp Val Glu Ile
370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
                420                 425                 430

Leu Pro Asp Asp Glu Ser Leu Phe Phe Gly Asp Thr Gly Leu Ser Lys
                435                 440                 445

Asn Pro Ile Glu Leu Val Glu Gly Trp Phe Ser Ser Trp Lys Ser Ser
450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
                485                 490                 495

Lys Arg Gln Ile Tyr Thr Asp Ile Glu Met Asn Arg Leu Gly Lys
                500                 505                 510

<210> SEQ ID NO 42
<211> LENGTH: 295
<212> TYPE: PRT
<213> ORGANISM: Vesicular stomatitis virus
<220> FEATURE:
<221> NAME/KEY: MOD_RES
<222> LOCATION: (1)..(295)
<223> OTHER INFORMATION: "Xaa" represents any, other or unknown amino
      acid

<400> SEQUENCE: 42

Met Lys Cys Leu Leu Xaa Leu Ala Phe Leu Phe Ile Gly Val Asn Cys
  1               5                  10                  15

Lys Phe Thr Ile Val Phe Pro Tyr Asn Gln Lys Gly Asn Trp Lys Asn
                 20                  25                  30

Val Pro Ser Asn Tyr His Tyr Cys Pro Ser Ser Ser Asp Leu Asn Xaa
             35                  40                  45

His Asn Asp Leu Ile Gly Thr Ala Leu Gln Val Lys Met Pro Lys Ser
         50                  55                  60

His Lys Ala Ile Gln Ala Asp Gly Trp Met Cys His Ala Ser Lys Trp
 65                  70                  75                  80

Val Thr Thr Cys Asp Phe Arg Trp Tyr Gly Pro Lys Tyr Ile Thr His
                 85                  90                  95

Ser Ile Arg Ser Phe Thr Pro Ser Val Glu Gln Cys Lys Glu Ser Ile
                100                 105                 110

Glu Gln Thr Lys Gln Gly Thr Trp Leu Asn Pro Gly Phe Pro Pro Gln
            115                 120                 125
```

```
Ser Cys Gly Tyr Ala Thr Val Thr Asp Ala Glu Ala Ile Val Gln
130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
                165                 170                 175

Val His Asn Ser Thr Thr Trp His Ser Asp Tyr Lys Val Lys Gly Leu
                180                 185                 190

Cys Asp Ser Asn Leu Ile Ser Met Asp Ile Thr Phe Phe Ser Glu Asp
                195                 200                 205

Gly Glu Leu Ser Ser Leu Gly Lys Glu Gly Thr Gly Phe Arg Ser Asn
210                 215                 220

Tyr Phe Ala Tyr Glu Thr Gly Asp Lys Ala Cys Lys Met Gln Tyr Cys
225                 230                 235                 240

Lys Arg Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
                260                 265                 270

Ser Ser Ile Ser Ala Pro Ser Gln Thr Ser Val Asp Val Ser Leu Ile
                275                 280                 285

Gln Asp Val Glu Arg Ile Leu
290                 295

<210> SEQ ID NO 43
<211> LENGTH: 234
<212> TYPE: PRT
<213> ORGANISM: Vesicular stomatitis virus

<400> SEQUENCE: 43

Pro Ser Gln Thr Ser Val Asp Val Ser Leu Ile Gln Asp Val Glu Arg
1               5                   10                  15

Ile Leu Asp Tyr Ser Leu Cys Gln Glu Thr Trp Ser Lys Ile Arg Ala
                20                  25                  30

Gly Leu Pro Ile Ser Pro Val Asp Leu Ser Tyr Leu Ala Pro Lys Asn
            35                  40                  45

Pro Gly Thr Gly Pro Val Phe Thr Ile Ile Asn Gly Thr Leu Lys Tyr
        50                  55                  60

Phe Glu Thr Arg Tyr Ile Arg Val Asp Ile Ala Ala Pro Ile Leu Ser
65                  70                  75                  80

Arg Met Val Gly Met Ile Ser Gly Thr Thr Thr Glu Arg Glu Leu Trp
                85                  90                  95

Asp Asp Trp Ala Pro Tyr Glu Asp Val Glu Ile Gly Pro Asn Gly Val
            100                 105                 110

Leu Arg Thr Ser Ser Gly Tyr Lys Phe Pro Leu Tyr Met Ile Gly His
        115                 120                 125

Gly Met Leu Asp Ser Asp Leu His Leu Ser Ser Lys Ala Gln Val Phe
130                 135                 140

Glu His Pro His Ile Gln Asp Ala Ala Ser Gln Leu Pro Asp Asp Glu
145                 150                 155                 160

Thr Leu Phe Phe Gly Asp Thr Gly Leu Ser Lys Asn Pro Ile Glu Phe
                165                 170                 175

Val Glu Gly Trp Phe Ser Ser Trp Lys Ser Ser Ile Ala Ser Phe Phe
            180                 185                 190

Phe Ile Ile Gly Leu Ile Ile Gly Leu Phe Leu Val Leu Arg Val Gly
        195                 200                 205
```

```
Ile Tyr Leu Cys Ile Lys Leu Lys His Thr Lys Arg Gln Ile Tyr
210                 215                 220

Thr Asp Ile Glu Met Asn Arg Leu Gly Lys
225                 230
```

<210> SEQ ID NO 44
<211> LENGTH: 511
<212> TYPE: PRT
<213> ORGANISM: Vesicular stomatitis virus
<220> FEATURE:
<221> NAME/KEY: MOD_RES
<222> LOCATION: (1)..(511)
<223> OTHER INFORMATION: "Xaa" represents any, other or unknown amino acid

<400> SEQUENCE: 44

```
Met Lys Cys Leu Leu Tyr Leu Ala Phe Leu Phe Ile Gly Val Asn Cys
 1               5                  10                  15

Lys Phe Thr Ile Val Phe Pro Tyr Asn Arg Lys Gly Asn Trp Lys Asn
                20                  25                  30

Val Pro Ser Asn Tyr His Tyr Cys Pro Ser Ser Ser Asp Leu Asn Trp
            35                  40                  45

His Asn Asp Leu Ile Gly Thr Ala Leu Gln Val Lys Met Pro Lys Ser
 50                  55                  60

His Lys Ala Ile Gln Ala Asp Gly Trp Met Cys His Ala Ser Lys Trp
 65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
            115                 120                 125

Ser Cys Gly Tyr Ala Thr Val Thr Asp Ala Glu Ala Ala Ile Val Gln
130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
            195                 200                 205

Gly Glu Leu Ser Ser Leu Gly Lys Glu Gly Thr Gly Phe Arg Ser Asn
210                 215                 220

Tyr Phe Ala Tyr Glu Thr Gly Asp Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
                260                 265                 270

Ser Ser Ile Ser Ala Pro Ser Gln Thr Ser Val Asp Val Ser Leu Ile
            275                 280                 285

Gln Asp Val Glu Arg Ile Leu Asp Tyr Ser Leu Cys Gln Glu Thr Trp
            290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
```

```
                         325                 330                 335
Gly Thr Leu Lys Tyr Phe Glu Thr Arg Tyr Ile Arg Val Asp Ile Ala
                340                 345                 350

Ala Pro Ile Leu Ser Arg Met Val Gly Met Ile Ser Gly Thr Thr Thr
            355                 360                 365

Glu Arg Glu Leu Trp Asp Asp Trp Ala Pro Tyr Glu Asp Val Glu Ile
        370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Xaa Ala Gln
                420                 425                 430

Leu Pro Asp Asp Glu Thr Leu Phe Phe Gly Asp Thr Gly Leu Ser Lys
            435                 440                 445

Asn Pro Ile Glu Phe Val Glu Gly Trp Phe Ser Ser Trp Lys Ser Ser
        450                 455                 460

Ile Ala Ser Phe Phe Ile Ile Gly Leu Ile Ile Gly Leu Phe Leu
465                 470                 475                 480

Val Leu Arg Val Gly Ile Tyr Leu Cys Ile Lys Leu Lys His Thr Lys
                485                 490                 495

Lys Arg Gln Ile Tyr Thr Asp Ile Glu Met Asn Arg Leu Gly Lys
            500                 505                 510

<210> SEQ ID NO 45
<211> LENGTH: 465
<212> TYPE: PRT
<213> ORGANISM: Vesicular stomatitis virus

<400> SEQUENCE: 45

Met Lys Cys Leu Leu Tyr Leu Ala Phe Leu Phe Ile Gly Val Asn Cys
  1               5                  10                  15

Lys Phe Thr Ile Val Phe Pro Tyr Asn Gln Lys Gly Asn Trp Lys Asn
                 20                  25                  30

Val Pro Ser Asn Tyr His Tyr Cys Pro Ser Ser Ser Asp Leu Asn Trp
             35                  40                  45

His Asn Asp Leu Ile Gly Thr Ala Leu Gln Val Lys Met Pro Lys Ser
         50                  55                  60

His Lys Ala Ile Gln Ala Asp Gly Trp Met Cys His Ala Ser Lys Trp
 65                  70                  75                  80

Val Thr Thr Cys Asp Phe Arg Trp Tyr Gly Pro Lys Tyr Ile Thr His
                 85                  90                  95

Ser Ile Arg Ser Phe Thr Pro Ser Val Glu Gln Cys Lys Glu Ser Ile
                100                 105                 110

Glu Gln Thr Lys Gln Gly Thr Trp Leu Asn Pro Gly Phe Pro Pro Gln
            115                 120                 125

Ser Cys Gly Tyr Ala Thr Val Thr Asp Ala Glu Ala Ala Ile Val Gln
        130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
```

```
                195                 200                 205
Gly Glu Leu Ser Ser Leu Gly Lys Glu Gly Thr Gly Phe Arg Ser Asn
    210                 215                 220

Tyr Phe Ala Tyr Glu Thr Gly Asp Lys Ala Cys Lys Met Gln Tyr Cys
225                 230                 235                 240

Lys Arg Trp Gly Val Arg Leu Pro Ser Gly Val Trp Phe Gly Met Ala
                245                 250                 255

Asp Lys Asp Leu Phe Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Tyr Phe Glu Thr Arg Tyr Ile Arg Val Asp
    290                 295                 300

Ile Ala Ala Pro Ile Leu Ser Arg Met Val Gly Met Ile Ser Gly Thr
305                 310                 315                 320

Thr Thr Glu Arg Glu Leu Trp Asp Asp Trp Ala Pro Tyr Glu Asp Val
                325                 330                 335

Glu Ile Gly Pro Asn Gly Val Leu Arg Thr Ser Ser Gly Tyr Lys Phe
            340                 345                 350

Pro Leu Tyr Met Ile Gly His Gly Met Leu Asp Ser Asp Leu His Leu
        355                 360                 365

Ser Ser Lys Ala Gln Val Phe Glu His Pro His Ile Gln Asp Ala Ala
    370                 375                 380

Ser Gln Leu Pro Asp Asp Glu Thr Leu Phe Phe Gly Asp Thr Gly Leu
385                 390                 395                 400

Ser Lys Asn Pro Ile Glu Phe Val Glu Gly Trp Phe Ser Ser Trp Lys
                405                 410                 415

Ser Ser Ile Ala Ser Phe Phe Phe Ile Ile Gly Leu Ile Ile Gly Leu
            420                 425                 430

Phe Leu Val Leu Arg Val Gly Ile Tyr Leu Cys Ile Lys Leu Lys His
        435                 440                 445

Thr Lys Lys Arg Gln Ile Tyr Thr Asp Ile Glu Met Asn Arg Leu Gly
    450                 455                 460

Lys
465

<210> SEQ ID NO 46
<211> LENGTH: 6330
<212> TYPE: DNA
<213> ORGANISM: Vesicular stomatitis virus

<400> SEQUENCE: 46
atggaagtcc acgattttga gaccgacgag ttcaatgatt tcaatgaaga tgactatgcc      60
acaagagaat tcctgaatcc cgatgagcgc atgacgtact tgaatcatgc tgattacaat     120
ttgaattctc ctctaattag tgatgatatt gacaatttga tcaggaaatt caattctctt     180
ccgattccct cgatgtggga tagtaagaac tgggatggag ttcttgagat gttaacatca     240
tgtcaagcca atcccatctc aacatctcag atgcataaat ggatgggaag ttggttaatg     300
tctgataatc atgatgccag tcaagggtat agttttttac atgaagtgga caaagaggca     360
gaaataacat tgacgtggt ggagaccttc atccgcggct ggggcaacaa accaattgaa      420
tacatcaaaa aggaaagatg gactgactca ttcaaaattc tcgcttattt gtgtcaaaag     480
tttttggact acacaagtt gacattaatc ttaaatgctg tctctgaggt ggaattgctc      540
aacttggcga ggactttcaa aggcaaagtc agaagaagtt ctcatggaac gaacatatgc     600
```

```
aggattaggg ttcccagctt gggtcctact tttatttcag aaggatgggc ttacttcaag      660
aaacttgata ttctaatgga ccgaaacttt ctgttaatgg tcaaagatgt gattataggg      720
aggatgcaaa cggtgctatc catggtatgt agaatagaca acctgttctc agagcaagac      780
atcttctccc ttctaaatat ctacagaatt ggagataaaa ttgtggagag gcagggaaat      840
ttttcttatg acttgattaa aatggtggaa ccgatatgca acttgaagct gatgaaatta      900
gcaagagaat caaggccttt agtcccacaa ttccctcatt ttgaaaatca tatcaagact      960
tctgttgatg aaggggcaaa aattgaccga ggtataagat tcctccatga tcagataatg     1020
agtgtgaaaa cagtggatct cacactggtg atttatggat cgttcagaca ttggggtcat     1080
ccttttatag attattacac tggactagaa aaattacatt cccaagtaac catgaagaaa     1140
gatattgatg tgtcatatgc aaaagcactt gcaagtgatt tagctcggat tgttctattt     1200
caacagttca atgatcataa aaagtggttc gtgaatggag acttgctccc tcatgatcat     1260 cccttaaaa gtcatgttaa agaaaataca tggcccacag ctgctcaagt tcaagatttt     1320
ggagataaat ggcatgaact tccgctgatt aaatgttttg aaatacccga cttactagac     1380
ccatcgataa tatactctga caaaagtcat tcaatgaata ggtcagaggt gttgaaacat     1440
gtccgaatga atccgaacac tcctatccct agtaaaaagg tgttgcagac tatgttggac     1500
acaaaggcta ccaattggaa agaatttctt aaagagattg atgagaaggg cttagatgat     1560
gatgatctaa ttattggtct taaaggaaag gagagggaac tgaagttggc aggtagattt     1620
ttctccctaa tgtcttggaa attgcgagaa tactttgtaa ttaccgaata tttgataaag     1680
actcatttcg tccctatgtt taaaggcctg acaatggcgg acgatctaac tgcagtcatt     1740
aaaaagatgt tagattcctc atccggccaa ggattgaagt catatgaggc aatttgcata     1800
gccaatcaca ttgattacga aaaatggaat aaccaccaaa ggaagttatc aaacggccca     1860
gtgttccgag ttatgggcca gttcttaggt tatccatcct taatcgagag aactcatgaa     1920
ttttttgaga aaagtcttat atactacaat ggaagaccag acttgatgcg tgttcacaac     1980
aacacactga tcaattcaac ctcccaacga gtttgttggc aaggacaaga gggtggactg     2040
gaaggtctac ggcaaaaagg atggactatc ctcaatctac tggttattca aagagaggct     2100
aaaatcagaa acactgctgt caaagtcttg gcacaaggtg ataatcaagt tatttgcaca     2160
cagtataaaa cgaagaaatc gagaaacgtt gtagaattac agggtgctct caatcaaatg     2220
gtttctaata atgagaaaat tatgactgca atcaaaatag ggacagggaa gttaggactt     2280
ttgataaatg acgatgagac tatgcaatct gcagattact tgaattatgg aaaaataccg     2340
attttccgtg gagtgattag agggttagag accaagagat ggtcacgagt gacttgtgtc     2400
accaatgacc aaatacccac ttgtgctaat ataatgagct cagtttccac aaatgctctc     2460
accgtagctc attttgctga aacccaatc aatgccatga tacagtacaa ttattttggg     2520
acatttgcta gactcttgtt gatgatgcat gatcctgctc ttcgtcaatc attgtatgaa     2580
gttcaagata agatacccgg cttgcacagt tctactttca aatacgccat gttgtatttg     2640 gaccccttcca ttggaggagt gtcgggcatg tctttgtcca ggttttttgat tagagccttc     2700 ccagatcccg taacagaaag tctctcattc tggagattca tccatgtaca tgctcgaagt     2760
gagcatctga aggagatgag tgcagtattt ggaaaccccg agatagccaa gtttcgaata     2820
actcacatag acaagctagt agaagatcca acctctctga acatcgctat gggaatgagt     2880
ccagcgaact tgttaaagac tgaggttaaa aaatgcttaa tcgaatcaag acaaaccatc     2940
aggaaccagg tgattaagga tgcaaccata tatttgtatc atgaagagga tcggctcaga     3000
```

```
agtttcttat ggtcaataaa tcctctgttc cctagatttt taagtgaatt caaatcaggc    3060
acttttttgg gagtcgcaga cgggctcatc agtctatttc aaaattctcg tactattcgg    3120
aactccttta agaaaagta tcatagggaa ttggatgatt tgattgtgag gagtgaggta    3180
tcctctttga cacatttagg gaaacttcat ttgagaaggg gatcatgtaa aatgtggaca    3240
tgttcagcta ctcatgctga cacattaaga tacaaatcct ggggccgtac agttattggg    3300
acaactgtac cccatccatt agaaatgttg ggtccacaac atcgaaaaga gactccttgt    3360
gcaccatgta acacatcagg gttcaattat gtttctgtgc attgtccaga cgggatccat    3420
gacgtcttta gttcacgggg accattgcct gcttatctag ggtctaaaac atctgaatct    3480
acatctattt tgcagccttg ggaaagggaa agcaaagtcc cactgattaa aagagctaca    3540
cgtcttagag atgctatctc ttggtttgtt gaacccgact ctaaactagc aatgactata    3600
ctttctaaca tccactcttt aacaggcgaa gaatggacca aaaggcagca tgggttcaaa    3660
agaacagggt ctgcccttca taggttttcg acatctcgga tgagccatgg tgggttcgca    3720
tctcagagca ctgcagcatt gaccaggttg atggcaacta cagacaccat gagggatctg    3780
ggagatcaga atttcgactt tttattccaa gcaacgttgc tctatgctca aattaccacc    3840
actgttgcaa gagacggatg gatcaccagt tgtacagatc attatcatat tgcctgtaag    3900
tcctgtttga gacccataga agagatcacc ctggactcaa gtatggacta cacgccccca    3960
gatgtatccc atgtgctgaa gacatggagg aatggggaag gttcgtgggg acaagagata    4020
aaacagatct atcctttaga agggaattgg aagaatttag cacctgctga gcaatcctat    4080
caagtcggca gatgtatagg ttttctatat ggagacttgg cgtatagaaa atctactcat    4140
gccgaggaca gttctctatt tcctctatct atacaaggtc gtattagagg tcgaggtttc    4200
ttaaaagggt tgctagacgg attaatgaga gcaagttgct gccaagtaat acaccggaga    4260
agtctggctc atttgaagag gccggccaac gcagtgtacg gaggtttgat ttacttgatt    4320
gataaattga gtgtatcacc tccattcctt tctcttacta gatcaggacc tattagagac    4380
gaattagaaa cgattcccca caagatccca acctcctatc cgacaagcaa ccgtgatatg    4440
ggggtgattg tcagaaatta cttcaaatac caatgccgtc taattgaaaa gggaaaatac    4500
agatcacatt attcacaatt atggttattc tcagatgtct tatccataga cttcattgga    4560
ccattctcta tttccaccac cctctgcaa atcctataca agccattttt atctgggaaa    4620
gataagaatg agttgagaga gctggcaaat cttctcttcat tgctaagatc aggagagggg    4680
tgggaagaca tacatgtgaa attcttcacc aaggacatat tattgtgtcc agaggaaatc    4740
agacatgctt gcaagttcgg gattgctaag gataataata aagacatgag ctatccccct    4800
tggggaaggg aatccagagg gacaattaca acaatccctg tttattatac gaccacccct    4860
tacccaaaga tgctagagat gcctccaaga atccaaaatc ccctgctgtc cggaatcagg    4920
ttgggccaat taccaactgg cgctcattat aaaattcgga gtatattaca tggaatggga    4980
atccattaca gggacttctt gagttgtgga gacggctccg gagggatgac tgctgcatta    5040
ctacgagaaa atgtgcatag cagaggaata ttcaatagtc tgttagaatt atcagggtca    5100
gtcatgcgag cgcctctcc tgagcccccc agtgccctag aaactttagg aggagataaa    5160
tcgagatgtg taaatggtga aacatgttgg gaatatccat ctgacttatg tgacccaagg    5220
acttgggact atttcctccg actcaaagca ggcttggggc ttcaaattga tttaattgta    5280
atggatatgg aagttcggga ttcttctact agcctgaaaa ttgagacgaa tgttagaaat    5340
tatgtgcacc ggattttgga tgagcaagga gttttaatct acaagactta tggaacatat    5400
```

```
atttgtgaga gcgaaaagaa tgcagtaaca atccttggtc ccatgttcaa gacggtcgac    5460
ttagttcaaa cagaatttag tagttctcaa acgtctgaag tatatatggt atgtaaaggt    5520
ttgaagaaat taatcgatga acccaatccc gattggtctt ccatcaatga atcctggaaa    5580
aacctgtacg cattccagtc atcagaacag gaatttgcca gagcaaagaa ggttagtaca    5640
tactttacct tgacaggtat tccctcccaa ttcattcctg atccttttgt aaacattgag    5700
actatgctac aaatattcgg agtacccacg ggtgtgtctc atgcggctgc cttaaaatca    5760
tctgatagac ctgcagattt attgaccatt agcctttttt atatggcgat tatatcgtat    5820
tataacatca atcatatcag agtaggaccg atacctccga accccccatc agatggaatt    5880
gcacaaaatg tggggatcgc tataactggt ataagctttt ggctgagttt gatggagaaa    5940
gacattccac tatatcaaca gtgtttagca gttatccagc aatcattccc gattaggtgg    6000
gaggctgttt cagtaaaagg aggatacaag cagaagtgga gtactagagg tgatgggctc    6060
ccaaaagata cccgaacttc agactccttg gccccaatcg ggaactggat cagatctctg    6120
gaattggtcc gaaaccaagt tcgtctaaat ccattcaatg agatcttgtt caatcagcta    6180
tgtcgtacag tggataatca tttgaaatgg tcaaatttgc gaagaaacac aggaatgatt    6240
gaatggatca atagacgaat tcaaaagaa gaccggtcta tactgatgtt gaagagtgac    6300
ctacacgagg aaaactcttg gagagattaa                                    6330

<210> SEQ ID NO 47
<211> LENGTH: 5327
<212> TYPE: DNA
<213> ORGANISM: Vesicular stomatitis virus

<400> SEQUENCE: 47
cattggggtc atccttttat agattattac gctggwctag aaaaattaca ttcccaagtw      60
accatkaaga aagatattga tgtgtcatat gcraaagcac ttgcaagtga tttagctcgg     120
attgttctat ttcaacagtt caatgatcat amaaagtggt tcgtgaatgg agacttgctc     180
cctcatgatc atcccttaa aagtcatgtt aaagaaaata catggcccac agctgctcaa     240
gttcaagatt ttggagataa atggcatgaa cttccgctga ttaaatgttt tgaaataccc     300
gacttactag acccatcgat aatatactct gacaaaagtc attcaatgaa taggtcagag     360
gtgttgaaac atgtccgaat gaatccgaac actcctatcc ctagtaaaaa ggtgttgcag     420
actatgttgg acacaaaggc taccaattgg aaagaatttc ttaaagagat tgatgagaag     480
ggcttagatg atgatgatct aattattggt cttaaaggaa aggagaggga actgaagttg     540
gcaggtagat ttttctccct aatgtcttgg aaattgcgag aatactttgt aattaccgaa     600
tatttgataa agactcattt cgtccctatg tttaaaggcc tgacaatggc ggacgatcta     660
actgcagtca ttaaaaagat gttagattcc tcatccggcc aaggattgaa gtcatatgag     720
gcaatttgca tagccaatca cattgattac gaaaaatgga ataaccacca aggaagtta     780 tcaaacggcc cagtgttccg agttatgggc cagttcttag ttatccatc cttaatcgag     840 agaactcatg aattttttga gaaaagtctt atatactaca atggaagacc agacttgatg     900
cgtgttcaca caacacact gatcaattca acctcccaac gagtttgttg gcaaggacaa     960
gagggtggac tggaaggtct acggcaaaaa ggatggagta tcctcaatct actggttatt    1020
caaagagagg ctaaaatcag aaacactgct gtcaaagtct tggcacaagg tgataatcaa    1080
gttatttgca cacagtataa aacgaagaaa tcgagaaacg ttgtagaatt acagggtgct    1140
ctcaatcaaa tggtttctaa taatgagaaa attatgactg caatcaaaat agggacaggg    1200
```

```
aagttaggac ttttgataaa tgacgatgag actatgcaat ctgcagatta cttgaattat    1260
ggaaaaatac cgatttttccg tggagtgatt agagggttag agaccaagag atggtcacga   1320
gtgacttgtg tcaccaatga ccaaataccc acttgtgcta atataatgag ctcagttttcc   1380 acaaatgctc tcaccgtagc tcattttgct gagaacccaa tcaatgccat gatacagtac   1440
aattattttg ggacatttgc tagactcttg ttgatgatgc atgatcctgc tcttcgtcaa    1500
tcattgtatg aagttcaaga taagataccg ggcttgcaca gttctacttt caaatacgcc    1560
atgttgtatt tggacccttc cattggagga gtgtcgggca tgtctttgtc caggtttttg    1620
attagagcct tcccagatcc cgtaacagaa agtctctcat tctggagatt catccatgta    1680
catgctcgaa gtgagcatct gaaggagatg agtgcagtat ttggaaaccc cgagatagcc    1740
aagtttcgaa taactcacat agacaagcta gtagaagatc caacctctct gaacatcgct    1800
atgggaatga gtccagcgaa cttgttaaag actgaggtta aaaaatgctt aatcgaatca    1860
agacaaacca tcaggaacca ggtgattaag gatgcaacca tatatttgta tcatgaagag    1920
gatcggctca gaagtttctt atggtcaata aatcctctgt tccctagatt tttaagtgaa    1980
ttcaaatcag gcacttttt gggagtcgca gacgggctca tcagtctatt tcaaaattct    2040
cgtactattc ggaactcctt taagaaaaag tatcataggg aattggatga tttgattgtg    2100
aggagtgagg tatcctcttt gacacattta gggaaacttc atttgagaag gggatcatgt    2160
aaaatgtgga catgttcagc tactcatgct gacacattaa gatacaaatc ctggggccgt    2220
acagttattg ggacaactgt acccatcca ttagaaatgt tgggtccaca acatcgaaaa     2280
gagactcctt gtgcaccatg taacacatca gggttcaatt atgtttctgt gcattgtcca    2340
gacgggatcc atgacgtctt tagttcacgg ggaccattgc ctgcttatct agggtctaaa    2400
acatctgaat ctacatctat tttgcagcct tgggaaaggg aaagcaaagt cccactgatt    2460
aaaagagcta cacgtcttag agatgctatc tcttggtttg ttgaacccga ctctaaaacta   2520 gcaatgacta tactttctaa catccactct ttaacaggcg aagaatggac caaaaggcag    2580
catgggttca aaagaacagg gtctgccctt cataggtttt cgacatctcg gatgagccat    2640
ggtgggttcg catctcagag cactgcagca ttgaccaggt tgatggcaac tacagacacc    2700
atgagggatc tgggagatca gaatttcgac tttttattcc aggcaacgtt gctctatgct    2760
cagattacca ccactgttgc aagagacgga tggatcacca gttgtacaga tcattatcat    2820
attgcctgta agtcctgttt gagacccata gaagagatca ccctggactc aagtatggac    2880
tacacgcccc cagatgtatc ccatgtgctg aagacatgga ggaatgggga aggttcgtgg    2940
ggacaagaga taaaacagat ctatccttta aagggaatt ggaagaattt agcacctgct    3000
gagcaatcct atcaagtcgg cagatgtata ggttttctat atggagactt ggcgtataga    3060
aaatctactc atgccgagga cagttctcta tttcctctat ctatacaagg tcgtattaga    3120
ggtcgaggtt tcttaaaagg gttgctagac ggattaatga gagcaagttg ctgccaagta    3180
atacaccgga gaagtctggc tcatttgaag aggccggcca acgcagtgta cggaggtttg    3240
atttacttga ttgataaatt gagtgtatca cctccattcc tttctcttac tagatcagga    3300
cctattagag acgaattaga aacgattccc cacaagatcc caacctccta tccgacaagc    3360
aaccgtgata tgggggtgat tgtcagaaat tacttcaaat accaatgccg tctaattgaa    3420
aagggaaaat acagatcaca ttattcacaa ttatggttat tctcagatgt cttatccata    3480
gacttcattg gaccattctc tatttccacc accctcttgc aaatcctata caagccattt    3540
ttatctggga aagataagaa tgagttgaga gagctggcaa atctttcttc attgctaaga    3600
```

```
tcaggagagg ggtgggaaga catacatgtg aaattcttca ccaaggacat attattgtgt    3660
ccagaggaaa tcagacatgc ttgcaagttc gggattgcta aggataataa taaagacatg    3720
agctatcccc cttggggaag ggaatccaga gggacaatta caacaatccc tgtttattat    3780
acgaccaccc cttacccaaa gatgctagag atgcctccaa gaatccaaaa tcccctgctg    3840
tccggaatca ggttgggcca gttaccaact ggcgctcatt ataaaattcg gagtatatta    3900
catggaatgg gaatccatta cagggacttc ttgagttgtg gagacggctc cggagggatg    3960
actgctgcat tactacgaga aaatgtgcat agcagaggaa tattcaatag tctgttagaa    4020
ttatcagggt cagtcatgcg aggcgcctct cctgagcccc ccagtgccct agaaacttta    4080
ggaggagata atcgagatg tgtaaatggt gaaacatgtt gggaatatcc atctgactta    4140
tgtgacccaa ggacttggga ctatttcctc cgactcaaag caggcttggg gcttcaaatt    4200
gatttaattg taatggatat ggaagttcgg gattcttcta ctagcctgaa aattgagacg    4260
aatgttagaa attatgtgca ccggattttg gatgagcaag gagttttaat ctacaagact    4320
tatggaacat atatttgtga gagcgaaaag aatgcagtaa caatccttgg tcccatgttc    4380
aagacggtcg acttagttca aacagaattt agtagttctc aaacgtctga agtatatatg    4440
gtatgtaaag gtttgaagaa attaatcgat gaacccaatc ccgattggtc ttccatcaat    4500
gaatcctgga aaaacctgta cgcattccag tcatcagaac aggaatttgc cagagcaaag    4560
aaggttagta catactttac cttgacaggt attccctccc aattcattcc tgatccttt    4620 gtgaacattg agactatgct acaaatattc ggagtaccca cggtgtgtc tcatgcggct    4680 gccttaaaat catctgatag acctgcagat ttattgacca ttagcctttt ttatatggcg    4740
attatatcgt attataacat caatcatatc agagtaggac cgatacctcc gaaccccca    4800 tcagatggaa ttgcacaaaa tgtggggatc gctataactg gtataagctt ttggctgagt    4860
ttgatggaga aagacattcc actatatcaa cagtgtttag cagttatcca gcaatcattc    4920
ccgattaggt gggaggctgt ttcagtaaaa ggaggataca agcagaagtg gagtactaga    4980
ggtgatgggc tcccaaaaga tacccgaatt tcagactcct tggccccaat cgggaactgg    5040
atcagatctc tggaattggt ccgaaaccaa gttcgtctaa atccattcaa tgagatcttg    5100
ttcaatcagc tatgtcgtac agtggataat catttgaaat ggtcaaattt gcgaaaaaac    5160
acaggaatga ttgaatggat caatagacga atttcaaaag aagaccggtc tatactgatg    5220
ttgaagagtg acctcatga ggaaaactct tggagagatt aaaaaatcat gaggagactc    5280
caaactttaa gtatgaaaaa aactttgatc cttaagaccc tcttgtg                 5327

<210> SEQ ID NO 48
<211> LENGTH: 348
<212> TYPE: DNA
<213> ORGANISM: Vesicular stomatitis virus

<400> SEQUENCE: 48
atggaagtcc acgattttga gaccgacgag ttcaatgatt tcaatgaaga tgactatgcc      60
acaagagaat tcctgaatcc cgatgagcgc atgacgtact tgaatcatgc tgattacaat      120
ttgaattctc ctctaattag tgatgatatt gacaatttga tcaggaaatt caattctctt     180
ccgattccct cgatgtggga tagtaagaac tgggatgagt tcttgagat gttaacatca      240 tgtcaagcca atcccatctc aacatctcag atgcataaat ggatgggaag ttggttaatg    300
tctgataatc atgatgccag tcaagggtat agtttttta cgaagtg                   348
```

<210> SEQ ID NO 49
<211> LENGTH: 6330
<212> TYPE: DNA
<213> ORGANISM: Vesicular stomatitis virus
<220> FEATURE:
<221> NAME/KEY: modified_base
<222> LOCATION: (1)..(6330)
<223> OTHER INFORMATION: "n" represents a, t, c, g, other or unknown

<400> SEQUENCE: 49

| | | | | | |
|---|---|---|---|---|---|
| atggaagtcc | acgattttga | gaccgacgag | ttcaatgatt | tcaatgaaga | tgactatgcc      60 |
| acaagagaat | tcctgaatcc | cgatgagcgc | atgacgtact | tgaatcatgc | tgattacaat     120 |
| ttgaattctc | ctctaattag | tgatgatatt | gacaatttga | tcaggaaatt | caattctctt     180 |
| ccgattccct | cgatgtggga | tagtaagaac | tgggatggag | ttcttgagat | gttaacatca     240 |
| tgtcaagcca | atcccatctc | aacatctcag | atgcataaat | ggatgggaag | ttggttaatg     300 |
| tctgataatc | atgatgccag | tcaagggtat | agttttttac | atgaagtgga | caaagaggca     360 |
| gaaataacat | ttgacgtggt | ggagaccttc | atccgcggct | ggggcaacaa | accaattgaa     420 |
| tacatcaaaa | aggaaagatg | gactgactca | ttcaaaattc | tcgcttattt | gtgtcaaaag     480 |
| tttttggact | tacacaagtt | gacattaatc | ttaaatgctg | tctctgaggt | ggaattgctc     540 |
| aacttggcga | ggactttcaa | aggcaaagtc | agaagaagtt | ctcatggaac | gaacatatgc     600 |
| aggcttaggg | ttcccagctt | gggtcctact | tttatttcag | aaggatgggc | ttacttcaag     660 |
| aaacttgata | ttctaatgga | ccgaaacttt | ctgttaatgg | tcaaagatgt | gattataggg     720 |
| aggatgcaaa | cggtgctatc | catggtatgt | agaatagaca | acctgttctc | agagcaagac     780 |
| atcttctccc | ttctaaatat | ctacagaatt | ggagataaaa | ttgtggagag | cagggaaat     840 |
| ttttcttatg | acttgattaa | aatggtggaa | ccgatatgca | acttgaggct | gatgaaatta     900 |
| gcaagagaat | caaggccttt | agtcccacaa | ttccctcatt | ttgaaaatca | tatcaagact     960 |
| tctgttgatg | aagggggcaaa | aattgaccga | ggtataagat | tcctccatga | tcagataatg    1020 |
| agtgtgaaaa | cagtggatct | cacactggtg | atttatggat | cgttcagaca | ttggggtcat    1080 |
| ccttttatag | attattacgc | tggactagaa | aaattacatt | cccaagtaac | catgaagaaa    1140 |
| gatattgatg | tgtcatatgc | aaaagcactt | gcaagtgatt | tagctcggat | tgttctattt    1200 |
| caacagttca | atgatcataa | aaagtggttc | gtgaatggag | acttgctccc | tcatgatcat    1260 |
| cccttttaaaa | gtcatgttaa | agaaaataca | tggcccacag | ctgctcaagt | tcaagatttt    1320 |
| ggagataaat | ggcatgaact | tccgctgatt | aaatgttttg | aaataccega | cttactagac    1380 |
| ccatcgataa | tatactctga | caaaagtcat | tcaatgaata | ggtcagaggt | gttgaaacat    1440 |
| gtccgaatga | atccgaacac | tcctatccct | agtaaaaagg | tgttgcagac | tatgttggac    1500 |
| acaaaggcta | ccaattggaa | agaatttctt | aaagagattg | atgagaaggg | cttagatgat    1560 |
| gatgatctaa | ttattggtct | taaaggaaag | gagagggaac | tgaagttggc | aggtagattt    1620 |
| ttctcccctaa | tgtcttggaa | attgcgagaa | tactttgtaa | ttaccgaata | tttgataaag    1680 |
| actcatttcg | tccctatgtt | taaaggcctg | acaatggcgg | acgatctaac | tgcagtcatt    1740 |
| aaaaagatgt | tagattcctc | atccggccaa | ggattgaagt | catatgaggc | aatttgcata    1800 |
| gccaatcaca | ttgattacga | aaaatggaat | aaccaccaaa | ggaagttatc | aaacggccca    1860 |
| gtgttccgag | ttatgggcca | gttcttaggt | tatccatcct | taatcgagag | aactcatgaa    1920 |
| ttttttgaga | aaagtcttat | atactacaat | ggaagaccag | acttgatgcg | tgttcacaac    1980 |
| aacacactga | tcaattcaac | ctcccaacga | gtttgttggc | aaggacaaga | gggtggactg    2040 |
| gaaggtctac | ggcaaaaagg | atggagtatc | ctcaatctac | tggttattca | aagagaggct    2100 |

```
aaaatcagaa acactgctgt caaagtcttg gcacaaggtg ataatcaagt tatttgcaca    2160
cagtataaaa cgaagaaatc gagaaacgtt gtagaattac agggtgctct caatcaaatg    2220
gtttctaata atgagaaaat tatgactgca atcaaaatag ggacagggaa gttaggactt    2280
ttgataaatg acgatgagac tatgcaatct gcagattact tgaattatgg aaaaatacca    2340
attttccgtg gagtgattag agggttagag accaagagat ggtcacgagt gacttgtgtc    2400
accaatgacc aaatacccac ttgtgctaat ataatgagct cagtttccac aaatgctctc    2460
accgtagctc attttgctga gaacccaatc aatgccatga tacagtacaa ttattttggg    2520
acatttgcta gactcttgtt gatgatgcat gatcctgctc ttcgtcaatc attgtatgaa    2580
gttcaagata agataccggg cttgcacagt tctactttca aatacgccat gttgtatttg    2640
gacccttcca ttggaggagt gtcgggcatg tctttgtcca ggttttgat tagagccttc     2700 ccagatcccg taacagaaag tctctcattc tggagattca tccatgtaca tgctcgaagt    2760
gagcatctga aggagatgag tgcagtattt ggaaaccccg atagccaa gtttcgaata      2820 actcacatag acaagctagt agaagatcca acctctctga acatcgctat gggaatgagt    2880
ccagcgaact tgttaaagac tgaggttaaa aaatgcttaa tcgaatcaag acaaaccatc    2940
aggaaccagg tgattaagga tgcaaccata tatttgtatc atgaagagga tcggctcaga    3000
agtttcttat ggtcaataaa tcctctgttc cctagatttt taagtgaatt caatcaggc     3060 acttttttgg gagtcgcaga cgggctcatc agtctatttc aaaattctcg tactattcgg    3120 aactcccttta agaaaagta tcatagggaa ttggatgatt tgattgtgag gagtgaggta    3180
tcctctttga cacatttagg gaaacttcat ttgagaaggg gatcatgtaa aatgtggaca    3240
tgttcagcta ctcatgctga cacattaaga tacaaatcct ggggccgtac agttattggg    3300
acaactgtac cccatccatt agaaatgttg ggtccacaac atcgaaaaga gactccttgt    3360
gcaccatgta acacatcagg gttcaattat gtttctgtgc attgtccaga cgggatccat    3420
gacgtcttta gttcacgggg accattgcct gcttatctag ggtctaaaac atctgaatct    3480
acatctattt tgcagccttg ggaaagggaa agcaaagtcc cactgattaa agagctaca    3540 cgtcttagag atgctatctc ttggtttgtt gaacccgact ctaaactagc aatgactata    3600 cttttctaaca tccactcttt aacaggcgaa gaatggacca aaaggcagca tgggttcaaa    3660
agaacagggt ctgcccttca taggttttcg acatctcgga tgagccatgg tgggttcgca    3720
tctcagagca ctgcagcatt gaccaggttg atggcaacta cagacaccat gagggatctg    3780
ggagatcaga atttcgactt tttattccan gcaacgttgc tctatgctca nattaccacc    3840
actgttgcaa gagacggatg gatcaccagt tgtacagatc attatcatat tgcctgtaag    3900
tcctgtttga gacccataga agagatcacc ctggactcaa gtatggacta cacgccccca    3960
gatgtatccc atgtgctgaa gacatggagg aatggggaag gttcgtgggg acaagagata    4020
aaacagatct atcctttaga agggaattgg aagaatttag cacctgctga gcaatcctat    4080
caagtcggca gatgtatagg ttttctatat ggagacttgg cgtatagaaa atctactcat    4140
gccgaggaca gttctctatt tcctctatct atacaaggtc gtattagagg tcgaggtttc    4200 ttaaagggt tgctagacgg attaatgaga gcaagttgct gccaagtaat acaccggaga    4260
agtctggctc atttgaagag gccggccaac gcagtgtacg gaggtttgat ttacttgatt    4320
gataaattga gtgtatcacc tccattcctt tctcttacta gatcaggacc tattagagac    4380
gaattagaaa cgattcccca caagatccca acctcctatc cgacaagcaa ccgtgatatg    4440
ggggtgattg tcagaaatta cttcaaatac caatgccgtc taattgaaaa gggaaaatac    4500
```

```
agatcacatt attcacaatt atggttattc tcagatgtct tatccataga cttcattgga    4560
ccattctcta tttccaccac cctcttgcaa atcctataca agccattttt atctgggaaa    4620
gataagaatg agttgagaga gctggcaaat ctttcttcat tgctaagatc aggagagggg    4680
tgggaagaca tacatgtgaa attcttcacc aaggacatat tattgtgtcc agaggaaatc    4740
agacatgctt gcaagttcgg gattgctaag gataataata aagacatgag ctatccccct    4800
tggggaaggg aatccagagg gacaattaca acaatccctg tttattatac gaccacccct    4860
tacccaaaga tgctagagat gcctccaaga atccaaaatc ccctgctgtc cggaatcagg    4920
ttgggccagt taccaactgg cgctcattat aaaattcgga gtatattaca tggaatggga    4980
atccattaca gggacttctt gagttgtgga gacggctccg gagggatgac tgctgcatta    5040
ctacgagaaa atgtgcatag cagaggaata ttcaatagtc tgttagaatt atcagggtca    5100
gtcatgcgag gcgcctctcc tgagcccccc agtgccctag aaactttagg aggagataaa    5160
tcgagatgtg taaatggtga acatgttggg aatatccat ctgacttatg tgacccaagg    5220
acttgggact atttcctccg actcaaagca ggcttggggc ttcaaattga tttaattgta    5280
atggatatgg aagttcggga ttcttctact agcctgaaaa ttgagacgaa tgttagaaat    5340
tatgtgcacc ggattttgga tgagcaagga gttttaatct acaagactta tggaacatat    5400
atttgtgaga gcgaaaagaa tgcagtaaca atccttggtc ccatgttcaa gacggtcgac    5460
ttagttcaaa cagaatttag tagttctcaa acgtctgaag tatatatggt atgtaaaggt    5520
ttgaagaaat taatcgatga acccaatccc gattggtctt ccatcaatga atcctggaaa    5580
aacctgtacg cattccagtc atcagaacag gaatttgcca gagcaaagaa ggttagtaca    5640
tactttacct tgacaggtat tccctcccaa ttcattcctg atccttttgt gaacattgag    5700
actatgctac aaatattcgg agtacccacg ggtgtgtctc atgcggctgc cttaaaatca    5760
tctgatagac ctgcagattt attgaccatt agcctttttt atatggcgat tatatcgtat    5820
tataacatca atcatatcag agtaggaccg atacctccga acccccatc agatggaatt    5880 gcacaaaatg tggggatcgc tataactggt ataagctttt ggctgagttt gatggagaaa    5940
gacattccac tatatcaaca gtgtttagca gttatccagc aatcattccc gattaggtgg    6000
gaggctgttt cagtaaaagg aggatacaag cagaagtgga gtactagagg tgatgggctc    6060
ccaaaagata cccgaatttc agactccttg gccccaatcg ggaactggat cagatctctg    6120
gaattggtcc gaaaccaagt tcgtctaaat ccattcaatg agatcttgtt caatcagcta    6180
tgtcgtacag tggataatca tttgaaatgg tcaaatttgc gaaaaaacac aggaatgatt    6240
gaatggatca atagacgaat ttcaaaagaa gaccggtcta tactgatgtt gaagagtgac    6300
ctacatgagg aaaactcttg gagagattaa                                   6330
```

<210> SEQ ID NO 50
<211> LENGTH: 2109
<212> TYPE: PRT
<213> ORGANISM: Vesicular stomatitis virus

<400> SEQUENCE: 50

```
Met Glu Val His Asp Phe Glu Thr Asp Glu Phe Asn Asp Phe Asn Glu
 1               5                  10                  15

Asp Asp Tyr Ala Thr Arg Glu Phe Leu Asn Pro Asp Glu Arg Met Thr
             20                  25                  30

Tyr Leu Asn His Ala Asp Tyr Asn Leu Asn Ser Pro Leu Ile Ser Asp
         35                  40                  45
```

-continued

```
Asp Ile Asp Asn Leu Ile Arg Lys Phe Asn Ser Leu Pro Ile Pro Ser
 50                  55                  60

Met Trp Asp Ser Lys Asn Trp Asp Gly Val Leu Glu Met Leu Thr Ser
 65                  70                  75                  80

Cys Gln Ala Asn Pro Ile Ser Thr Ser Gln Met His Lys Trp Met Gly
                 85                  90                  95

Ser Trp Leu Met Ser Asp Asn His Asp Ala Ser Gln Gly Tyr Ser Phe
            100                 105                 110

Leu His Glu Val Asp Lys Glu Ala Glu Ile Thr Phe Asp Val Val Glu
        115                 120                 125

Thr Phe Ile Arg Gly Trp Gly Asn Lys Pro Ile Glu Tyr Ile Lys Lys
130                 135                 140

Glu Arg Trp Thr Asp Ser Phe Lys Ile Leu Ala Tyr Leu Cys Gln Lys
145                 150                 155                 160

Phe Leu Asp Leu His Lys Leu Thr Leu Ile Leu Asn Ala Val Ser Glu
                165                 170                 175

Val Glu Leu Leu Asn Leu Ala Arg Thr Phe Lys Gly Lys Val Arg Arg
            180                 185                 190

Ser Ser His Gly Thr Asn Ile Cys Arg Ile Arg Val Pro Ser Leu Gly
        195                 200                 205

Pro Thr Phe Ile Ser Glu Gly Trp Ala Tyr Phe Lys Lys Leu Asp Ile
210                 215                 220

Leu Met Asp Arg Asn Phe Leu Leu Met Val Lys Asp Val Ile Ile Gly
225                 230                 235                 240

Arg Met Gln Thr Val Leu Ser Met Val Cys Arg Ile Asp Asn Leu Phe
                245                 250                 255

Ser Glu Gln Asp Ile Phe Ser Leu Leu Asn Ile Tyr Arg Ile Gly Asp
            260                 265                 270

Lys Ile Val Glu Arg Gln Gly Asn Phe Ser Tyr Asp Leu Ile Lys Met
        275                 280                 285

Val Glu Pro Ile Cys Asn Leu Lys Leu Met Lys Leu Ala Arg Glu Ser
    290                 295                 300

Arg Pro Leu Val Pro Gln Phe Pro His Phe Glu Asn His Ile Lys Thr
305                 310                 315                 320

Ser Val Asp Glu Gly Ala Lys Ile Asp Arg Gly Ile Arg Phe Leu His
                325                 330                 335

Asp Gln Ile Met Ser Val Lys Thr Val Asp Leu Thr Leu Val Ile Tyr
            340                 345                 350

Gly Ser Phe Arg His Trp Gly His Pro Phe Ile Asp Tyr Tyr Thr Gly
        355                 360                 365

Leu Glu Lys Leu His Ser Gln Val Thr Met Lys Lys Asp Ile Asp Val
    370                 375                 380

Ser Tyr Ala Lys Ala Leu Ala Ser Asp Leu Ala Arg Ile Val Leu Phe
385                 390                 395                 400

Gln Gln Phe Asn Asp His Lys Lys Trp Phe Val Asn Gly Asp Leu Leu
                405                 410                 415

Pro His Asp His Pro Phe Lys Ser His Val Lys Glu Asn Thr Trp Pro
            420                 425                 430

Thr Ala Ala Gln Val Gln Asp Phe Gly Asp Lys Trp His Glu Leu Pro
        435                 440                 445

Leu Ile Lys Cys Phe Glu Ile Pro Asp Leu Leu Asp Pro Ser Ile Ile
    450                 455                 460

Tyr Ser Asp Lys Ser His Ser Met Asn Arg Ser Glu Val Leu Lys His
465                 470                 475                 480
```

```
Val Arg Met Asn Pro Asn Thr Pro Ile Pro Ser Lys Lys Val Leu Gln
                485                 490                 495

Thr Met Leu Asp Thr Lys Ala Thr Asn Trp Lys Glu Phe Leu Lys Glu
            500                 505                 510

Ile Asp Glu Lys Gly Leu Asp Asp Asp Leu Ile Ile Gly Leu Lys
        515                 520                 525

Gly Lys Glu Arg Glu Leu Lys Leu Ala Gly Arg Phe Phe Ser Leu Met
    530                 535                 540

Ser Trp Lys Leu Arg Glu Tyr Phe Val Ile Thr Glu Tyr Leu Ile Lys
545                 550                 555                 560

Thr His Phe Val Pro Met Phe Lys Gly Leu Thr Met Ala Asp Asp Leu
                565                 570                 575

Thr Ala Val Ile Lys Lys Met Leu Asp Ser Ser Ser Gly Gln Gly Leu
            580                 585                 590

Lys Ser Tyr Glu Ala Ile Cys Ile Ala Asn His Ile Asp Tyr Glu Lys
        595                 600                 605

Trp Asn Asn His Gln Arg Lys Leu Ser Asn Gly Pro Val Phe Arg Val
    610                 615                 620

Met Gly Gln Phe Leu Gly Tyr Pro Ser Leu Ile Glu Arg Thr His Glu
625                 630                 635                 640

Phe Phe Glu Lys Ser Leu Ile Tyr Tyr Asn Gly Arg Pro Asp Leu Met
                645                 650                 655

Arg Val His Asn Asn Thr Leu Ile Asn Ser Thr Ser Gln Arg Val Cys
            660                 665                 670

Trp Gln Gly Gln Glu Gly Gly Leu Glu Gly Leu Arg Gln Lys Gly Trp
        675                 680                 685

Thr Ile Leu Asn Leu Leu Val Ile Gln Arg Glu Ala Lys Ile Arg Asn
    690                 695                 700

Thr Ala Val Lys Val Leu Ala Gln Gly Asp Asn Gln Val Ile Cys Thr
705                 710                 715                 720

Gln Tyr Lys Thr Lys Lys Ser Arg Asn Val Val Glu Leu Gln Gly Ala
                725                 730                 735

Leu Asn Gln Met Val Ser Asn Asn Glu Lys Ile Met Thr Ala Ile Lys
            740                 745                 750

Ile Gly Thr Gly Lys Leu Gly Leu Leu Ile Asn Asp Asp Glu Thr Met
        755                 760                 765

Gln Ser Ala Asp Tyr Leu Asn Tyr Gly Lys Ile Pro Ile Phe Arg Gly
    770                 775                 780

Val Ile Arg Gly Leu Glu Thr Lys Arg Trp Ser Arg Val Thr Cys Val
785                 790                 795                 800

Thr Asn Asp Gln Ile Pro Thr Cys Ala Asn Ile Met Ser Ser Val Ser
                805                 810                 815

Thr Asn Ala Leu Thr Val Ala His Phe Ala Glu Asn Pro Ile Asn Ala
            820                 825                 830

Met Ile Gln Tyr Asn Tyr Phe Gly Thr Phe Ala Arg Leu Leu Leu Met
        835                 840                 845

Met His Asp Pro Ala Leu Arg Gln Ser Leu Tyr Glu Val Gln Asp Lys
    850                 855                 860

Ile Pro Gly Leu His Ser Ser Thr Phe Lys Tyr Ala Met Leu Tyr Leu
865                 870                 875                 880

Asp Pro Ser Ile Gly Gly Val Ser Gly Met Ser Leu Ser Arg Phe Leu
                885                 890                 895

Ile Arg Ala Phe Pro Asp Pro Val Thr Glu Ser Leu Ser Phe Trp Arg
```

-continued

```
                900             905             910
Phe Ile His Val His Ala Arg Ser Glu His Leu Lys Glu Met Ser Ala
        915                 920                 925
Val Phe Gly Asn Pro Glu Ile Ala Lys Phe Arg Ile Thr His Ile Asp
        930                 935                 940
Lys Leu Val Glu Asp Pro Thr Ser Leu Asn Ile Ala Met Gly Met Ser
945                 950                 955                 960
Pro Ala Asn Leu Leu Lys Thr Glu Val Lys Lys Cys Leu Ile Glu Ser
                965                 970                 975
Arg Gln Thr Ile Arg Asn Gln Val Ile Lys Asp Ala Thr Ile Tyr Leu
            980                 985                 990
Tyr His Glu Glu Asp Arg Leu Arg Ser Phe Leu Trp Ser Ile Asn Pro
        995                 1000                1005
Leu Phe Pro Arg Phe Leu Ser Glu Phe Lys Ser Gly Thr Phe Leu Gly
        1010                1015                1020
Val Ala Asp Gly Leu Ile Ser Leu Phe Gln Asn Ser Arg Thr Ile Arg
1025                1030                1035                1040
Asn Ser Phe Lys Lys Lys Tyr His Arg Glu Leu Asp Asp Leu Ile Val
                1045                1050                1055
Arg Ser Glu Val Ser Ser Leu Thr His Leu Gly Lys Leu His Leu Arg
            1060                1065                1070
Arg Gly Ser Cys Lys Met Trp Thr Cys Ser Ala Thr His Ala Asp Thr
        1075                1080                1085
Leu Arg Tyr Lys Ser Trp Gly Arg Thr Val Ile Gly Thr Thr Val Pro
        1090                1095                1100
His Pro Leu Glu Met Leu Gly Pro Gln His Arg Lys Glu Thr Pro Cys
1105                1110                1115                1120
Ala Pro Cys Asn Thr Ser Gly Phe Asn Tyr Val Ser Val His Cys Pro
                1125                1130                1135
Asp Gly Ile His Asp Val Phe Ser Ser Arg Gly Pro Leu Pro Ala Tyr
            1140                1145                1150
Leu Gly Ser Lys Thr Ser Glu Ser Thr Ser Ile Leu Gln Pro Trp Glu
        1155                1160                1165
Arg Glu Ser Lys Val Pro Leu Ile Lys Arg Ala Thr Arg Leu Arg Asp
        1170                1175                1180
Ala Ile Ser Trp Phe Val Glu Pro Asp Ser Lys Leu Ala Met Thr Ile
1185                1190                1195                1200
Leu Ser Asn Ile His Ser Leu Thr Gly Glu Glu Trp Thr Lys Arg Gln
                1205                1210                1215
His Gly Phe Lys Arg Thr Gly Ser Ala Leu His Arg Phe Ser Thr Ser
            1220                1225                1230
Arg Met Ser His Gly Gly Phe Ala Ser Gln Ser Thr Ala Ala Leu Thr
        1235                1240                1245
Arg Leu Met Ala Thr Thr Asp Thr Met Arg Asp Leu Gly Asp Gln Asn
        1250                1255                1260
Phe Asp Phe Leu Phe Gln Ala Thr Leu Leu Tyr Ala Gln Ile Thr Thr
1265                1270                1275                1280
Thr Val Ala Arg Asp Gly Trp Ile Thr Ser Cys Thr Asp His Tyr His
                1285                1290                1295
Ile Ala Cys Lys Ser Cys Leu Arg Pro Ile Glu Glu Ile Thr Leu Asp
            1300                1305                1310
Ser Ser Met Asp Tyr Thr Pro Pro Asp Val Ser His Val Leu Lys Thr
        1315                1320                1325
```

-continued

Trp Arg Asn Gly Glu Gly Ser Trp Gly Gln Glu Ile Lys Gln Ile Tyr
    1330                1335                1340

Pro Leu Glu Gly Asn Trp Lys Asn Leu Ala Pro Ala Glu Gln Ser Tyr
1345                1350                1355                1360

Gln Val Gly Arg Cys Ile Gly Phe Leu Tyr Gly Asp Leu Ala Tyr Arg
        1365                1370                1375

Lys Ser Thr His Ala Glu Asp Ser Ser Leu Phe Pro Leu Ser Ile Gln
            1380                1385                1390

Gly Arg Ile Arg Gly Arg Gly Phe Leu Lys Gly Leu Leu Asp Gly Leu
        1395                1400                1405

Met Arg Ala Ser Cys Cys Gln Val Ile His Arg Arg Ser Leu Ala His
    1410                1415                1420

Leu Lys Arg Pro Ala Asn Ala Val Tyr Gly Gly Leu Ile Tyr Leu Ile
1425                1430                1435                1440

Asp Lys Leu Ser Val Ser Pro Pro Phe Leu Ser Leu Thr Arg Ser Gly
            1445                1450                1455

Pro Ile Arg Asp Glu Leu Glu Thr Ile Pro His Lys Ile Pro Thr Ser
        1460                1465                1470

Tyr Pro Thr Ser Asn Arg Asp Met Gly Val Ile Val Arg Asn Tyr Phe
        1475                1480                1485

Lys Tyr Gln Cys Arg Leu Ile Glu Lys Gly Lys Tyr Arg Ser His Tyr
    1490                1495                1500

Ser Gln Leu Trp Leu Phe Ser Asp Val Leu Ser Ile Asp Phe Ile Gly
1505                1510                1515                1520

Pro Phe Ser Ile Ser Thr Thr Leu Leu Gln Ile Leu Tyr Lys Pro Phe
        1525                1530                1535

Leu Ser Gly Lys Asp Lys Asn Glu Leu Arg Glu Leu Ala Asn Leu Ser
        1540                1545                1550

Ser Leu Leu Arg Ser Gly Glu Gly Trp Glu Asp Ile His Val Lys Phe
        1555                1560                1565

Phe Thr Lys Asp Ile Leu Leu Cys Pro Glu Glu Ile Arg His Ala Cys
    1570                1575                1580

Lys Phe Gly Ile Ala Lys Asp Asn Asn Lys Asp Met Ser Tyr Pro Pro
1585                1590                1595                1600

Trp Gly Arg Glu Ser Arg Gly Thr Ile Thr Thr Ile Pro Val Tyr Tyr
        1605                1610                1615

Thr Thr Thr Pro Tyr Pro Lys Met Leu Glu Met Pro Pro Arg Ile Gln
            1620                1625                1630

Asn Pro Leu Leu Ser Gly Ile Arg Leu Gly Gln Leu Pro Thr Gly Ala
        1635                1640                1645

His Tyr Lys Ile Arg Ser Ile Leu His Gly Met Gly Ile His Tyr Arg
        1650                1655                1660

Asp Phe Leu Ser Cys Gly Asp Gly Ser Gly Gly Met Thr Ala Ala Leu
1665                1670                1675                1680

Leu Arg Glu Asn Val His Ser Arg Gly Ile Phe Asn Ser Leu Leu Glu
            1685                1690                1695

Leu Ser Gly Ser Val Met Arg Gly Ala Ser Pro Glu Pro Pro Ser Ala
            1700                1705                1710

Leu Glu Thr Leu Gly Gly Asp Lys Ser Arg Cys Val Asn Gly Glu Thr
        1715                1720                1725

Cys Trp Glu Tyr Pro Ser Asp Leu Cys Asp Pro Arg Thr Trp Asp Tyr
    1730                1735                1740

Phe Leu Arg Leu Lys Ala Gly Leu Gly Leu Gln Ile Asp Leu Ile Val
1745                1750                1755                1760

Met Asp Met Glu Val Arg Asp Ser Ser Thr Ser Leu Lys Ile Glu Thr
                1765                1770                1775

Asn Val Arg Asn Tyr Val His Arg Ile Leu Asp Glu Gln Gly Val Leu
            1780                1785                1790

Ile Tyr Lys Thr Tyr Gly Thr Tyr Ile Cys Glu Ser Glu Lys Asn Ala
        1795                1800                1805

Val Thr Ile Leu Gly Pro Met Phe Lys Thr Val Asp Leu Val Gln Thr
    1810                1815                1820

Glu Phe Ser Ser Ser Gln Thr Ser Glu Val Tyr Met Val Cys Lys Gly
1825                1830                1835                1840

Leu Lys Lys Leu Ile Asp Glu Pro Asn Pro Asp Trp Ser Ser Ile Asn
                1845                1850                1855

Glu Ser Trp Lys Asn Leu Tyr Ala Phe Gln Ser Ser Glu Gln Glu Phe
            1860                1865                1870

Ala Arg Ala Lys Lys Val Ser Thr Tyr Phe Thr Leu Thr Gly Ile Pro
        1875                1880                1885

Ser Gln Phe Ile Pro Asp Pro Phe Val Asn Ile Glu Thr Met Leu Gln
    1890                1895                1900

Ile Phe Gly Val Pro Thr Gly Val Ser His Ala Ala Ala Leu Lys Ser
1905                1910                1915                1920

Ser Asp Arg Pro Ala Asp Leu Leu Thr Ile Ser Leu Phe Tyr Met Ala
                1925                1930                1935

Ile Ile Ser Tyr Tyr Asn Ile Asn His Ile Arg Val Gly Pro Ile Pro
            1940                1945                1950

Pro Asn Pro Pro Ser Asp Gly Ile Ala Gln Asn Val Gly Ile Ala Ile
        1955                1960                1965

Thr Gly Ile Ser Phe Trp Leu Ser Leu Met Glu Lys Asp Ile Pro Leu
    1970                1975                1980

Tyr Gln Gln Cys Leu Ala Val Ile Gln Gln Ser Phe Pro Ile Arg Trp
1985                1990                1995                2000

Glu Ala Val Ser Val Lys Gly Gly Tyr Lys Gln Lys Trp Ser Thr Arg
                2005                2010                2015

Gly Asp Gly Leu Pro Lys Asp Thr Arg Thr Ser Asp Ser Leu Ala Pro
            2020                2025                2030

Ile Gly Asn Trp Ile Arg Ser Leu Glu Leu Val Arg Asn Gln Val Arg
        2035                2040                2045

Leu Asn Pro Phe Asn Glu Ile Leu Phe Asn Gln Leu Cys Arg Thr Val
    2050                2055                2060

Asp Asn His Leu Lys Trp Ser Asn Leu Arg Arg Asn Thr Gly Met Ile
2065                2070                2075                2080

Glu Trp Ile Asn Arg Arg Ile Ser Lys Glu Asp Arg Ser Ile Leu Met
                2085                2090                2095

Leu Lys Ser Asp Leu His Glu Glu Asn Ser Trp Arg Asp
            2100                2105

<210> SEQ ID NO 51
<211> LENGTH: 1753
<212> TYPE: PRT
<213> ORGANISM: Vesicular stomatitis virus
<220> FEATURE:
<221> NAME/KEY: MOD_RES
<222> LOCATION: (1)..(1753)
<223> OTHER INFORMATION: "Xaa" represents any, other or unknown amino
      acid

<400> SEQUENCE: 51

-continued

```
His Trp Gly His Pro Phe Ile Asp Tyr Tyr Ala Gly Leu Glu Lys Leu
  1               5                  10                  15

His Ser Gln Val Thr Xaa Lys Lys Asp Ile Asp Val Ser Tyr Ala Lys
             20                  25                  30

Ala Leu Ala Ser Asp Leu Ala Arg Ile Val Leu Phe Gln Gln Phe Asn
         35                  40                  45

Asp His Xaa Lys Trp Phe Val Asn Gly Asp Leu Leu Pro His Asp His
     50                  55                  60

Pro Phe Lys Ser His Val Lys Glu Asn Thr Trp Pro Thr Ala Ala Gln
 65                  70                  75                  80

Val Gln Asp Phe Gly Asp Lys Trp His Glu Leu Pro Leu Ile Lys Cys
                 85                  90                  95

Phe Glu Ile Pro Asp Leu Leu Asp Pro Ser Ile Ile Tyr Ser Asp Lys
             100                 105                 110

Ser His Ser Met Asn Arg Ser Glu Val Leu Lys His Val Arg Met Asn
         115                 120                 125

Pro Asn Thr Pro Ile Pro Ser Lys Lys Val Leu Gln Thr Met Leu Asp
     130                 135                 140

Thr Lys Ala Thr Asn Trp Lys Glu Phe Leu Lys Glu Ile Asp Glu Lys
145                 150                 155                 160

Gly Leu Asp Asp Asp Leu Ile Ile Gly Leu Lys Gly Lys Glu Arg
                 165                 170                 175

Glu Leu Lys Leu Ala Gly Arg Phe Phe Ser Leu Met Ser Trp Lys Leu
             180                 185                 190

Arg Glu Tyr Phe Val Ile Thr Glu Tyr Leu Ile Lys Thr His Phe Val
         195                 200                 205

Pro Met Phe Lys Gly Leu Thr Met Ala Asp Asp Leu Thr Ala Val Ile
     210                 215                 220

Lys Lys Met Leu Asp Ser Ser Gly Gln Gly Leu Lys Ser Tyr Glu
225                 230                 235                 240

Ala Ile Cys Ile Ala Asn His Ile Asp Tyr Glu Lys Trp Asn Asn His
                 245                 250                 255

Gln Arg Lys Leu Ser Asn Gly Pro Val Phe Arg Val Met Gly Gln Phe
             260                 265                 270

Leu Gly Tyr Pro Ser Leu Ile Glu Arg Thr His Glu Phe Phe Glu Lys
         275                 280                 285

Ser Leu Ile Tyr Tyr Asn Gly Arg Pro Asp Leu Met Arg Val His Asn
     290                 295                 300

Asn Thr Leu Ile Asn Ser Thr Ser Gln Arg Val Cys Trp Gln Gly Gln
305                 310                 315                 320

Glu Gly Gly Leu Glu Gly Leu Arg Gln Lys Gly Trp Ser Ile Leu Asn
                 325                 330                 335

Leu Leu Val Ile Gln Arg Glu Ala Lys Ile Arg Asn Thr Ala Val Lys
             340                 345                 350

Val Leu Ala Gln Gly Asp Asn Gln Val Ile Cys Thr Gln Tyr Lys Thr
         355                 360                 365

Lys Lys Ser Arg Asn Val Val Glu Leu Gln Gly Ala Leu Asn Gln Met
     370                 375                 380

Val Ser Asn Asn Glu Lys Ile Met Thr Ala Ile Lys Ile Gly Thr Gly
385                 390                 395                 400

Lys Leu Gly Leu Leu Ile Asn Asp Asp Glu Thr Met Gln Ser Ala Asp
                 405                 410                 415

Tyr Leu Asn Tyr Gly Lys Ile Pro Ile Phe Arg Gly Val Ile Arg Gly
             420                 425                 430
```

Leu Glu Thr Lys Arg Trp Ser Arg Val Thr Cys Val Thr Asn Asp Gln
        435                 440                 445

Ile Pro Thr Cys Ala Asn Ile Met Ser Ser Val Ser Thr Asn Ala Leu
    450                 455                 460

Thr Val Ala His Phe Ala Glu Asn Pro Ile Asn Ala Met Ile Gln Tyr
465                 470                 475                 480

Asn Tyr Phe Gly Thr Phe Ala Arg Leu Leu Met Met His Asp Pro
                485                 490                 495

Ala Leu Arg Gln Ser Leu Tyr Glu Val Gln Asp Lys Ile Pro Gly Leu
        500                 505                 510

His Ser Ser Thr Phe Lys Tyr Ala Met Leu Tyr Leu Asp Pro Ser Ile
        515                 520                 525

Gly Gly Val Ser Gly Met Ser Leu Ser Arg Phe Leu Ile Arg Ala Phe
        530                 535                 540

Pro Asp Pro Val Thr Glu Ser Leu Ser Phe Trp Arg Phe Ile His Val
545                 550                 555                 560

His Ala Arg Ser Glu His Leu Lys Glu Met Ser Ala Val Phe Gly Asn
                565                 570                 575

Pro Glu Ile Ala Lys Phe Arg Ile Thr His Ile Asp Lys Leu Val Glu
        580                 585                 590

Asp Pro Thr Ser Leu Asn Ile Ala Met Gly Met Ser Pro Ala Asn Leu
        595                 600                 605

Leu Lys Thr Glu Val Lys Lys Cys Leu Ile Glu Ser Arg Gln Thr Ile
        610                 615                 620

Arg Asn Gln Val Ile Lys Asp Ala Thr Ile Tyr Leu Tyr His Glu Glu
625                 630                 635                 640

Asp Arg Leu Arg Ser Phe Leu Trp Ser Ile Asn Pro Leu Phe Pro Arg
                645                 650                 655

Phe Leu Ser Glu Phe Lys Ser Gly Thr Phe Leu Gly Val Ala Asp Gly
                660                 665                 670

Leu Ile Ser Leu Phe Gln Asn Ser Arg Thr Ile Arg Asn Ser Phe Lys
        675                 680                 685

Lys Lys Tyr His Arg Glu Leu Asp Asp Leu Ile Val Arg Ser Glu Val
        690                 695                 700

Ser Ser Leu Thr His Leu Gly Lys Leu His Leu Arg Arg Gly Ser Cys
705                 710                 715                 720

Lys Met Trp Thr Cys Ser Ala Thr His Ala Asp Thr Leu Arg Tyr Lys
                725                 730                 735

Ser Trp Gly Arg Thr Val Ile Gly Thr Thr Val Pro His Pro Leu Glu
                740                 745                 750

Met Leu Gly Pro Gln His Arg Lys Glu Thr Pro Cys Ala Pro Cys Asn
        755                 760                 765

Thr Ser Gly Phe Asn Tyr Val Ser Val His Cys Pro Asp Gly Ile His
        770                 775                 780

Asp Val Phe Ser Ser Arg Gly Pro Leu Pro Ala Tyr Leu Gly Ser Lys
785                 790                 795                 800

Thr Ser Glu Ser Thr Ser Ile Leu Gln Pro Trp Glu Arg Glu Ser Lys
                805                 810                 815

Val Pro Leu Ile Lys Arg Ala Thr Arg Leu Arg Asp Ala Ile Ser Trp
        820                 825                 830

Phe Val Glu Pro Asp Ser Lys Leu Ala Met Thr Ile Leu Ser Asn Ile
        835                 840                 845

His Ser Leu Thr Gly Glu Glu Trp Thr Lys Arg Gln His Gly Phe Lys

```
                850                 855                 860
Arg Thr Gly Ser Ala Leu His Arg Phe Ser Thr Ser Arg Met Ser His
865                 870                 875                 880

Gly Gly Phe Ala Ser Gln Ser Thr Ala Ala Leu Thr Arg Leu Met Ala
                885                 890                 895

Thr Thr Asp Thr Met Arg Asp Leu Gly Asp Gln Asn Phe Asp Phe Leu
                900                 905                 910

Phe Gln Ala Thr Leu Leu Tyr Ala Gln Ile Thr Thr Val Ala Arg
            915                 920                 925

Asp Gly Trp Ile Thr Ser Cys Thr Asp His Tyr His Ile Ala Cys Lys
            930                 935                 940

Ser Cys Leu Arg Pro Ile Glu Glu Ile Thr Leu Asp Ser Ser Met Asp
945                 950                 955                 960

Tyr Thr Pro Pro Asp Val Ser His Val Leu Lys Thr Trp Arg Asn Gly
                965                 970                 975

Glu Gly Ser Trp Gly Gln Glu Ile Lys Gln Ile Tyr Pro Leu Glu Gly
                980                 985                 990

Asn Trp Lys Asn Leu Ala Pro Ala Glu Gln Ser Tyr Gln Val Gly Arg
            995                 1000                1005

Cys Ile Gly Phe Leu Tyr Gly Asp Leu Ala Tyr Arg Lys Ser Thr His
    1010                1015                1020

Ala Glu Asp Ser Ser Leu Phe Pro Leu Ser Ile Gln Gly Arg Ile Arg
1025                1030                1035                1040

Gly Arg Gly Phe Leu Lys Gly Leu Leu Asp Gly Leu Met Arg Ala Ser
                1045                1050                1055

Cys Cys Gln Val Ile His Arg Arg Ser Leu Ala His Leu Lys Arg Pro
                1060                1065                1070

Ala Asn Ala Val Tyr Gly Gly Leu Ile Tyr Leu Ile Asp Lys Leu Ser
            1075                1080                1085

Val Ser Pro Pro Phe Leu Ser Leu Thr Arg Ser Gly Pro Ile Arg Asp
    1090                1095                1100

Glu Leu Glu Thr Ile Pro His Lys Ile Pro Thr Ser Tyr Pro Thr Ser
1105                1110                1115                1120

Asn Arg Asp Met Gly Val Ile Val Arg Asn Tyr Phe Lys Tyr Gln Cys
                1125                1130                1135

Arg Leu Ile Glu Lys Gly Lys Tyr Arg Ser His Tyr Ser Gln Leu Trp
                1140                1145                1150

Leu Phe Ser Asp Val Leu Ser Ile Asp Phe Ile Gly Pro Phe Ser Ile
    1155                1160                1165

Ser Thr Thr Leu Leu Gln Ile Leu Tyr Lys Pro Phe Leu Ser Gly Lys
    1170                1175                1180

Asp Lys Asn Glu Leu Arg Glu Leu Ala Asn Leu Ser Ser Leu Leu Arg
1185                1190                1195                1200

Ser Gly Glu Gly Trp Asp Ile His Val Lys Phe Phe Thr Lys Asp
            1205                1210                1215

Ile Leu Leu Cys Pro Glu Glu Ile Arg His Ala Cys Lys Phe Gly Ile
            1220                1225                1230

Ala Lys Asp Asn Asn Lys Asp Met Ser Tyr Pro Pro Trp Gly Arg Glu
            1235                1240                1245

Ser Arg Gly Thr Ile Thr Thr Ile Pro Val Tyr Tyr Thr Thr Thr Pro
    1250                1255                1260

Tyr Pro Lys Met Leu Glu Met Pro Pro Arg Ile Gln Asn Pro Leu Leu
1265                1270                1275                1280
```

-continued

Ser Gly Ile Arg Leu Gly Gln Leu Pro Thr Gly Ala His Tyr Lys Ile
            1285                1290                1295

Arg Ser Ile Leu His Gly Met Gly Ile His Tyr Arg Asp Phe Leu Ser
        1300                1305                1310

Cys Gly Asp Gly Ser Gly Gly Met Thr Ala Ala Leu Leu Arg Glu Asn
    1315                1320                1325

Val His Ser Arg Gly Ile Phe Asn Ser Leu Leu Glu Leu Ser Gly Ser
1330                1335                1340

Val Met Arg Gly Ala Ser Pro Glu Pro Pro Ser Ala Leu Glu Thr Leu
1345                1350                1355                1360

Gly Gly Asp Lys Ser Arg Cys Val Asn Gly Glu Thr Cys Trp Glu Tyr
            1365                1370                1375

Pro Ser Asp Leu Cys Asp Pro Arg Thr Trp Asp Tyr Phe Leu Arg Leu
        1380                1385                1390

Lys Ala Gly Leu Gly Leu Gln Ile Asp Leu Ile Val Met Asp Met Glu
    1395                1400                1405

Val Arg Asp Ser Ser Thr Ser Leu Lys Ile Glu Thr Asn Val Arg Asn
1410                1415                1420

Tyr Val His Arg Ile Leu Asp Glu Gln Gly Val Leu Ile Tyr Lys Thr
1425                1430                1435                1440

Tyr Gly Thr Tyr Ile Cys Glu Ser Glu Lys Asn Ala Val Thr Ile Leu
            1445                1450                1455

Gly Pro Met Phe Lys Thr Val Asp Leu Val Gln Thr Glu Phe Ser Ser
        1460                1465                1470

Ser Gln Thr Ser Glu Val Tyr Met Val Cys Lys Gly Leu Lys Lys Leu
    1475                1480                1485

Ile Asp Glu Pro Asn Pro Asp Trp Ser Ser Ile Asn Glu Ser Trp Lys
    1490                1495                1500

Asn Leu Tyr Ala Phe Gln Ser Ser Glu Gln Glu Phe Ala Arg Ala Lys
1505                1510                1515                1520

Lys Val Ser Thr Tyr Phe Thr Leu Thr Gly Ile Pro Ser Gln Phe Ile
            1525                1530                1535

Pro Asp Pro Phe Val Asn Ile Glu Thr Met Leu Gln Ile Phe Gly Val
        1540                1545                1550

Pro Thr Gly Val Ser His Ala Ala Ala Leu Lys Ser Ser Asp Arg Pro
    1555                1560                1565

Ala Asp Leu Leu Thr Ile Ser Leu Phe Tyr Met Ala Ile Ile Ser Tyr
1570                1575                1580

Tyr Asn Ile Asn His Ile Arg Val Gly Pro Ile Pro Pro Asn Pro Pro
1585                1590                1595                1600

Ser Asp Gly Ile Ala Gln Asn Val Gly Ile Ala Ile Thr Gly Ile Ser
            1605                1610                1615

Phe Trp Leu Ser Leu Met Glu Lys Asp Ile Pro Leu Tyr Gln Gln Cys
        1620                1625                1630

Leu Ala Val Ile Gln Gln Ser Phe Pro Ile Arg Trp Glu Ala Val Ser
    1635                1640                1645

Val Lys Gly Gly Tyr Lys Gln Lys Trp Ser Thr Arg Gly Asp Gly Leu
    1650                1655                1660

Pro Lys Asp Thr Arg Ile Ser Asp Ser Leu Ala Pro Ile Gly Asn Trp
1665                1670                1675                1680

Ile Arg Ser Leu Glu Leu Val Arg Asn Gln Val Arg Leu Asn Pro Phe
            1685                1690                1695

Asn Glu Ile Leu Phe Asn Gln Leu Cys Arg Thr Val Asp Asn His Leu
        1700                1705                1710

-continued

Lys Trp Ser Asn Leu Arg Lys Asn Thr Gly Met Ile Glu Trp Ile Asn
        1715                1720                1725

Arg Arg Ile Ser Lys Glu Asp Arg Ser Ile Leu Met Leu Lys Ser Asp
    1730                1735                1740

Leu His Glu Glu Asn Ser Trp Arg Asp
1745                1750

<210> SEQ ID NO 52
<211> LENGTH: 2109
<212> TYPE: PRT
<213> ORGANISM: Vesicular stomatitis virus
<220> FEATURE:
<221> NAME/KEY: MOD_RES
<222> LOCATION: (1)..(2109)
<223> OTHER INFORMATION: "Xaa" represents any, other or unknown amino
      acid

<400> SEQUENCE: 52

Met Glu Val His Asp Phe Glu Thr Asp Glu Phe Asn Asp Phe Asn Glu
 1               5                  10                  15

Asp Asp Tyr Ala Thr Arg Glu Phe Leu Asn Pro Asp Glu Arg Met Thr
             20                  25                  30

Tyr Leu Asn His Ala Asp Tyr Asn Leu Asn Ser Pro Leu Ile Ser Asp
         35                  40                  45

Asp Ile Asp Asn Leu Ile Arg Lys Phe Asn Ser Leu Pro Ile Pro Ser
     50                  55                  60

Met Trp Asp Ser Lys Asn Trp Asp Gly Val Leu Glu Met Leu Thr Ser
 65                  70                  75                  80

Cys Gln Ala Asn Pro Ile Ser Thr Ser Gln Met His Lys Trp Met Gly
                 85                  90                  95

Ser Trp Leu Met Ser Asp Asn His Asp Ala Ser Gln Gly Tyr Ser Phe
            100                 105                 110

Leu His Glu Val Asp Lys Glu Ala Glu Ile Thr Phe Asp Val Val Glu
        115                 120                 125

Thr Phe Ile Arg Gly Trp Gly Asn Lys Pro Ile Glu Tyr Ile Lys Lys
    130                 135                 140

Glu Arg Trp Thr Asp Ser Phe Lys Ile Leu Ala Tyr Leu Cys Gln Lys
145                 150                 155                 160

Phe Leu Asp Leu His Lys Leu Thr Leu Ile Leu Asn Ala Val Ser Glu
                165                 170                 175

Val Glu Leu Leu Asn Leu Ala Arg Thr Phe Lys Gly Lys Val Arg Arg
            180                 185                 190

Ser Ser His Gly Thr Asn Ile Cys Arg Leu Arg Val Pro Ser Leu Gly
        195                 200                 205

Pro Thr Phe Ile Ser Glu Gly Trp Ala Tyr Phe Lys Lys Leu Asp Ile
    210                 215                 220

Leu Met Asp Arg Asn Phe Leu Leu Met Val Lys Asp Val Ile Ile Gly
225                 230                 235                 240

Arg Met Gln Thr Val Leu Ser Met Val Cys Arg Ile Asp Asn Leu Phe
                245                 250                 255

Ser Glu Gln Asp Ile Phe Ser Leu Leu Asn Ile Tyr Arg Ile Gly Asp
            260                 265                 270

Lys Ile Val Glu Arg Gln Gly Asn Phe Ser Tyr Asp Leu Ile Lys Met
        275                 280                 285

Val Glu Pro Ile Cys Asn Leu Arg Leu Met Lys Leu Ala Arg Glu Ser
    290                 295                 300

```
Arg Pro Leu Val Pro Gln Phe Pro His Phe Glu Asn His Ile Lys Thr
305                 310                 315                 320

Ser Val Asp Glu Gly Ala Lys Ile Asp Arg Gly Ile Arg Phe Leu His
            325                 330                 335

Asp Gln Ile Met Ser Val Lys Thr Val Asp Leu Thr Leu Val Ile Tyr
                340                 345                 350

Gly Ser Phe Arg His Trp Gly His Pro Phe Ile Asp Tyr Tyr Ala Gly
            355                 360                 365

Leu Glu Lys Leu His Ser Gln Val Thr Met Lys Lys Asp Ile Asp Val
        370                 375                 380

Ser Tyr Ala Lys Ala Leu Ala Ser Asp Leu Ala Arg Ile Val Leu Phe
385                 390                 395                 400

Gln Gln Phe Asn Asp His Lys Lys Trp Phe Val Asn Gly Asp Leu Leu
                405                 410                 415

Pro His Asp His Pro Phe Lys Ser His Val Lys Glu Asn Thr Trp Pro
            420                 425                 430

Thr Ala Ala Gln Val Gln Asp Phe Gly Asp Lys Trp His Glu Leu Pro
        435                 440                 445

Leu Ile Lys Cys Phe Glu Ile Pro Asp Leu Leu Asp Pro Ser Ile Ile
450                 455                 460

Tyr Ser Asp Lys Ser His Ser Met Asn Arg Ser Glu Val Leu Lys His
465                 470                 475                 480

Val Arg Met Asn Pro Asn Thr Pro Ile Pro Ser Lys Lys Val Leu Gln
                485                 490                 495

Thr Met Leu Asp Thr Lys Ala Thr Asn Trp Lys Glu Phe Leu Lys Glu
            500                 505                 510

Ile Asp Glu Lys Gly Leu Asp Asp Asp Leu Ile Ile Gly Leu Lys
        515                 520                 525

Gly Lys Glu Arg Glu Leu Lys Leu Ala Gly Arg Phe Phe Ser Leu Met
        530                 535                 540

Ser Trp Lys Leu Arg Glu Tyr Phe Val Ile Thr Glu Tyr Leu Ile Lys
545                 550                 555                 560

Thr His Phe Val Pro Met Phe Lys Gly Leu Thr Met Ala Asp Asp Leu
                565                 570                 575

Thr Ala Val Ile Lys Lys Met Leu Asp Ser Ser Ser Gly Gln Gly Leu
            580                 585                 590

Lys Ser Tyr Glu Ala Ile Cys Ile Ala Asn His Ile Asp Tyr Glu Lys
        595                 600                 605

Trp Asn Asn His Gln Arg Lys Leu Ser Asn Gly Pro Val Phe Arg Val
                610                 615                 620

Met Gly Gln Phe Leu Gly Tyr Pro Ser Leu Ile Glu Arg Thr His Glu
625                 630                 635                 640

Phe Phe Glu Lys Ser Leu Ile Tyr Tyr Asn Gly Arg Pro Asp Leu Met
                645                 650                 655

Arg Val His Asn Asn Thr Leu Ile Asn Ser Thr Ser Gln Arg Val Cys
            660                 665                 670

Trp Gln Gly Gln Glu Gly Gly Leu Glu Gly Leu Arg Gln Lys Gly Trp
        675                 680                 685

Ser Ile Leu Asn Leu Leu Val Ile Gln Arg Glu Ala Lys Ile Arg Asn
690                 695                 700

Thr Ala Val Lys Val Leu Ala Gln Gly Asp Asn Gln Val Ile Cys Thr
705                 710                 715                 720

Gln Tyr Lys Thr Lys Lys Ser Arg Asn Val Val Glu Leu Gln Gly Ala
                725                 730                 735
```

```
Leu Asn Gln Met Val Ser Asn Glu Lys Ile Met Thr Ala Ile Lys
            740                 745                 750

Ile Gly Thr Gly Lys Leu Gly Leu Leu Ile Asn Asp Asp Glu Thr Met
            755                 760                 765

Gln Ser Ala Asp Tyr Leu Asn Tyr Gly Lys Ile Pro Ile Phe Arg Gly
            770                 775                 780

Val Ile Arg Gly Leu Glu Thr Lys Arg Trp Ser Arg Val Thr Cys Val
785                 790                 795                 800

Thr Asn Asp Gln Ile Pro Thr Cys Ala Asn Ile Met Ser Ser Val Ser
            805                 810                 815

Thr Asn Ala Leu Thr Val Ala His Phe Ala Glu Asn Pro Ile Asn Ala
            820                 825                 830

Met Ile Gln Tyr Asn Tyr Phe Gly Thr Phe Ala Arg Leu Leu Leu Met
            835                 840                 845

Met His Asp Pro Ala Leu Arg Gln Ser Leu Tyr Glu Val Gln Asp Lys
            850                 855                 860

Ile Pro Gly Leu His Ser Ser Thr Phe Lys Tyr Ala Met Leu Tyr Leu
865                 870                 875                 880

Asp Pro Ser Ile Gly Gly Val Ser Gly Met Ser Leu Ser Arg Phe Leu
            885                 890                 895

Ile Arg Ala Phe Pro Asp Pro Val Thr Glu Ser Leu Ser Phe Trp Arg
            900                 905                 910

Phe Ile His Val His Ala Arg Ser Glu His Leu Lys Glu Met Ser Ala
            915                 920                 925

Val Phe Gly Asn Pro Glu Ile Ala Lys Phe Arg Ile Thr His Ile Asp
            930                 935                 940

Lys Leu Val Glu Asp Pro Thr Ser Leu Asn Ile Ala Met Gly Met Ser
945                 950                 955                 960

Pro Ala Asn Leu Leu Lys Thr Glu Val Lys Lys Cys Leu Ile Glu Ser
            965                 970                 975

Arg Gln Thr Ile Arg Asn Gln Val Ile Lys Asp Ala Thr Ile Tyr Leu
            980                 985                 990

Tyr His Glu Glu Asp Arg Leu Arg Ser Phe Leu Trp Ser Ile Asn Pro
            995                 1000                1005

Leu Phe Pro Arg Phe Leu Ser Glu Phe Lys Ser Gly Thr Phe Leu Gly
            1010                1015                1020

Val Ala Asp Gly Leu Ile Ser Leu Phe Gln Asn Ser Arg Thr Ile Arg
1025                1030                1035                1040

Asn Ser Phe Lys Lys Lys Tyr His Arg Glu Leu Asp Asp Leu Ile Val
            1045                1050                1055

Arg Ser Glu Val Ser Ser Leu Thr His Leu Gly Lys Leu His Leu Arg
            1060                1065                1070

Arg Gly Ser Cys Lys Met Trp Thr Cys Ser Ala Thr His Ala Asp Thr
            1075                1080                1085

Leu Arg Tyr Lys Ser Trp Gly Arg Thr Val Ile Gly Thr Thr Val Pro
            1090                1095                1100

His Pro Leu Glu Met Leu Gly Pro Gln His Arg Lys Glu Thr Pro Cys
1105                1110                1115                1120

Ala Pro Cys Asn Thr Ser Gly Phe Asn Tyr Val Ser Val His Cys Pro
            1125                1130                1135

Asp Gly Ile His Asp Val Phe Ser Ser Arg Gly Pro Leu Pro Ala Tyr
            1140                1145                1150

Leu Gly Ser Lys Thr Ser Glu Ser Thr Ser Ile Leu Gln Pro Trp Glu
```

-continued

```
            1155                1160                1165

Arg Glu Ser Lys Val Pro Leu Ile Lys Arg Ala Thr Arg Leu Arg Asp
    1170                1175                1180

Ala Ile Ser Trp Phe Val Glu Pro Asp Ser Lys Leu Ala Met Thr Ile
1185                1190                1195                1200

Leu Ser Asn Ile His Ser Leu Thr Gly Glu Glu Trp Thr Lys Arg Gln
            1205                1210                1215

His Gly Phe Lys Arg Thr Gly Ser Ala Leu His Arg Phe Ser Thr Ser
            1220                1225                1230

Arg Met Ser His Gly Gly Phe Ala Ser Gln Ser Thr Ala Ala Leu Thr
            1235                1240                1245

Arg Leu Met Ala Thr Thr Asp Thr Met Arg Asp Leu Gly Asp Gln Asn
    1250                1255                1260

Phe Asp Phe Leu Phe Xaa Ala Thr Leu Leu Tyr Ala Xaa Ile Thr Thr
1265                1270                1275                1280

Thr Val Ala Arg Asp Gly Trp Ile Thr Ser Cys Thr Asp His Tyr His
            1285                1290                1295

Ile Ala Cys Lys Ser Cys Leu Arg Pro Ile Glu Glu Ile Thr Leu Asp
            1300                1305                1310

Ser Ser Met Asp Tyr Thr Pro Pro Asp Val Ser His Val Leu Lys Thr
            1315                1320                1325

Trp Arg Asn Gly Glu Gly Ser Trp Gly Gln Glu Ile Lys Gln Ile Tyr
    1330                1335                1340

Pro Leu Glu Gly Asn Trp Lys Asn Leu Ala Pro Ala Glu Gln Ser Tyr
1345                1350                1355                1360

Gln Val Gly Arg Cys Ile Gly Phe Leu Tyr Gly Asp Leu Ala Tyr Arg
            1365                1370                1375

Lys Ser Thr His Ala Glu Asp Ser Ser Leu Phe Pro Leu Ser Ile Gln
            1380                1385                1390

Gly Arg Ile Arg Gly Arg Gly Phe Leu Lys Gly Leu Leu Asp Gly Leu
            1395                1400                1405

Met Arg Ala Ser Cys Cys Gln Val Ile His Arg Ser Leu Ala His
    1410                1415                1420

Leu Lys Arg Pro Ala Asn Ala Val Tyr Gly Gly Leu Ile Tyr Leu Ile
1425                1430                1435                1440

Asp Lys Leu Ser Val Ser Pro Pro Phe Leu Ser Leu Thr Arg Ser Gly
            1445                1450                1455

Pro Ile Arg Asp Glu Leu Glu Thr Ile Pro His Lys Ile Pro Thr Ser
            1460                1465                1470

Tyr Pro Thr Ser Asn Arg Asp Met Gly Val Ile Val Arg Asn Tyr Phe
            1475                1480                1485

Lys Tyr Gln Cys Arg Leu Ile Glu Lys Gly Lys Tyr Arg Ser His Tyr
    1490                1495                1500

Ser Gln Leu Trp Leu Phe Ser Asp Val Leu Ser Ile Asp Phe Ile Gly
1505                1510                1515                1520

Pro Phe Ser Ile Ser Thr Thr Leu Leu Gln Ile Leu Tyr Lys Pro Phe
            1525                1530                1535

Leu Ser Gly Lys Asp Lys Asn Glu Leu Arg Glu Leu Ala Asn Leu Ser
            1540                1545                1550

Ser Leu Leu Arg Ser Gly Glu Gly Trp Glu Asp Ile His Val Lys Phe
    1555                1560                1565

Phe Thr Lys Asp Ile Leu Leu Cys Pro Glu Glu Ile Arg His Ala Cys
    1570                1575                1580
```

-continued

```
Lys Phe Gly Ile Ala Lys Asp Asn Asn Lys Asp Met Ser Tyr Pro Pro
1585                1590                1595                1600

Trp Gly Arg Glu Ser Arg Gly Thr Ile Thr Thr Ile Pro Val Tyr Tyr
            1605                1610                1615

Thr Thr Thr Pro Tyr Pro Lys Met Leu Glu Met Pro Pro Arg Ile Gln
        1620                1625                1630

Asn Pro Leu Leu Ser Gly Ile Arg Leu Gly Gln Leu Pro Thr Gly Ala
    1635                1640                1645

His Tyr Lys Ile Arg Ser Ile Leu His Gly Met Gly Ile His Tyr Arg
1650                1655                1660

Asp Phe Leu Ser Cys Gly Asp Gly Ser Gly Gly Met Thr Ala Ala Leu
1665                1670                1675                1680

Leu Arg Glu Asn Val His Ser Arg Gly Ile Phe Asn Ser Leu Leu Glu
            1685                1690                1695

Leu Ser Gly Ser Val Met Arg Gly Ala Ser Pro Glu Pro Pro Ser Ala
        1700                1705                1710

Leu Glu Thr Leu Gly Gly Asp Lys Ser Arg Cys Val Asn Gly Glu Thr
    1715                1720                1725

Cys Trp Glu Tyr Pro Ser Asp Leu Cys Asp Pro Arg Thr Trp Asp Tyr
1730                1735                1740

Phe Leu Arg Leu Lys Ala Gly Leu Gly Leu Gln Ile Asp Leu Ile Val
1745                1750                1755                1760

Met Asp Met Glu Val Arg Asp Ser Ser Thr Ser Leu Lys Ile Glu Thr
            1765                1770                1775

Asn Val Arg Asn Tyr Val His Arg Ile Leu Asp Glu Gln Gly Val Leu
        1780                1785                1790

Ile Tyr Lys Thr Tyr Gly Thr Tyr Ile Cys Glu Ser Glu Lys Asn Ala
    1795                1800                1805

Val Thr Ile Leu Gly Pro Met Phe Lys Thr Val Asp Leu Val Gln Thr
1810                1815                1820

Glu Phe Ser Ser Ser Gln Thr Ser Glu Val Tyr Met Val Cys Lys Gly
1825                1830                1835                1840

Leu Lys Lys Leu Ile Asp Glu Pro Asn Pro Asp Trp Ser Ser Ile Asn
            1845                1850                1855

Glu Ser Trp Lys Asn Leu Tyr Ala Phe Gln Ser Ser Glu Gln Glu Phe
        1860                1865                1870

Ala Arg Ala Lys Lys Val Ser Thr Tyr Phe Thr Leu Thr Gly Ile Pro
    1875                1880                1885

Ser Gln Phe Ile Pro Asp Pro Phe Val Asn Ile Glu Thr Met Leu Gln
    1890                1895                1900

Ile Phe Gly Val Pro Thr Gly Val Ser His Ala Ala Ala Leu Lys Ser
1905                1910                1915                1920

Ser Asp Arg Pro Ala Asp Leu Leu Thr Ile Ser Leu Phe Tyr Met Ala
            1925                1930                1935

Ile Ile Ser Tyr Tyr Asn Ile Asn His Ile Arg Val Gly Pro Ile Pro
        1940                1945                1950

Pro Asn Pro Pro Ser Asp Gly Ile Ala Gln Asn Val Gly Ile Ala Ile
    1955                1960                1965

Thr Gly Ile Ser Phe Trp Leu Ser Leu Met Glu Lys Asp Ile Pro Leu
    1970                1975                1980

Tyr Gln Gln Cys Leu Ala Val Ile Gln Gln Ser Phe Pro Ile Arg Trp
1985                1990                1995                2000

Glu Ala Val Ser Val Lys Gly Gly Tyr Lys Gln Lys Trp Ser Thr Arg
            2005                2010                2015
```

-continued

```
Gly Asp Gly Leu Pro Lys Asp Thr Arg Ile Ser Asp Ser Leu Ala Pro
            2020            2025            2030

Ile Gly Asn Trp Ile Arg Ser Leu Glu Leu Val Arg Asn Gln Val Arg
        2035            2040            2045

Leu Asn Pro Phe Asn Glu Ile Leu Phe Asn Gln Leu Cys Arg Thr Val
    2050            2055            2060

Asp Asn His Leu Lys Trp Ser Asn Leu Arg Lys Asn Thr Gly Met Ile
2065            2070            2075            2080

Glu Trp Ile Asn Arg Arg Ile Ser Lys Glu Asp Arg Ser Ile Leu Met
            2085            2090            2095

Leu Lys Ser Asp Leu His Glu Glu Asn Ser Trp Arg Asp
            2100            2105
```

ONCOLYTIC VIRUS

This application claims the benefit of U.S. Provisional Application No. 60/287,590, having an effective filing date of Sep. 17, 1999 now abandoned, as obtained by the petition dated Sep. 8, 2000 under 37 CFR 1.53(c)(2) from U.S. application Ser. No. 09/397,873, filed Sep. 17, 1999, the contents of which are incorporated herein by reference.

The present invention relates to a novel cancer therapeutic. More specifically, this invention relates to viruses that selectively infect and inhibit tumour cell growth.

BACKGROUND OF THE INVENTION

The use of oncolytic bacteria, or compositions of oncolytic bacterias, for combatting neoplasms in humans and animals is known. For example EP 564 121, GB 1,587,244 and U.S. Pat. No. 3,192,116 disclose the use of non-pathogenic bacteria that result in the liquification and lysis of tumours in vertebrates. However in many instances, for example with the use of *Clostridium*, the tumours are only partially destroyed, and tumour regrowth may still occur. To ensure control of tumour growth the administration of bacteria, followed by chemotherapeutic drugs, for example 5-fluorodeoxyuridine or alkylating agents, has been suggested (e.g. GB 1,069,144).

Several viruses have also been shown to exhibit tumoricidal properties, for example parvovirus H-1 (Dupressoir et al., 1996. Cancer Res, 49:3203-3208), Newcastle disease virus (Reichand et al., 1992. J. Surg. Res, 52:448-453) or retroviral vectors containing drug susceptibility genes (Takamiya et al., 1993. J. Neurosurg, 79:104-110). WO97/26904 and WO96/03997 disclose a mutant herpes simplex virus (HSV-1761) that inhibits tumour cell growth. Administration of HSV-1716 comprising a 759 base pair deletion in each copy of $\gamma34.5$ of the long repeat region ($R_L$) to tumour cells kills these cells. However, this virus is specific for neuronal cells as HSV is known to selectively inhabit the neuronal system. Furthermore, the use of common human pathogens as an oncolytic virus is limited as it is likely that the general population has been infected and acquired an immune response to such viruses. A preexisting immune response to a viral strain similar to the one used as a therapeutic agent in the treatment of a cancer may attenuate the effectiveness of the virus as therapeutic agent.

Other virus strains have reported oncolytic activity. The ONYX-015 human adenovirus (produced by ONYX pharmaceuticals) is believed to replicate preferentially in p53 negative tumour cells. This virus shows promise in clinical trials with head and neck cancer patients (Kirn, D., T. et al., Nat Med, 1998. 4:1341-1342). Reovirus type 3 is being developed by Oncolytic Biotech as a cancer therapeutic, which preferentially grows in PKR −/− cells (Yin, H. S., J Virol Methods, 1997. 67:93-101; Strong, J. E. and P. W. Lee, J Virol, 1996. 70:612-616; Strong, J. E., et al., Virology, 1993. 197:405-411; Minuk, G. Y., et al., J Hepatol, 1987. 5:8-13; Rozee, K. R., et al., Appl Environ Microbiol, 1978. 35:297-300). Reovirus, type III exhibited enhanced replication properties in cells which expressed the mutant ras oncogene (Coffey, M. C., et al., Science, 1998. 282:1332-1334; Strong, J. E., et al., Embo J, 1998. 17:3351-1362). Mundschau and Faller (Mundschau, L. J. and D. V. Faller, J Biol Chem, 1992. 267:23092-23098) have shown that the ras oncogene product activated an inhibitor of PKR, and this coupled with the observation that the PKR chemical inhibitor 2-aminopurine increased the growth of Reo type III in normal cells implicates PKR is a critical regulator of the growth of reovirus.

WO 99/04026 teaches the use of VSV as a vector in gene therapy for the expression of a wide range of products including antibodies, immunogens, toxins, etc. for the treatment of a variety of disease disorders.

Interferons are circulating factors which bind to cell surface receptors activating a signalling cascade ultimately leading to a number of biological responses. Two of the outcomes of interferon signalling are tightly linked: (1) an antiviral response and (2) induction of growth inhibitory and/or apoptotic signals.

U.S. Pat. No. 4,806,347 discloses the use of $\gamma$ Interferon and a fragment of INF-$\gamma$ (known as $\Delta4\alpha2$) against human tumour cells.

WO 99/18799 reports the cytotoxic activity of Newcastle Disease Virus (NDV) and Sindbis virus towards several human cancer cells. However, both viruses demonstrated selectivity in their cytotoxic activity towards tumor cells.

WO 99/18799 discloses that interferon addition to normal cells renders these cells resistant to NDV, yet, this effect was not observed with interferon-treated tumor cells which continued to exhibit NDV-induced sensitivity. WO 99/18799 also discloses the cytotoxic activity of VSV cells against KB cells (head and neck carcinoma) and HT 1080 (Fibrosarcoma), and alleviation of cytotoxicity in normal and tumor cells, by VSV, in the presence of interferon. No other cell types were tested against VSV cytotoxic activity.

Certain mutant strains of VSV have been reported. Stanners, et al., Virology (1987) 160 (1):255-8. Francoeur, et al., Virology (1987) 160 (1):236-45. Stanners, et al., J. Gen. Virol. (1975) 29 (3):281-96. Stanners, et al., Cell (1977) 11 (2):273-81.

The present invention relates to viral formulations that are useful in the treatment of diseases and cancers, preferably leukaemia. Such formulations may also comprise an oncolytic VSV strain and a chemical agent, for example a cytokine which confers to normal cells, resistance to viral infection, but leaves diseased or cancerous cells susceptible to viral infection and lysis.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to a novel cancer therapeutic. More specifically, this invention relates to viruses that selectively infect and inhibit tumour cell growth.

According to the present invention there is provided a method of reducing the viability of a tumour cell comprising administering a virus to the tumour cell, wherein the virus is characterized as not being a common human pathogen. Preferably the tumour cell lacks PKR activity, and the virus is selected from the group consisting of rhabdovirus. More preferably the virus is VSV.

This invention is also directed to a method of reducing the viability of a tumour cell comprising administering a virus to the tumour cell, wherein the virus is characterized as being unable to inactivate PKR activity within a host cell. Preferably the virus is selected from the group consisting of vesicular stomatitis virus, picornavirus, influenza virus, and adenovirus.

The present invention also pertains to a method of reducing the viability a tumour cell within a population of cells comprising administering a virus to the population of cells, wherein the virus is characterized as being able to selectively infect and kill the tumour cell. Preferably the virus is further characterized by being unable to inactivate PKR activity in a host cell.

This invention also relates to the method as defined above, wherein the population of cells is treated with interferon prior to administering the virus.

This invention provides a method for identifying a tumor susceptible to treatment with a virus, comprising: (a) dividing a sample containing cells of the tumor into a first portion and a second portion; (b) treating the first portion with the virus; and (c) determining whether the percentage of dead cells in the first portion is higher than in the second portion, wherein the tumor is susceptible to treatment with the virus if the percentage of dead cells in the first portion is higher than in the second portion.

This invention provides a method for identifying a tumor susceptible to treatment with a virus, comprising: (a) dividing a sample containing cells of the tumor into a first portion and a second portion; (b) treating the first portion with the virus and an amount of interferon sufficient to improve survival of interferon-responsive cells in the presence of the virus, and treating the second portion with the virus in the absence of interferon; and (c) determining whether the percentage of dead cells in the first portion is higher than in the second portion, wherein the tumor is susceptible to treatment with the virus if the percentage of dead cells in the first portion is higher than in the second portion.

The present invention is directed to a mutant VSV, characterized in that the mutant VSV grows poorly in interferon-responsive cells. Such strains are also referred to herein as attenuated strains of VSV, or VSV strains that grow poorly in interferon-responsive cells. They can be identified by their producing smaller plaques in monolayers of interferon-responsive cells than in interferon-nonresponsive cells, as described below. Attenuated VSV strains can also be identified by their having a higher LD50 when administered intranasally to PKR+/- mice as compared to WT Indiana, in the assay described below.

The present invention also pertains to a method for isolating VSV using an affinity matrix, comprising adding the VSV to the affinity matrix to produce bound VSV, washing the bound VSV, and eluting the VSV from the affinity matrix. Also included in the present invention is a modified VSV that comprises a non-native fusion protein on the outer surface of the virus. The non-native protein may be fusion protein comprising an affinity tag and a viral envelope protein, or it may be derived from a producer cell.

The present invention is also directed to isolated nucleic acid molecules (DNA or RNA) having a sequence coding for mutant VSV proteins and sequences complementary thereto. Such nucleic acid molecules can be used in the preparation of a recombinant VSV or as a DNA vaccine.

There are several advantages for the use of a virus as described herein as a therapeutic virus over other viruses:

- Rhabdoviruses are not common human pathogens. For example, VSV is found mostly in insects, rodents and domestic farm animals, and therefore a large proportion of individuals will not have been infected or immunized to VSV infection. On the other hand, Adenovirus or Reovirus are human pathogens and most of the general population have been infected and acquired an immune response to both of these viruses. A preexisting immune response to a viral strain similar to the one used as a therapeutic agent in the treatment of a cancer may attenuate the effectiveness of the virus as therapeutic agent;
- VSV replicates much more quickly than either Adenovirus or Reovirus, and can be readily concentrated to high titres. Production of high titre virus preparations is a significant limitation of other potential viral therapeutic strains;
- VSV is simple virus comprising only five genes, easily amenable to genetic manipulation. No such system is currently available for Reovirus;
- Cellular infection by VSV is highly responsive to additional chemical agents such as interferon, a feature which enhances its therapeutic value.
- VSV has a broad host range and is capable of infecting most types of human cells, whereas other viruses are more limited in regard to the types of cells they may infect.
- VSV is a RNA virus and spends its entire lifecycle in the cytoplasm. Therefore it involves less danger of unwanted integration into the genome of a patient.

Collectively, these VSV attributes provide significant advantages over the use of the other viruses known to exhibit oncolytic activity.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1 shows a general schematic of the interferon cascade.

FIG. 2 shows the effect of VSV on normal human fibroblasts, human melanoma cell line SK-MEL3, LNCaP a prostate cancer cell line, and the ovarian carcinoma cell A2780 in the presence and absence of interferon as determined by a modified cpe assay. Monolayers of cells were infected at an moi of 0.1 pfu in a 12 well plate. At time 0 and every 12 hours subsequent up to 48 hours, one well of infected cells was fixed with 0.5 ml Leukostat fixative for 2 minutes. At the end of the experiment monolayers were stained with Leukostat stains.

FIG. 3 shows the cytopathic effect of VSV in normal fibroblasts cells (FIG. 3 (*a*)), and tumour cell lines, including ovarian tumour cells (FIG. 3 (*b*)) and KB tumour cells (FIG. 3 (*c*)).

FIG. 4 shows the effect of VSV on normal human fibroblasts co-cultured with 293T tumour cells over a period of 24 hours. Co-cultures were infected at an moi of 0.1 pfu/cell and the infection allowed to proceed in the presence (IFN+) or absence (IFN−) of interferon. Cultures were stained with antibodies to large T antigen (red nuclei) to detect the 293T cells and with DAPI (blue nuclei) which stains all cell types.

FIG. 5 shows the effect of VSV in vivo on tumors implanted within nude mice. Human melanoma cells were implanted within nude mice and either mock injected (VSV (−)), injected with wild type VSV (data not presented), or injected with additional melanoma cells infected in vitro with VSV for one hour prior to injection into the tumour site VSV(+)). Size of the tumors were determined over a 7 day period.

FIG. 6 shows ulcers formed on a tumor produced within a nude mouse as described in FIG. 5.

FIG. 7: VSV and VSV infected cells inhibit growth of human melanoma xenografts in nude mice.

FIGS. 8A and 8B: PKR −/− mice are acutely sensitive to intranasal VSV infection and demonstrate a deficiency in IFN mediated resistance.

FIG. 9: Interferon can protect xenograft bearing nude mice during VSV treatment.

Figure 10A:
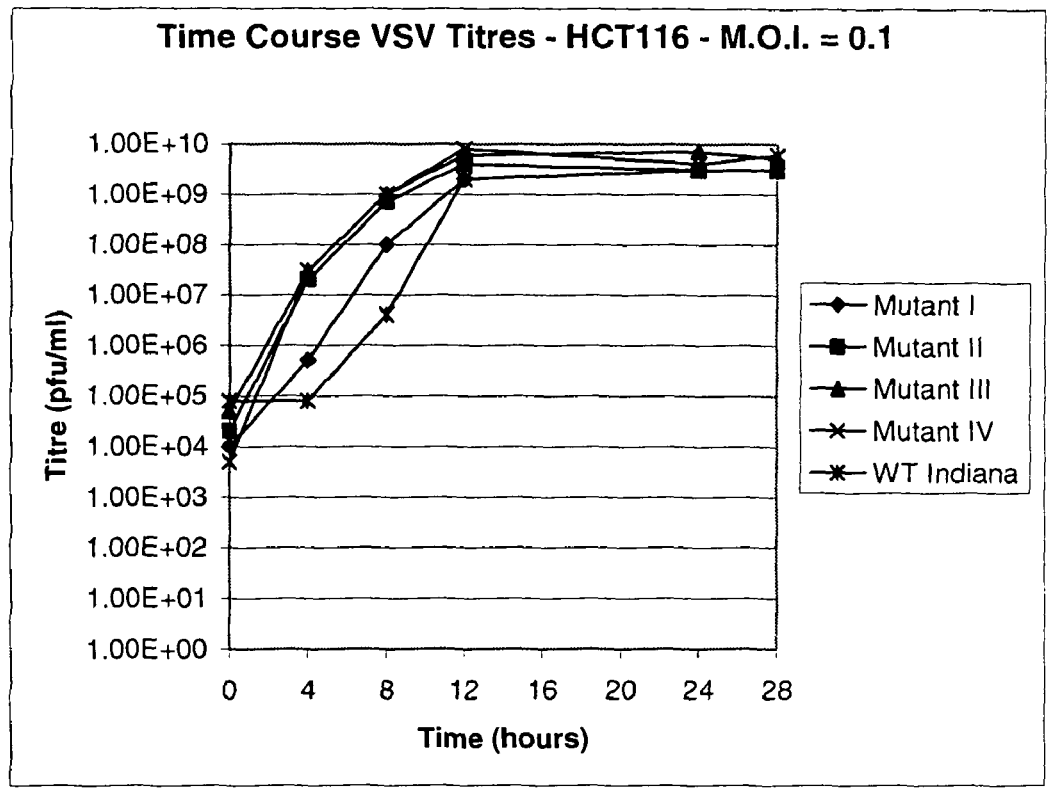
Figure 10B:
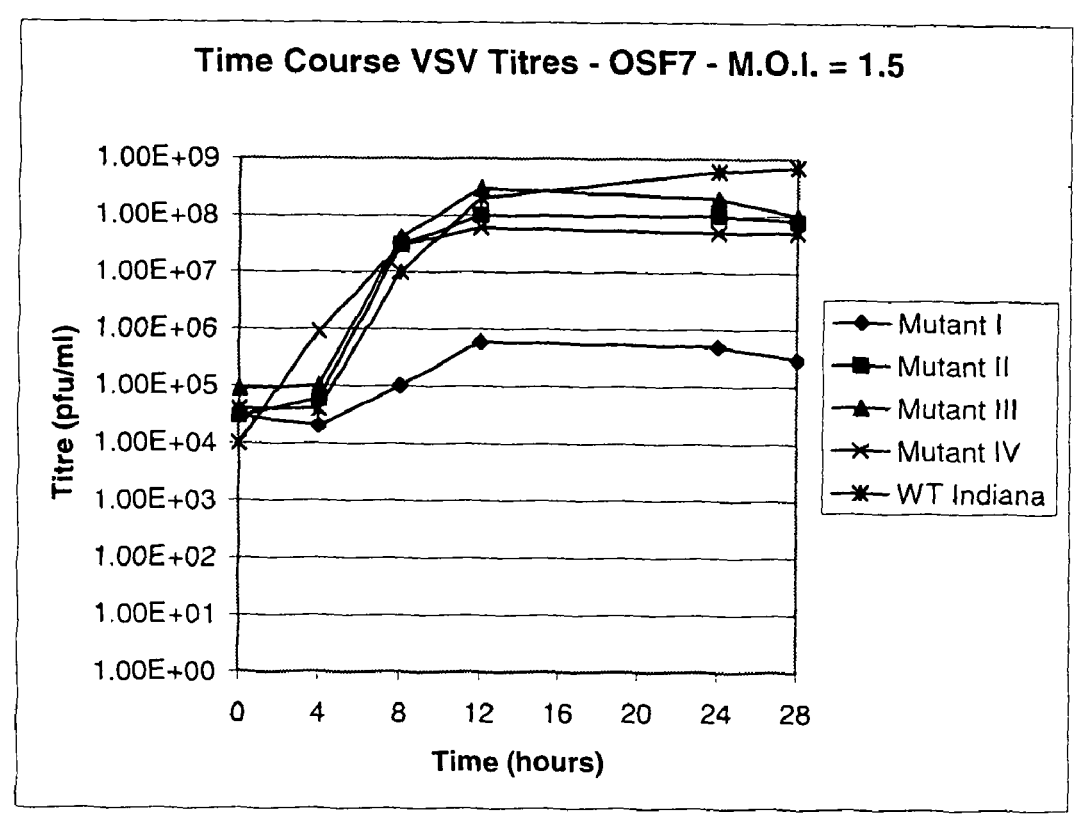

FIGS. 10A and 10B: Virus production from tumour cells and normal cells infected with wild type Indiana and various mutant VSV strains.

Figure 11:
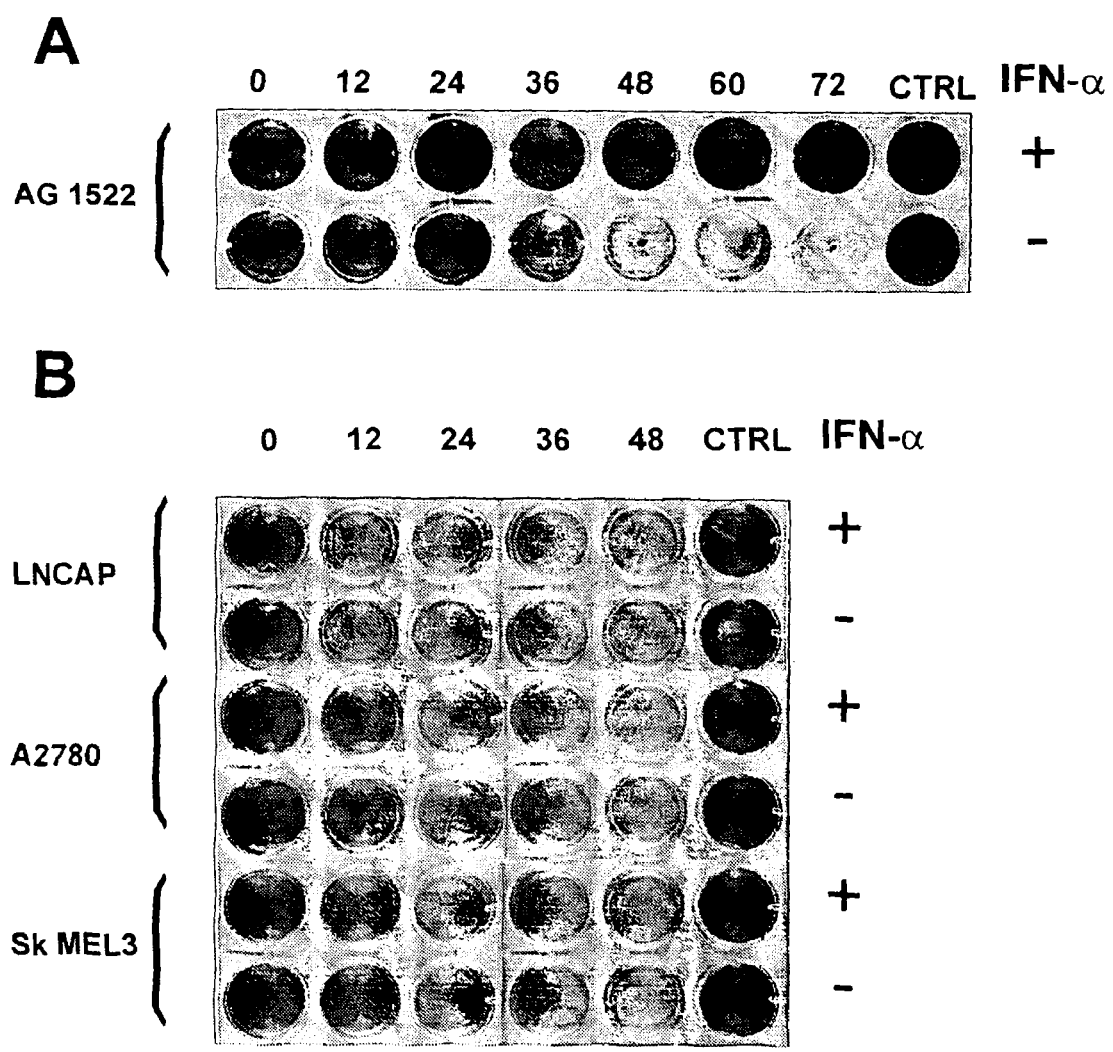

FIG. 11: Malignant cells are rapidly killed following VSV (WT Indiana) infection and are not protected by IFN-α.

Figure 12:
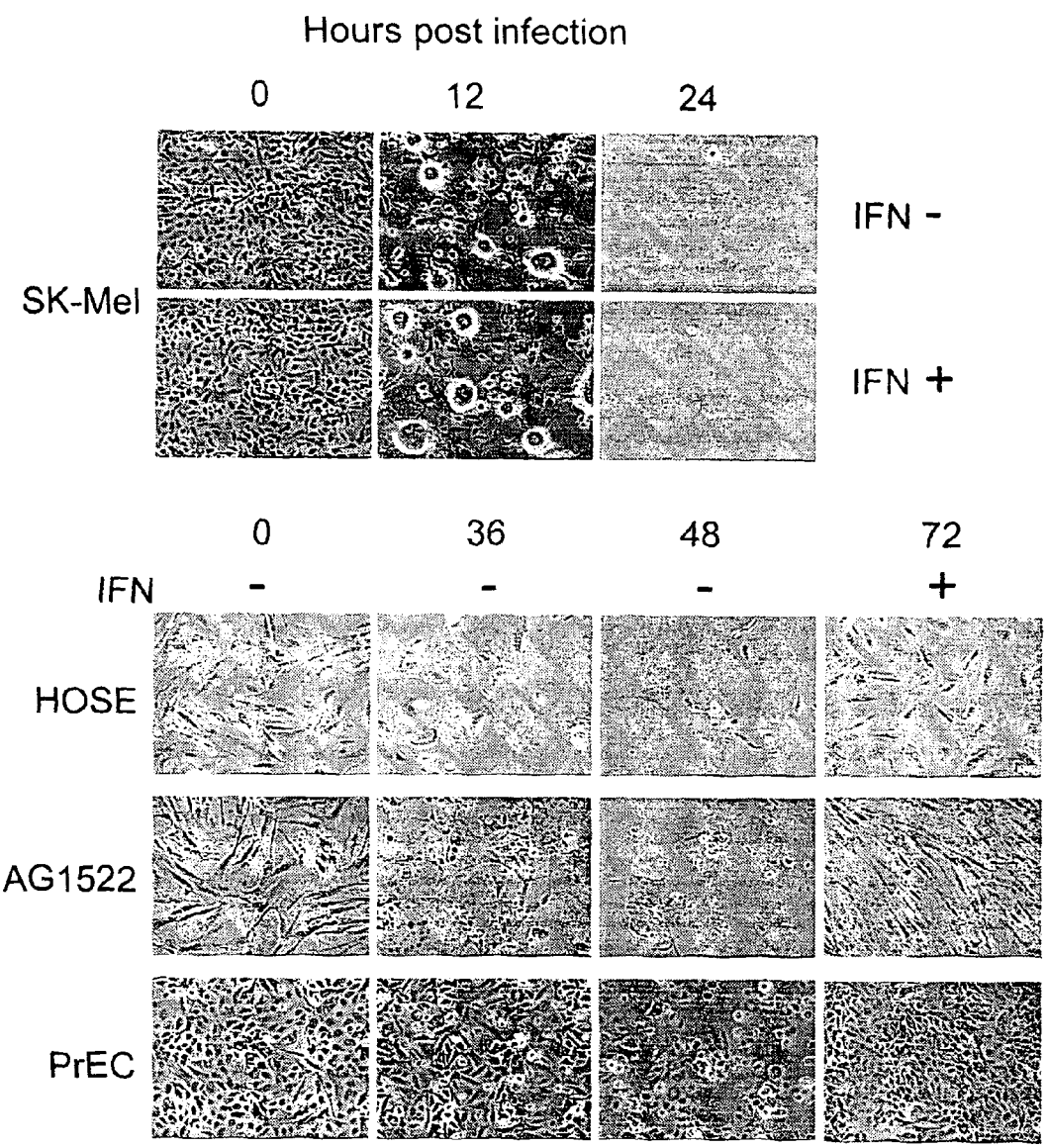

FIG. 12: VSV induced cytopathic effect visible in human melanoma cells but not in primary human cells with or without IFN-α.

Figure 13:
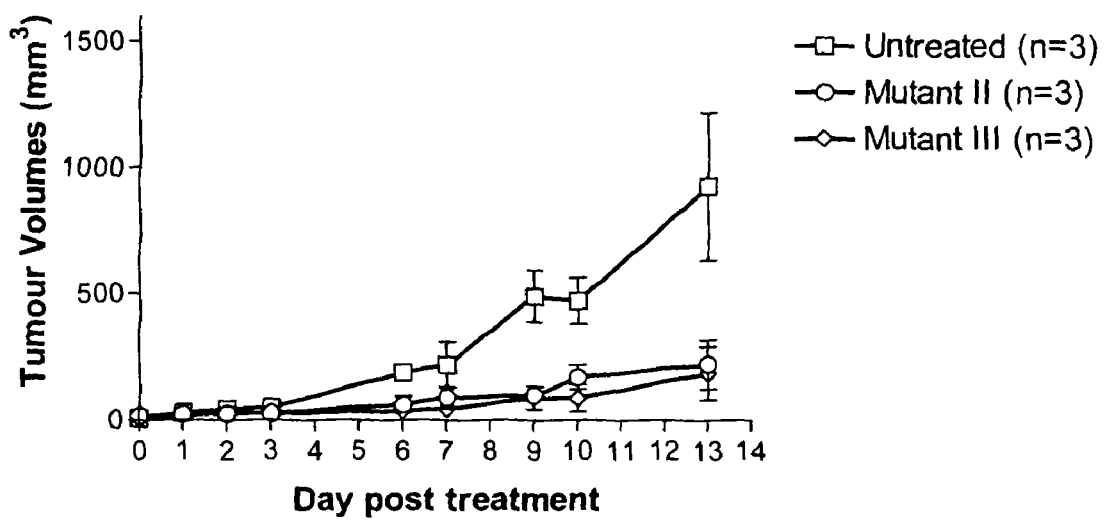

FIG. 13: Efficacy of a single intravenous dose of mutant VSV in treating human melanoma xenografts in nude mice.

FIG. 14: N Protein cDNA sequence (SEQ ID NOS 9-13, respectively, in order of appearance) of wild type and mutant VSVs.

FIG. 15: N Protein amino acid sequence (SEQ ID NOS 14-17, respectively, in order of appearance) of wild type and mutant VSVs.

FIG. 16: P Protein cDNA sequence (SEQ ID NOS 18-22, respectively, in order of appearance) of wild type and mutant VSVs.

FIG. 17: P Protein amino acid sequence (SEQ ID NOS 23-27, respectively, in order of appearance) of wild type and mutant VSVs.

FIG. 18: M Protein cDNA sequence (SEQ ID NOS 28-31, respectively, in order of appearance) of wild type and mutant VSVs.

FIG. 19: M Protein amino acid sequence (SEQ ID NOS 32-35, respectively, in order of appearance) of wild type and mutant VSVs.

FIG. 20: G Protein cDNA sequence (SEQ ID NOS 36-40, respectively, in order of appearance) of wild type and mutant VSVs.

FIG. 21: G Protein amino acid sequence (SEQ ID NOS 41.45, respectively, in order of appearance) of wild type and mutant VSVs.

FIG. 22: L Protein cDNA sequence (SEQ ID NOS 46-49, respectively, in order of appearance) of wild type and mutant VSVs.

FIG. 23: L Protein amino acid sequence (SEQ ID NOS 50-52, respectively, in order of appearance) of wild type and mutant VSVs.

DESCRIPTION OF PREFERRED EMBODIMENTS

The present invention relates to a novel cancer therapeutic. More specifically, this invention relates to viruses that selectively infect and inhibit tumour cell growth.

The following description is of a preferred embodiment by way of example only and without limitation to the combination of features necessary for carrying the invention into effect.

Cancer cells gain a survival advantage over their normal counterparts by acquiring mutations in growth inhibitory or apoptotic pathways and, in the case of interferons, would do so at the expense of critical antiviral defense mechanisms. As tumour cells gain a significant growth advantage by mutating interferon response genes, they will be more susceptible to virus infection.

By "reducing the viability" of a tumour cell it is meant either killing the tumour cell or limiting its growth for a period of time.

By "not a common human pathogen" it is meant a virus that is found mostly in non-human hosts, for example, but not limited to insects, rodents, and farm animals. Such viruses are not typically found within the general human population.

As used herein Mutant I, Mutant 1, Mut 1 and M1 refer to attenuated mutant strain T1026. Mutants II, III, IV and V (and variant nomenclature analogous to Mutant I) refer to attenuated mutants T1026R, TP3, TP6 and G31, respectively.

The novel cancer therapeutic of the present invention incorporates the use of at least one oncolytic virus that selectively targets tumour cells and leads to their destruction. Preferably the oncolytic virus is a Vesicular stomatitis virus (VSV), for example the Indiana strain, or other strains, or a derivative thereof. By a derivative of VSV, it is meant a VSV virus obtained by either selecting the virus under different growth conditions, or one that has been subjected to a range of selection pressures, or one that has been genetically modified using recombinant techniques known within the art. For example, which are not to be considered limiting in any manner, a derivative of VSV may include a mutant VSV selected following infection on a human cell that has been treated with interferon as described herein, or a VSV that displays an affinity tag useful for affinity purification.

The effectiveness of oncolytic virus suppression of tumour cell growth in part resides in the differential susceptibility of tumour cells, compared to normal cells, to viral infection. Without wishing to be bound by theory, the differential susceptibility may in part be due to the down regulation or inactivation of factors within a cell that otherwise function to protect the cell from tumorous growth and virus infection. Examples of factors that when inactivated result in tumorous cell growth, and that are also involved in mediating virus infection include but are not limited to PKR (double stranded RNA dependent kinase) and PML (Promyelocytic Leukemia gene), however, it is to be understood that other factors may also play a role.

The down regulation or inactivation of PKR, through a variety of mechanisms including but not limited to PKR-related mediators, is known to be associated with tumour cell growth, while normal cells exhibit active PKR. Furthermore, wild type cells exposed to viral infection exhibit elevated PKR expression which results in the suppression of viral replication, while cells that exhibit reduced, or no, PKR activity are susceptible to viral attack and exhibit cancerous growth. Similarly, the PML gene product functions as a tumour suppressor and it is also known to suppress viral replication.

By "differential susceptibility", it is meant a property associated with a cell that results in both tumour cell growth and the inability of the cell to suppress viral replication. Cells exhibiting differential susceptibility are preferred candidates for treatment of tumorous cell growth using the cancer therapeutic of the present invention. This differential susceptibility may be accentuated through the addition of one or more chemical agents prior to or during treatment of the tumour cell. Preferably, this chemical agent increases the resistance of a wild-type cell to viral infection, but has little or no effect on the response of a tumour cell to viral infection. An example, which is not to be considered limiting in any manner, of such a chemical agent is interferon.

By "PKR" it is meant a serine/threonine kinase that exhibits multiple functions including roles in the control of mRNA translation and gene transcription (1,2). The kinase harbors two double-stranded RNA dsRNA binding motifs in its amino terminal regulatory half and catalytic kinase domain in its carboxyl tail. Binding of dsRNA to the amino terminus induces a conformational change in the enzyme revealing and activating the catalytic kinase domain. The expression of PKR is induced by several PKR-mediators, including but not limited to, interferon.

By "PKR-mediator" it is meant proteins or compounds that directly, or indirectly affect PKR activity either at the gene or protein level and include both PKR-activators and PKR-inhibitors. Examples of PKR-activators include, but are not limited to STAT1 (see FIG. 1), Interferon regulatory factor (IRF-1), and interferon. Examples of PKR-inhibitors, include, but are not limited to, VA RNAs, p58(IPK), factors associated with the Ras pathway, the ribosomal protein L18, or proteases that degrade PKR protein. PKR activity may also be mediated through mutations to the gene encoding PKR, or to the regulatory region that drives the expression of PKR. These mutations may either increase or decrease PKR activity. Mutations to PKR that reduce PKR activity include, but are not limited to, the loss of dsRNA binding ability of PKR, or mutations that result in negative catalytic mutants. Mutations that increase PKR activity include, but are not limited to over-expression of PKR, or mutations that resulted in a more active PKR protein.

PKR regulates translation through the phosphorylation of eIF-2α, a factor involved in the initiation of protein translation. Once phosphorylated, eIF-2α-GDP, forms an inactive complex with eIF-2B resulting in a rapid inhibition of protein synthesis. PKR impinges on gene transcription indirectly via activation of NFκB. This activation appears to be carried out by PKR phosphorylation of an IκB kinase (3) which in turn phosphorylates IκB leading to its targeted destruction.

PKR Antiviral Activity

Infection of a cell by many distinct virus types leads to the formation of dsRNA (e.g. as replicative intermediates) resulting in the activation of PKR and its subsequent downstream effectors (see FIG. 1). In particular, protein synthesis is rapidly terminated and an apoptotic cascade is initiated (4,5). As a result of the activation of PKR, the production of new virions is curtailed and the spread of virus through the organism is limited. Der et al (12) report a requirement for PKR in the induction of cellular apoptosis in response to a variety of stress inducers.

Without being bound by theory, it is possible that malignancies arise as a result of multiple mutations in genes that control cell proliferation and apoptosis. PKR's role in regulating protein synthesis coupled with its antiproliferative and pro-apoptotic properties make it a target for oncogenic mutations, which directly or indirectly affect its activity.

As described in more detail in the examples an initial screen of several viruses using PKR –/– animals indicated that PKR null animals are susceptible to infection by Vesicular stomatitis virus (VSV). Similar results were obtained in vitro, where VSV infection proceeded more rapidly in PKR–/– fibroblasts, when compared to infection in PKR+/+ fibroblasts. These results demonstrate that PKR is required by mammalian cells to resist infections by VSV. Furthermore, certain cell lines, for example, but not limited to primary human bone marrow, were resistant to VSV infection, while leukemia cell lines were susceptible to VSV infection.

It is contemplated that viruses related to VSV, or other viruses that exhibit similar mechanisms of viral infection can be identified that exhibit the property of selectively infecting cells with reduced or no PKR activity. One of skill in the art can readily screen other viruses using the methods as described herein, for their ability to reduce the viability of cells, or kill cells lacking PKR activity, or PKR–/– cells, PKR –/– animals, or both PKR–/– cells and animals.

As indicated in the examples below, pretreatment of cells with interferon reduces virus infectivity by several orders of magnitude. Without wishing to be bound by theory, the addition of interferon may upregulate PKR expression resulting in this increased resistance to viral infection.

Because of its potent antiviral activity, viruses have evolved strategies to circumvent PKR. For example, HIV and Hepatitis C encode proteins dedicated to the binding and inactivation of PKR (6,7). Adenovirus encodes small RNA molecules (VA RNAs) which bind to but do not activate PKR (8). Influenza virus usurps a cellular protein p58(IPK) to inhibit PKR while polio virus initiates the proteolytic degradation of PKR (9,10). Large T antigen of SV-40 appears to function downstream of eIF-2α to promote protein translation even in the presence of activated PKR (10).

PKR and Tumour Suppression

Expression of dominant negative PKR catalytic mutants in NIH 3T3 cells leads to their malignant transformation and facilitates their growth as tumours in nude mouse models (13,14). A similar phenomena has been observed using PKR mutants which have lost dsRNA binding activity. Induced expression of PKR in S. cerevisiae leads to growth arrest in the yeast—a phenomena that can be reversed by co-expression of a non-phosphorylatable version of eIF-2α. Therefore, PKR has anti-proliferative activity and functions as a tumour suppressor.

There are several lines of evidence that PKR is inactivated, absent or reduced in expression in a broad spectrum of human malignancies:

Oncogenic Ras mutations occur in about 30% of all human tumours while mutations in upstream Ras activators (ie EGF receptor, Neu receptor, PDGF receptor) are even more common. Mundschau and Faller (15,16) have described an oncogenic Ras induced PKR inhibitor. Furthermore, Strong et al (17) demonstrated that activation of the Ras pathway results in down regulation of PKR activity.

The ribosomal protein L18 is overexpressed in primary colorectal cancer tissues and has recently been shown to bind to and inactivate PKR (18).

Patients with 5q translocations exhibit diminished PKR expression (19-21). Interferon regulatory factor 1 (IRF-1) is a transcription factor with tumour suppressor activity, which maps to the human chromosomal region 5q. PKR gene transcription is regulated in part by IRF-1.

Human PKR maps to 2p21-22 and has been recently identified as the site of translocation in a case of acute myelogenous leukemia.

In biopsies from poorly differentiated, highly malignant tumours, PKR protein was present at very low levels or was undetectable (23-25).

STAT1

STAT1 is an essential mediator of the interferon pathway and its activation results in an upregulation of PKR mRNA and protein (see FIG. 1).

There is marked deficiency in the level/activity of STAT1 protein in interferon resistant melanoma cell lines and primary melanoma biopsy material (26), in a variety of human tumour cell lines including a myeloid leukemia, cervical carcinomas, ovarian cancer, and a lung carcinoma (27), and in a gastric adenocarcinoma (28,29). Furthermore, cutaneous T cell lymphoma (CTCL) is a malignancy which in general is responsive to interferon (however frequently clinical resistance arises in a substantial portion of cases). Sun et al (30) have reported that STAT1 protein is absent in a CTCL cell line suggesting that development of clinical resistance to interferon may arise due to STAT1 mutations.

PML: Promyelocytic Leukemia Gene

PML is an interferon induced gene that normally functions as a tumour suppressor and a key regulator of Fas, TNFα and interferon induced apoptosis. Recently, Chelbi-Alix et al have shown that another normal function of the PML gene product is to suppress virus replication. The PML-RAR fusion protein functions as a dominant negative inhibitor of interferon induced apoptosis and we would predict will also make APL cells preferentially susceptible to virus infection.

Down regulation of PKR protein or activity occurs in a broad spectrum of human malignancies. While cancer cells have attained a growth advantage and unbridled protein translation capacity by eliminating PKR or PKR-mediators, these cells have simultaneously eliminated one of the cell's primary and potent antiviral defence mechanisms. Therefore, tumour cells with reduced PKR activity will be more susceptible to infection than their normal counterparts. As indicated above, other components (e.g. STAT1 and PML) of the interferon pathway are frequently mutated in human malignancies, and loss of their activity will render tumour cells sensitive to virus infection. This differential susceptibility forms the basis for the use of viral-based cancer therapeutics of the present invention for the treatment of tumorous cell growth.

Screening of PKR null mouse strains with several different viruses indicated that PKR null animals are capable of suppressing a number of virus infections including vaccinia, influenza and EMCV. However, Vesicular Stomatitis Virus (VSV) exhibited an ability to infect PKR-/- animals. VSV, a member of the Rhabdovirus family, was observed to kill 100% of PKR null animals following intranasal infection by as little as 50 infectious virus particles (or plaque forming units, pfu). In contrast, over 20,000 times as many VSV particles were required to kill half of infected wild type littermates.

VSV is an enveloped, negative sense RNA virus with a simple five gene genome. This is a very well characterized virus family with several serologically distinct laboratory strains and a multitude of characterized mutants. The natural hosts of VSV include insects, rodents and domestic farm animals. In general, very few North Americans have come in contact with the virus—most human infections occurring in laboratory personnel and farmers. In humans infections are either asymptomatic or manifested as mild "flu". There are no reported cases of severe illness or death amongst infected humans.

The ability of VSV to selectively infect tumour cells over wild-type cells was also observed. Tumour cell lines, following an overnight infection exhibited a 100 to 1000 times higher rate of infection than that detected in normal primary fibroblasts. Furthermore, the cytopathic effect (cpe) was accelerated in the tumour cell cultures.

Figure 2:
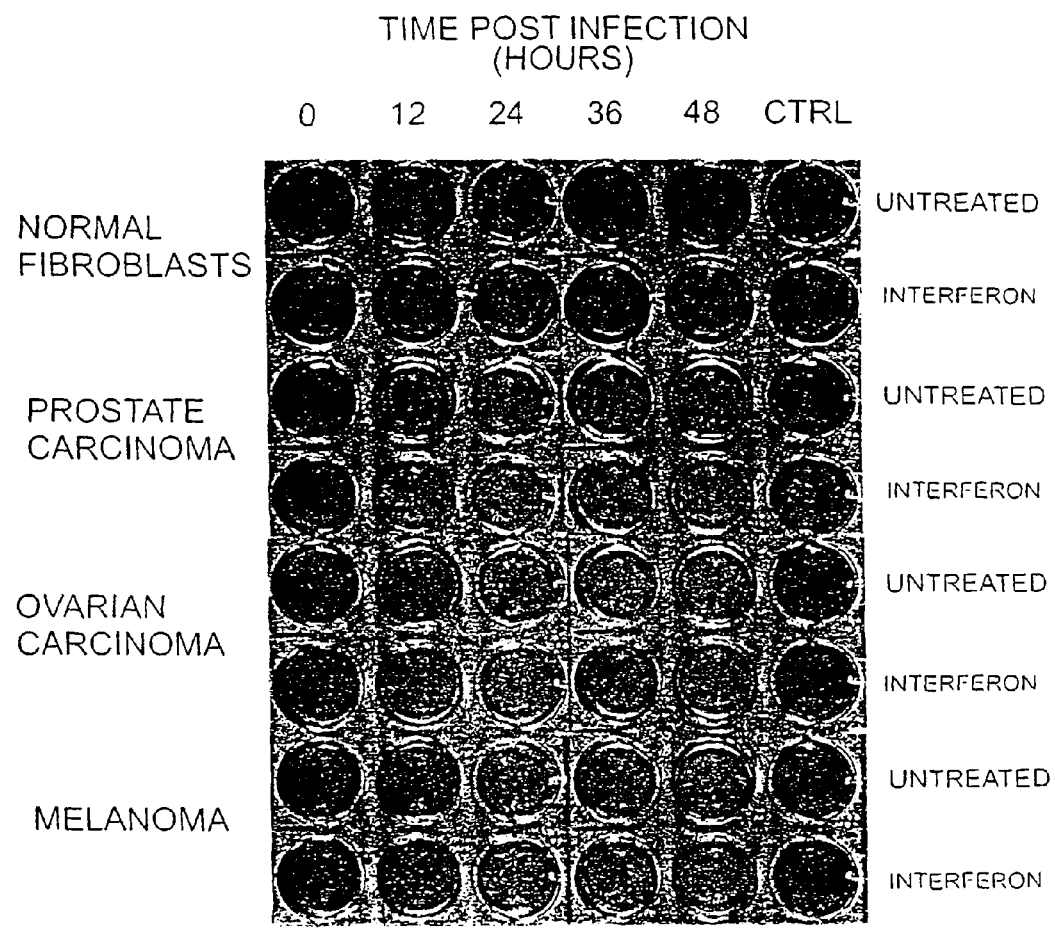

Since PKR is an interferon inducible gene product, pretreatment of cells with interferon prior to exposure to VSV was tested to determined the effect of viral infection. Wild-type cell cultures, that were pretreated with interferon, were resistant to VSV infection, while tumour cell lines, for example, but not limited to, fibrosarcoma, melanoma, prostate carcinoma, leukaemia and ovarian sarcoma, were susceptible to virus infection (see Table 1, Example 2; FIG. 2). Lung carcinoma cells (LC80) were also susceptible to VSV infection in the presence and absence of interferon (data not presented). However, several tumour cell lines were resistant to VSV infection in the presence of interferon.

Ovarian carcinoma cells, fibrosarcoma, lung carcinoma, melanoma, prostate carcinoma, lung carcinoma, and leukaemia cells are VSV sensitive, and this sensitivity was maintained in the presence of interferon, therefore, such tumor cells and cancers derived therefrom may be particularly amenable to VSV treatment. However, other cancers may also be amenable to viral treatment as described herein. Studies with respect to VSV sensitivity using primary tumour material is readily available in ascites fluid. Further, since the tumour is contained within the peritoneal cavity it may prove particularly suited to localized administration of a virally based therapeutic. In this regard, live tissue from patient's ascitic fluid can be tested for the ability of the tumour cells to support VSV infection in the presence and absence of interferon.

Figure 5:
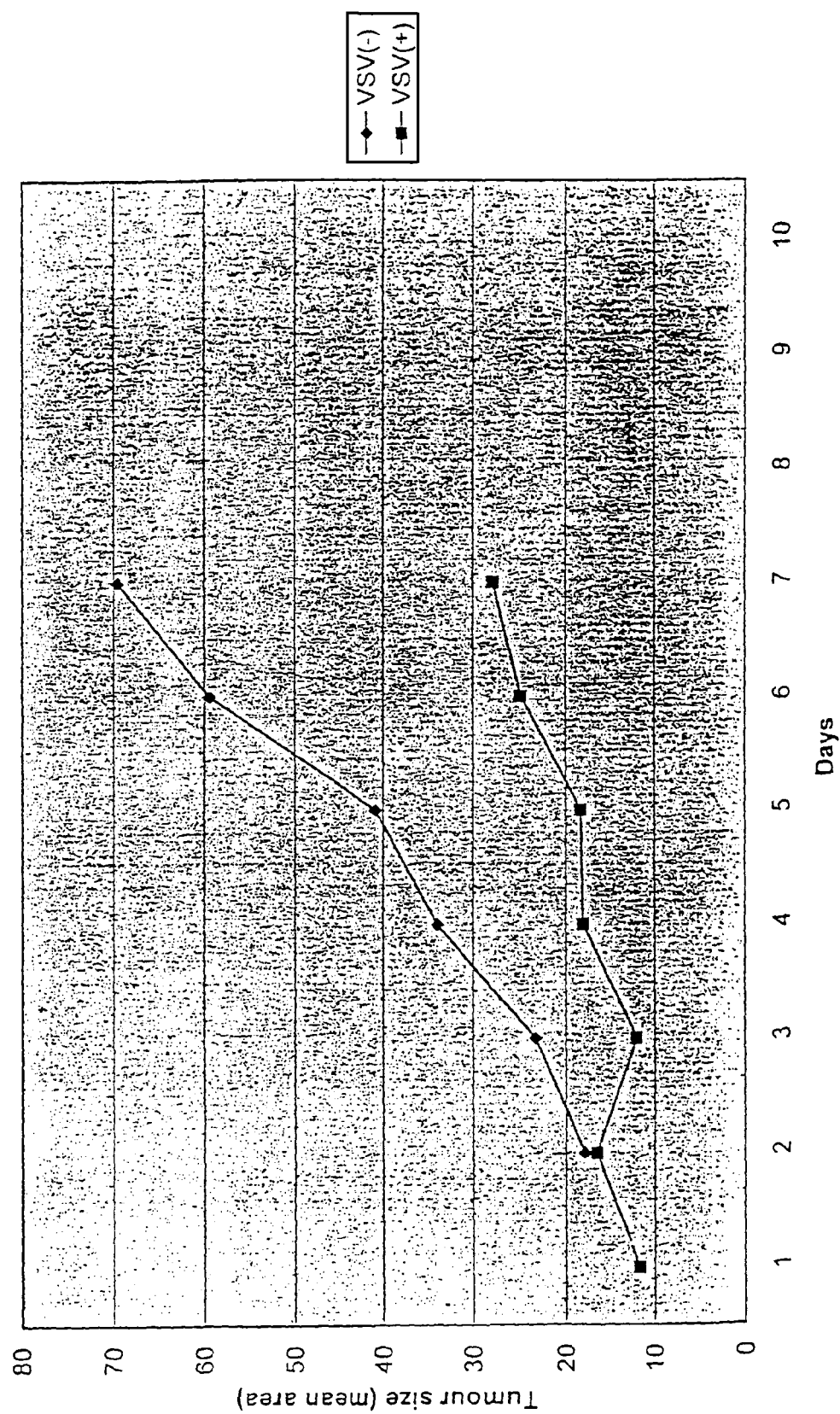
Figure 6:

It is expected that VSV will have therapeutic activity in vivo, and will have the ability to kill distant (metastatic) tumour growths. To date no significant organ pathology in treated mice have been observed, however, the kinetics of VSV viremia need to be further studied. Nude mice, implanted with human melanoma cells received VSV, or additional melanoma cells infected in vitro with VSV (see Example 5), to ensure the continuous production of infective particles to the tumour over a several hour period, via injection (FIG. 5). In mock-injected animals (VSV(-); injection with vehicle alone) tumours grew continuously over the course of the experiment. Animals which received only pure virus showed initially continuous growth of tumours over the first four day period, after this time the tumours began to reduce in size and continued to do so over the course of this experiment. Tumours that were injected with infected cells stopped growing and regressed to small hard nodules resembling scar tissue. In some of the larger injected tumours, ulcers formed on the tumour within 1-2 days, (see FIG. 6). While both injection of purified virus and infected melanoma cells caused significant regressions, infected producer cells were more effective.

Studies with an immunocompetent mouse tumour model (i.e. as described by Strong et al; 17) will examine the affects of antibody response to therapeutic VSV infection, and determine if VSV infection of tumour cells increases their immunogenicity and promotes recognition of tumour antigens by the host organism.

Primary human bone marrow was also found to be resistant to VSV infection in the absence of interferon pretreatment (see Table 1, Example 2), indicating that these cells have an innate resistance to VSV infection. In contrast two leukemia cell lines (M07E and L1210) were also tested and found to be susceptible to VSV infection as evidenced by cytopathic effect, virus growth and loss of cell viability.

While the results disclosed herein relate to VSV, it is to be understood that one of skill in the art, by following the methods outlined in this document, will be readily able to screen other VSV strains, derivatives of VSV including mutants of VSV, or related viruses for the ability to selectively kill tumour cells. There are several other serologically and biologically distinct strains of VSV, which can be tested for this property. Such VSV strains include, but are not limited to New Jersey, Piry, Coccal, and Chandipura. Identification of other suitable serologically unrelated strains may be useful if sequential VSV injections are required to completely eradicate tumours. Furthermore, picornaviruses (eg rhinoviruses) are known to be relatively innocuous to normal human tissues yet grow extremely well in transformed cells in tissue culture, and these viruses may also be used. Furthermore, combinations of viruses may be used to enhance the cytopathic effect observed with VSV.

Figure 4:
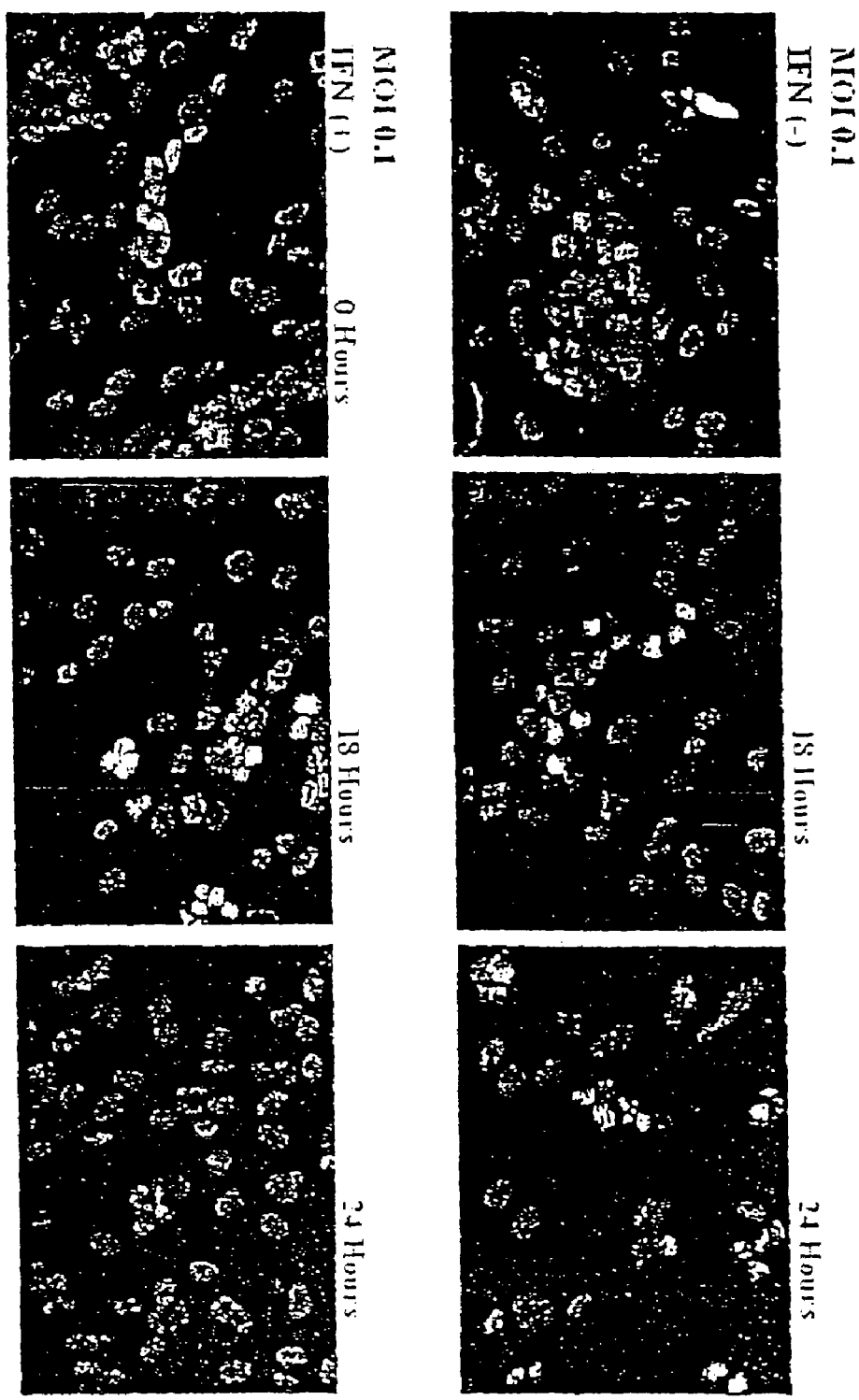

In order to determine whether the presence of either a normal or tumor cell could affect the other cell type (either normal and tumor cell) and alter the resistance or susceptibility of either of these cells to VSV infection, normal cells and fibroblasts were co-cultured in the present of VSV. The culture was infected at an moi of 0.1 pfu/cell and the infection allowed to proceed in the presence or absence of interferon. At 0, 12 and 24 hours (FIG. 4) the cultures were fixed and stained with antibodies to large T antigen (red nuclei) to detect the 293T cells and with DAPI (blue nuclei) which stains all cell types (FIG. 4). The number of 293T cells (red nuclei) steadily declined during the time course and displayed severely condensed or fragmented nuclei characteristic of a cell dying from virally induced apoptosis. This selective destruction of the transformed cells was seen both in the presence and absence of interferon. The normal fibroblasts did not develop nuclear changes nor were their numbers reduced in response to VSV infection even though 293T cells were producing copious amounts of virus within the co-culture. This indicates that mixtures of cell populations may be treated with VSV while still maintaining tumor cell sensitivity, and normal cell resistance to VSV.

In addition there are a number of mutants of VSV, for example, but not limited to mutants which are impaired in the shut down of host protein synthesis or are more or less sensitive to interferon, which may exhibit differential infection between normal and tumour cells. For example, which is not intended to be limiting in any manner, other viral mutants are known which show tropism for STAT1 or PKR negative cells include an influenza virus strain which is unable to inactivate PKR has been described (36) Adenovirus mutants which lack the PKR inactivating VA gene are known to grow better in the absence of PKR.

As described herein, VSV mutants were isolated that grew poorly on interferon responsive cells. These mutants were selected based upon their ability to form small plaques in monolayers of interferon-responsive cells. On interferon non-responsive cells (i.e. tumor cells) these mutants form large plaques. The selection of mutants by size of plaque in interferon-responsive cells allows for the isolation of virus that grows poorly in normal cells. However, other VSV mutants may be obtained under different selection criteria. Mutants isolated using interferon-responsive cells were amplified and tested for their ability to kill tumour and normal cells. The rationale here is that VSV mutants, which can induce interferon in target cells, would limit their own replication in an interferon responsive cell population. These same viruses would however have unrestricted growth in tumour cells that lack interferon responsiveness. These mutants are of value, as they have even less cytopathic effect on normal tissues while maintaining oncolytic activity than wild type VSV.

Four mutants (Mut 1-4) were obtained based on their ability to form plaques in monolayers of interferon-responsive cells. These mutants, and wild type virus (moi of 1.0 pfu/cell) were used to infect melanoma cells and normal human foreskin fibroblasts. All of the mutants were able to kill tumour cells efficiently but normal cells infected with the mutants even after long periods of infection appeared completely uninfected. At this same moi wild type VSV demonstrated a cytopathic effect on the normal cells. These results indicate that the mutant virus have a greater therapeutic effect in that they kill tumour cells efficiently while sparing normal cells, and that they also have the ability to produce more virus particles and increase virus spread throughout the tumour (see Example 4). Surprisingly these mutants grew more rapidly than wild type VSV (Indiana) in HCT 116 colon carcinoma cells but not in OSF7 cells (See Example 21 and FIGS. 10A and 10B). VSV mutants that display rapid growth in the tumour cell of interest but not in normal cells are preferred.

Earlier experiments indicated that PKR –/– mice were killed with VSV by several routes of infection, however, these mice were not affected by intravenous injections of the virus. In order to determine whether plasma components were inactivating the virus upon contact, VSV produced from several sources including within mouse L cells was incubated with human serum (from normal uninfected donor) and the virus titer after incubation determined (Example 6). The viral titer of L cell-produced VSV dropped four hundred fold, while VSV produced in human melanoma cells was unaffected by incubation in plasma. These results indicate that the choice of cell line for the production of VSV is critical. Based on this observation it is possible to screen human cell lines for those that produce optimum amounts of virus that is not sensitive to human serum.

Without wishing to be bound by theory, it may be that the difference in these two virus preparations reflects the nature of the cohort of proteins found on the surface of the virus producing cells. As part of its replicative cycle, VSV buds through the plasma membrane and acquires cellular protein on its envelope. Certain proteins found on L cells when expressed in the context of the virus particle could activate complement. Indeed, it has been shown earlier that retrovirus particles produced in certain mouse cells are inactivated by serum while the same virus produced in a subset of human cell lines was unaffected by plasma. (Pensiero, M. N., et al. Hum Gene Ther, 1996. 7:1095-1101).

Conventional techniques for VSV production are difficult to scale up for industrial production. Therefore, the purification of VSV, using an affinity matrix, for example affinity chromatography was explored. (See Example 7). However, other protocols for affinity purification may also be used as known within the art, for example, but not limited to, batch processing a solution of virus and affinity matrix, pelleting the VSV-bound matrix by centrifugation, and isolating the virus. In order to provide the virus with an affinity tag to be used for the purification of the virus, the virus may be genetically modified, using techniques well known in the art, to express one or more affinity tags on its surface, preferably as a fusion viral envelope protein, or producer cell lines may be engineered to express one or more affinity tags on their plasma membranes which would be acquired by the virus as it buds through membrane, however, endogenous viral envelope proteins may also be used. One well characterized affinity tag involve the use of Histidine residues which binds to immobilized nickel columns, however, it is to be understood that other affinity tags may also be employed.

Cell lines can be prepared that act as a universal producer of VSV, or other virus, that expresses a chimeric VSV protein with nickel binding, or other affinity tag properties. This universal producer cell may be used for the production of a chimeric protein (affinity tag) for any enveloped virus (including all enveloped RNA and DNA viruses). For the purification of virus which bud through the nuclear membrane (such as Herpes virus), a tag to be expressed on the viral envelope protein expressed in the nuclear membrane is engineered.

Other affinity tags include antibodies, preferably an antibody which recognizes a particular peptide under conditions of low salt, low temperature or in the presence of a critical cation/anion. Physiological salt concentrations, thermal elution or chelation could effect elution. Antibodies generated against di or tripeptides may also be used for purification. In this manner, two or more of these tags on the surface of a single virus particle would allow for the sequential affinity purification of the virus.

VSV may be genetically modified in order alter its properties for use in vivo. Methods for the genetic modification of VSV are well established within the art. For example a reverse genetic system has been established for VSV (Roberts A. and J. K. Rose, Virology, 1998. 247:1-6) making it possible to alter the genetic properties of the virus. Furthermore, standard techniques well known to one of skill in the art may be used to genetically modify VSV and introduce desired genes within the VSV genome to produce recombinant VSVs (e.g. Sambrook et al., 1989, A Laboratory Manual. New York: Cold Spring Harbor Laboratory Press).

VSV may be targeted to a desired site in vivo to increase viral efficacy. For example, modification of VSV G protein to produce fusions that target specific sites may be used to enhance VSV efficiency in vivo. However, it is to be understood that other protein targets in addition to the VSV G protein may also be modified to produce such fusion proteins. Such fusion proteins may comprise, for example, but not limited to, Single chain Fv fragments (Lorimer, I. A., et al. Proc. Natl. Acad. Sci. U.S.A., 1996. 93:14815-20) that have specificity for tumour antigens. An example of such a single chain Fv fragment that may be used to prepared a VSV G fusion protein, is an Fv fragment that targets a mutant EGF receptor found on about 80% of human breast tumour cells.

VSV may also be modified to express one or more suicide genes capable of metabolizing a pro-drug into a toxic metabolite thereby permitting VSV infected cells to be killed by administration of a pro-drug. For example, VSV comprising the herpes virus thymidine kinase gene or the cytosine deaminase gene encodes an enzyme that can convert ganciclovir or 5-FC, respectively, into a toxic compound. However, it is to be understood that other suicide genes may also be employed. As it is well established that ganciclovir metabolites kill not only cell expressing HSV TK but also cells in the immediate vicinity, rVSV comprising these suicide genes exhibit several advantages. For example, the effective killing by the virus is increased since one infected cell kills ten or more surrounding tumour cells, furthermore rVSV comprising a suicide gene permits the elimination of virus if desired from an individual infected with the virus. This may be important in situations where it is unclear how VSV may affect an individual. For instance, an immune comprised individual may be unexpectedly susceptible to VSV. Thus the addition of a suicide gene would be an improvement on the safety of the viral therapeutic.

VSV may also be modified by the introduction of a mammalian gene product. Such a mammalian gene product would limit VSV growth in normal cells, but not the growth of VSV in tumour or diseased cells. For example, rVSV capable of expressing one or more transactivators of p53, activates apoptotic pathways in normal cells but not tumor cells. Such rVSVs therefore selectively limit virus spread in normal tissues. However, it is to be understood that other mammalian gene products may also be expressed within VSV for this purpose. Another example, which is not to be considered limiting in any manner is the PKR gene. A rVSV expressing the PKR gene limits virus replication in all normal cells, however, in cells that express PKR inhibitors, the virally encoded PKR is inactivated. An example of a cell that expresses one or more PKR inhibitors is a chronically Hepatitis C infected cell. Since Hepatitis C encodes and expresses two known inhibitors of PKR (i.e. NS5A and E2), a VSV encoded PKR gene product is be neutralized, and VSV allowed to replicate freely.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

Example 1

PKR Negative Cells are Susceptible to VSV Infection

In Vivo Experiments

Initial studies were directed to identifying viruses that are capable of infecting PKR−/− animals and cells. Using homologous recombination strategies, PKR null mouse strains were generated (35, which is incorporated by reference) and tested for their ability to fight virus infections. Since these mice are PKR−/−, they should be susceptible to virus infection. Several species of virus were administered to PKR null animals over a range of concentrations.

Infection of PKR Null Mice:

A PKR null mouse line was generated using conventional knockout technology (Abraham, N., et al., J Biol Chem, 1999. 274:5953-5962). Groups of five female mice, 3 months of age or greater, were infected intranasally with varying amounts of vesicular stomatitis virus (Indiana strain). Age matched wild type animals were infected in parallel and both sets of animals were monitored on a daily basis for signs of infection. These include, hydration, piloerection, activity level, appetite, hind limb paralysis, respiratory rate, body weight and any other symptoms indicating that the animal was in distress.

Wild type animals showed few and only transient symptoms at multiplicities of infection up to $10^5$ pfu with VSV. In contrast, PKR null animals very rapidly developed dehydration, piloerection, loss of appetite, rapid respiratory rate, decreased activity and squinting crusty eyes. At high doses of VSV infection ($10^5$ pfu) the animals showed symptoms in less than 24 hours and usually succumbed to the infection within 48 hours. At doses of infection as low as 25 pfu, 100 percent of the PKR null animals died of VSV infection within 5 days. In separate experiments groups of five wild type and PKR null animals were sacrificed at 48 hours post infection with VSV and organs were removed to assess viral titres. In the PKR animals titres in excess of one million PFU/ml of lung homogenate were found at this time while in wild type animals virus titres ranged from 0 to 100 pfu per ml of lung homogenate. In the wild type and PKR null animals similar amounts of virus were found in the brain. The remainder of the tissues in both mouse strains had undetectable virus at this time post infection.

Vesicular stomatitis virus, a member of the Rhabdovirus family was able to kill 100% of PKR null animals following intranasal infection by as little as 50 infectious virus particles (or plaque forming units, pfu). In contrast, over 20,000 times as many VSV particles were required to kill half of infected normal littermates. These results indicate that PKR null animals are capable of suppressing a number of virus infections including vaccinia, influenza and EMCV. However, VSV exhibited an ability to infect PKR−/− animals. These results also indicate that PKR is required by mammalian cells to resist infections by VSV (Indiana laboratory strain).

Example 2

Selective Killing of Tumour Cells with VSV

In Vitro Experiments

Several tumour cell lines were chosen at random from the Ottawa Regional Cancer Center and tested for their susceptibility to VSV infection. Primary fibroblast cultures from healthy adult volunteers or primary bone marrow samples from healthy donors were used as control cells.

Infection of Tumour Cells with VSV:

As a first test of the oncolytic properties of VSV, virus production and cytopathic effect following an overnight incubation with VSV was assessed. Monolayers of cells were incubated with the Indiana strain of VSV at a multiplicity of infection (moi) of 0.1 plaque forming units (pfu). After allowing virus to adsorb for minutes at 37 C, the cultures were rinsed thoroughly with phosphate buffered saline (PBS) and then cultured an additional 18 hours at 37 C. At this time, the cultures were examined microscopically for cytopathic effect (cpe) and photographed. The 18 hour supernatant was removed and virus titres per ml of medium determined. In some experiments, cultures were preincubated for 12 hours with human alpha interferon (100 units/ml) prior to infection.

Figure 3A:
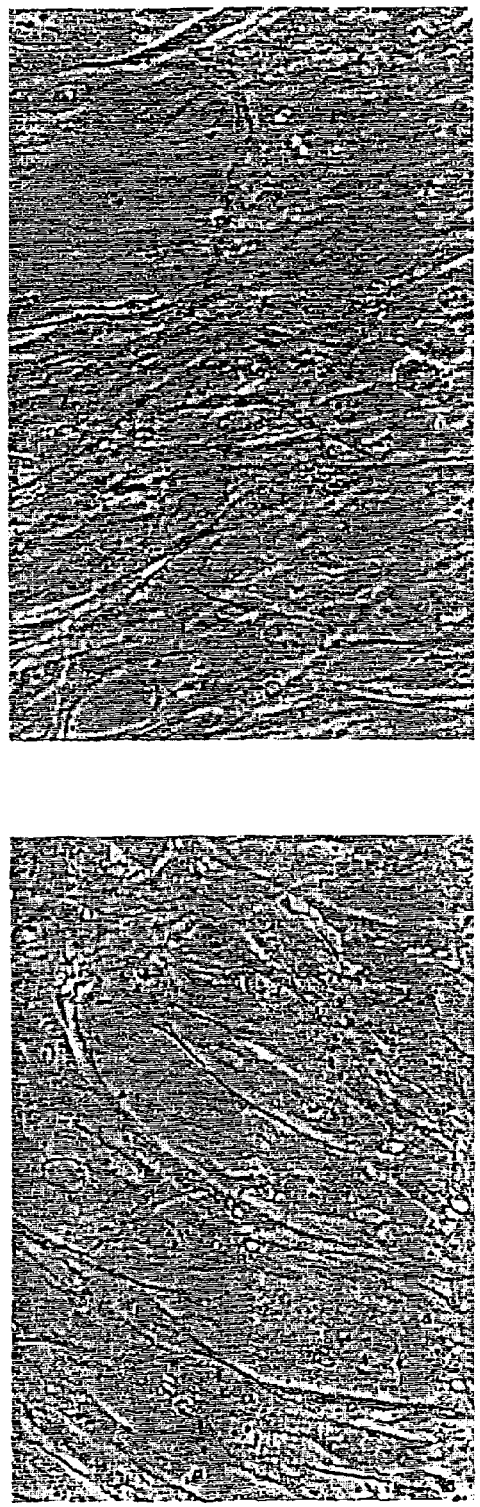
Figure 3B:
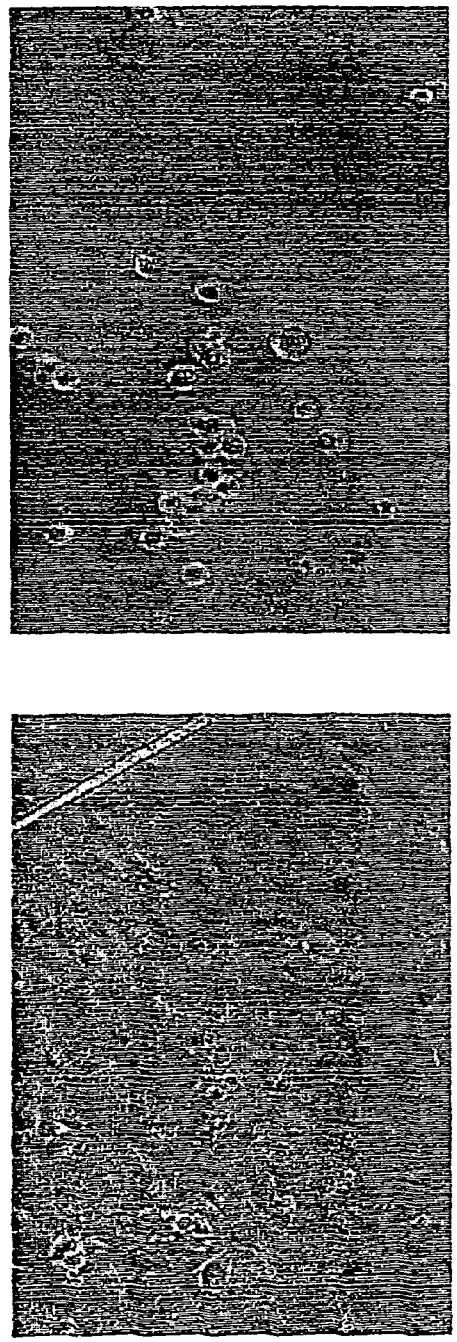

To examine the kinetics of infection of the assorted cell types a modified cpe assay (Heise, C., et al., Nat Med, 1997. 3:639-645) was used. Essentially, monolayers of cells were infected at an moi of 0.1 pfu in a 12 well plate. At time 0 and every 12 hours subsequent up to 48 hours, one well of infected cells was fixed with 0.5 ml Leukostat fixative (Fisher Diagnostics) for 2 minutes. At the end of the experiment monolayers were stained with Leukostat stains 1 and 2 following manufacturers instructions. Since PKR is an interferon inducible gene product, the pretreatment with interferon, 100 units/ml of human alpha interferon 12 hours prior to infection, was tested to determined if interferon could enhance protection within the assorted cell cultures. The data are presented in Table 1 and FIGS. 2-3.

TABLE 1

Cell lines tested for VSV sensitivity

| Cell line | cell type | Reference | Untreated Overnight Virus Yield | Interferon Overnight Virus Yield |
|---|---|---|---|---|
| OSF 16 | human normal fibroblast | ORCC[1] | $1 \times 10^5$ pfu | 0 pfu |
| AG1522 | human foreskin fibroblast | [20] | | 0 pfu |
| OSF 7 | human normal fibroblast | ORCC | $1 \times 10^6$ | 0 pfu |
| OSF 12 | human normal fibroblast | ORCC | $2 \times 10^5$ pfu | 0 pfu |
| MN11 | mouse fibrosarcoma | [21] | $1 \times 10^8$ | $1 \times 10^4$ |
| A2780 | human ovarian carcinoma | [22] | $2 \times 10^8$ | $1 \times 10^7$ |
| H-1078 | normal human bone marrow | ORCC | 0 pfu (moi 10 pfu) | Not determined |
| M07E | human leukemic cell line | [23] | $2 \times 10^6$ (moi 1.0 pfu) | Not determined |
| L1210 | mouse leukemic cell line | [24] | $4 \times 10^6$ | $2 \times 10^4$ |
| SK-MEL3 | human melanoma | [25] | Not determined: cpe assay positive | Not determined: cpe assay positive |
| LNCAP | human prostate carcinoma | [26] | Not determined: cpe assay positive | Not determined; cpe assay positive |
| 293T | fibrosarcoma transformed with SV-40 Large T and Adeno E1A | [27] | $1 \times 10^8$ | $8 \times 10^7$ |
| OVCA 432 | | [28] | $1 \times 10^7$ | 0 pfu |
| C13 | ovarian carcinoma | [29] | $1 \times 10^8$ | $1 \times 10^5$ |
| OVCA 3 | | [30] | $5 \times 10^7$ | Not determined |
| COS | Large T transformed simian kidney cell line | [31] | $2 \times 10^8$ | Not determined |
| HCT 116 | colon carcinoma | [32] | Not determined: cpe assay positive | Not determined cpe assay positive |
| OVCA 420 | | [28] | $1 \times 10^8$ | $3 \times 10^6$ |

1 established at the ORCC from forearm biopsy.

From the data in Table 1 it can be seen that although normal human fibroblasts can support viral replication, the amount of virus produced and the progression to cell lysis was substantially delayed when compared to tumour cells. An even more substantial difference in virus production was observed following pretreatment with interferon. While normal human fibroblast monolayers were completely protected from the cytolytic affect of VSV by interferon, tumour cells remained sensitive, producing copious amounts of viral particles and rapidly undergoing cytolysis.

Other cells lines, including a lung carcinoma cell line (LC80) and a leukaemia cell line, AML5 (acute myelogenous leukemia 5) cells were also found to be effectively killed by VSV. In the case of AML5, at a moi of 1.0 pfu/ml cells were completely killed within 24 hours, while at 0.0001 pfu/ml the cells were killed within 72 hours, further indicating the sensitivity of leukaemia cells to VSV.

As can be seen in FIG. 2, monolayers of tumour cells were much more rapidly destroyed by VSV infection as compared to normal human fibroblasts. The human melanoma cell line SK-MEL3, the LNCaP prostate cancer cell line and the ovarian carcinoma cell A2780 all showed substantial cpe as early as 12 hours post infection. Although the normal human fibroblast cultures were infected and capable of producing virus (see Table 1), the kinetics of infection was substantially slower than in the three tumour cell lines tested in this experiment. In addition, as with the overnight virus growth assay (Table 1, FIG. 2), interferon alpha treatment completely protected the normal human fibroblasts, but was ineffective at protecting the three tumor cell lines from the cytopathic effect of VSV.

The results obtained for Table 1 demonstrate that a screening strategy for determining the types of tumours which are susceptible to killing by VSV may be employed using for example, but not limited to, the NIH/NCI standard panel of tumour cell lines available from ATCC. These cell lines are screened in order to determine the time to complete cpe and/or virus growth using various initial multiplicities of infection. These experiments are done in the presence and absence of interferon so that the number of and types of tumours that are VSV sensitive and are resistant to interferon's antiviral activity are determined.

VSV Treatment of Leukemia

VSV does not productively infect bone marrow stem cells, even at high moi of 10 pfu/cell (H-1078; Table 1). The treated cultures retained all of their stem cell characteristics. Two leukemia cell lines (MO7E and L1210; Table 1) were killed following an overnight infection and produced large amounts of virus.

To determine whether VSV could kill primary leukemia cells from a cancer patient, a peripheral blood sample was obtained from an AML patient and white blood cells collected and plated in RPMI media plus 10% FBS ($10^7$/well in 6 well plate, each infection in duplicate). Cells were mock infected or infected at an moi of 10.0/cell. VSV selectively killed myeloid leukemic cells as indicated by the decrease in the percentage of blast cells (leukemic blasts), while the overall cell number was minimally affected (i.e. neutrophils flourished). The leukemic sample produced titres of VSV exceeding $10^7$ pfu/ml at 16 hours post infection. The number of blast cells in the sample was dramatically reduced at 21 hours post infection while the proportion of normal neutrophils increased. Mock infected cells (−VSV) contained almost 70% blast cells in a monolayer, while in cells infected with VSV (+VSV) normal cells predominated. These results demonstrate VSV is able to preferentially kill primary leukemic blast cells while sparing normal blood cells.

Example 3

Killing of Tumour Cells in Mixed Cultures

Normal human fibroblasts and 293T tumour cells were co-cultured in a 50:50 mixture. Since 293T cells express the large T antigen which is not found in normal cells, the two cell types can be distinguished by immunofluoresence.

In this experiment cultures were infected at an moi of 0.1 pfu/cell and the infection allowed to proceed in the presence or absence of interferon. At 0, 18 and 24 hours (FIG. 4) the cultures were fixed and stained with antibodies to large T antigen (red nuclei) to detect the 293T cells and with DAPI (blue nuclei) which stains all cell types (FIG. 4). Initially both cell types displayed a spindle-like morphology with large oval nuclei. After 18 hours the number of 293T cells (red nuclei) were reduced and many of the remaining 293T cells displayed altered nuclear morphology. By 24 hours post-infection very few 293T cells were detected and those few that remained displayed severely condensed or fragmented nuclei characteristic of a cell dying from virally induced apoptosis.

This selective destruction of the transformed cells was seen both in the presence and absence of interferon. The normal fibroblasts did not develop nuclear changes nor were their numbers reduced in response to VSV infection even though 293T cells were producing copious amounts of virus within the co-culture.

Example 4

VSV Mutants as Oncolytic Agents

VSV mutants were isolated based upon their ability to form small plaques in monolayers of interferon-responsive cells, as compared to the size of plaques in monolayers of interferon-nonresponsive cells. Viral isolates, which form small plaques in interferon-responsive cells were picked, amplified and re-cloned. Mutants isolated in this way were amplified and tested for their ability to kill tumour and normal cells. The rationale here is that VSV mutants, which can induce interferon in target cells, would limit their own replication in an interferon responsive cell population. These same viruses would however have unrestricted growth in tumour cells that lack interferon responsiveness. These mutants would be of value, as they should have even less cytopathic effect on normal tissues while maintaining oncolytic activity.

Four mutants (Mut 1-4) were obtained based on their ability to form small plaques in monolayers of interferon-responsive cells. These mutants were initially identified by Dr. Lauren Poliquin (University of Quebec at Montreal) and provided by him. After five rounds of plaque purification, these mutants and wild type virus (moi of 1.0 pfu/cell) were used to infect melanoma cells and normal human foreskin fibroblasts and titres of released virus determined 12 and 24 hours post infection.

All of the mutants were able to kill tumour cells efficiently but normal cells infected with the mutants even after long time points appeared completely uninfected. At this same moi wild type VSV demonstrated a cytopathic effect on the normal cells. It was also observed that all of the VSV mutants produced approximately ten times more virus than the wild type VSV following an overnight infection of melanoma cells. On normal cells, while the Mutants 1-4 had significantly less cytopathic effect than wild type VSV, similar amounts of virus were produced from the infected cultures. These results indicate that the mutant virus have a greater therapeutic effect in that they kill tumour cells efficiently while sparing normal cells, and that they also have the ability to produce more virus particles and increase virus spread throughout the tumour.

Example 5

Infection of Nude Mice Bearing Human Tumour Xenografts

Nude mice were implanted with human melanoma cells and divided into groups. One group received a mock injection (VSV(−)), and the other were injected with wild type VSV or injected with additional melanoma cells infected in vitro with VSV for one hour prior to injection into the tumour site in order to deliver cells that would continuously produce infective particles to the tumour over a several hour period (VSV (+)). The results of these experiments are seen in FIG. 5 which shows the average of the tumour area with time in treated and mock injected animals.

In the case of mock-injected animals (VSV(−); injection with vehicle alone) tumours grew continuously over the course of the experiment. Animals which received only pure virus showed initially continuous growth of tumours although at day 4 post infection the tumours began to shrink and continued to do so over the course of this experiment. Tumours that were injected with infected cells demonstrated the most dramatic regressions. Essentially most tumours stopped growing and regressed to small hard nodules resembling scar tissue.

In some of the larger injected tumours, ulcers formed on the tumour within 1-2 days, (see FIG. 6), followed by continuous shrinkage of the once rapidly growing malignancy. While both injection of purified virus and infected melanoma cells caused significant regressions, infected producer cells were more effective.

Example 6

The Choice of Cell Line for Producing VSV Affects Sensitivity of the Virus to Plasma Earlier experiments indicated that PKR −/− mice were killed with VSV by several routes of infection, however, these mice were not affected by intravenous injections of the virus. Without wishing to be bound by theory, this could be because the PKR −/− vascular endothelial cells provide a barrier to tissue infection or because plasma components were inactivating the virus upon contact. To test this latter idea VSV produced from several sources including within mouse L cells was incubated with human serum (from normal uninfected donor) and the virus titer after incubation determined.

Following incubation of VSV in human serum, the viral titer of L cell-produced VSV dropped four hundred fold. On the on the other hand VSV produced in human melanoma cells was unaffected by incubation in plasma.

These results indicate that the choice of cell line for the production of VSV is critical. Based on this observation it is possible to screen human cell lines for those that produce optimum amounts of virus that is not sensitive to human serum.

Example 7

Strategy for VSV Concentration and Purification

Conventional techniques for VSV production include centrifugation steps and gradient purification—both of these approaches difficult to scale up for industrial production. Therefore, alternate protocols for the purification of VSV, for example affinity columns for the simultaneous concentration and purification of virus particles has been explored.

In order to provide the virus with an affinity tag to be used for the purification of the virus, endogenous proteins may be used or, the virus may be engineered to express one or more affinity tags on its surface, or producer cell lines may be engineered to express one or more affinity tags on their plasma membranes which would be acquired by the virus as it buds through membrane. The unique viral envelope proteins can be purified using affinity chromatography.

One such affinity tag may involve the use of Histidine residues which binds to immobilized nickel columns, however, it is to be understood that other affinity tags may also be employed. This approach has been tested using the bacterial virus M13. Using a phage peptide display system (Koivunen, E., et al., J. Nucl Med, 1999. 40:883-888), viral particles expressing Histidine containing peptides which bind to nickel columns, but that can be eluted with imidazole, were selected including:
CTTHRHHTSNC (SEQ ID NO:1); CLNAHRTTHHHC (SEQ ID NO:2); CHGLHSNMRHC (SEQ ID NO:3); CHHHHRLNC (SEQ ID NO:4); CSHHHRGC (SEQ ID NO:5); CWDHHNHHC (SEQ ID NO:6); CDNNHHHHC (SEQ ID NO:7); CHHHRISSHC (SEQ ID NO:8). The expression of these peptides on the surface of M13 phage resulted in the purification concentration of the virus on nickel resins and their elution using low concentrations of imidazole.

One or more of these sequences can be integrated into the VSV G protein to result in an increased concentration of the viral particles bearing these peptides on nickel residues. The eluted virus is expected to retain its infectivity.

In this manner a cell line that can be a universal producer of VSV, or other virus, that expresses a chimeric VSV protein with nickel binding properties is produced. This universal producer cell may be used for the production of such a chimeric protein (affinity tag) for any enveloped virus (including all enveloped RNA and DNA viruses). For the purification of virus which bud through the nuclear membrane (such as Herpes virus), a tag to be expressed on the viral envelope protein expressed in the nuclear membrane is engineered.

Other affinity tags include antibodies, preferably an antibody which recognizes a particular peptide under conditions of low salt, low temperature or in the presence of a critical cation/anion. Physiological salt concentrations, thermal elution or chelation could effect elution. Antibodies generated against di or tripeptides may also be used for purification. In this manner, two or more of these tags on the surface of a single virus particle would allow for the sequential affinity purification of the virus.

Example 8

Use of VSV to Treat Chronic Infections

Some human disorders arise as a result of chronic viral infections including latent herpes infection, hepatitis, AIDS and cervical cancer. In each of these cases, the causative viral agent has evolved mechanisms to inactivate components of the interferon response pathway including PKR (e.g. Chelbi-Alix, M. K. and H. de The, Oncogene, 1999. 18:935-941; Gale, M. J., Jr., et al., Virology, 1997. 230: 217-227; Gale, M. J., et al., Clin Diagn Virol, 1998. 10:157-162; Gale, M., Jr. and M. G. Katze, Methods, 1997. 11:383-401; Barnard, P. and N. A. McMillan, Virology, 1999. 259:305-313). Therefore, the administration of VSV, or interferon inducing VSV mutants, or a combination thereof, to individuals suffering from these disorders, selectively ablates the chronically infected cells. Further therapeutic efficacy could be found by targeting through cell or viral receptors only the chronically infected cells.

Example 9

Genetic Modification of VSV

A reverse genetic system has been established for VSV (Roberts A. and J. K. Rose, Virology, 1998. 247:1-6) making it possible to alter the genetic properties of the virus.
Targeting VSV to Desired Sites In Vivo Presently VSV can bind to most mammalian cell types although its replication once inside the cell can be restricted (i.e. by interferon responsive gene products including PKR). Thus the effective dose of virus that can actually find target cells (i.e. tumour cells) for productive infection can be greatly limited simply by the "sink" that other normal tissues provide. Therefore, VSV may be genetically modified in order to bind and infect only tumour cells.

Recombinant DNA techniques well known in the art (e.g. Sambrook et al., 1989, A Laboratory Manual. New York: Cold Spring Harbor Laboratory Press) are used to modify VSV G protein. Single chain Fv fragments (Lorimer, I. A., et al. Proc. Natl. Acad. Sci. U.S.A., 1996. 93:14815-20) that have specificity for tumour antigens are fused to VSV G protein. An example of such a single chain Fv fragment is one that targets the mutant EGF receptor that is found on about 80% of human breast tumour cells.
Expression of Suicide Genes within VSV The VSV genome is modified so that it comprises the herpes virus thymidine kinase gene or the cytosine deaminase gene. Both of these genes encode enzymes which can convert pro-drugs into toxic compounds (e.g. ganciclovir or 5-FC). Viruses modified in this way express these suicide genes, thereby permitting VSV infected cells to be killed by administration of the pro-drug. This provides two advantages since (1) it is well established that ganciclovir metabolites kill not only cell expressing HSV TK but also can cells in the immediate vicinity. This "by-stander effect" can increase the effective killing by the virus (i.e. one infected cell could result in the killing of ten or more surrounding tumour cells); and (2) having a VSV with a suicide gene could allow the elimination of virus if desired from an individual infected with the virus.
Controlling VSV Growth In Vivo A mammalian gene product is introduced within VSV to limit VSV growth in normal cells, but this gene product does not affect VSV growth in tumour or diseased cells.

Recombinant VSVs (rVSV) comprising one or more transactivators of p53, activate apoptotic pathways in normal cells but not tumour cells. Such rVSVs limit virus spread in normal tissues but allow virus growth in tumour cells.

rVSV comprising the PKR gene limits virus replication in all normal cells, however, in cells that express PKR inhibitors, the virally encoded PKR is inactivated.

An example of a cell that expresses one or more PKR inhibitors is a chronically Hepatitis C infected cell. Since Hepatitis C encodes and expresses two known inhibitors of PKR (i.e. NS5A and E2), a VSV encoded PKR gene product is be neutralized, and VSV allowed to replicate freely.

Example 10

Progressive Loss of Interferon Responsiveness with Oncogenic Transformation

Murine fibroblasts at various stages of transformation, either pretreated with 100 units of interferon alpha or left untreated, were infected with WT Indiana VSV at an MOI of 0.1 pfu/cell. Viral production was measured 18 hours pi by standard plaque assay. MEF: mouse fibroblast primary cultures isolated from Balb/C mouse embryos. NIH 3T3 cells: immortalized mouse embryo fibroblasts. PVSrc: NIH 3T3 cells transformed with the viral src gene. MOP 8: NIH 3T3 cells transformed with the polyoma virus Large T antigen. Results are shown in Table 2.

In this example, loss of interferon responsiveness correlates with susceptibility to VSV infection and progression of the malignant phenotype. The MEF cells are mortal (ie have a limited lifespan in culture) and completely interferon responsive. NIH 3T3 cells although not tumourigenic are immortalized and are about ten thousand fold less responsive to interferon than MEFs. The PVSrc and MOP 8 cells are fully tumourigenic, support robust VSV replication and are minimally protected by interferon treatment.

TABLE 2

| Cell Line | Viral Titre (pfu/ml) | |
| --- | --- | --- |
|  | Untreated | IFN-α |
| MEF (Mouse Embryonic Fibroblast) | $4 \times 10^6$ | <10 |
| NIH3T3 | $8 \times 10^7$ | $1 \times 10^4$ |
| PVSrc | $3 \times 10^9$ | $2 \times 10^7$ |
| MOP 8 | $1 \times 10^8$ | $5 \times 10^6$ |

Example 11

Virus Yield after Overnight Infection of Various Cell Lines Either Untreated or Treated with IFN A variety of normal and transformed cell lines were either untreated or pre-treated with 100 units of IFN-α, infected at an MOI of 0.1 pfu/ml with WT Indiana VSV and incubated for 18 hours at 37° C. Culture media from each sample was titred for VSV production. Results are shown in Table 3.

This example demonstrates that viral production is ten to ten thousand times more efficient in a range of tumour cell types as compared to normal primary tissues. In the presence of interferon alpha, virus production in normal primary cells is almost completely blocked while in tumour cells interferon has little or no effect on VSV replication.

TABLE 3

| Cell Line | Viral Titre (pfu/ml) | |
| --- | --- | --- |
|  | Untreated | IFN-α |
| OSF7 (primary normal human fibroblast) | $1 \times 10^6$ | <10 |
| OSF12 (primary normal human fibroblast) | $2 \times 10^5$ | <10 |
| OSF16 (primary normal human fibroblast) | $1 \times 10^5$ | <10 |
| PrEC (primary normal human prostate epithelium) | $8 \times 10^6$ | <10 |
| HOSE (primary normal human ovarian surface epithelium) | $1 \times 10^7$ | <1000 |
| A2780 (human ovarian carcinoma) | $2 \times 10^8$ | $1 \times 10^7$ |
| OVCA 420 (human ovarian carcinoma) | $1 \times 10^8$ | $3 \times 10^6$ |
| C13 (human ovarian carcinoma) | $1 \times 10^8$ | $1 \times 10^5$ |
| LC80 (human lung carcinoma) | $2 \times 10^9$ | $6 \times 10^7$ |
| SK-MEL3 (human melanoma) | $1 \times 10^9$ | $1 \times 10^9$ |
| LNCAP (human prostate carcinoma) | $4 \times 10^9$ | $5 \times 10^9$ |
| HCT116 (human colon carcinoma) | $1 \times 10^9$ | $2 \times 10^9$ |
| 293T (HEK cells transformed with T antigen and Ad virus E1A) | $1 \times 10^8$ | $8 \times 10^7$ |

Example 12

$LD_{50}$ for WT and Mutant VSV Delivered Intranasally to PKR$^{+/-}$ (129xBalb/c) Mice 8-10 week old female mice were an anesthetized and infected intranasally with virus diluted in 50 μl of phosphate buffered saline (PBS) into the nares of each animal (PKR$^{+/-}$; 129 x Balb/c strain). Lethal dose 50 values were calculated using the Korler-Spearman method. Results are shown in Table 4.

This example demonstrates that mutants I, II and III in particular, are attenuated as compared to the wild type Indiana strain of virus when tested for toxicity in 129X Balb/c mice.

TABLE 4

| Virus | Intranasal $LD_{50}$ (pfu) |
|---|---|
| WT Indiana | $1 \times 10^4$ |
| Mutant I | $1 \times 10^{10}$ |
| Mutant II | $>1 \times 10^{10}$ |
| Mutant III | $3 \times 10^8$ |
| Mutant IV | $<1 \times 10^5$ |

Example 13

$PKR^{-/-}$ Mice are Exquisitely Sensitive to VSV Compared to Various $PKR^{+/+}$ Mouse Strains $PKR^{-/-}$ and $PKR^{+/+}$ mice were infected intranasally at various doses and their survival monitored over time. All $PKR^{-/-}$ mice succumbed to the infection between days 2 and 5 depending on the dose, while control mice remained alive beyond this point. Results are shown in Table 5.

This example demonstrates the importance of the PKR gene product in the resistance of mice to VSV infection.

TABLE 5

| Genetic Background | | IN Dose (pfu) | Survival at day 5 |
|---|---|---|---|
| $PKR^{+/+}$ | Balb/c | $5 \times 10^4$ | 5/5 |
| | CD-1 | $5 \times 10^4$ | 5/5 |
| | Balb/c × 129 | $5 \times 10^4$ | 5/5 |
| $PKR^{-/-}$ | Balb/c × 129 | $5 \times 10^4$ | 0/5 |
| | | $5 \times 10^3$ | 0/4 |
| | | $5 \times 10^2$ | 0/3 |
| | | $5 \times 10^1$ | 0/3 |

Example 14

AML3 Cells Die by Apoptosis Following Infection with VSV

OCI/AML3 (acute myelogenous leukemia) cells were infected with VSV at an MOI of 3.0 pfu/cell. Fourteen and twenty hours post-infection unfixed samples were analyzed. Apoptotic cells with phosphatidylserine membrane translocation were detected by flow cytometry using Annexin-V-Biotin-X/NeutrAvidin-PE red fluorescent protein (Molecular Probes). Mitochondrial membrane depolarization in early apoptotic cells were analyzed by flow cytometry using JC-1 potential-sensitive dye (Molecular Probes). JC-1 is accumulated by polarized mitochondria shifting fluorescence emission from green to red spectra. Non-viable AMID cells were identified using Ethidium (EthD-1) homodimer-1 red fluorescent vital dye (Molecular probes). Assays were performed following the manufacturers specifications. Results are shown in Table 6.

This example demonstrates that VSV kills AML cells at least in part through a virally induced apoptotic pathway.

TABLE 6

|  | Tests | MOI 0.0 Percent Positive | MOI 3.0 Percent Positive | Net Positive (Dead) |
|---|---|---|---|---|
| 14 hrs p.i. | EthD-1 | 6.6 | 32.3 | 25.7 |
|  | Annexin V | 14.3 | 52.7 | 38.4 |
|  | JC-1 | 7.5 | 21.4 | 13.4 |
| 20 hrs p.i. | EthD-1 positive | 6.4 | 58.5 | 52.1 |
|  | Annexin-V positive | 10.8 | 79.6 | 68.8 |
|  | JC-1 | 3.9 | 43.2 | 39.3 |

Example 15

Mutant VSV Strains Infect and Kill AML Cells

OCI/AML3 (acute myelogenous leukemia) cells were infected at an MOI of 1.0 and incubated for 23 hours. Unfixed cells were stained with Eth-D1 (ethidium dimer, Molecular Probes) to detect non-viable cells following manufacturers specifications. Number of stained cells per 10,000 counted used to calculate percent dead. Results are shown in Table 7.

This example demonstrates that the mutant VSV strains used are as effective as the wild type Indiana strain in killing AML cells.

TABLE 7

|  | Mock | WT IND | Mut I | Mut II | Mut III | Mut IV | Mut V |
|---|---|---|---|---|---|---|---|
| Percent Dead | 30.0 | 64.7 | 60.7 | 86.7 | 72.1 | 74.4 | 82.8 |

Example 16

Figure 7:
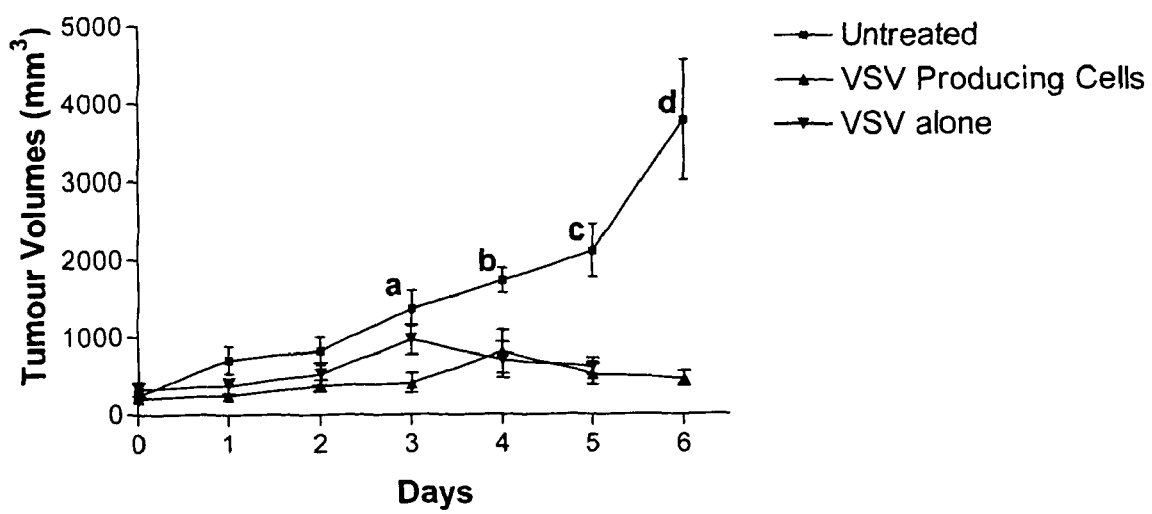

VSV and VSV Infected Cells Exhibit Antitumor Activity Against Human Melanoma Xenografts in Nude Mice SK-MEL 3 (melanoma) derived tumours were developed in 8-10 week old female Balb/c athymic mice. On day 0, tumours were either left untreated or were infected with $10^8$ pfu WT Indiana VSV in culture media or $2.5 \times 10^6$ WT Indiana VSV infected SK-MEL 3 cells (VSV producing cells). Statistical differences were calculated between treated and untreated groups at each data point with the following confidence values (b: $p<0.01$; c: $p<0.001$; d: $p=0.007$). Results are shown in FIG. 7. On day 3, only tumours treated with VSV producing cells were significantly smaller than untreated tumours (a: $p<0.001$). No statistically significant differences in tumour volumes between groups were apparent from day 0 to day 2. Data points represent means+/−SEM from multiple tumours (untreated n=8; VSV producing cells n=8; VSV alone n=4).

This example demonstrates that a single injection of VSV, directly into solid tumours profoundly affects tumour growth resulting in partial to complete regression. The use of infected tumour cells as a vehicle to deliver virus is also efficacious.

Example 17

Figures 8A, 8B:
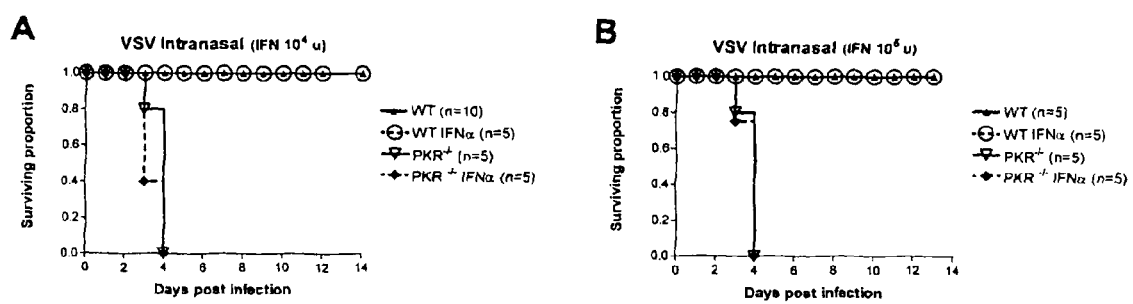

PKR$^{-/-}$ Mice are Acutely Sensitive to Intranasal VSV Infection and Demonstrate a Deficiency in IFN Mediated Resistance (A & B) PKR$^{-/-}$ and control mice (Balb/c X129) were infected intranasally with $5 \times 10^4$ pfu of VSV and monitored for morbidity and survival over the course of 14 days, after which remaining animals were deemed to have survived the infection. Results are shown in FIGS. 8A and 8B. PKR$^{-/-}$ mice showed a severe decrease in survival compared to control mice (WT), succumbing by day 3 or 4, while all control mice survived the infection. IFN-α/β pretreatment (18 h prior to infection) with either $2 \times 10^4$ IU (FIG. 8A) or $2 \times 10^5$ IU (FIG. 8B) had no protective effect in PKR$^{-/-}$ animals.

This example demonstrates that a single defect in the interferon pathway (absence of PKR gene product) is sufficient to render mice unable to resist VSV infections. This defect cannot be rescued by interferon.

Example 18

Interferon can Protect Xenograft Bearing Nude Mice During VSV Treatment

Figure 9:
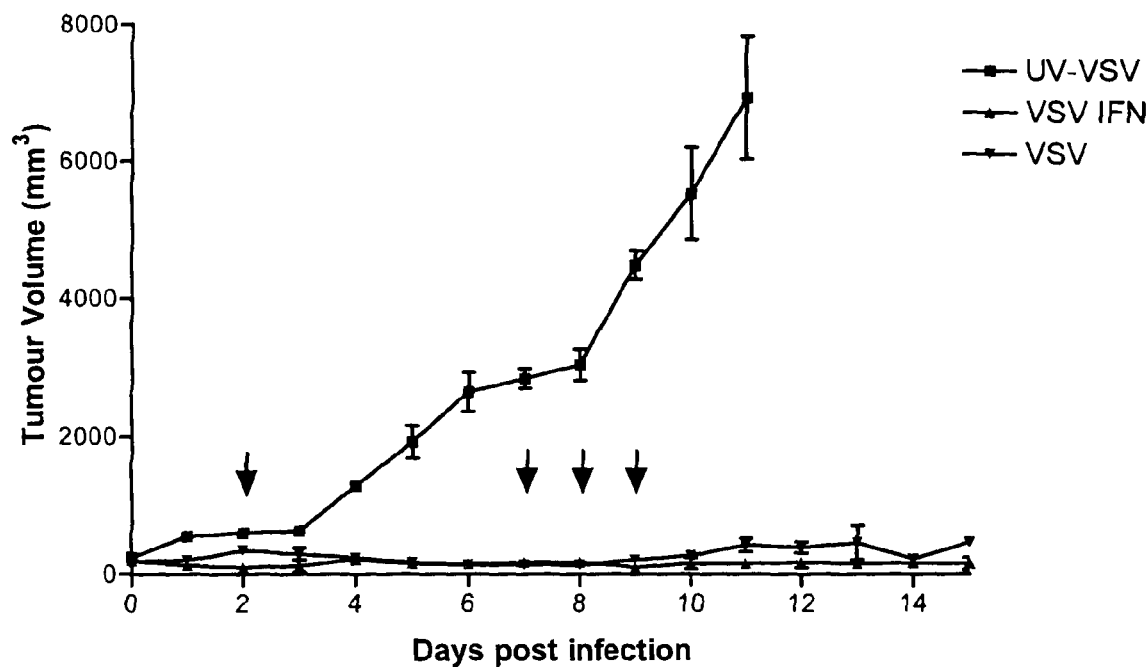

SK-MEL 3 melanoma cells were injected intradermally into CD-1 athymic nude mice. On day 0, tumours were injected with either live WT Indiana VSV ($1 \times 10^9$ pfu) or an equivalent amount of UV inactivated VSV, and measured daily. Results are shown in FIG. 9. Interferon was administered to a subset of animals (VSV IFN) at the times indicated (black arrows). (UV-VSV n=4; VSV IFN n=6; VSV n=6). In these experiments a single intratumoural injection of VSV is tumour-inhibiting in all cases. All tumours had at least a partial regression and in three of twelve mice treated a complete tumour regression. Tumours receiving UV inactivated virus continued to grow unabated until these animals were sacrificed at day 11. Nude mice not receiving interferon and injected with live virus began to die at day 10 and only two of six remained viable by day 15. In contrast, all interferon treated, infected, nude mice were protected from VSV toxicity and remained symptom free for more than 45 days.

This example demonstrates that a single intratumoural injection of live VSV is efficacious against tumours. Furthermore infected, tumour bearing, nude mice can be rescued from VSV toxicity by interferon injection.

Example 19

VSV Infects and Kills Leukemia and Myeloma Cells

The indicated cell lines were infected with VSV Indiana HR strain at a multiplicity of infection of one plaque forming unit per cell. At 24, 48 and 72 hours post infection (p.i.) samples were taken from the infected cultures and stained directly with propidium iodide following manufacturers instructions (Molecular Probes). Samples were then analysed by flow cytometry using the FACSsort WinMDI Version 2.7 program. In Table 8 the percentage of cells dead for each leukemic cell type is shown for the indicated times post infection.

This example shows that VSV is able to infect and kill a diverse set of leukemia types. The K-562 cell is isolated from a chronic myelogenous leukemia (CML) patient while MOLT-4 is a T cell leukemia and SR and H929 are myelomas.

TABLE 8

| Cell Line | 24 hr. p.i. | 48 hr. p.i. | 72 hr. p.i. |
|---|---|---|---|
| K-562 (CML) | 15.38% | 52.36% | N/D |
| MOLT-4 (T cell Leukemia) | 53.94% | 48.80% | N/D |
| SR (Myeloma) | 32.10% | 46.38% | N/D |
| H929(Myeloma) | 10.73% | 17.35% | 64.41% |

Example 20

Vesicular Stomatitis Virus (VSV) Strains Including Wild Type Indiana and Five Attenuated VSV Mutants Demonstrate Selective Cytotoxicity Toward Human Prostate Carcinoma Cells Compared to Normal Human Fibroblasts Vesicular stomatitis virus strains including wild type Indiana and attenuated mutant strains I (TR1026), II (TR1026R), III (TP3), IV (TP6) and V (G31) were obtained from Dr. Lauren Poliquin, University of Quebec at Montreal. Each of these virus strains was plaque purified five times prior to use in this experiment.

Human prostate carcinoma cells (LNCAP) and normal human cells (OSF 7 forearm fibroblast) were grown in 96-well tissue culture plates to a density of approximately $5 \times 10^4$ cells per well. Virus was added in 10-fold dilutions ranging from $5 \times 10^5$ pfu to 5 pfu. Control wells with no virus were included on each plate. The plates were incubated for 48 hours at 37° C. in 5% CO2. Cytotoxicity was quantified using a colorimetric MTS ((3-[4,5-dimethylthiazol-2-yl]-5-[3-carboxymethoxyphenyl]-2-[4-sulfophenyl]-2H-tetrazolium, inner salt) assay (CellTiter 96 Aqueous, catalog #G1112, Promega Corporation, Madison Wis. 53711-5399), monitored at 490 nm, that detects mitochondrial enzyme activity. The amount of cell killing in the virus treated wells was determined by the loss in viability in the virus treated wells relative to the untreated wells. The data was plotted graphically as pfu/cell vs. percentage cell killing relative to control. The TC50 for these cells was calculated as the amount of virus in pfu/cell causing a 50% reduction in the amount of viable cells. Lower TC50 values reflect increased sensitivity of the cells to the lytic effects of the virus. The in vitro therapeutic index for each VSV strain was calculated as the ratio of TC50 for the OSF7 cells compared to the TC50 for the LNCAP cells.

The results are shown in Table 9. Wild type VSV-Indiana and each of the five mutants demonstrated a high degree of cytotoxicity toward the human prostate carcinoma cells as reflected in the low TC50 values, all less than 0.01 pfu/cell. The normal human fibroblasts cells were one to more than 3 orders of magnitude more resistant to the cytotoxic effects of all six VSV strains. All five mutants had less toxicity on the normal OSF7 fibroblasts cells and had a higher in vitro therapeutic index than the wild-type Indiana VSV.

TABLE 9

Cytotoxicity Assay Results for VSV Strains (Wild type Indiana and Mutants I through V) Against Prostate Carcinoma Cells and Normal Fibroblasts.

| | Mutant I | Mutant II | Mutant III | Mutant IV | Mutant V | WT Indiana |
|---|---|---|---|---|---|---|
| LNCAP Prostate Carcinoma TC50 (pfu/cell) | 0.0064 | 0.0048 | 0.0014 | 0.0006 | 0.0012 | 0.0017 |
| OSF7 Normal Fibroblasts TC50 (pfu/cell) | >42 | 22 | 4.3 | 0.031 | 9.8 | 0.022 |
| Therapeutic Index (TC50 OSF7/ TC50 LNCAPP) | >6562 | 4583 | 3071 | 52 | 8167 | 13 |

Example 21

Virus Production from Tumour Cells and Normal Cells Infected with Wild Type Indiana and Various Mutant VSV Strains HCT 116 colon carcinoma cells and OSF 7 forearm fibroblasts were grown to confluence in 35 mm tissue culture dishes. Media was removed and virus was added in a volume of 30 µl with a multiplicity of infection of 0.1 pfu/cell for the HCT 116 cells and 1.5 pfu/cell for the OSF 7 cells. After a 1 hour incubation period at 37° C., 5% CO2, 1 ml of tissue culture media was added to the dishes. Results are shown in FIGS. 10A and B. At the indicated time points, 10 µl samples of media were removed from the dishes. The virus titre of these samples was determined by a plaque assay.

This example demonstrates the rapid replication kinetics of wild type and mutant VSV strains in HCT 116 colon carcinoma cells. All four mutant VSV strains had more rapid growth in HCT116 tumor cells than the wild type VSV. Note that in the normal OSF-7 cell cultures a ten fold higher input of virus is required to attain similar replication kinetics.

Example 22

Malignant Cells are Rapidly Killed Following VSV (WT Indiana) Infection and are not Protected by IFN-α

Monolayers of normal primary human fibroblasts (AG 1522) and several tumour cell lines were either untreated or pretreated with IFN-α (100 units) and then infected with VSV at an MOI of 0.1 pfu/ml. At 12 hours increments the infections were terminated by cell fixation and staining to determine the kinetics of cell killing. Control (CNTL) monolayers were left to grow, uninfected, over the course of the experiment and therefore stain more intensely. Results are shown in FIG. 11. LNCAP is a human prostate carcinoma; A2780 is an human ovarian epithelial carcinoma, and Sk MEL3 is a human melanoma.

This example demonstrates the rapid kinetics of tumour cell killing by VSV Indiana even in the presence of interferon alpha. While normal cells are also killed by VSV, the kinetics are slower and normal cells can be completely protected by interferon alpha.

Example 23

VSV Induced Cytopathic Effect Visible in Human Melanoma Cells but Not in Primary Human Cells with or without IFN-α

Gelatin-coated coverslips with normal human cells and SK-MEL3 cells untreated or pretreated with IFN-α (100

U/ml) were infected with WT Indiana VSV at an MOI of 0.1 pfu/ml. Results are shown in FIG. 12. The human melanoma cells (SK-MEL3) displayed cpe at 12 hours post-infection even in the presence of interferon. At 24 hours post-infection these malignant cells had died and lifted from the coverslip. Human primary cells including foreskin fibroblasts (AG1522), ovarian surface epithelial cells (HOSE) and prostate epithelial cells (PrEC) did not show CPE (cytopathic effect) until 36 hours in the absence of interferon and were completely protected in the presence of interferon beyond 72 hours post-infection.

This example demonstrates that VSV Indiana is able to rapidly destroy melanoma cells even in the presence of interferon alpha whereas normal fibroblasts and epithelial cells are slower to be killed and can be completely protected by interferon alpha.

Example 24

VSV Selectively Kills Transformed Cells Co-Cultured with Normal Fibroblasts

Equal numbers of 293T cells (human embryo kidney cells transformed with adenovirus E1A and Large T antigen) and normal human foreskin fibroblasts were plated on gelatin-coated coverslips and infected (WT Indiana VSV) at an MOI of 0.1 both in the presence and absence of interferon. Cells were fixed at 12 (not shown), 24 and 36 hours post-infection. Fixed cells were stained with an anti-TAg antibody and DAPI. The red staining 293T cells were quickly killed as early as 12 hours post-infection, regardless of interferon treatment, with those few remaining cells displaying condensed or fragmented nuclei. The normal fibroblasts displayed altered nuclei by 36 hours post-infection in the absence of interferon but were protected from the virus in the presence of interferon beyond this time point.

This example demonstrates that in a mixed culture of normal and tumour cells, VSV Indiana preferentially replicates and kills tumour cells. Normal cells in the infected co-cultures are slower to die and can be completely rescued by interferon treatment.

Example 25

Efficacy of a Single Intravenous Dose of Mutant VSV in Treating Human Melanoma Xenografts in Nude Mice SK-Mel3 human melanoma xenografts were established in 5-6 week old CD-1 athymic mice. On day 0, tumours were either left untreated or were treated intravenously with $5\times10^9$ pfu of mutant VSV as indicated. Results are shown in FIG. 13.

This example demonstrates that mutants II and III are able to inhibit tumour growth following a single intravenous injection. Thus virus need not be administered at the tumour site to be effective in inhibiting tumour growth. Furthermore, the mutants while being attenuated for growth in normal mouse tissues, are still able to target tumour cells in vivo.

Example 26

Selective Killing of AML Cells Co-Cultured with Normal Bone Marrow

The growth factor independent cell line OCI/AML3 was mixed 1:9 with normal bone marrow and infected for 24 hours with WT Indiana VSV. Various dilutions of cells were then plated in methylcellulose plus and minus growth factors and colony counts were performed 14 days later. Table 10 shows data for dishes receiving $10^4$ cells. The asterisk (*) signifies that no leukemic colonies were detected on the growth factor minus dishes even when $10^5$ cells were plated per dish.

This example demonstrates the rapid and selective killing of leukemia cells in the presence of normal bone stem cells. Furthermore it demonstrates that bone marrow is not a dose-limiting target of VSV oncolytic therapy as it is with most other conventional cancer therapies.

TABLE 10

| | Multiplicity of Infection | | |
|---|---|---|---|
| Colony Type | 0.0 | 1.0 | 5.0 |
| Leukemic | 172 | 0* | 0* |
| Neutrophil | 12 | 7 | 5 |
| Mixed | 6 | 3 | 4 |
| Monocyte | 10 | 7 | 5 |

Example 27

VSV Sequences

The genome of VSV contains genes that encode viral proteins N, P, M, G and L. The cDNA sequences of the open reading frames (ORF) for these proteins from wild type heat resistant VSV (HR) and three mutant VSVs were determined (based on sequencing five times each) and compared with the sequences of GenBank Accession No. NC 001560 (derived from Colorado and San Juan strains of VSV). The mutants are M2 (TR1026R), M3 (TP3) and M4 (TP6). The nucleic acid sequences are shown in FIGS. 14, 16, 18, 20 and 22. The corresponding deduced amino acid sequences are shown in FIGS. 15, 17, 19, 21 and 23, respectively. Differences are indicated by highlighted letters. Dotted lines represent incomplete sequencing.

Some of the differences between the amino acid sequences are shown in Table 11 using notation based on column heading (i.e. for column heading "Differences Between GenBank and HR" notation K155R means that the amino acid at position 155 is K in GenBank and R in HR). In those cases where HR sequence is not yet available comparisons can only be made between GenBank and a particular mutant. M3* denotes a difference between mutant 3 and HR but in this case the amino acid matches the GenBank deposit at that position (i.e. mutant 3 and the Genbank sequence agree at that position while HR is different).

This data demonstrates the many differences in sequence between the HR strain and the GenBank deposit (which is primarily derived from the San Juan strain). It also demonstrates some of the differences between the mutants and the HR strain from which they were derived. These genetic differences correlate with phenotypic differences.

TABLE 11

| Gene | Differences Between GenBank and HR | Differences Between HR and Mutants | Differences Between Genbank and Mutant #2 | Differences Between GenBank and Mutant #4 |
|---|---|---|---|---|
| N | D10A, K155R, N353S | A10D (M3*)<br>None (M4) | | |

TABLE 11-continued

| Gene | Differences Between GenBank and HR | Differences Between HR and Mutants | Differences Between Genbank and Mutant #2 | Differences Between GenBank and Mutant #4 |
|---|---|---|---|---|
| P | K50R, A76V, Q77P, E99D P110Q, S126L, S140L Y151H, M168I, E170K D237N | None (M2, M3 and M4) | | |
| M | S32N, Y54H, N57H, T133A, I171V, I226V | M51R (M3) None (M4) | | |
| G | H24Y, I57L, Q96H, V141A, Y172D, G132D H242R, S438T, L453F H487Y | Q26R, R242H, S431A (all M3) E254G (M4) | A331V | |
| L | T367A, T689S, T2026I R2075K | None (M4) | | I202L, K296R |

All citations are herein incorporated by reference.

The present invention has been described with regard to preferred embodiments. However, it will be obvious to persons skilled in the art that a number of variations and modifications can be made without departing from the scope of the invention as described herein.

REFERENCES

1. Stark, G. R., et al., How cells respond to interferons. Annu Rev Biochem, 1998. 67: p. 227-64.
2. Jaramillo, M. L., N. Abraham, and J. C. Bell, The interferon system: a review with emphasis on the role of PKR in growth control. Cancer Invest, 1995. 13 (3): p. 327-38.
3. Cuddihy, A. R., et al., Double-stranded-RNA-activated protein kinase PKR enhances transcriptional activation by tumor suppressor p53. Mol Cell Biol, 1999. 19 (4): p. 2475-84.
4. Lee, S. B., et al., The apoptosis pathway triggered by the interferon-induced protein kinase PKR requires the third basic domain, initiates upstream of Bcl-2, and involves ICE-like proteases. Virology, 1997. 231 (1): p. 81-8.
5. Lee, S. B. and M. Esteban, The interferon-induced double-stranded RNA-activated protein kinase induces apoptosis. Virology, 1994. 199 (2): p. 491-6.
6. Gale, M. J., Jr., et al., Evidence that hepatitis C virus resistance to interferon is mediated through repression of the PKR protein kinase by the nonstructural 5A protein. Virology, 1997. 230 (2): p. 217-27.
7. McMillan, N. A., et al., HIV-1 Tat directly interacts with the interferon-induced, double-stranded RNA-dependent kinase, PKR. Virology, 1995. 213 (2): p. 413-24.
8. Kitajewski, J., et al., Adenovirus VAI RNA antagonizes the antiviral action of interferon by preventing activation of the interferon-induced eIF-2 alpha kinase. Cell, 1986. 45 (2): p. 195-200.
9. Black, T. L., G. N. Barber, and M. G. Katze, Degradation of the interferon-induced 68,000-M(r) protein kinase by polio virus requires RNA. J Virol, 1993. 67 (2): p. 791-800.
10. Melville, M. W., et al., The molecular chaperone hsp40 regulates the activity of P58IPK, the cellular inhibitor of PKR. Proc Natl Acad Sci USA, 1997. 94 (1): p. 97-102.
11. Swaminathan, S., et al., Simian Virus 40 Large-T Bypasses the Translational Block Imposed by the Phosphorylation of eIF-2alpha. Virology, 1996. 219 (1): p. 321-3.
12. Der, S. D., et al., A double-stranded RNA-activated protein kinase-dependent pathway mediating stress-induced apoptosis. Proc Natl Acad Sci USA, 1997. 94 (7): p. 3279-83.
13. Meurs, E. F., et al., Tumor suppressor function of the interferon-induced double-stranded RNA-activated protein kinase. Proc Natl Acad Sci USA, 1993. 90 (1): p. 232-6.
14. Koromilas, A. E., et al., Malignant transformation by a mutant of the IFN-inducible dsRNA-dependent protein kinase. Science, 1992. 257 (5077): p. 1685-9.
15. Mundschau, L. J. and D. V. Faller, Oncogenic ras induces an inhibitor of double-stranded RNA-dependent eukaryotic initiation factor 2 alpha-kinase activation. J Biol Chem, 1992. 267 (32): p. 23092-8.
16. Mundschau, L. J. and D. V. Faller, Endogenous inhibitors of the dsRNA-dependent eIF-2 alpha protein kinase PKR in normal and ras-transformed cells. Biochimie, 1994. 76 (8): p. 792-800.
17. Strong, J. E., et al., The molecular basis of viral oncolysis: usurpation of the Ras signalling pathway by reovirus. Embo J, 1998. 17 (12): p. 3351-62.
18. Kumar, K. U., S. P. Srivastava, and R. J. Kaufman, Double-stranded RNA-activated protein kinase (PKR) is negatively regulated by 60S ribosomal subunit protein L18. Mol Cell Biol, 1999. 19 (2): p. 1116-25.
19. Peralta, R. C., et al., Distinct regions of frequent loss of heterozygosity of chromosome 5p and 5q in human esophageal cancer. Int J Cancer, 1998. 78 (5): p. 600-5.
20. Kirchhoff, S., et al., IRF-1 induced cell growth inhibition and interferon induction requires the activity of the protein kinase PKR. Oncogene, 1995. 11 (3): p. 439-45.
21. Beretta, L., et al., Expression of the protein kinase PKR in modulated by IRF-1 and is reduced in 5q-associated leukemias. Oncogene, 1996. 12 (7): p. 1593-6.
22. Lossos, I. S., et al., A novel translocation (1; 2)(p34; p21-22) in acute myelomonoblastic leukemia. Cancer Genet Cytogenet, 1998. 106 (1): p. 78-9.
23. Haines, G. K. d., et al., Expression of the double-stranded RNA-dependent protein kinase (p68) in squamous cell carcinoma of the head and neck region. Arch Otolaryngol Head Neck Surg, 1993. 119 (10): p. 1142-7.
24. Haines, G. K., et al., Correlation of the expression of double-stranded RNA-dependent protein kinase (p68) with differentiation in head and neck squamous cell carcinoma. Virchows Arch B Cell Pathol Incl Mol Pathol, 1993. 63 (5): p. 289-95.
25. Shimada, A., et al., Aberrant expression of double-stranded RNA-dependent protein kinase in hepatocytes of chronic hepatitis and differentiated hepatocellular carcinoma. Cancer Res, 1998. 58 (19): p. 4434-8.
26. Wong, L. H., et al., Interferon-resistant human melanoma cells are deficient in ISGF3 components, STAT1, STAT2, and p48-ISGF3gamma. J Biol Chem, 1997. 272 (45): p. 28779-85.
27. Petricoin, E., 3rd, et al., Human cancer cell lines express a negative transcriptional regulator of the interferon regulatory factor family of DNA binding proteins. Mol Cell Biol, 1994. 14 (2): p. 1477-86.
28. Abril, E., et al., Characterization of a gastric tumor cell line defective in MHC class I inducibility by both alpha- and gamma-interferon. Tissue Antigens, 1996. 47 (5): p. 391-8.

29. Abril, E., et al., Unresponsiveness to interferon associated with STAT1 protein deficiency in a gastric adenocarcinoma cell line. Cancer Immunol Immunother, 1998. 47 (2): p. 113-20.
30. Sun, W. H., et al., Interferon-alpha resistance in a cutaneous T-cell lymphoma cell line is associated with lack of STAT1 expression. Blood, 1998. 91 (2): p. 570-6.
31. Chelbi-Alix, M. K., et al., Resistance to virus infection conferred by the interferon-induced promyelocytic leukemia protein. J Virol, 1998. 72 (2): p. 1043-51.
32. Chelbi-Alix, M. K., et al., Induction of the PML protein by interferons in normal and APL cells. Leukemia, 1995. 9 (12): p. 2027-33.
33. Stadler, M., et al., Transcriptional induction of the PML growth suppressor gene by interferons is mediated through an ISRE and a GAS element. Oncogene, 1995. 11 (12): p. 2565-73.
34. Koken, M. H., et al., Leukemia-associated retinoic acid receptor alpha fusion partners, PML and PLZF, heterodimerize and colocalize to nuclear bodies. Proc Natl Acad Sci USA, 1997. 94 (19): p. 10255-60.
35. Abraham, N., et al., Characterization of transgenic mice with targeted disruption of the catalytic domain of the double-stranded RNA-dependent protein kinase, PKR. J Biol Chem, 1999. 274 (9): p. 5953-62.
36. Garcia-Sastre, A., et al., Influenza A virus lacking the NS1 gene replicates in interferon-deficient systems. Virology, 1998. 252 (2): p. 324-30.

What is claimed is:

1. A method of reducing the viability of a tumor cell, comprising administering to the tumor cell a virus, such that the virus is delivered to the tumor cell,
wherein said virus is a vesicular stomatitis virus and said tumor cell is a hematopoietic tumor cell and
wherein the virus is contained in a cell infected with the virus and the administering comprises administering the virus-infected cell.

2. The method of claim 1, wherein the hematopoietic tumor cell is a leukemia, a lymphoma, or a myeloma.

3. The method of claim 1, wherein the hematopoietic tumor cell is a leukemia.

4. The method of claim 3, wherein the leukemia is acute myelogenous leukemia.

5. The method of claim 3, wherein the leukemia is chronic myelogenous leukemia.

6. The method of claim 3, wherein the leukemia is promyelocytic leukemia.

7. The method of claim 3, wherein the leukemia is T cell leukemia.

8. The method of claim 1, wherein the hematopoietic tumor cell is a lymphoma.

9. The method of claim 1, wherein the hematopoietic tumor cell is a myeloma.

10. The method of claim 1, wherein the tumor cell is PKR−/−; STAT1−/−; or both PKR−/− and STAT1−/−.

11. The method of claim 1, further comprising administering interferon to the tumor cell prior to administering VSV, such that the interferon is delivered to the tumor cell.

12. The method of claim 1, wherein the virus is unable to inactivate PKR activity within the tumor cell.

13. The method of claim 1, wherein the virus is an attenuated strain of vesicular stomatitis virus.

14. The method of claim 1, wherein the virus is vesicular stomatitis virus strain M1.

15. The method of claim 1, wherein the virus is vesicular stomatitis virus strain M2.

16. The method claim 1, wherein the virus is vesicular stomatitis virus strain M3.

17. The method of claim 1, wherein the virus is vesicular stomatitis virus strain M4.

18. The method of claim 1, wherein the virus is vesicular stomatitis virus strain M5.

19. The method of claim 1, wherein the tumor cell is in a mammalian subject.

20. The method of claim 19, wherein the mammalian subject is a non-human mammal.

21. The method of claim 19, further comprising treating the mammalian subject with an interferon.

22. The method of claim 19, wherein the mammalian subject is a human.

23. The method of claim 19, wherein the administering comprises administering the virus-infected cell to the subject by a route selected from intratumorally, intravenously and intraperitoneally.

24. A method of reducing the viability of a tumor cell within a population of cells comprising administering a vesicular stomatitis virus to the population of cells, such that the virus is delivered to the population of cells,
wherein the virus is contained in a cell infected with the virus and the administering comprises administering the virus-infected cell,
wherein the population of cells comprises hematopoietic tumor cells and non-tumor cells and
wherein the virus is able to selectively reduce the viability of the hematopoietic tumor cells.

25. The method of claim 24, wherein the virus is unable to inactivate PKR activity in the tumor cell.

26. The method of claim 25, further comprising treating the population of cells with interferon prior to administering the virus.

27. The method of claim 24, wherein the hematopoietic tumor cells are leukemia cells.

28. The method of claim 27, wherein the leukemia cells are acute myelogenous leukemia cells.

29. The method of claim 27, wherein the leukemia cells are chronic myelogenous leukemia cells.

30. The method of claim 27, wherein the leukemia cells are promyelocytic leukemia cells.

31. The method of claim 27, wherein the leukemia cells are T cell leukemia cells.

32. The method of claim 24, wherein the hematopoietic tumor cells are lymphoma cells.

33. The method of claim 24, wherein the hematopoietic tumor cells are myeloma cells.

34. The method of claim 24, wherein the tumor cells are PKR−/−; STAT1−/−; or both PKR−/− and STAT1−/−.

35. The method of claim 24, wherein the virus is an attenuated strain of vesicular stomatitis virus.

36. The method of claim 24, wherein the virus is vesicular stomatitis virus strain M1.

37. The method of claim 24, wherein the virus is vesicular stomatitis virus strain M2.

38. The method of claim 24, wherein the virus is vesicular stomatitis virus strain M3.

39. The method of claim 24, wherein the virus is vesicular stomatitis virus strain M4.

40. The method of claim 24, wherein the virus is vesicular stomatitis virus strain M5.

41. The method of claim 24, wherein the administering of the vesicular stomatitis virus to the population of cells is performed in vitro.

* * * * *